US012152017B2

United States Patent
Liu et al.

(10) Patent No.: US 12,152,017 B2
(45) Date of Patent: Nov. 26, 2024

(54) KETOAMIDE COMPOUND AND PREPARATION METHOD, PHARMACEUTICAL COMPOSITION, AND USE THEREOF

(71) Applicants: Shanghai Institute of Materia Medica, Chinese Academy of Sciences, Shanghai (CN); Fudan University, Shanghai (CN)

(72) Inventors: Hong Liu, Shanghai (CN); Shibo Jiang, Shanghai (CN); Wenhao Dai, Shanghai (CN); Lu Lu, Shanghai (CN); Jingjing Peng, Shanghai (CN); Shuai Xia, Shanghai (CN); Jiang Wang, Shanghai (CN); Jian Li, Shanghai (CN); Hualiang Jiang, Shanghai (CN); Kaixian Chen, Shanghai (CN)

(73) Assignees: Shanghai Institute of Materia Medica, Chinese Academy of Sciences, Shanghai (CN); Fudan University, Shanghai (CN)

( * ) Notice: Subject to any disclaimer, the term of this patent is extended or adjusted under 35 U.S.C. 154(b) by 955 days.

(21) Appl. No.: 17/267,375

(22) PCT Filed: Aug. 9, 2019

(86) PCT No.: PCT/CN2019/100060
§ 371 (c)(1),
(2) Date: Apr. 19, 2021

(87) PCT Pub. No.: WO2020/030143
PCT Pub. Date: Feb. 13, 2020

(65) Prior Publication Data
US 2022/0112177 A1   Apr. 14, 2022

(30) Foreign Application Priority Data
Aug. 9, 2018 (CN) .......................... 201810903062.1

(51) Int. Cl.
| | |
|---|---|
| C07D 403/12 | (2006.01) |
| A61P 31/12 | (2006.01) |
| C07D 209/20 | (2006.01) |
| C07D 241/44 | (2006.01) |
| C07D 401/12 | (2006.01) |
| C07D 405/12 | (2006.01) |
| C07D 409/12 | (2006.01) |
| C07D 413/12 | (2006.01) |
| C07D 471/04 | (2006.01) |

(52) U.S. Cl.
CPC ............ *C07D 403/12* (2013.01); *A61P 31/12* (2018.01); *C07D 209/20* (2013.01); *C07D 241/44* (2013.01); *C07D 401/12* (2013.01); *C07D 405/12* (2013.01); *C07D 409/12* (2013.01); *C07D 413/12* (2013.01); *C07D 471/04* (2013.01)

(58) Field of Classification Search
CPC .. C07D 403/12; C07D 209/20; C07D 241/44; C07D 401/12; C07D 405/12; C07D 409/12; C07D 413/12; C07D 471/04; A61P 31/12
USPC ....................................................... 546/278.1
See application file for complete search history.

(56) References Cited

U.S. PATENT DOCUMENTS

2022/0112177 A1   4/2022   Liu et al.

FOREIGN PATENT DOCUMENTS

| CN | 103145608 A | 6/2013 |
|---|---|---|
| CN | 104592349 A | 5/2015 |
| CN | 105837487 A | 8/2016 |
| CN | 106928206 A | 7/2017 |
| JP | 2021507010 A | 2/2021 |
| WO | 2006061714 A2 | 6/2006 |
| WO | 2013049382 A2 | 4/2013 |

(Continued)

OTHER PUBLICATIONS

Kher et al., "Substrate Derived Peptidic α-Ketoamides as Inhibitors of the Malarial Protease PfSUB1," Bioorganic & Medicinal Chemistry Letters, vol. 18, No. 24, 2014, pp. 4486-4489.

(Continued)

*Primary Examiner* — Kahsay Habte
(74) *Attorney, Agent, or Firm* — Ice Miller LLP

(57) ABSTRACT

A ketoamide compound and a preparation method, a pharmaceutical composition, and a use thereof. Specifically, the ketoamide compound shown in formula (A), a racemate, an enantiomer, or a diastereoisomer thereof, or any mixture of same, or a pharmaceutically active metabolite thereof, or a pharmaceutically acceptable salt, solvate, or prodrug thereof. The ketoamide compound can effectively inhibit coronavirus or Ebola virus, and thereby implement the prevention or treatment of diseases related to coronavirus or diseases related to Ebola virus.

10 Claims, 3 Drawing Sheets

(56) References Cited

FOREIGN PATENT DOCUMENTS

| WO | 2017114509 A1 | 7/2017 |
| WO | 2018042343 A2 | 3/2018 |
| WO | 2018067847 A1 | 4/2018 |
| WO | 2019121682 A | 6/2019 |
| WO | 2020030143 A1 | 2/2020 |

OTHER PUBLICATIONS

Chen et al., "Synthesis and Evaluation of Tripeptidyl a-Ketoamides as Human Rhinovirus 3C Protease Inhibitors," Bioorganic & Medicinal Chemistry Letters, vol. 20, No. 13, 2003, pp. 3531-3536.

Gibadullin et al., "GalNAc-Tyrosine is a Ligand of Plant Lectins, Antibodies, and Human and Murine Macrophage Galactose-Type Lectins," ACS Chemical Biology, vol. 8, No. 12, 2017, pp. 2172-2182.

International Search Report dated Oct. 12, 2019 issued in International Application No. PCT/CN2019/100060.

Thanigaimalai, Pillaiyar, et al., "Development of potent dipeptide-type Sars-Cov 3CL protease inhibitors with novel P3 scaffolds: Design, synthesis, biological evaluation, and docking studies," European Journal of Medicinal Chemistry, vol. 68, pp. 372-384, Aug. 9, 2013.

Zhai, Yangyang, et al., "Cyanohydrin as an Anchoring Group for Potent and Selective Inhibitors of Enterovirus 71 3C Protease," Journal of Medicinal Chemistry, vol. 58, pp. 9414-9420, Nov. 16, 2015.

Sacco, Michael Dominic, et al., "Structure and inhibition of the SARS-CoV-2 main protease reveal strategy for developing dual inhibitors against Mpro and cathepsin L," Science Advances, vol. 6, Dec. 9, 2020.

Xu, Zhijian, et al., "Nelfinavir was predicted to be a potential inhibitor of 2019-nCov main protease by an integrative approach combining homology modelling, molecular docking and binding free energy calculation," bioRxiv preprint doi: https://doi.org/10.1101/2020.01.27.921627; this version posted Jan. 28, 2020.

Zeng, Debin, et al., "Synthesis and structure-activity relationship of a-keto amides as enterovirus 71 3C protease inhibitors," Bioorganic & Medicinal Chemistry Letters, vol. 26, pp. 1762-1766, Feb. 16, 2016.

Wang, Yaxin, et al., "Inhibition of enterovirus 71 replication by an a-hydroxy-nitrile derivative NK-1.9k," Antiviral Research, vol. 141 (2017).

Zhang, Linlin, et al., "a-Ketoamides as Broad-Spectrum Inhibitors of Coronavirus and enterovirus Repliaction: Structure-Based Design, Synthesis, and Activity Assessment," J. Med. Chem., vol. 63, pp. 4562-4578 (2020).

Frecer, Vladimir, et al., "Antiviral agents against COVID-19: structure-based design of specific peptidomimetic inhibitors of SARS-CoV-2 main protease," RSC Adv. vol. 10, pp. 40244-40263 (2020).

Genovese, Luigi, et al., "Microscopic factors modulating the interactions between the SARS-Cov-2 main protease and a-ketoamide inhibitors," 19 pp. Sep. 11, 2020.

Liu, Xin, et al., "Potential inhibitors for 2019-nCOV coronavirus M protease from clinically approved medicines," 13 pages.

Extended European Search Report issued Jan. 30, 2024 in corresponding European application No. 21748369.2.

Nie, Quandeng, et al., "3D-quantitative structure-activity relationship study for the design of novel enterovirus A71 3C proteas inhibitors," Chemical Biology & Drug Design, vol. 92, No. 4, Jun. 26, 2018 pp. 1750-1762.

Lopez-Leon, Sandra, et al, "More than 50 long-term effects of COVID-19: a systematic review and meta-analysis," Scientific Reports (2021) 11:16144, retrieved from the Internet (https://doi.org/10.1038/s41598-021-95565-8 ).

Bai, Bing, et al., "Peptidomimetic a-Acyloxymethylketone Warheads with Six-Membered Lactam P1 Glutamine Mimic: SARS-CoV-2 3CL Protease Inhibition, Coronavirus Antiviral Activity, and In Vitro Biological Stability," Journal of Medical Chemistry, vol. 65, pp. 2905-2925 (2022).

Fig. 3C

ECₐ₀ of mice serum for MERS-CoV PsV infection (serum dilution multiples)

| time after administration(h) | administered drug | |
|---|---|---|
| | Compound A13 | DMSO |
| 2 | 3,181 | 130 |
| 12 | 1,133 | 76 |
| 24 | 260 | 124 |

KETOAMIDE COMPOUND AND PREPARATION METHOD, PHARMACEUTICAL COMPOSITION, AND USE THEREOF

CROSS-REFERENCE TO RELATED APPLICATION

This application is a Section 371 of International Application No. PCT/CN2019/100060 filed Aug. 9, 2019, which was published in the Chinese language Feb. 13, 2020, under International Publication No. WO 2020/030143 A1, which claims priority to Chinese Application No. 201810903062.1 filed Aug. 9, 2018, the disclosures of which are incorporated herein by reference in their entireties.

TECHNICAL FIELD

The present invention relates to the fields of medicinal chemistry and pharmacotherapy, and in particular to keto-amide compounds as inhibitors for coronavirus or Ebola virus, preparation methods thereof, pharmaceutical compositions containing such compounds, and uses thereof.

BACKGROUND ART

Coronavirus belongs to Coronavirus Genus under Coronaviridae Family in the systematic classification. The diameter of mature coronavirus is about 60 nm-220 nm and under the electron microscope, it looks like a corona or crown, so it is named as coronavirus. It is an important pathogen causing diseases in many spinal animals including human.

Coronavirus is a single-stranded positive-stranded RNA virus with a genome size of 27-32 kb, and is a RNA virus with the largest genome known at present. It contains 6-12 open reading frames and similar to the mRNA of eukaryotic cells, the replication of the coronavirus is carried out in the cytoplasm. After infecting the cell, the virus is unshelled in the cytoplasm, and then the positive-strand genomic RNA is activated, thereby showing the role of mRNA. Coronavirus infection is distributed in many regions around the world, and the existence of this virus has been found in China, the United Kingdom, the United States, Germany, Japan, Russia, Finland, India and other countries. Infections caused by the virus mainly occur in winter and early spring. In a home inspection in Michigan, USA, it was proved that the coronavirus can infect all age groups, 0-4 years old accounted for 29.2%, 40 years old and above accounted for 22%, with the highest incidence in the group of 15-19 years old age. This is not the same as the prevalence of other upper respiratory viruses, such as respiratory syncytial virus, which usually decreases with age.

Coronaviruses can be divided into four genera α, β, γ and δ according to their serological characteristics. Among them, a new type of β genus coronavirus MERS-CoV (Middle East Respiratory Syndrome-coronavirus) is having a major impact on global public health. MERS-CoV was first discovered in Saudi Arabia in 2012 and was renamed as Middle East Respiratory Syndrome in 2013. According to data released by the World Health Organization (WHO), as of Mar. 19, 2018, there were a total of 2143 patients who were confirmed to be infected with MERS-CoV in 27 countries around the world, wherein 750 cases were dead with a fatality rate close to 35%, and the virus has spread into China.

After humans are infected with MERS-CoV, the clinical manifestations include fever, cough, and shortness of breath. Most of these patients will also experience symptoms such as fever, feel cold/chills, cough, shortness of breath, and muscle pain. The majority of MERS-CoV patients are people suffering from chronic diseases. Children under the age of 15 and the elderly over 65, pregnant women, patients with chronic diseases such as cardiovascular disease and pneumonia, and patients with poor resistance are all susceptible.

MERS-CoV is highly pathogenic and can not only spread across species, but also spread from person to person. MERS-CoV has a fatality rate of more than 30%. The main modes of transmission are droplet transmission and contact transmission.

SARS-CoV and MERS-CoV both belong to the 13 genus of coronavirus. SARS-CoV caused severe acute respiratory syndrome in Shunde, Guangdong, China in 2002, and spread to Southeast Asia and the world. It was not until mid-2003 that the epidemic was gradually controlled. SARS virus is excreted from the body through the secretions of the respiratory tract, and it is transmitted through oral fluid, sneeze, contact, and it can spread through air droplets. The peak of infection is in autumn and winter and early spring.

In summary, there is an urgent need in this field to develop inhibitors against MERS-CoV and SARS-CoV. This is not only a focus in international antiviral research, but also an important work in the prevention and control of infectious diseases in China.

SUMMARY OF THE INVENTION

The purpose of the present invention is to provide a kind of ketoamide compounds represented by formula A, its racemates, enantiomers, diastereomers, or mixture thereof, or its pharmaceutically active metabolite, or its pharmaceutically acceptable salt, solvate or prodrug that have an inhibitory effect on Coronavirus or Ebola virus, and its preparation method, pharmaceutical composition and use.

In the first aspect of the present invention, it provides a ketoamide compound represented by the formula A, or a racemate, an enantiomer, a diastereomer, or a mixture thereof, or a pharmaceutically active metabolite, or a pharmaceutically acceptable salt, a solvate or a prodrug thereof:

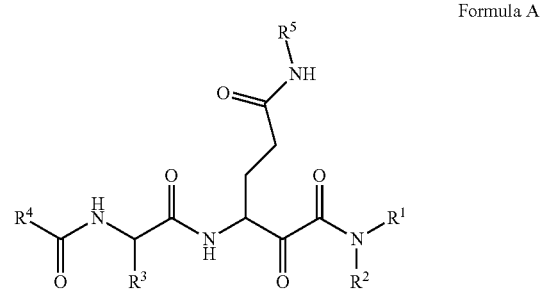

Formula A wherein:
$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl, and sulfonyl;

$R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C6-C20 aryl C2-C6 alkynylene, substituted or unsubstituted C3-C20 heteroaryl C1-C9 alkylene, substituted or unsubstituted C3-C20 heteroaryl C2-C9 alkenylene, and substituted or unsubstituted C3-C20 heteroaryl C2-C9 alkynylene;

when —$NHR^5$ and its adjacent —(C=O)—$CH_2$— form a ring, $R^5$ is —$(CH_2)_n$—, and n is 2 or 3;

when —$NHR^5$ does not form a ring with its adjacent —(C=O)—$CH_2$—, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl, and sulfonyl;

wherein, in $R^1$, $R^2$, $R^3$, $R^4$ and $R^5$, each of the term "substituted" independently refers to substitution by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, trifluoromethyl; the heterocycloalkyl and the heteroaryl each independently comprise 1, 2, 3 or 4 heteroatoms selected from N, O, and S.

In another preferred embodiment, $R^1$ and $R^2$ are each independently selected from the group consisting of hydrogen, deuterium, tritium, amino, hydroxyl, substituted or unsubstituted C1-C6 alkyl, substituted or unsubstituted C3-C8 cycloalkyl, substituted or unsubstituted C3-C8 cycloalkyl C1-C5 alkylene, substituted or unsubstituted C3-C10 heterocycloalkyl, substituted or unsubstituted C3-C10 heterocycloalkyl C1-C5 alkylene, substituted or unsubstituted C6-C14 aryl, substituted or unsubstituted C3-C10 heteroaryl, substituted or unsubstituted C6-C14 aryl C1-C5 alkylene, substituted or unsubstituted C3-C10 heteroaryl C1-C5 alkylene, substituted or unsubstituted C6-C10 aryl C2-C5 alkenylene, substituted or unsubstituted C3-C10 heteroaryl C2-C5 alkenylene, acyl, and sulfonyl;

$R^3$ is selected from the group consisting of substituted or unsubstituted C1-C6 alkyl, substituted or unsubstituted C2-C6 alkenyl, substituted or unsubstituted C2-C6 alkynyl, substituted or unsubstituted C3-C8 cycloalkyl, substituted or unsubstituted C3-C8 cycloalkyl C1-C5 alkylene, substituted or unsubstituted C3-C8 heterocycloalkyl, substituted or unsubstituted C3-C8 heterocycloalkyl C1-C5 alkylene, substituted or unsubstituted C6-C10 aryl, substituted or unsubstituted C3-C10 heteroaryl, substituted or unsubstituted C6-C10 aryl C1-C5 alkylene, substituted or unsubstituted C3-C10 heteroaryl C1-C5 alkylene, substituted or unsubstituted C6-C10 aryl C2-C4 alkenylene, substituted or unsubstituted C3-C10 heteroaryl C2-C4 alkenylene, substituted or unsubstituted C6-C10 aryl C2-C4 alkynylene, and substituted or unsubstituted C3-C10 heteroaryl C2-C4 alkynylene;

wherein, in $R^1$, $R^2$ and $R^3$, the term "substituted" each independently refers to substitution by 1, 2, or 3 substituents selected from the group consisting of halogen, hydroxy, C1-C6 alkyl, halogenated C1-C6 alkyl, C1-C6 alkoxy, halogenated C1-C6 alkoxy, C1-C4 alkylcarbonyl, C1-C4 alkylthio, C1-C6 alkoxycarbonyl, and trifluoromethyl; and the heterocycloalkyl and the heteroaryl each independently include 1 or 2 heteroatoms selected from N, O and S.

In another preferred embodiment, the compound is a compound represented by formula AA,

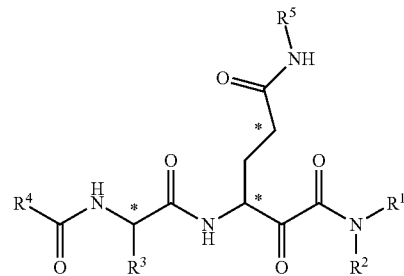

Formula AA wherein, $R^1$, $R^2$, $R^3$, $R^4$, $R^5$ and n are as defined above;
* indicates that the stereochemical isomerism of carbon atoms can independently be R or S.

In another preferred embodiment, $R^4$ is selected from the group consisting of 9-10 membered heteroaromatic ring containing 1, 2 or 3 heteroatoms selected from N, O and S, 5-6 membered heteroaromatic ring containing 1, 2 or 3 heteroatoms selected from N, O and S; the above-mentioned groups are substituted or unsubstituted; wherein, the term "substituted" means that the hydrogen atoms on the group are substituted by 1, 2, 3 or 4 substituents selected from the group consisting of halogen, hydroxy, C1-C6 alkyl, halogenated C1-C6 alkyl, C3-C6 cycloalkyl, halogenated C3-C6 cycloalkyl, C1-C6 alkoxy, halogenated C1-C6 alkoxy, C1-C6 alkylthio, and halogenated C1-C6 alkylthio.

In another preferred embodiment, the heteroaryl is a 5-, 6-, 7-, 8-, 9- or 10-membered saturated or partially saturated heteroaromatic ring.

In another preferred embodiment, the heterocycloalkyl is a 5-, 6-, 7-, 8-, 9- or 10-membered unsaturated heterocyclic ring.

In another preferred embodiment, $R^4$ is selected from the group consisting of:
  substituted or unsubstituted quinoxalinyl, substituted or unsubstituted quinazolinyl,
  substituted or unsubstituted cinnolinyl,
  substituted or unsubstituted indolyl, substituted or unsubstituted isoindolyl,
  substituted or unsubstituted 1,3-benzodioxolanyl,
  substituted or unsubstituted benzimidazolyl, substituted or unsubstituted indazolyl,
  substituted or unsubstituted imidazole[1,2-A]pyridyl, substituted or unsubstituted imidazole[1,5-A]pyridyl,
  substituted or unsubstituted pyrazolyl, substituted or unsubstituted imidazolyl, substituted or unsubstituted thiazolyl, substituted or unsubstituted oxazolyl, substituted or unsubstituted isoxazolyl, substituted or unsubstituted 1,2,3-triazolyl, substituted or unsubstituted 1,2-thiadiazolyl, substituted or unsubstituted 1,2,4-triazinyl,
  substituted or unsubstituted pyridyl, substituted or unsubstituted pyrrolyl, substituted or unsubstituted pyrazinyl, substituted or unsubstituted pyrimidinyl,
  substituted or unsubstituted 3,8a-dihydro-2H-benzopyranyl, substituted or unsubstituted benzopyranyl,
  substituted or unsubstituted quinolinyl, substituted or unsubstituted isoquinolinyl,
  substituted or unsubstituted benzoxazolyl, substituted or unsubstituted benzothiazolyl,
  substituted or unsubstituted benzothienyl,
  substituted or unsubstituted benzofuranyl;
  wherein, the term "substituted" means that the hydrogen atoms on the group are substituted by 1, 2 or 3 substituents selected from the group consisting of F, Cl, Br, I, hydroxyl, C1-C6 alkyl, halogenated C1-C6 alkyl, C3-C6 cycloalkyl, halogenated C3-C6 cycloalkyl, C1-C6 alkoxy, halogenated C1-C6 alkoxy, C1-C6 alkylthio, and halogenated C1-C6 alkylthio.

In the present invention, $R^4$ is imidazole[1,2-A]pyridine corresponding to the compounds numbered as A156 to A161 of the present invention.

In the present invention, "imidazole[1,2-A]pyridine", "imidazole[1,2-a]pyridine", "imidazo[1,2-A]pyridine" and "imidazo[1,2-a]pyridine" can be used interchangeably.

In the present invention, "imidazole[1,5-A]pyridine", "imidazole[1,5-a]pyridine", "imidazo[1,5-A]pyridine" and "imidazo[1,5-a]pyridine" can be used interchangeably.

In the present invention, $R^4$ is 3,8a-dihydro-2H-benzopyran corresponding to the compounds numbered as A132 to A137 of the present invention.

In another preferred embodiment, when —$NHR^5$ forms a ring with its adjacent —(C=O)—$CH_2$—, $R^5$ is —$(CH_2)_n$—, and n is 3;
  when —$NHR^5$ does not form a ring with its adjacent —(C=O)—$CH_2$—, $R^5$ is selected from the group consisting of hydrogen, deuterium, tritium, hydroxyl, substituted or unsubstituted C1-C6 alkyl, substituted or unsubstituted C3-C8 cycloalkyl, substituted or unsubstituted C3-C8 heterocycloalkyl, substituted or unsubstituted C6-C10 aryl, substituted or unsubstituted C3-C10 heteroaryl, substituted or unsubstituted C6-C10 aryl C1-C4 alkylene, substituted or unsubstituted C6-C10 aryl C2-C4 alkenylene, substituted or unsubstituted C3-C10 heteroaryl C1-C4 alkylene, and substituted or unsubstituted C3-C10 heteroaryl C2-C4 alkenylene;
  wherein, the term "substituted" each independently refers to substitution by 1, 2, or 3 substituents selected from the group consisting of F, Cl, Br, I, hydroxyl, C1-C6 alkyl, C1-C6 alkoxy, C1-C6 alkylthio; the heterocycloalkyl and the heteroaryl each independently contain 1, 2 or 3 heteroatoms selected from N, O, and S.

In another preferred embodiment, the compound is selected from the compounds listed in Table 1.

In the second aspect of the present invention, it provides a method for preparing the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention, wherein it comprises the following steps:

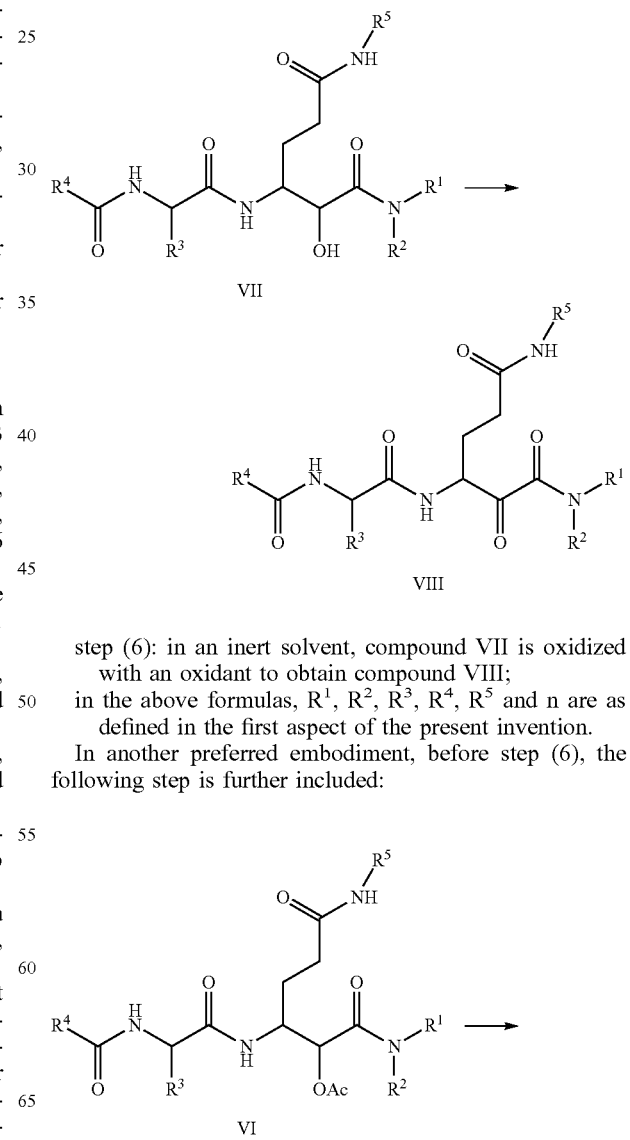

step (6): in an inert solvent, compound VII is oxidized with an oxidant to obtain compound VIII;
in the above formulas, $R^1$, $R^2$, $R^3$, $R^4$, $R^5$ and n are as defined in the first aspect of the present invention.

In another preferred embodiment, before step (6), the following step is further included:

-continued

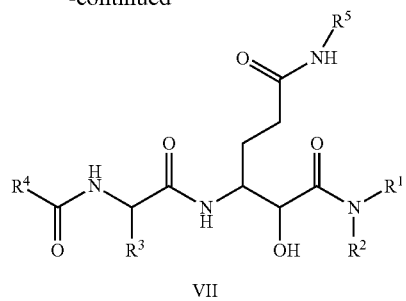

VII step (5): in the presence of an organic solvent, compound VI is reacted with a basic substance to obtain compound VII.

In another preferred embodiment, the organic solvent is an alcohol solvent, and preferably is selected from the group consisting of methanol, ethanol, propanol, isopropanol, butanol, ethylene glycol and aromatic alcohol.

In another preferred embodiment, the basic substance is selected from the group consisting of LiOH, NaOH, KOH, lithium carbonate, sodium carbonate, potassium carbonate, lithium bicarbonate, sodium bicarbonate, potassium bicarbonate, potassium tert-butoxide, sodium tert-butoxide, lithium tert-butoxide, and 1,8-diazabicycloundec-7-ene.

In another preferred embodiment, the inert solvent is selected from the group consisting of dichloromethane, tetrahydrofuran, N, N-dimethylformamide, dioxane and chloroform.

In another preferred embodiment, the oxidant is selected from the group consisting of Dess-Martin oxidant, dimethyl sulfoxide, oxalyl chloride, PCC oxidant and PDC oxidant.

In another preferred embodiment, before step (5), the following step is further included:

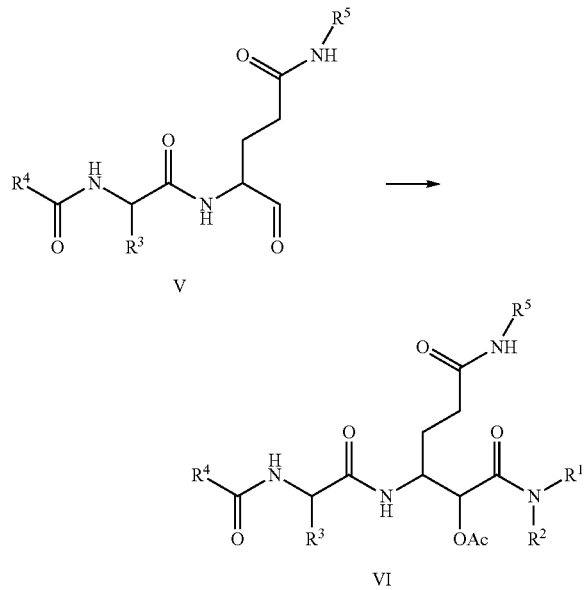

step (4): in an inert solvent, in the presence of acetic acid, compound V is reacted with an isocyanide compound to obtain the compound VI.

In another preferred embodiment, the isocyanide compound is selected from the group consisting of benzyl isocyanide, cyclohexyl isocyanide, methyl isocyanoacetate, tert-butyl isocyanide and tert-butyl 2-isocyanopropionate.

In another preferred embodiment, before step (4), the following step is further included:

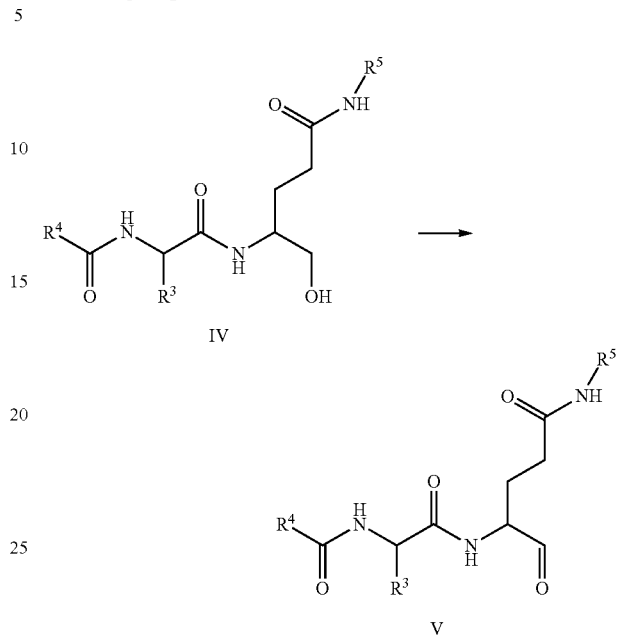

step (3): compound IV is oxidized with an oxidant in an inert solvent to obtain compound V.

In another preferred embodiment, before step (3), the following step is further included:

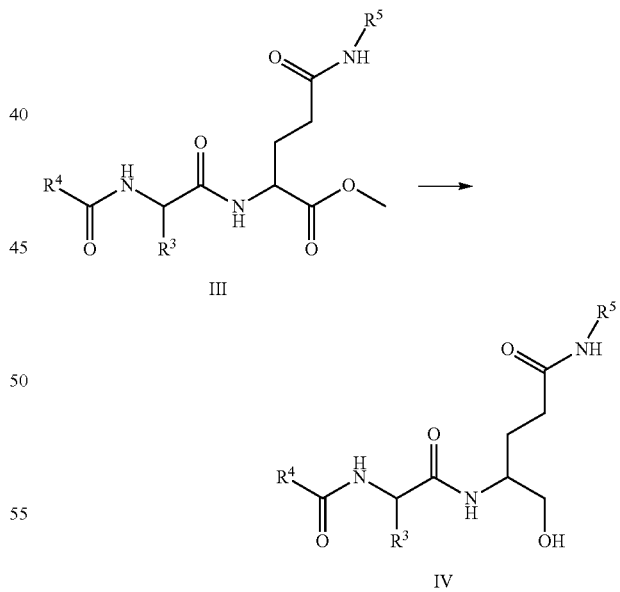

step (2): compound III is reduced with a reducing agent in an inert solvent to obtain compound IV.

In another preferred embodiment, the reducing agent is a borohydride, and is preferably selected from the group consisting of sodium borohydride, lithium borohydride and sodium cyanoborohydride.

In another preferred embodiment, before step (2), the following step is further included:

[Chemical scheme showing compound II + compound Ic → compound III]

step (1): in an inert solvent and in the presence of a condensing agent, compound II is reacted with compound Ic to obtain the compound III.

In another preferred embodiment, the condensing agent is preferably EDCI (1-ethyl-(3-dimethylaminopropyl)carbodiimide hydrochloride) and/or HATU (2-(7-oxybenzotriazole)-N,N,N',N'-tetramethylurea hexafluorophosphate).

In the third aspect of the present invention, it provides a pharmaceutical composition, which comprises the following components:
  i) a therapeutically effective amount of one or more of the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention; and
  ii) a pharmaceutically acceptable carrier or excipient.

In the fourth aspect of the present invention, it provides a ketoamide inhibitor containing one or more of the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention.

In the fifth aspect of the present invention, it provides a use of the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention in preparing a pharmaceutical composition or a preparation for the treatment or prevention of a disease related to coronavirus or a disease related to Ebola virus.

In another preferred embodiment, the coronavirus is selected from the group consisting of SARS virus and MERS virus.

In another preferred embodiment, the disease related to coronavirus is selected from the group consisting of common cold, upper respiratory tract infection, severe acute respiratory syndrome, multiple sclerosis, otitis media and gastrointestinal disorder.

In another preferred embodiment, the disease related to Ebola virus is selected from the group consisting of hemorrhagic fever, acute onset fever, myalgia and bleeding rash.

In another preferred embodiment, the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention is used in combination with other antiviral drugs.

In the sixth aspect of the present invention, it provides a non-therapeutic in vitro method for inhibiting Coronavirus or Ebola virus, wherein the ketoamide compound, or a racemate, an enantiomer, a diastereomer, or a mixture thereof, or a pharmaceutically active metabolite, or a pharmaceutically acceptable salt, a solvate or a prodrug thereof according to the first aspect of the present invention is in contact with Coronavirus or Ebola virus.

In the seventh aspect of the present invention, it provides a method for preventing or treating a disease related to Coronavirus or a disease related to Ebola virus, which comprises a step of: administering a therapeutically effective amount of one or more of the ketoamide compounds, or a racemate, an enantiomer, a diastereomer, or a mixture thereof, or a pharmaceutically active metabolite, or a pharmaceutically acceptable salt, a solvate or a prodrug thereof according to the first aspect of the present invention to a subject or patient in need.

It should be understood that in the present invention, any of the technical features specifically described above and below (such as in the Examples) can be combined with each other, which will not redundantly be described one by one herein.

DESCRIPTION OF FIGURES

FIG. 3A-3D shows antiviral activity wherein the compound A13 (100 mg/kg) or DMSO (100 μL) was administered intraperitoneally to Balb/c mice (n=4), and then blood samples were taken 2 hours (A), 12 hours (B) and 24 hours (C) after administration, and serum was separated, the anti-MERS-CoV pseudovirus activity was tested, and then the antiviral activity of the serum was compared (D). ($EC_{50}$: Half-effect concentration, in units of serum dilution multiples).

FIG. 4 shows weight change wherein the compound A13 (100 mg/kg) or DMSO (100 μL) was administered to Balb/c mice intraperitoneally (n=4) for 7 consecutive days (once a day), and then weight changes of the mice were recorded during this period.

DETAILED DESCRIPTION OF THE INVENTION

Figure 1A:
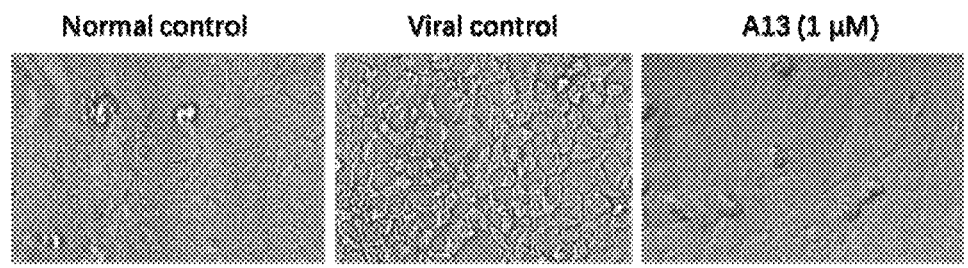
FIG. 1A shows that HCoV-OC43 can cause vacuolation and other cytopathic phenomena (CPE) after infection of target cells HCT-8, while compound A13 (1 μM) can effectively inhibit the infection of HCoV-OC43. Each figure is measured under the same magnification.

Through long-term, extensive and intensive researches, the inventors have synthesized a class of compounds of formula A that can inhibit Coronavirus and/or Ebola virus. Compared with the existing Coronavirus inhibitors, the compounds of the invention have higher inhibitory activity. On this basis, the inventors have completed the present invention.

Terms

In the present invention, unless specifically indicated, the terms used have the general meaning well known to those skilled in the art.

In the present invention, the term "halogen" refers to F, Cl, Br or I.

In the present invention, the term "C1-C10 alkyl" refers to a straight or branched chain alkyl having 1 to 10 carbon atoms, preferably a C1-C6 alkyl, more preferably a C1-C4 alkyl, and it includes without limitation methyl, ethyl, propyl, isopropyl, butyl, isobutyl, sec-butyl, tert-butyl, pentyl, hexyl, etc.

In the present invention, the term "C3-C10 cycloalkyl" refers to a cyclic alkyl having 3 to 10 carbon atoms on the ring, and it includes without limitation cyclopropyl, cyclobutyl, cyclopentyl, cyclohexyl, cycloheptyl, cyclooctyl and cyclodecyl, etc. Preferably, it is C3-C8 cycloalkyl, C3-C7 cycloalkyl or C3-C6 cycloalkyl.

In the present invention, the terms "aromatic ring" or "aryl" have the same meaning, preferably "C6-C20 aryl", more preferably "C6-C14 aryl", and more preferably "C6-C10 aryl". The term "C6-C10 aryl" refers to an aromatic ring group having 6 to 10 carbon atoms in the ring that does not contain heteroatoms, such as phenyl, naphthyl and the like.

In the present invention, the term "aromatic heterocycle" or "heteroaryl" has the same meaning and refers to a heteroaromatic group containing one or more heteroatoms. For example, "C3-C20 heteroaryl" refers to an aromatic heterocyclic ring containing 1 to 4 heteroatoms selected from oxygen, sulfur and nitrogen and 3-20 carbon atoms. Non-limiting examples include: furyl, thienyl, pyridyl, pyrazolyl, pyrrolyl, N-alkylpyrrolyl, pyrimidinyl, pyrazinyl, imidazolyl, tetrazolyl and the like. The heteroaryl ring may be fused to an aryl, heterocyclic or cycloalkyl ring, wherein the ring connected to the parent structure is a heteroaryl ring. Heteroaryl groups can be optionally substituted or unsubstituted.

In the present invention, the term "halogenated" means substituted by halogen.

In the present invention, the term "C2-C10 alkenyl" refers to a straight or branched chain alkenyl group having 2 to 10 carbon atoms and containing a double bond, and it includes but is not limited to vinyl, propenyl, butenyl, isobutenyl, pentenyl and hexenyl etc. Preferably, it is a C2-C6 alkenyl.

In the present invention, the term "C2-C10 alkynyl" refers to a straight-chain or branched alkynyl having 2 to 10 carbon atoms and containing a triple bond, and it includes but is not limited to, ethynyl, propynyl, butynyl, isobutynyl, pentynyl and hexynyl, etc. Preferably, it is C2-C6 alkynyl.

In the present invention, the term "C1-C8 alkoxy" refers to a straight or branched chain alkoxy group having 1 to 8 carbon atoms, and includes, without limitation, methoxy, ethoxy, propoxy, isopropoxy and butoxy, etc. Preferably, it is C1-C4 alkoxy.

In the present invention, the term "acyl" refers to a straight or branched acyl group having 1 to 8 carbon atoms, and includes, without limitation, formyl, acetyl, propionyl and the like. Preferably, it is a C1-C4 alkanoyl.

In the present invention, the term "sulfonyl" refers to a linear or branched sulfonyl group having 1 to 8 carbon atoms, and includes, without limitation, methylsulfonyl, ethylsulfonyl, propylsulfonyl and the like. Preferably, it is a C1-C4 alkylsulfonyl.

In the present invention, the term "substituted" means that one or more hydrogen atoms on a specific group are replaced with a specific substituent. The specific substituents are the substituents described correspondingly hereinabove, or the substituents appearing in the respective embodiments. Unless otherwise specified, a substituted group may have a substituent selected from a specific group at any substitutable position of the group, and the substituent may be the same or different at each position. Those skilled in the art will understand that the combinations of substituents contemplated by the present invention are those that are stable or chemically achievable. The substituents are for example (but not limited to): halogen, hydroxyl, carboxy (—COOH), C1-C8 alkyl, C2-C8 alkenyl, C2-C8 alkynyl, C3-C8 cycloalkyl, 3-12-membered heterocyclic group, aryl, heteroaryl, C1-C8 aldehyde group, C2-C10 acyl, C2-C10 ester group, amino, C1-C8 alkoxy, C1-C10 sulfonyl, etc.

Compound

The present invention provides a ketoamide compound represented by formula A, its racemates, enantiomers, diastereomers, or their mixtures, or their pharmaceutically active metabolites, or their pharmaceutically acceptable salts, or solvates or prodrugs thereof:

Formula A wherein, $R^1$, $R^2$, $R^3$, $R^4$, $R^5$ and n are as defined above.

In another preferred embodiment, in the compound, any one of $R^1$, $R^2$, $R^3$, $R^4$, $R^5$ and n is the corresponding group in the specific compound described in Table 1.

In another preferred embodiment, the compound is preferably a compound prepared in the examples.

In another preferred embodiment, the compounds A1-A236 are the compounds prepared in Examples 1-236, respectively.

In another preferred embodiment, the compound is selected from the compounds listed in Table 1.

TABLE 1

| number | structure | name |
| --- | --- | --- |
| A1 | 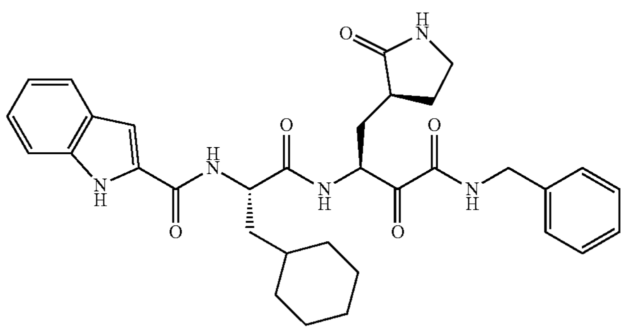 [SMILES: O=C(NCc1ccccc1)C(=O)[C@H](C[C@@H]1CCNC1=O)NC(=O)[C@H](CC1CCCCC1)NC(=O)c1cc2ccccc2[nH]1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-1H-indole-2-carboxamide |
| A2 | 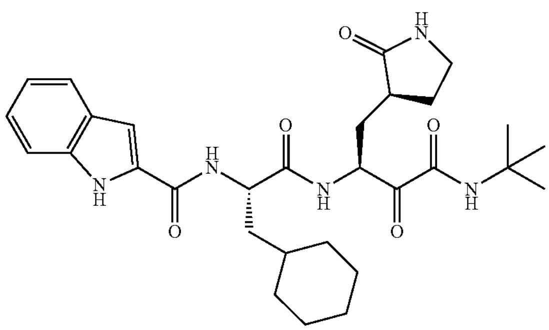 [SMILES: CC(C)(C)NC(=O)C(=O)[C@H](C[C@@H]1CCNC1=O)NC(=O)[C@H](CC1CCCCC1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-1H-indole-2-carboxamide |
| A3 | 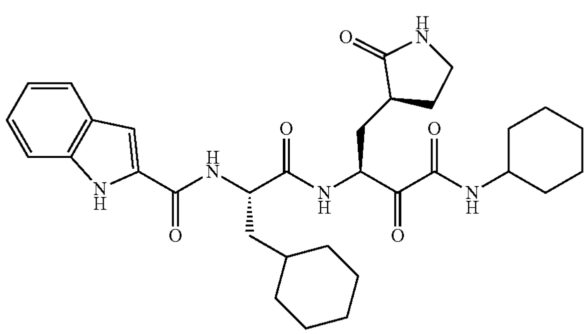 [SMILES: O=C(NC1CCCCC1)C(=O)[C@H](C[C@@H]1CCNC1=O)NC(=O)[C@H](CC1CCCCC1)NC(=O)c1cc2ccccc2[nH]1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-1H-indole-2-carboxamide |
| A4 | 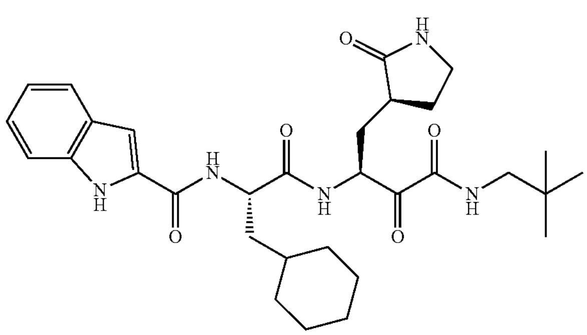 [SMILES: CC(C)(C)CNC(=O)C(=O)[C@H](C[C@@H]1CCNC1=O)NC(=O)[C@H](CC1CCCCC1)NC(=O)c1cc2ccccc2[nH]1] | N-((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-1H-indole-2-carboxamide |

TABLE 1-continued

| number | structure | name |
|---|---|---|
| A5 | 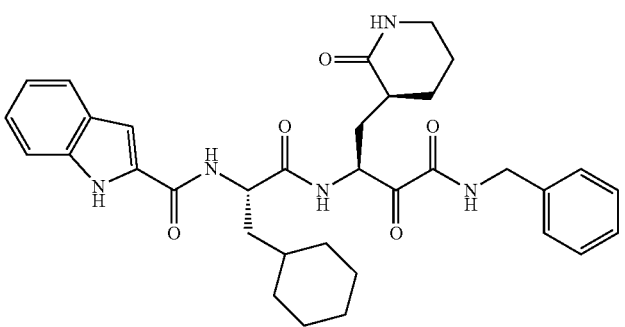 [SMILES: O=C(NCc1ccccc1)C(=O)[C@H](C[C@@H]1CCCNC1=O)NC(=O)[C@H](CC1CCCCC1)NC(=O)c1cc2ccccc2[nH]1] | N-((S)-1-(((S)-4-(benzylamino)-3,4-dione-1-((S)-2-oxopiperidine-3-yl)but-2-yl)amino)-3-cyclohexyl-1-oxopropan-2-yl)-1H-indole-2-carboxamide |
| A6 | 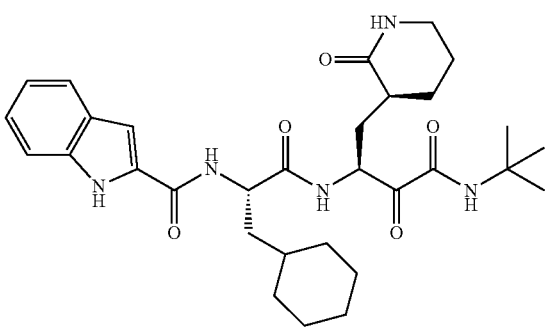 [SMILES: CC(C)(C)NC(=O)C(=O)[C@H](C[C@@H]1CCCNC1=O)NC(=O)[C@H](CC1CCCCC1)NC(=O)c1cc2ccccc2[nH]1] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-1H-indole-2-carboxamide |
| A7 | 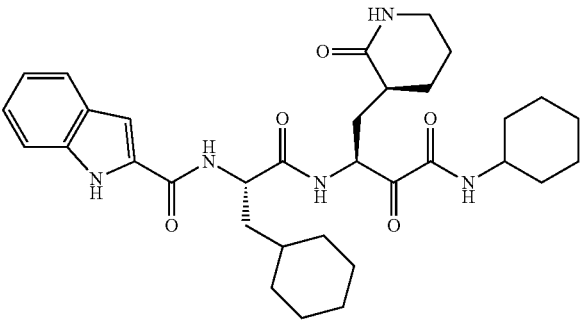 [SMILES: O=C(NC1CCCCC1)C(=O)[C@H](C[C@@H]1CCCNC1=O)NC(=O)[C@H](CC1CCCCC1)NC(=O)c1cc2ccccc2[nH]1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-1H-indole-2-carboxamide |
| A8 | 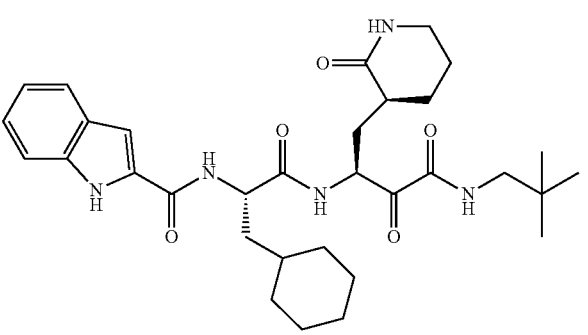 [SMILES: CC(C)(C)CNC(=O)C(=O)[C@H](C[C@@H]1CCCNC1=O)NC(=O)[C@H](CC1CCCCC1)NC(=O)c1cc2ccccc2[nH]1] | N-((S)-3-cyclohexyl-1-(((S)-4-(neopentylamino)-3,4-dione-1-((S)-2-oxopiperidine-3-yl)but-2-yl)amino)-3-cyclohexyl-1-oxopropan-2-yl)-1H-indole-2-carboxamide |

TABLE 1-continued

| number | structure | name |
| --- | --- | --- |
| A9 | 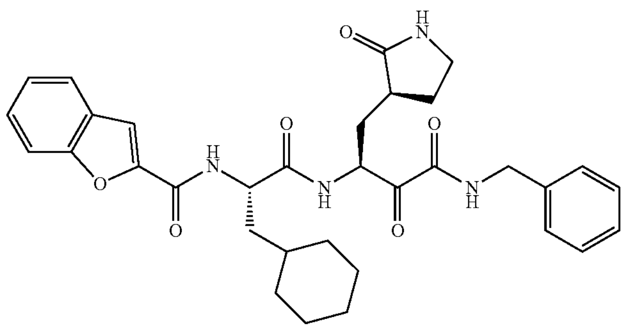 [SMILES: O=C(NCc1ccccc1)C(=O)[C@H](C[C@@H]1CCNC1=O)NC(=O)[C@H](CC1CCCCC1)NC(=O)c1cc2ccccc2o1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-benzofuran-2-carboxamide |
| A10 | 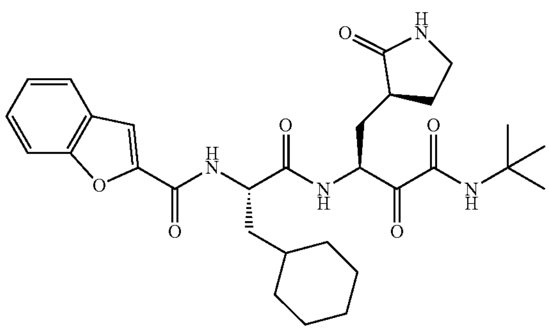 [SMILES: CC(C)(C)NC(=O)C(=O)[C@H](C[C@@H]1CCNC1=O)NC(=O)[C@H](CC1CCCCC1)NC(=O)c1cc2ccccc2o1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-benzofuran-2-carboxamide |
| A11 | 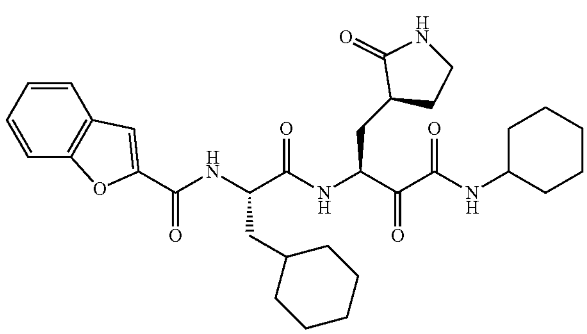 [SMILES: O=C(NC1CCCCC1)C(=O)[C@H](C[C@@H]1CCNC1=O)NC(=O)[C@H](CC1CCCCC1)NC(=O)c1cc2ccccc2o1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-benzofuran-2-carboxamide |
| A12 | 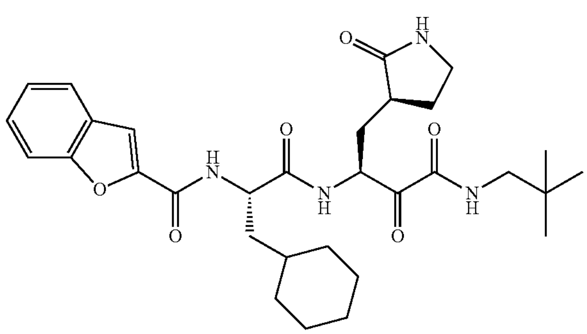 | N-((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-benzofuran-2-carboxamide |

TABLE 1-continued

| number | structure | name |
|---|---|---|
| A13 | 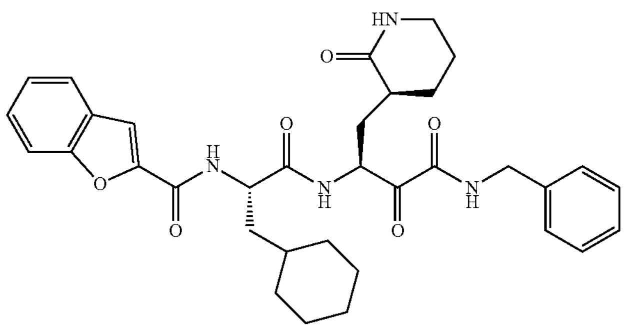 [SMILES: O=C(NCc1ccccc1)C(=O)[C@H](C[C@@H]1CCCNC1=O)NC(=O)[C@H](CC1CCCCC1)NC(=O)c1cc2ccccc2o1] | N-((S)-1-(((S)-4-(benzylamino)-3,4-dione-1-((S)-2-oxopiperidine-3-yl)but-2-yl)amino)-3-cyclohexyl-1-oxopropan-2-yl)-benzofuran-2-carboxamide |
| A14 | 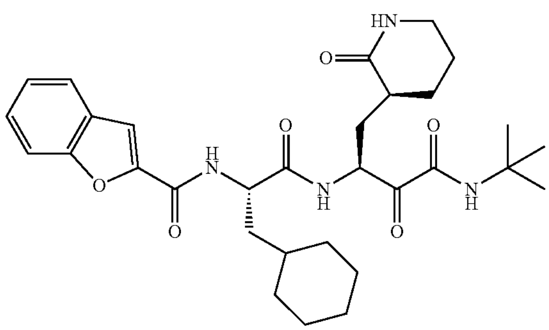 [SMILES: CC(C)(C)NC(=O)C(=O)[C@H](C[C@@H]1CCCNC1=O)NC(=O)[C@H](CC1CCCCC1)NC(=O)c1cc2ccccc2o1] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-benzofuran-2-carboxamide |
| A15 | 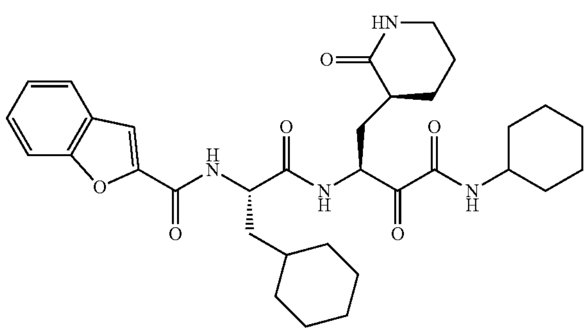 [SMILES: O=C(NC1CCCCC1)C(=O)[C@H](C[C@@H]1CCCNC1=O)NC(=O)[C@H](CC1CCCCC1)NC(=O)c1cc2ccccc2o1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-benzofuran-2-carboxamide |
| A16 | 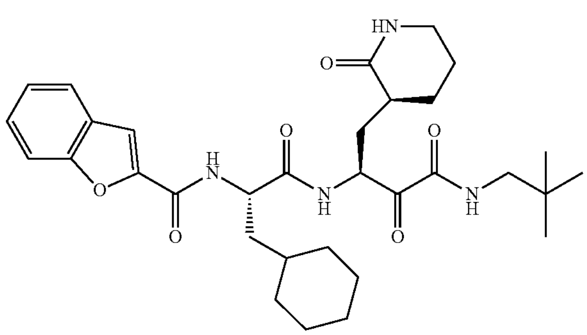 [SMILES: CC(C)(C)CNC(=O)C(=O)[C@H](C[C@@H]1CCCNC1=O)NC(=O)[C@H](CC1CCCCC1)NC(=O)c1cc2ccccc2o1] | N-((S)-3-cyclohexyl-1-(((S)-4-(neopentylamino)-3,4-dione-1-((S)-2-oxopiperidine-3-yl)but-2-yl)amino)-3-cyclohexyl-1-oxopropan-2-yl)-benzofuran-2-carboxamide |

TABLE 1-continued

| number | structure | name |
|---|---|---|
| A17 | 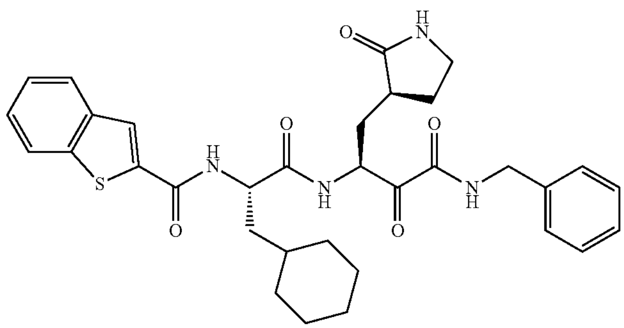 [SMILES: O=C(NCc1ccccc1)C(=O)[C@H](C[C@@H]1CCNC1=O)NC(=O)[C@H](CC1CCCCC1)NC(=O)c1cc2ccccc2s1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-benzothiophene-2-carboxamide |
| A18 | 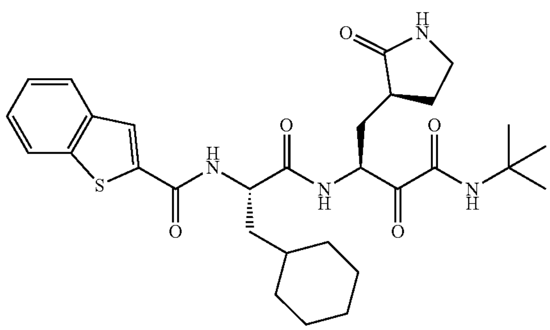 [SMILES: CC(C)(C)NC(=O)C(=O)[C@H](C[C@@H]1CCNC1=O)NC(=O)[C@H](CC1CCCCC1)NC(=O)c1cc2ccccc2s1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-benzothiophene-2-carboxamide |
| A19 | 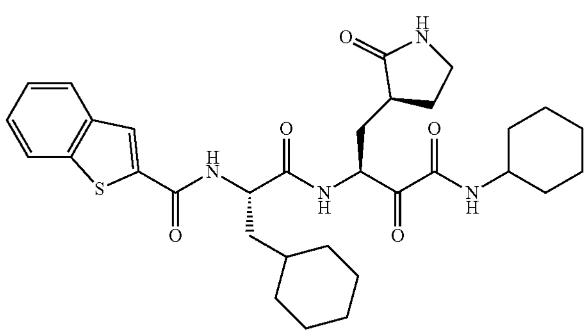 [SMILES: O=C(NC1CCCCC1)C(=O)[C@H](C[C@@H]1CCNC1=O)NC(=O)[C@H](CC1CCCCC1)NC(=O)c1cc2ccccc2s1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-benzothiophene-2-carboxamide |
| A20 | 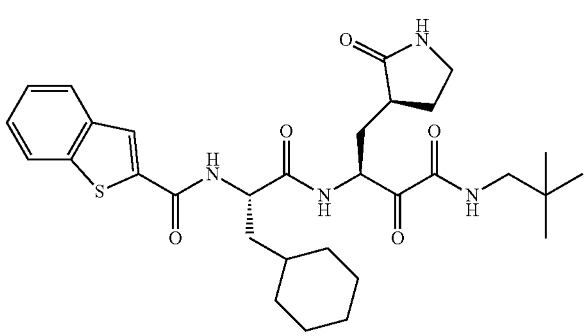 | N-((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-benzothiophene-2-carboxamide |

TABLE 1-continued

| number | structure | name |
|---|---|---|
| A21 | 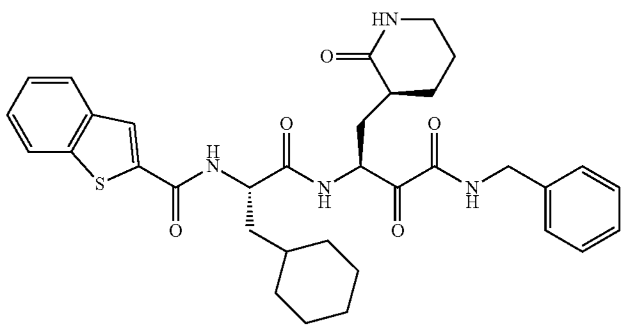 [SMILES: O=C(NCc1ccccc1)C(=O)[C@H](C[C@@H]1CCCNC1=O)NC(=O)[C@H](CC1CCCCC1)NC(=O)c1cc2ccccc2s1] | N-((S)-1-(((S)-4-(benzylamino)-3,4-dione-1-((S)-2-oxopiperidine-3-yl)but-2-yl)amino)-3-cyclohexyl-1-oxopropan-2-yl)-benzothiophene-2-carboxamide |
| A22 | 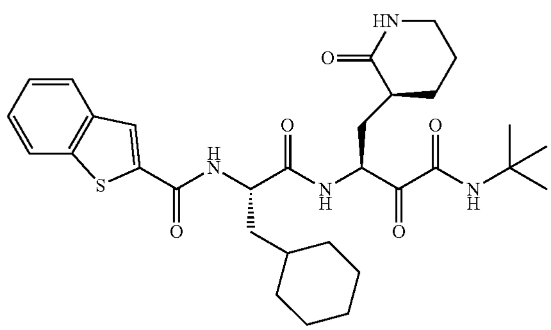 [SMILES: CC(C)(C)NC(=O)C(=O)[C@H](C[C@@H]1CCCNC1=O)NC(=O)[C@H](CC1CCCCC1)NC(=O)c1cc2ccccc2s1] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-benzothiophene-2-carboxamide |
| A23 | 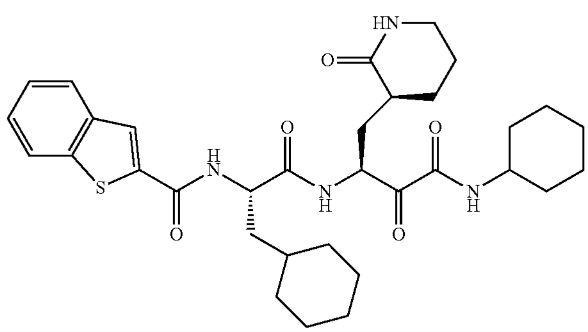 [SMILES: O=C(NC1CCCCC1)C(=O)[C@H](C[C@@H]1CCCNC1=O)NC(=O)[C@H](CC1CCCCC1)NC(=O)c1cc2ccccc2s1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-benzothiophene-2-carboxamide |
| A24 | 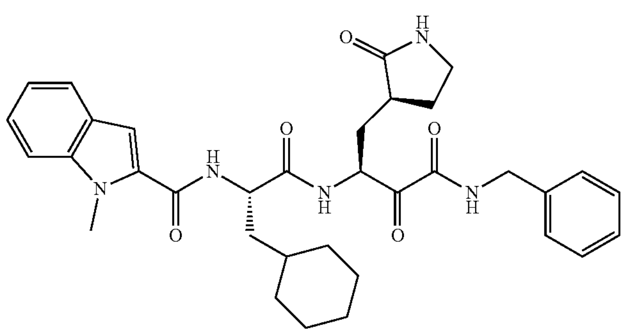 | N-((S)-1-(((S)-4-(benzylamino)-3,4-dione-1-((S)-2-oxopyrrolidine-3-yl)but-2-yl)amino)-3-cyclohexyl-1-oxopropan-2-yl)-1-methyl-1H-indole-2-carboxamide |

TABLE 1-continued

| number | structure | name |
|---|---|---|
| A25 | 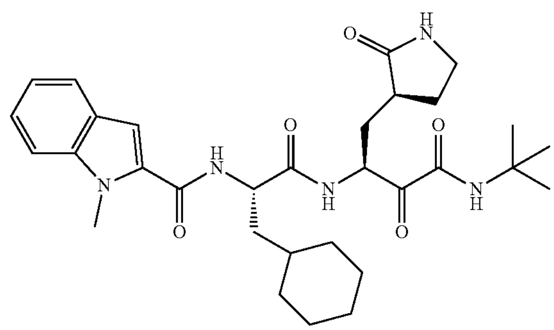 [SMILES: Cn1c(C(=O)N[C@@H](CC2CCCCC2)C(=O)N[C@@H](C[C@@H]2CCNC2=O)C(=O)C(=O)NC(C)(C)C)cc2ccccc21] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-1-methyl-1H-indole-2-carboxamide |
| A26 | 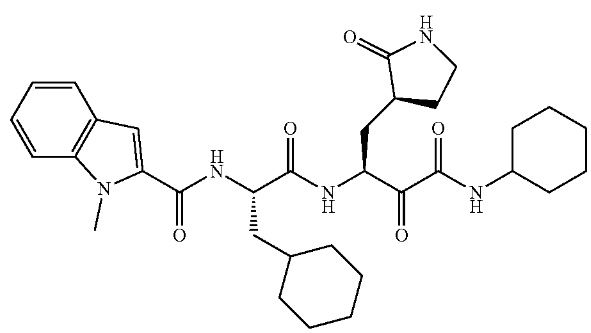 [SMILES: Cn1c(C(=O)N[C@@H](CC2CCCCC2)C(=O)N[C@@H](C[C@@H]2CCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-1-methyl-1H-indole-2-carboxamide |
| A27 | 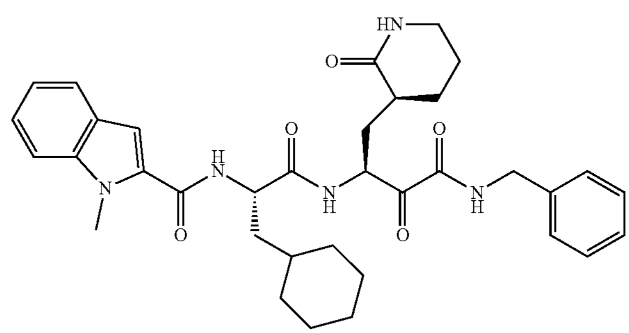 [SMILES: Cn1c(C(=O)N[C@@H](CC2CCCCC2)C(=O)N[C@@H](C[C@@H]2CCCNC2=O)C(=O)C(=O)NCc2ccccc2)cc2ccccc21] | N-((S)-1-(((S)-4-(benzylamino)-3,4-dione-1-((S)-2-oxopiperidine-3-yl)but-2-yl)amino)-3-cyclohexyl-1-oxopropan-2-yl)-1-methyl-1H-indole-2-carboxamide |
| A28 | 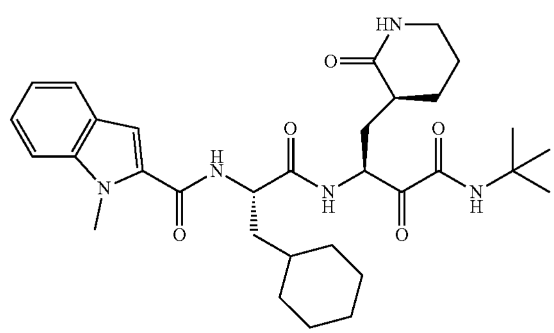 [SMILES: Cn1c(C(=O)N[C@@H](CC2CCCCC2)C(=O)N[C@@H](C[C@@H]2CCCNC2=O)C(=O)C(=O)NC(C)(C)C)cc2ccccc21] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-1-methyl-1H-indole-2-carboxamide |

TABLE 1-continued

| number | structure | name |
|---|---|---|
| A29 | 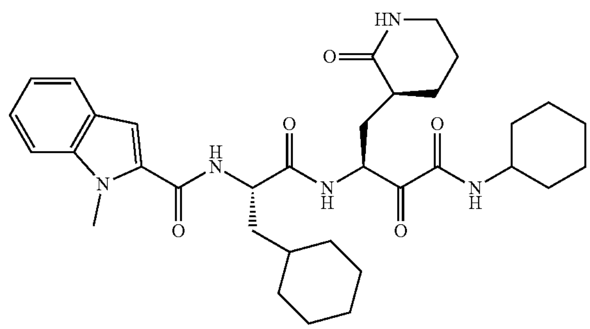 [SMILES: Cn1c(C(=O)N[C@@H](CC2CCCCC2)C(=O)N[C@@H](C[C@@H]2CCCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-1-methyl-1H-indole-2-carboxamide |
| A30 | 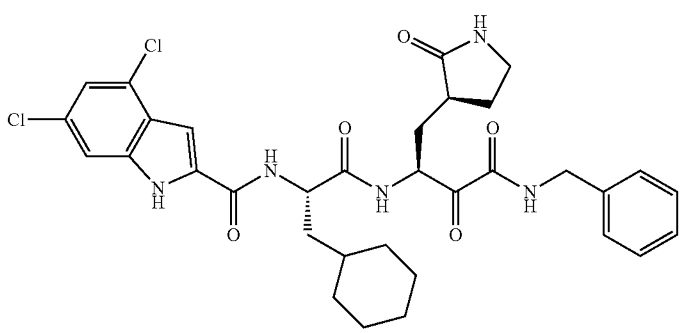 [SMILES: O=C(NCc1ccccc1)C(=O)[C@H](C[C@@H]1CCNC1=O)NC(=O)[C@H](CC1CCCCC1)NC(=O)c1cc2c(Cl)cc(Cl)cc2[nH]1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-4,6-dichloro-1H-indole-2-carboxamide |
| A31 | 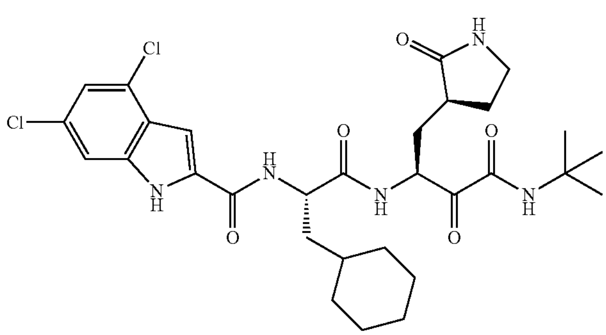 [SMILES: CC(C)(C)NC(=O)C(=O)[C@H](C[C@@H]1CCNC1=O)NC(=O)[C@H](CC1CCCCC1)NC(=O)c1cc2c(Cl)cc(Cl)cc2[nH]1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-4,6-dichloro-1H-indole-2-carboxamide |
| A32 | 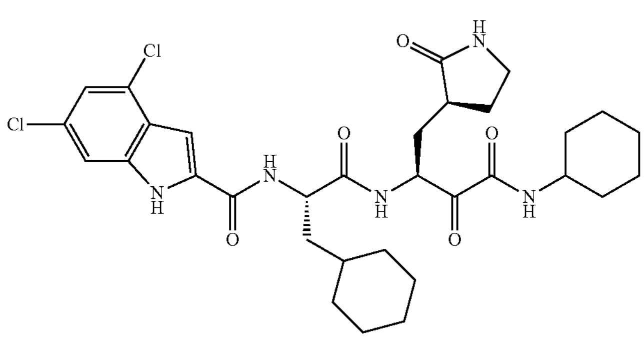 [SMILES: O=C(NC1CCCCC1)C(=O)[C@H](C[C@@H]1CCNC1=O)NC(=O)[C@H](CC1CCCCC1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-4,6-dichloro-1H-indole-2-carboxamide |

TABLE 1-continued

| number | structure | name |
|---|---|---|
| A33 | 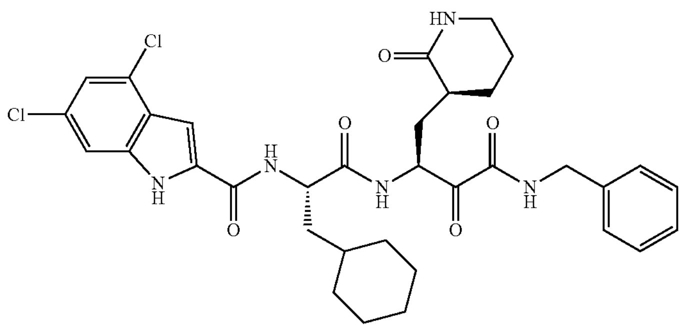 [SMILES: O=C(NCc1ccccc1)C(=O)[C@H](C[C@@H]1CCCNC1=O)NC(=O)[C@H](CC1CCCCC1)NC(=O)c1cc2c(Cl)cc(Cl)cc2[nH]1] | N-((S)-1-(((S)-4-(benzylamino)-3,4-dione-1-((S)-2-oxopiperidine-3-yl)but-2-yl)amino)-3-cyclohexyl-1-oxopropan-2-yl)-4,6-dichloro-1H-indole-2-carboxamide |
| A34 | 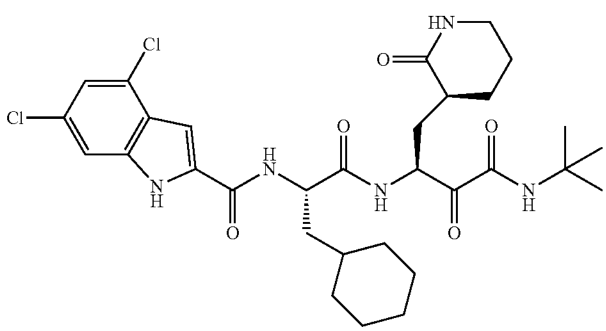 | N-((S)-1-(((S)-4-(tert-butylamino)-3,4-dione-1-((S)-2-oxopiperidine-3-yl)but-2-yl)amino)-3-cyclohexyl-1-oxopropan-2-yl)-4,6-dichloro-1H-indole-2-carboxamide |
| A35 | 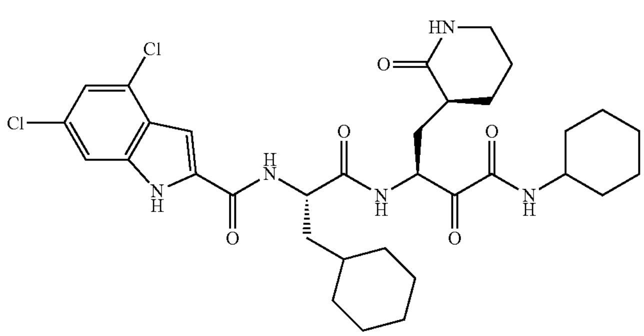 [SMILES: O=C(NC1CCCCC1)C(=O)[C@H](C[C@@H]1CCCNC1=O)NC(=O)[C@H](CC1CCCCC1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-4,6-dichloro-1H-indole-2-carboxamide |
| A36 | 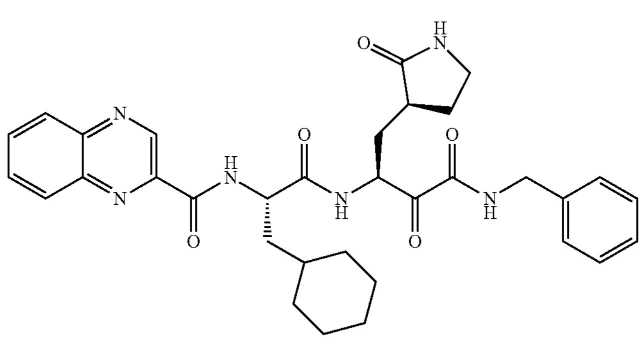 [SMILES: O=C(NCc1ccccc1)C(=O)[C@H](C[C@@H]1CCNC1=O)NC(=O)[C@H](CC1CCCCC1)NC(=O)c1cnc2ccccc2n1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-quinoxaline-2-carboxamide |

TABLE 1-continued

| number | structure | name |
|---|---|---|
| A37 | 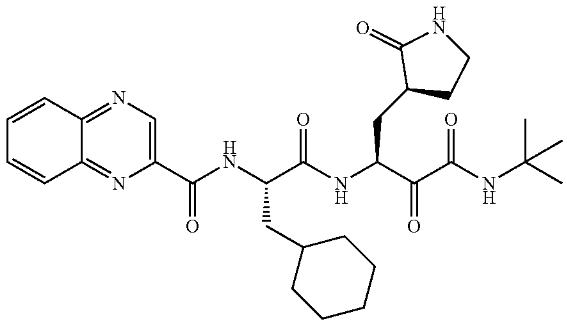 [SMILES: CC(C)(C)NC(=O)C(=O)[C@H](C[C@@H]1CCNC1=O)NC(=O)[C@H](CC1CCCCC1)NC(=O)c1cnc2ccccc2n1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-quinoxaline-2-carboxamide |
| A38 | 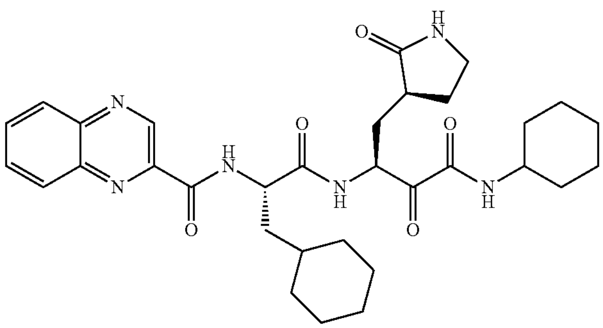 [SMILES: O=C(NC1CCCCC1)C(=O)[C@H](C[C@@H]1CCNC1=O)NC(=O)[C@H](CC1CCCCC1)NC(=O)c1cnc2ccccc2n1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-quinoxaline-2-carboxamide |
| A39 | 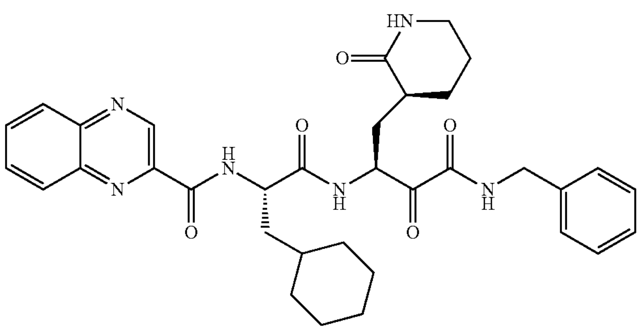 [SMILES: O=C(NCc1ccccc1)C(=O)[C@H](C[C@@H]1CCCNC1=O)NC(=O)[C@H](CC1CCCCC1)NC(=O)c1cnc2ccccc2n1] | N-((S)-1-(((S)-4-(benzylamino)-3,4-dione-1-((S)-2-oxopiperidine-3-yl)but-2-yl)amino)-3-cyclohexyl-1-oxopropan-2-yl)-quinoxaline-2-carboxamide |
| A40 | 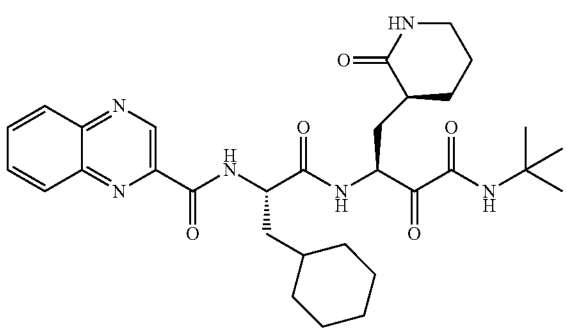 [SMILES: CC(C)(C)NC(=O)C(=O)[C@H](C[C@@H]1CCCNC1=O)NC(=O)[C@H](CC1CCCCC1)NC(=O)c1cnc2ccccc2n1] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-quinoxaline-2-carboxamide |

TABLE 1-continued

| number | structure | name |
|---|---|---|
| A41 | 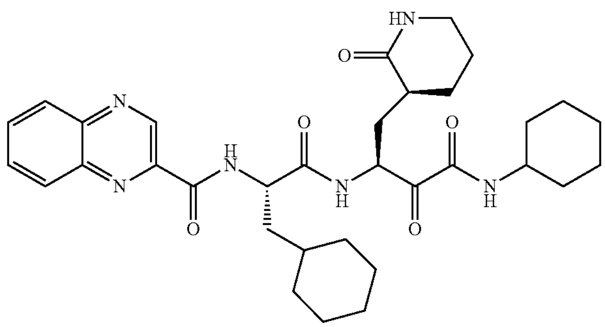 [SMILES: O=C(NC1CCCCC1)C(=O)[C@H](C[C@@H]1CCCNC1=O)NC(=O)[C@H](CC1CCCCC1)NC(=O)c1cnc2ccccc2n1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-quinoxaline-2-carboxamide |
| A42 | 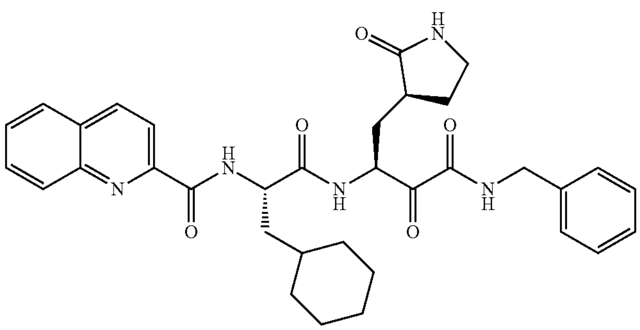 [SMILES: O=C(NCc1ccccc1)C(=O)[C@H](C[C@@H]1CCNC1=O)NC(=O)[C@H](CC1CCCCC1)NC(=O)c1ccc2ccccc2n1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-quinoline-2-carboxamide |
| A43 | 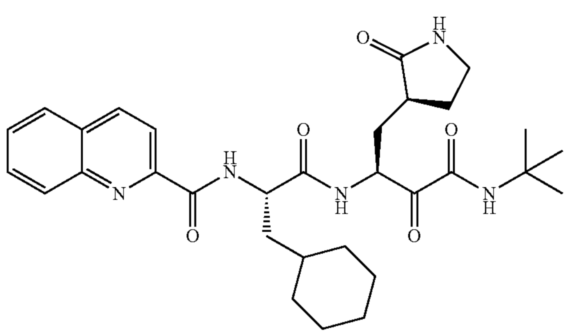 [SMILES: CC(C)(C)NC(=O)C(=O)[C@H](C[C@@H]1CCNC1=O)NC(=O)[C@H](CC1CCCCC1)NC(=O)c1ccc2ccccc2n1] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-quinoline-2-carboxamide |
| A44 | 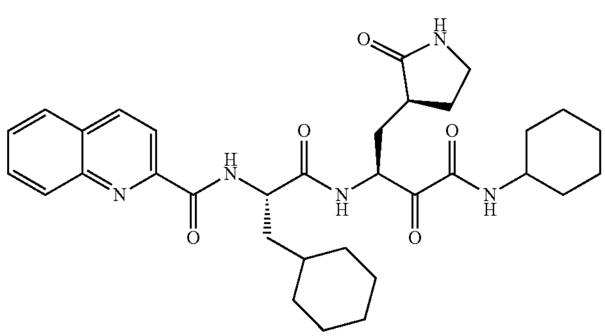 [SMILES: O=C(NC1CCCCC1)C(=O)[C@H](C[C@@H]1CCNC1=O)NC(=O)[C@H](CC1CCCCC1)NC(=O)c1ccc2ccccc2n1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-quinoline-2-carboxamide |

TABLE 1-continued

| number | structure | name |
| --- | --- | --- |
| A45 | 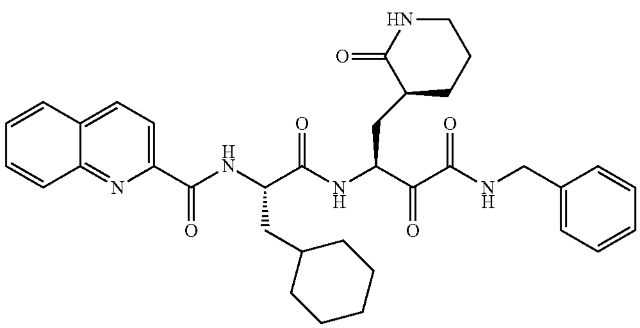 | N-((S)-1-(((S)-4-(benzylamino)-3,4-dione-1-((S)-2-oxopiperidine-3-yl)but-2-yl)amino)-3-cyclohexyl-1-oxopropan-2-yl)-quinoline-2-carboxamide |
| A46 | 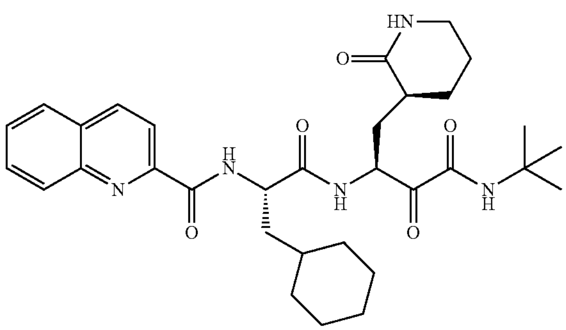 [SMILES: CC(C)(C)NC(=O)C(=O)[C@H](C[C@@H]1CCCNC1=O)NC(=O)[C@H](CC1CCCCC1)NC(=O)c1ccc2ccccc2n1] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-quinoline-2-carboxamide |
| A47 | 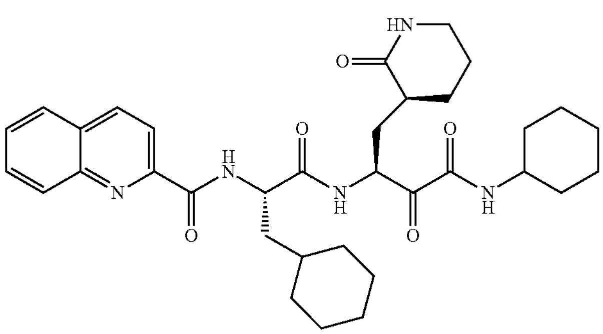 [SMILES: O=C(NC1CCCCC1)C(=O)[C@H](C[C@@H]1CCCNC1=O)NC(=O)[C@H](CC1CCCCC1)NC(=O)c1ccc2ccccc2n1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopropan-2-yl)-quinoline-2-carboxamide |
| A48 | 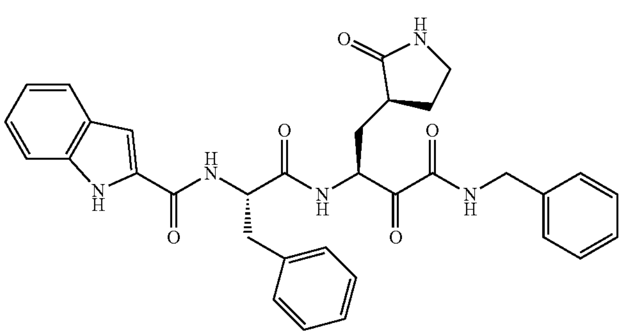 | N-((S)-1-(((S)-4-(benzylamino)-3,4-dione-1-((S)-2-oxopyrrolidine-3-yl)but-2-yl)amino)-1-oxo-3-phenylpropan-2-yl)-1H-indole-2-carboxamide |

TABLE 1-continued

| number | structure | name |
|---|---|---|
| A49 | 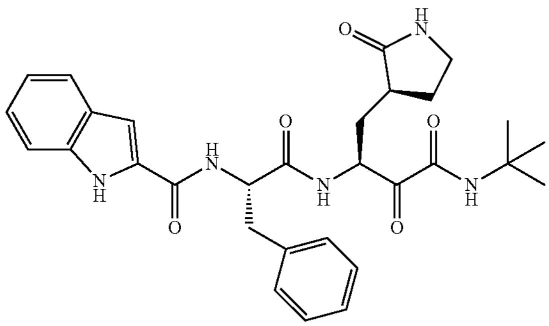 [SMILES: CC(C)(C)NC(=O)C(=O)[C@H](C[C@@H]1CCNC1=O)NC(=O)[C@H](Cc1ccccc1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-1H-indole-2-carboxamide |
| A50 | 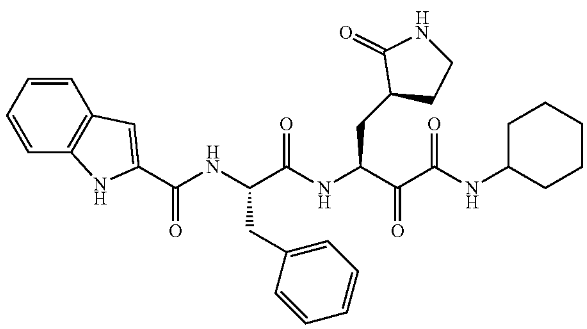 [SMILES: O=C(NC1CCCCC1)C(=O)[C@H](C[C@@H]1CCNC1=O)NC(=O)[C@H](Cc1ccccc1)NC(=O)c1cc2ccccc2[nH]1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-1H-indole-2-carboxamide |
| A51 | 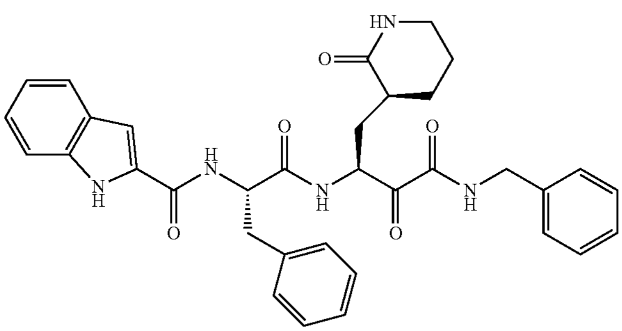 | N-((S)-1-(((S)-4-(benzylamino)-3,4-dione-1-((S)-2-oxopiperidine-3-yl)but-2-yl)amino)-1-oxo-3-phenylpropan-2-yl)-1H-indole-2-carboxamide |
| A52 | 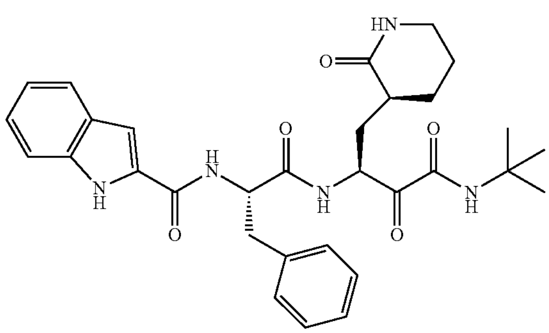 [SMILES: CC(C)(C)NC(=O)C(=O)[C@H](C[C@@H]1CCCNC1=O)NC(=O)[C@H](Cc1ccccc1)NC(=O)c1cc2ccccc2[nH]1] | N-((S)-1-(((S)-4-(tert-butylamino)-3,4-dione-1-((S)-2-oxopiperidine-3-yl)but-2-yl)amino)-1-oxo-3-phenylpropan-2-yl)-1H-indole-2-carboxamide |

TABLE 1-continued

| number | structure | name |
|---|---|---|
| A53 | 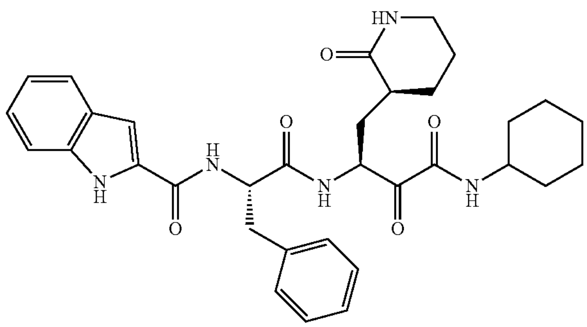 | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-1H-indole-2-carboxamide |
| A54 | 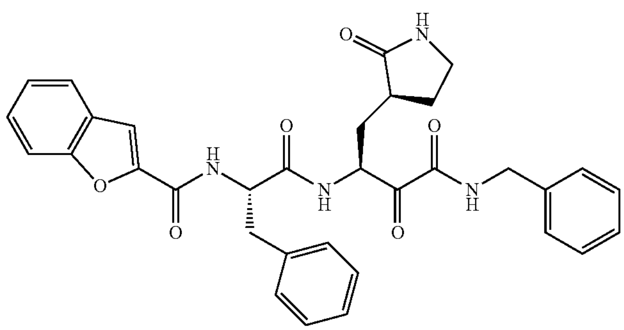 | N-((S)-1-(((S)-4-(benzylamino)-3,4-dione-1-((S)-2-oxopyrrolidine-3-yl)but-2-yl)amino)-1-oxo-3-phenylpropan-2-yl)-benzofuran-2-carboxamide |
| A55 | 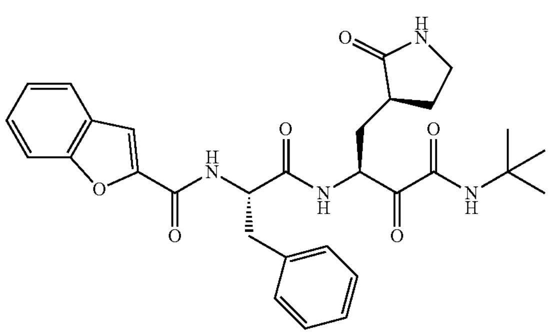 [SMILES: CC(C)(C)NC(=O)C(=O)[C@H](C[C@@H]1CCNC1=O)NC(=O)[C@H](Cc1ccccc1)NC(=O)c1cc2ccccc2o1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-benzofuran-2-carboxamide |
| A56 | 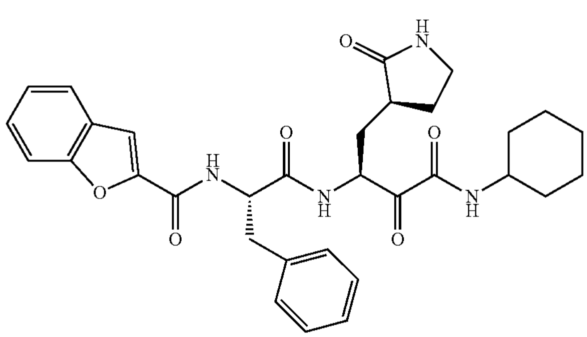 [SMILES: O=C(NC1CCCCC1)C(=O)[C@H](C[C@@H]1CCNC1=O)NC(=O)[C@H](Cc1ccccc1)NC(=O)c1cc2ccccc2o1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-benzofuran-2-carboxamide |

TABLE 1-continued

| number | structure | name |
|---|---|---|
| A57 | 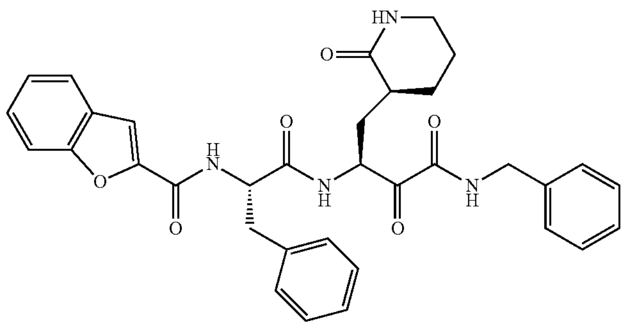 [SMILES: O=C(NCc1ccccc1)C(=O)[C@H](C[C@@H]1CCCNC1=O)NC(=O)[C@H](Cc1ccccc1)NC(=O)c1cc2ccccc2o1] | N-((S)-1-(((S)-4-(benzylamino)-3,4-dione-1-((S)-2-oxopiperidine-3-yl)but-2-yl)amino)-1-oxo-3-phenylpropan-2-yl)-benzofuran-2-carboxamide |
| A58 | 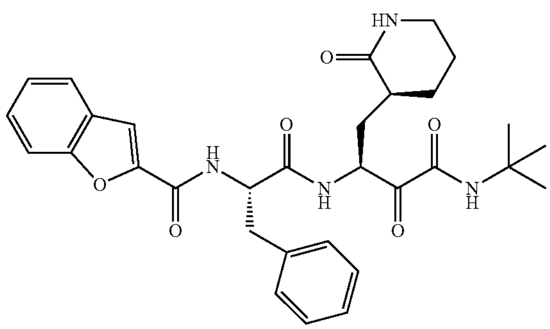 [SMILES: CC(C)(C)NC(=O)C(=O)[C@H](C[C@@H]1CCCNC1=O)NC(=O)[C@H](Cc1ccccc1)NC(=O)c1cc2ccccc2o1] | N-((S)-1-(((S)-4-(tert-butylamino)-3,4-dione-1-((S)-2-oxopiperidine-3-yl)but-2-yl)amino)-1-oxo-3-phenylpropan-2-yl)-benzofuran-2-carboxamide |
| A59 | 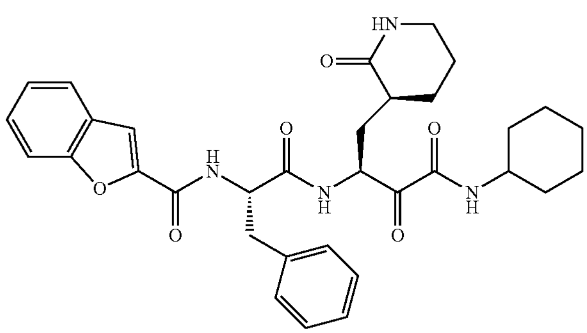 [SMILES: O=C(NC1CCCCC1)C(=O)[C@H](C[C@@H]1CCCNC1=O)NC(=O)[C@H](Cc1ccccc1)NC(=O)c1cc2ccccc2o1] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-benzofuran-2-carboxamide |
| A60 | 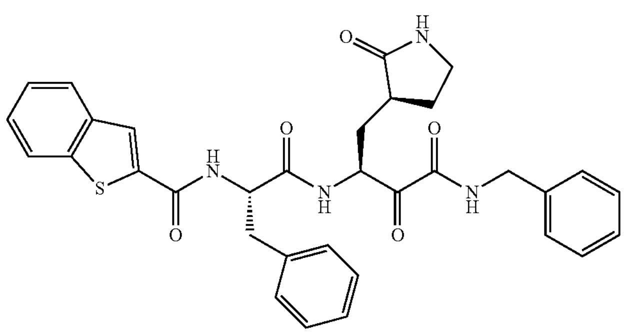 | N-((S)-1-(((S)-4-(benzylamino)-3,4-dione-1-((S)-2-oxopyrrolidine-3-yl)but-2-yl)amino)-1-oxo-3-phenylpropan-2-yl)-benzothiophene-2-carboxamide |

TABLE 1-continued

| number | structure | name |
|---|---|---|
| A61 | 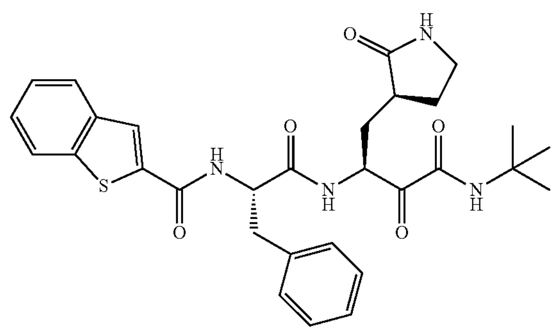 [SMILES: CC(C)(C)NC(=O)C(=O)[C@H](C[C@@H]1CCNC1=O)NC(=O)[C@H](Cc1ccccc1)NC(=O)c1cc2ccccc2s1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-benzothiophene-2-carboxamide |
| A62 | 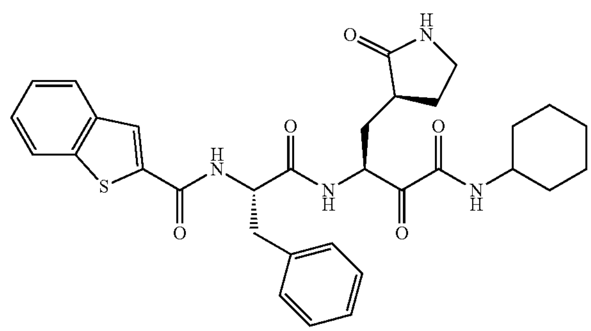 [SMILES: O=C(NC1CCCCC1)C(=O)[C@H](C[C@@H]1CCNC1=O)NC(=O)[C@H](Cc1ccccc1)NC(=O)c1cc2ccccc2s1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-benzothiophene-2-carboxamide |
| A63 | 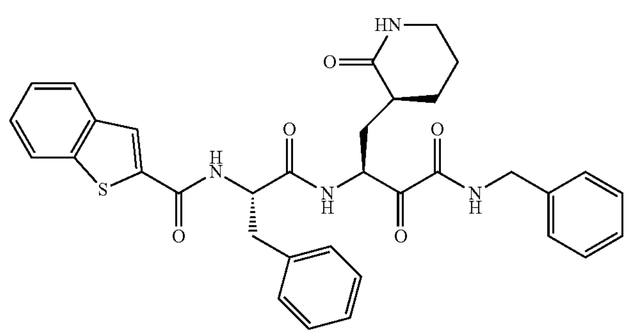 [SMILES: O=C(NCc1ccccc1)C(=O)[C@H](C[C@@H]1CCCNC1=O)NC(=O)[C@H](Cc1ccccc1)NC(=O)c1cc2ccccc2s1] | N-((S)-1-(((S)-4-(benzylamino)-3,4-dione-1-((S)-2-oxopiperidine-3-yl)but-2-yl)amino)-1-oxo-3-phenylpropan-2-yl)-benzothiophene-2-carboxamide |
| A64 | 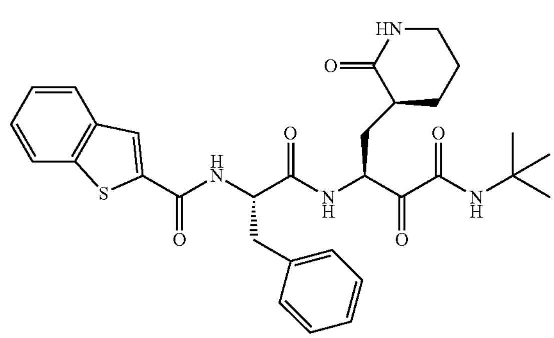 [SMILES: CC(C)(C)NC(=O)C(=O)[C@H](C[C@@H]1CCCNC1=O)NC(=O)[C@H](Cc1ccccc1)NC(=O)c1cc2ccccc2s1] | N-((S)-1-(((S)-4-(tert-butylamino)-3,4-dione-1-((S)-2-oxopiperidine-3-yl)but-2-yl)amino)-1-oxo-3-phenylpropan-2-yl)-benzothiophene-2-carboxamide |

TABLE 1-continued

| number | structure | name |
|---|---|---|
| A65 | 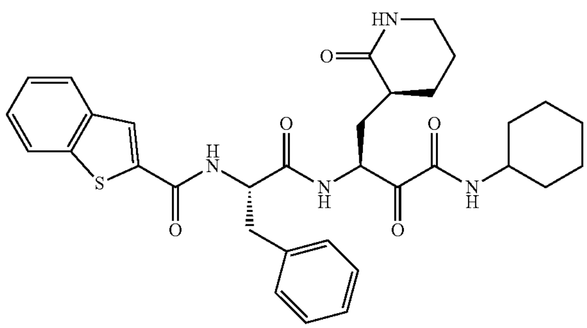 [SMILES: O=C(NC1CCCCC1)C(=O)[C@H](C[C@@H]1CCCNC1=O)NC(=O)[C@H](Cc1ccccc1)NC(=O)c1cc2ccccc2s1] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-benzothiophene-2-carboxamide |
| A66 | 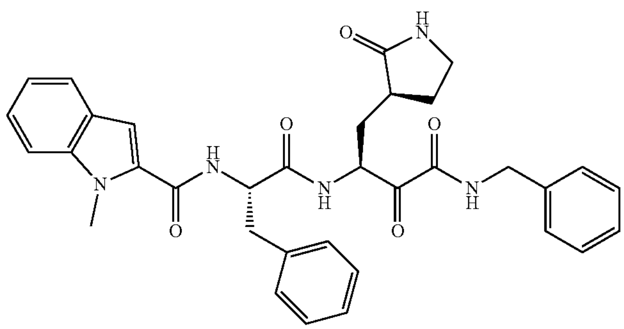 | N-((S)-1-(((S)-4-(benzylamino)-3,4-dione-1-((S)-2-oxopyrrolidine-3-yl)but-2-yl)amino)-1-oxo-3-phenylpropan-2-yl)-1-methyl-1H-indole-2-carboxamide |
| A67 | 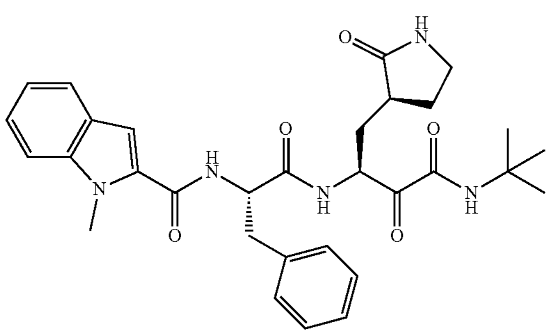 [SMILES: Cn1c(C(=O)N[C@@H](Cc2ccccc2)C(=O)N[C@@H](C[C@@H]2CCNC2=O)C(=O)C(=O)NC(C)(C)C)cc2ccccc21] | N-((S)-1-(((S)-4-(tert-butylamino)-3,4-dione-1-((S)-2-oxopyrrolidine-3-yl)but-2-y)amino)-1-oxo-3-phenylpropan-2-yl)-1-methyl-1H-indole-2-carboxamide |
| A68 | 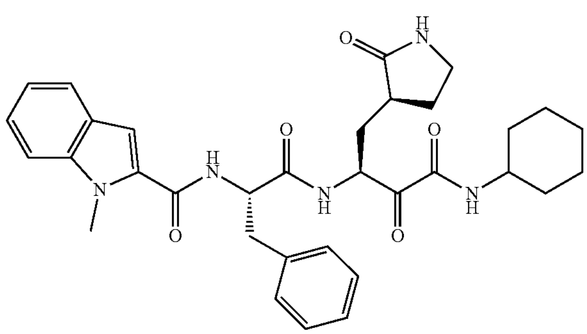 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-1-methyl-1H-indole-2-carboxamide |

TABLE 1-continued

| number | structure | name |
|---|---|---|
| A69 | 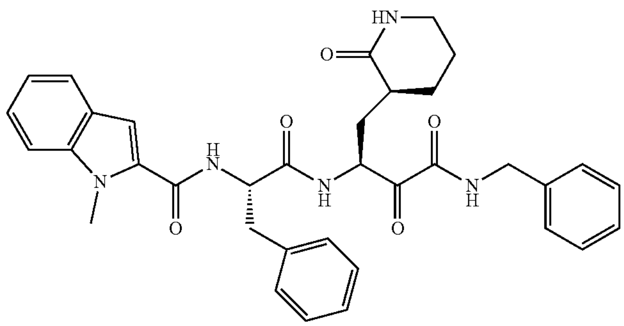 [SMILES: Cn1c(C(=O)N[C@@H](Cc2ccccc2)C(=O)N[C@@H](C[C@@H]2CCCNC2=O)C(=O)C(=O)NCc2ccccc2)cc2ccccc21] | N-((S)-1-(((S)-4-(benzylamino)-3,4-dione-1-((S)-2-oxopiperidine-3-yl)but-2-yl)amino)-1-oxo-3-phenylpropan-2-yl)-1-methyl-1H-indole-2-carboxamide |
| A70 | 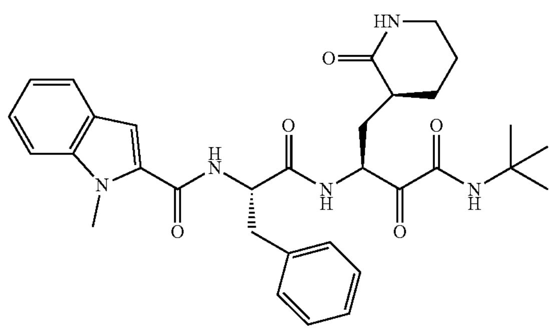 [SMILES: Cn1c(C(=O)N[C@@H](Cc2ccccc2)C(=O)N[C@@H](C[C@@H]2CCCNC2=O)C(=O)C(=O)NC(C)(C)C)cc2ccccc21] | N-((S)-1-(((S)-4-(tert-butylamino)-3,4-dione-1-((S)-2-oxopiperidine-3-yl)but-2-yl)amino)-1-oxo-3-phenylpropan-2-yl)-1-methyl-1H-indole-2-carboxamide |
| A71 | 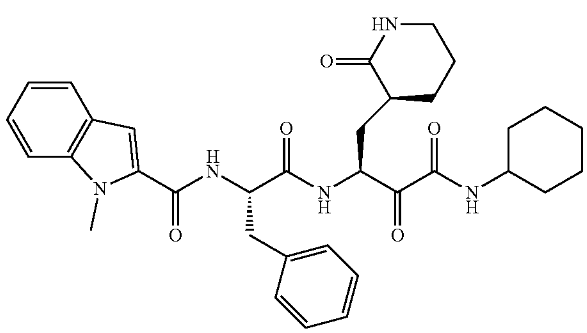 [SMILES: Cn1c(C(=O)N[C@@H](Cc2ccccc2)C(=O)N[C@@H](C[C@@H]2CCCNC2=O)C(=O)C(=O)NC2CCCCC2)cc2ccccc21] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-1-methyl-1H-indole-2-carboxamide |
| A72 | 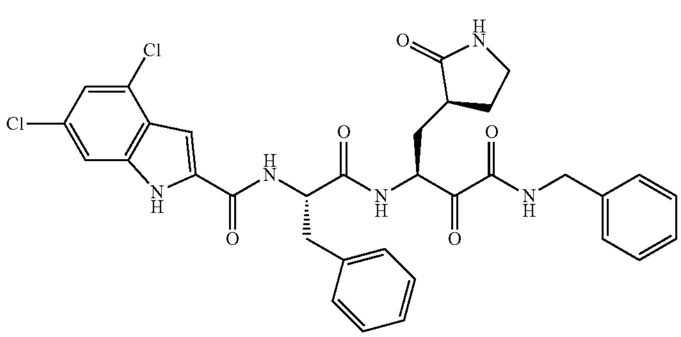 [SMILES: O=C(NCc1ccccc1)C(=O)[C@H](C[C@@H]1CCNC1=O)NC(=O)[C@H](Cc1ccccc1)NC(=O)c1cc2c(Cl)cc(Cl)cc2[nH]1] | N-((S)-1-(((S)-4-(benzylamino)-3,4-dione-1-((S)-2-oxopyrrolidine-3-yl)but-2-yl)amino)-1-oxo-3-phenylpropan-2-yl)-4,6-dichloro-1H-indole-2-carboxamide |

TABLE 1-continued

| number | structure | name |
|---|---|---|
| A73 | 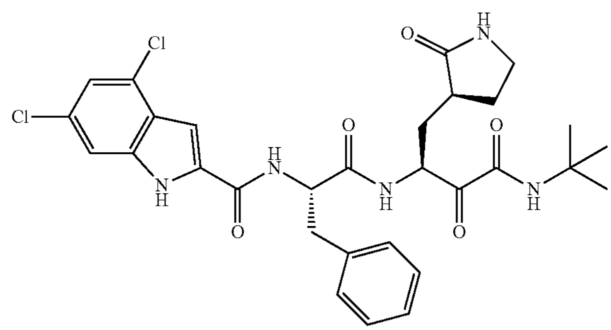 [SMILES: CC(C)(C)NC(=O)C(=O)[C@H](C[C@@H]1CCNC1=O)NC(=O)[C@H](Cc1ccccc1)NC(=O)c1cc2c(Cl)cc(Cl)cc2[nH]1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-4,6-dichloro-1H-indole-2-carboxamide |
| A74 | 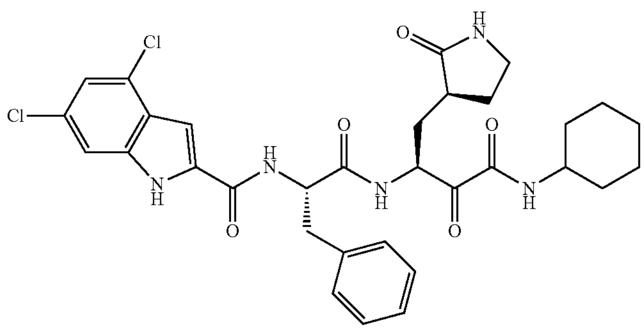 [SMILES: O=C(NC1CCCCC1)C(=O)[C@H](C[C@@H]1CCNC1=O)NC(=O)[C@H](Cc1ccccc1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-4,6-dichloro-1H-indole-2-carboxamide |
| A75 | 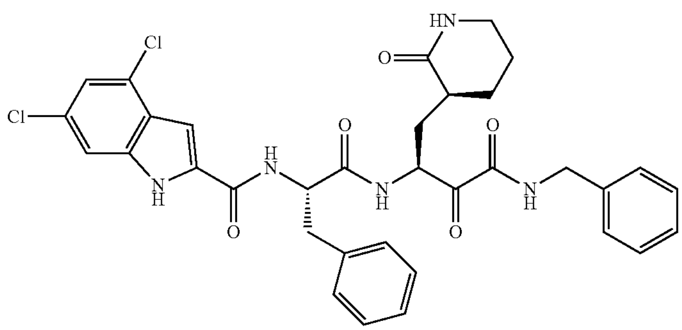 [SMILES: O=C(NCc1ccccc1)C(=O)[C@H](C[C@@H]1CCCNC1=O)NC(=O)[C@H](Cc1ccccc1)NC(=O)c1cc2c(Cl)cc(Cl)cc2[nH]1] | N-((S)-1-(((S)-4-(benzylamino)-3,4-dione-1-((S)-2-oxopiperidine-3-yl)but-2-yl)amino)-1-oxo-3-phenylpropan-2-yl)-4,6-dichloro-1H-indole-2-carboxamide |
| A76 | 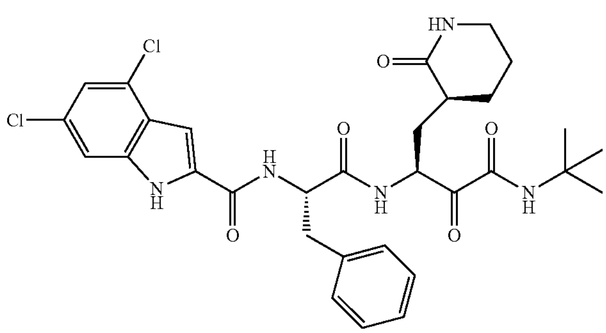 | N-((S)-1-(((S)-4-(tert-butylamino)-3,4-dione-1-((S)-2-oxopiperidine-3-yl)but-2-yl)amino)-1-oxo-3-phenylpropan-2-yl)-4,6-dichloro-1H-indole-2-carboxamide |

TABLE 1-continued

| number | structure | name |
| --- | --- | --- |
| A77 | 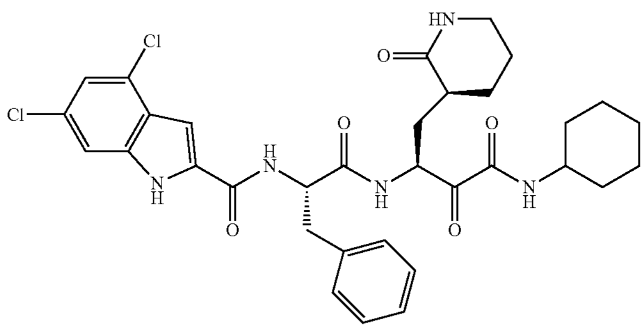 [SMILES: O=C(NC1CCCCC1)C(=O)[C@H](C[C@@H]1CCCNC1=O)NC(=O)[C@H](Cc1ccccc1)NC(=O)c1cc2c(Cl)cc(Cl)cc2[nH]1] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-4,6-dichloro-1H-indole-2-carboxamide |
| A78 | 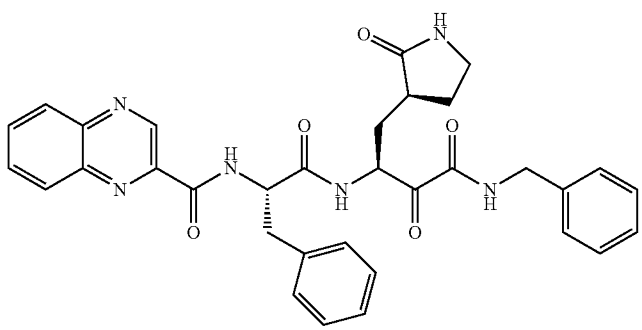 [SMILES: O=C(NCc1ccccc1)C(=O)[C@H](C[C@@H]1CCNC1=O)NC(=O)[C@H](Cc1ccccc1)NC(=O)c1cnc2ccccc2n1] | N-((S)-1-(((S)-4-(benzylamino)-3,4-dione-1-((S)-2-oxopyrrolidine-3-yl)but-2-yl)amino)-1-oxo-3-phenylpropan-2-yl)-quinoxaline-2-carboxamide |
| A79 | 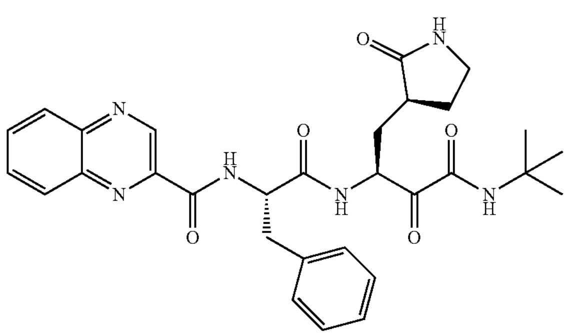 [SMILES: CC(C)(C)NC(=O)C(=O)[C@H](C[C@@H]1CCNC1=O)NC(=O)[C@H](Cc1ccccc1)NC(=O)c1cnc2ccccc2n1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-quinoxaline-2-carboxamide |
| A80 | 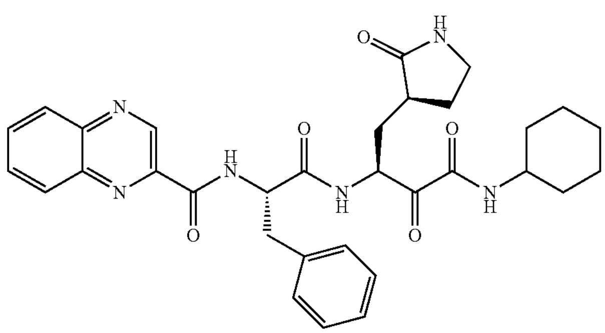 [SMILES: O=C(NC1CCCCC1)C(=O)[C@H](C[C@@H]1CCNC1=O)NC(=O)[C@H](Cc1ccccc1)NC(=O)c1cnc2ccccc2n1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-quinoxaline-2-carboxamide |

TABLE 1-continued

| number | structure | name |
| --- | --- | --- |
| A81 | 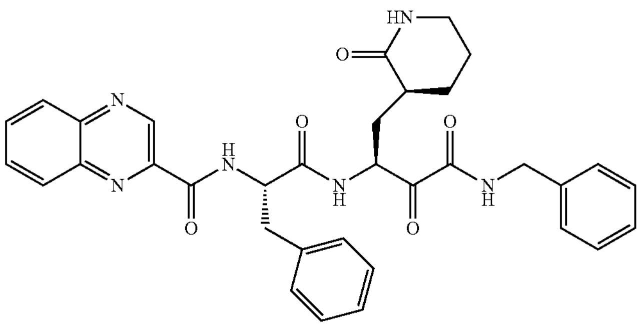 [SMILES: O=C(NCc1ccccc1)C(=O)[C@H](C[C@@H]1CCCNC1=O)NC(=O)[C@H](Cc1ccccc1)NC(=O)c1cnc2ccccc2n1] | N-((S)-1-(((S)-4-(benzylamino)-3,4-dione-1-((S)-2-oxopiperidine-3-yl)but-2-yl)amino)-1-oxo-3-phenylpropan-2-yl)-quinoxaline-2-carboxamide |
| A82 | 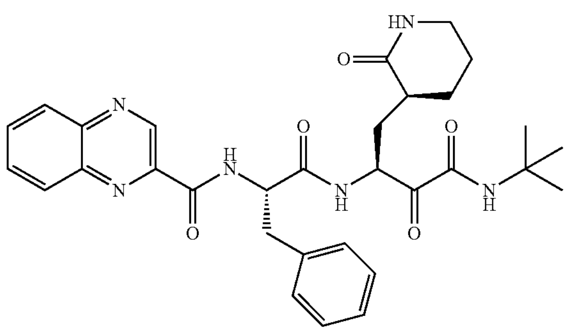 [SMILES: CC(C)(C)NC(=O)C(=O)[C@H](C[C@@H]1CCCNC1=O)NC(=O)[C@H](Cc1ccccc1)NC(=O)c1cnc2ccccc2n1] | N-((S)-1-(((S)-4-(tert-butylamino)-3,4-dione-1-((S)-2-oxopiperidine-3-yl)but-2-yl)amino)-1-oxo-3-phenylpropan-2-yl)-quinoxaline-2-carboxamide |
| A83 | 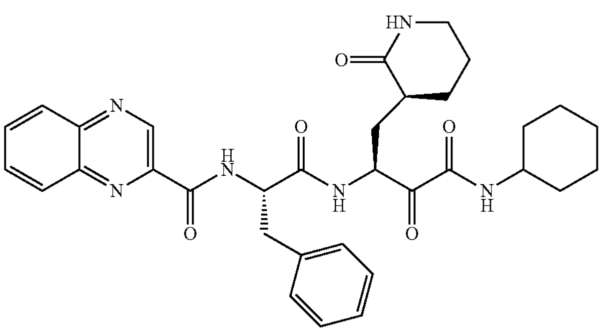 [SMILES: O=C(NC1CCCCC1)C(=O)[C@H](C[C@@H]1CCCNC1=O)NC(=O)[C@H](Cc1ccccc1)NC(=O)c1cnc2ccccc2n1] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-quinoxaline-2-carboxamide |
| A84 | 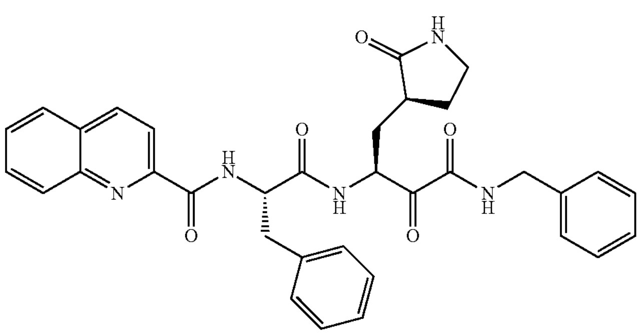 [SMILES: O=C(NCc1ccccc1)C(=O)[C@H](C[C@@H]1CCNC1=O)NC(=O)[C@H](Cc1ccccc1)NC(=O)c1ccc2ccccc2n1] | N-((S)-1-(((S)-4-(benzylamino)-3,4-dione-1-((S)-2-oxopyrrolidine-3-yl)but-2-yl)amino)-1-oxo-3-phenylpropan-2-yl)-quinoline-2-carboxamide |

TABLE 1-continued

| number | structure | name |
|---|---|---|
| A85 | 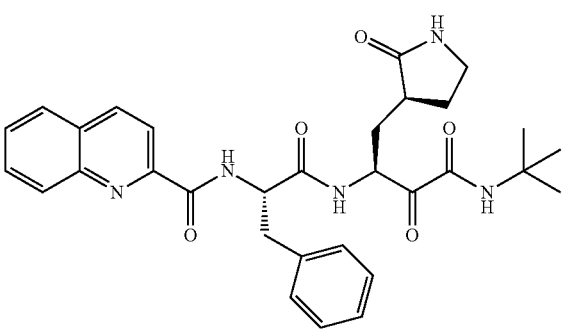 [SMILES: CC(C)(C)NC(=O)C(=O)[C@H](C[C@@H]1CCNC1=O)NC(=O)[C@H](Cc1ccccc1)NC(=O)c1ccc2ccccc2n1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-quinoline-2-carboxamide |
| A86 | 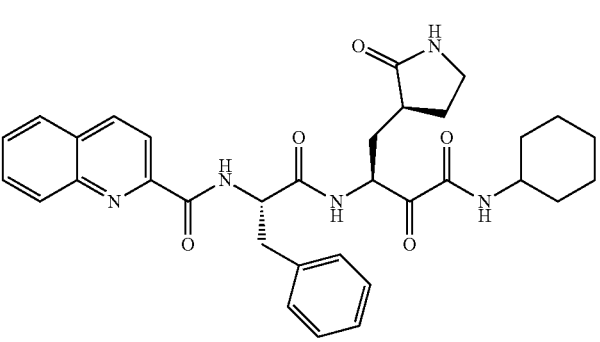 [SMILES: O=C(NC1CCCCC1)C(=O)[C@H](C[C@@H]1CCNC1=O)NC(=O)[C@H](Cc1ccccc1)NC(=O)c1ccc2ccccc2n1] | N-((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-quinoline-2-carboxamide |
| A87 | 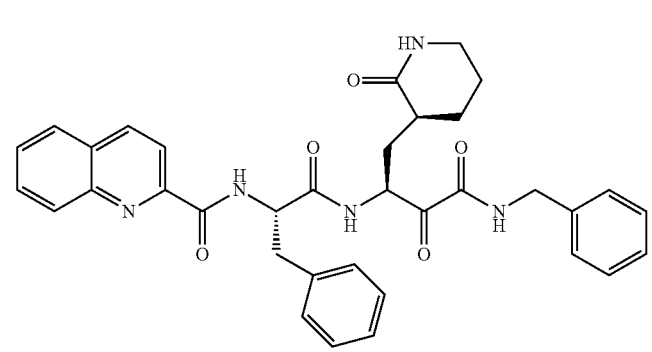 [SMILES: O=C(NCc1ccccc1)C(=O)[C@H](C[C@@H]1CCCNC1=O)NC(=O)[C@H](Cc1ccccc1)NC(=O)c1ccc2ccccc2n1] | N-((S)-1-(((S)-4-(benzylamino)-3,4-dione-1-((S)-2-oxopiperidine-3-yl)but-2-yl)amino)-1-oxo-3-phenylpropan-2-yl)-quinoline-2-carboxamide |
| A88 | 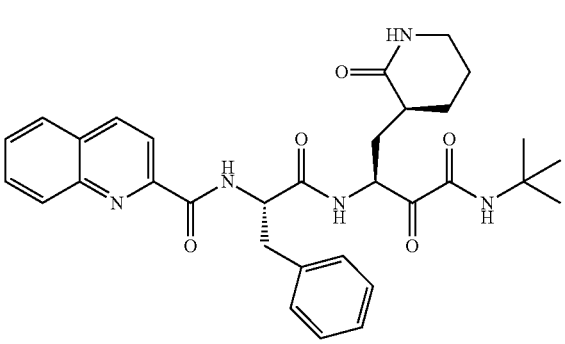 [SMILES: CC(C)(C)NC(=O)C(=O)[C@H](C[C@@H]1CCCNC1=O)NC(=O)[C@H](Cc1ccccc1)NC(=O)c1ccc2ccccc2n1] | N-((S)-1-(((S)-4-(tert-butylamino)-3,4-dione-1-((S)-2-oxopiperidine-3-yl)but-2-yl)amino)-1-oxo-3-phenylpropan-2-yl)-quinoline-2-carboxamide |

TABLE 1-continued

| number | structure | name |
|---|---|---|
| A89 | 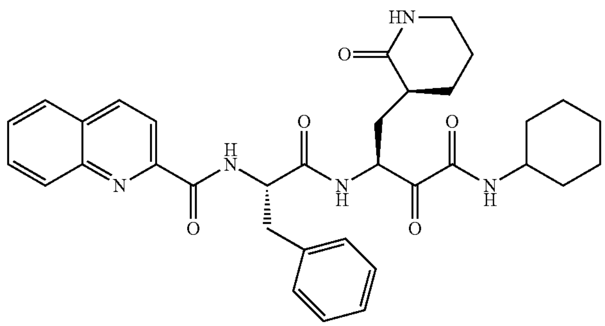 [SMILES: O=C(NC1CCCCC1)C(=O)[C@H](C[C@@H]1CCCNC1=O)NC(=O)[C@H](Cc1ccccc1)NC(=O)c1ccc2ccccc2n1] | N-((S)-3-cyclohexyl-1-(((S)-4-(cyclohexylamino)-3,4-dione-1-((S)-2-oxopiperidine-3-yl)but-2-yl)amino)-1-oxo-3-phenylpropan-2-yl)-quinoline-2-carboxamide |
| A90 | 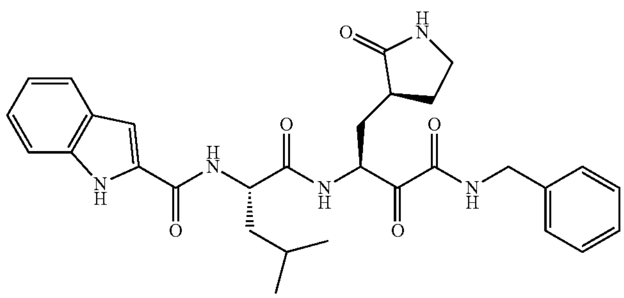 [SMILES: CC(C)C[C@H](NC(=O)c1cc2ccccc2[nH]1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-1H-indole-2-carboxamide |
| A91 | 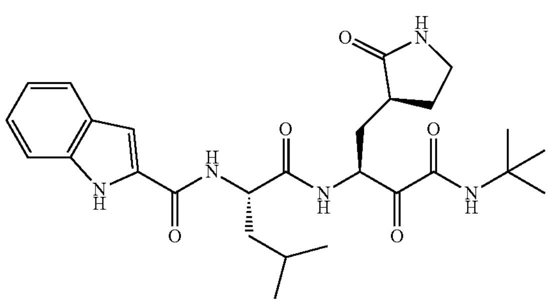 [SMILES: CC(C)C[C@H](NC(=O)c1cc2ccccc2[nH]1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-1H-indole-2-carboxamide |
| A92 | 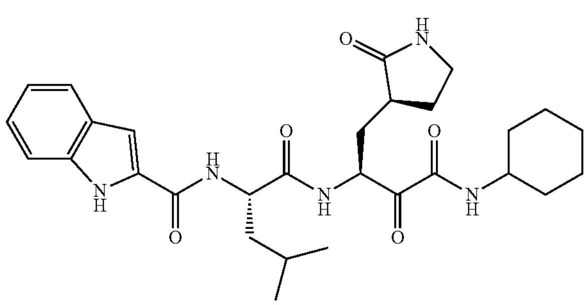 | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-1H-indole-2-carboxamide |

TABLE 1-continued

| number | structure | name |
|---|---|---|
| A93 | 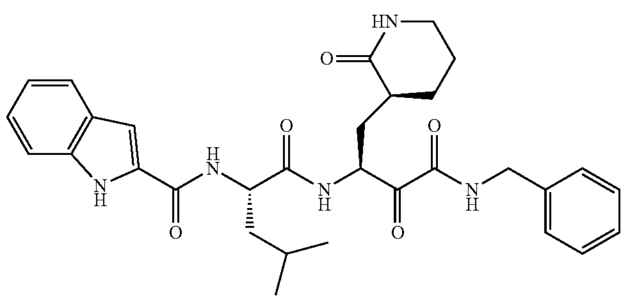 [SMILES: CC(C)C[C@H](NC(=O)c1cc2ccccc2[nH]1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-1H-indole-2-carboxamide |
| A94 | 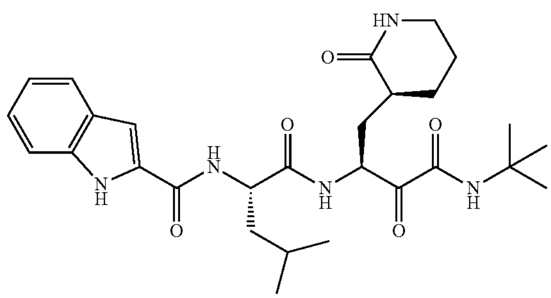 [SMILES: CC(C)C[C@H](NC(=O)c1cc2ccccc2[nH]1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-1H-indole-2-carboxamide |
| A95 | 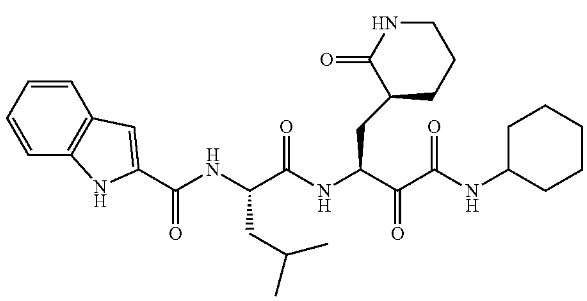 [SMILES: CC(C)C[C@H](NC(=O)c1cc2ccccc2[nH]1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-1H-indole-2-carboxamide |
| A96 | 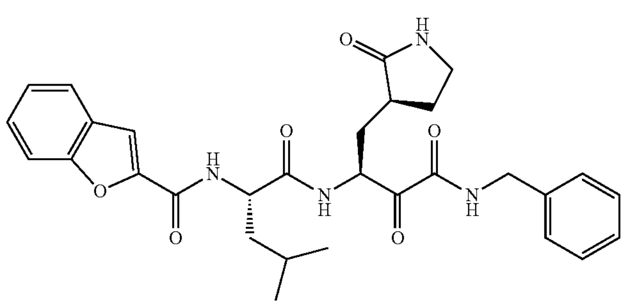 [SMILES: CC(C)C[C@H](NC(=O)c1cc2ccccc2o1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-benzofuran-2-carboxamide |

TABLE 1-continued

| number | structure | name |
|---|---|---|
| A97 | 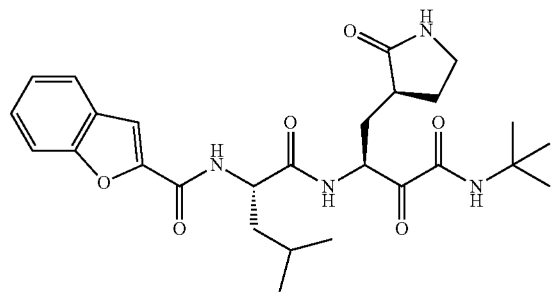 [SMILES: CC(C)C[C@H](NC(=O)c1cc2ccccc2o1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-benzofuran-2-carboxamide |
| A98 | 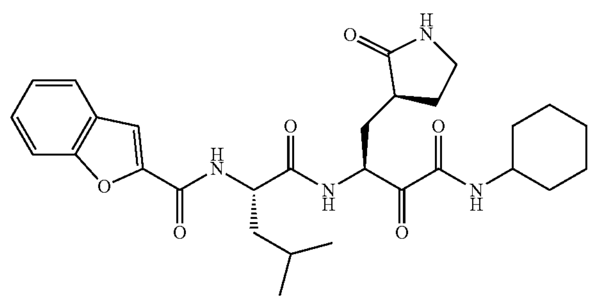 | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-benzofuran-2-carboxamide |
| A99 | 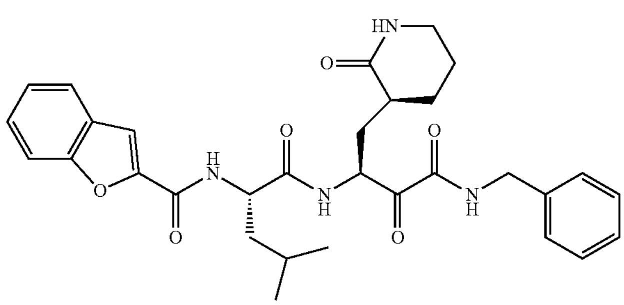 | N-((S)-1-(((S)-4-(benzylamino)-3,4-dione-1-((S)-2-oxopiperidine-3-yl)but-2-yl)amino)-4-methyl-1-oxopentan-2-yl)-benzofuran-2-carboxamide |
| A100 | 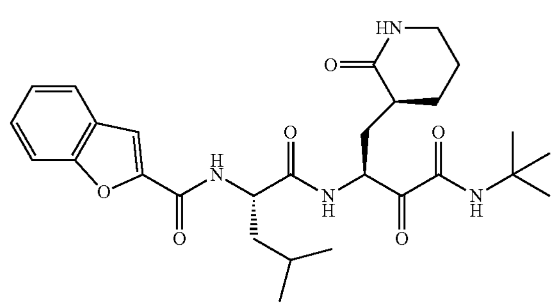 [SMILES: CC(C)C[C@H](NC(=O)c1cc2ccccc2o1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-benzofuran-2-carboxamide |

TABLE 1-continued

| number | structure | name |
|---|---|---|
| A101 | 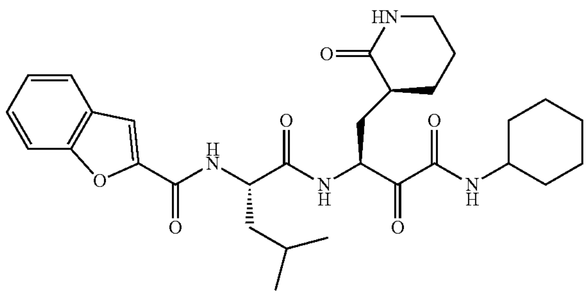 [SMILES: CC(C)C[C@H](NC(=O)c1cc2ccccc2o1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-benzofuran-2-carboxamide |
| A102 | 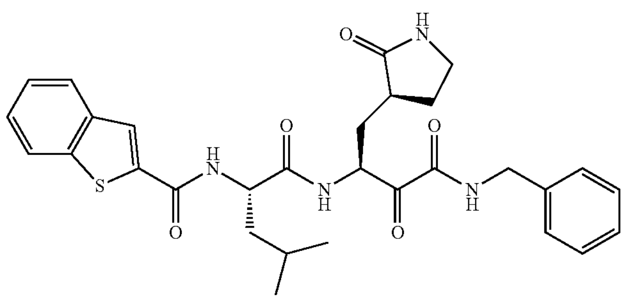 [SMILES: CC(C)C[C@H](NC(=O)c1cc2ccccc2s1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-benzothiophene-2-carboxamide |
| A103 | 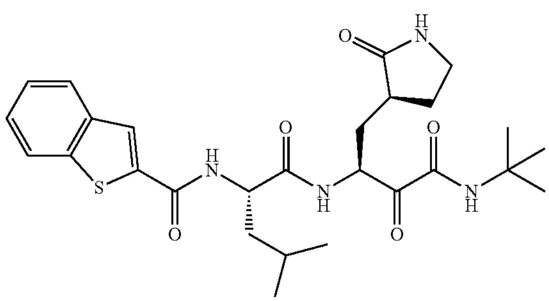 [SMILES: CC(C)C[C@H](NC(=O)c1cc2ccccc2s1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-benzothiophene-2-carboxamide |
| A104 | 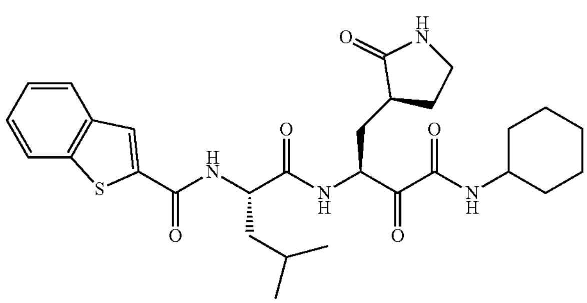 [SMILES: CC(C)C[C@H](NC(=O)c1cc2ccccc2s1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-benzothiophene-2-carboxamide |

TABLE 1-continued

| number | structure | name |
|---|---|---|
| A105 | 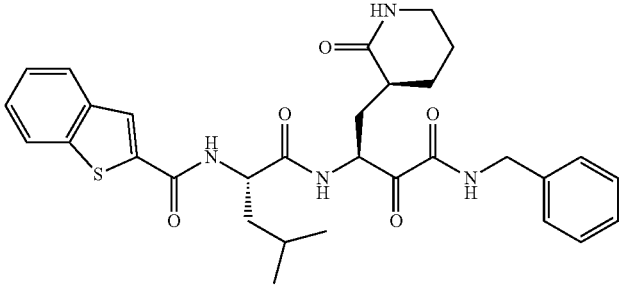 [SMILES: CC(C)C[C@H](NC(=O)c1cc2ccccc2s1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-benzothiophene-2-carboxamide |
| A106 | 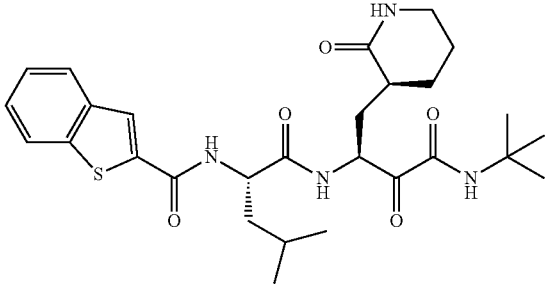 | N-((S)-1-(((S)-4-(tert-butylamino)-3,4-dione-1-((S)-2-oxopiperidine-3-yl)but-2-yl)amino)-3-cyclohexyl-1-oxopentan-2-yl)-benzothiophene-2-carboxamide |
| A107 | 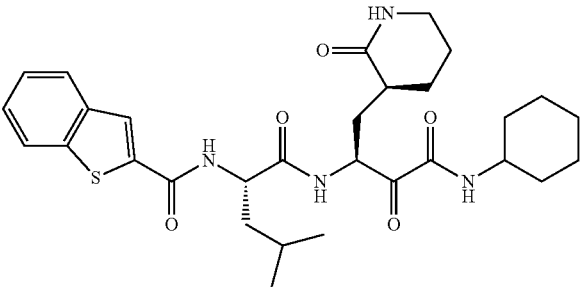 [SMILES: CC(C)C[C@H](NC(=O)c1cc2ccccc2s1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-benzothiophene-2-carboxamide |
| A108 | 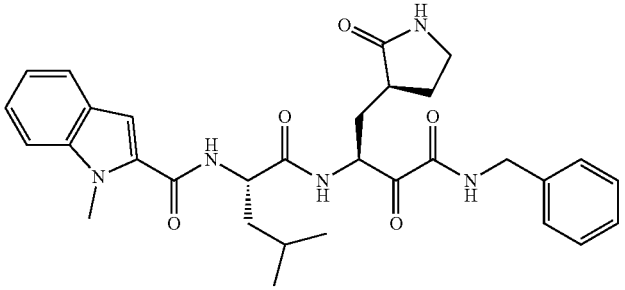 [SMILES: CC(C)C[C@H](NC(=O)c1cc2ccccc2n1C)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-1-methyl-1H-indole-2-carboxamide |

TABLE 1-continued

| number | structure | name |
| --- | --- | --- |
| A109 | 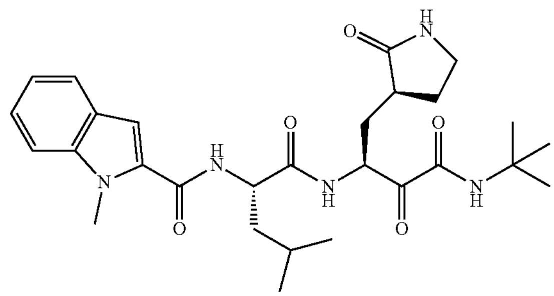 [SMILES: CC(C)C[C@H](NC(=O)c1cc2ccccc2n1C)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-1-methyl-1H-indole-2-carboxamide |
| A110 | 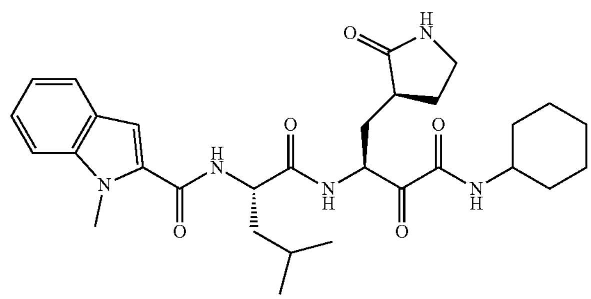 [SMILES: CC(C)C[C@H](NC(=O)c1cc2ccccc2n1C)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-1-methyl-1H-indole-2-carboxamide |
| A111 | 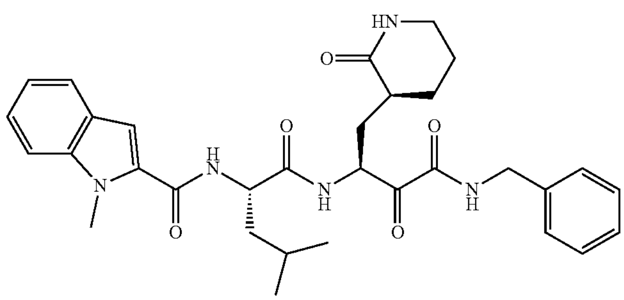 [SMILES: CC(C)C[C@H](NC(=O)c1cc2ccccc2n1C)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-1-methyl-1H-indole-2-carboxamide |
| A112 | 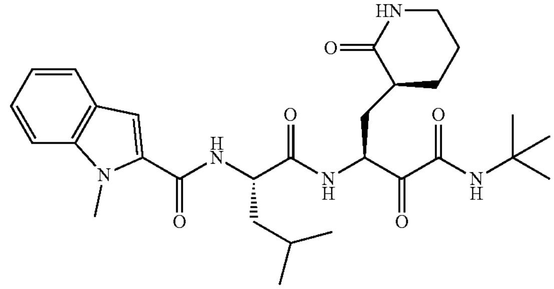 [SMILES: CC(C)C[C@H](NC(=O)c1cc2ccccc2n1C)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-1-methyl-1H-indole-2-carboxamide |

TABLE 1-continued

| number | structure | name |
| --- | --- | --- |
| A113 | 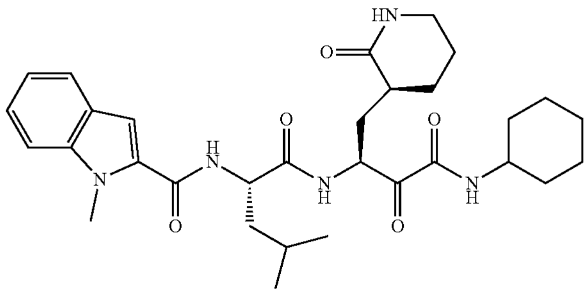 [SMILES: CC(C)C[C@H](NC(=O)c1cc2ccccc2n1C)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-1-methyl-1H-indole-2-carboxamide |
| A114 | 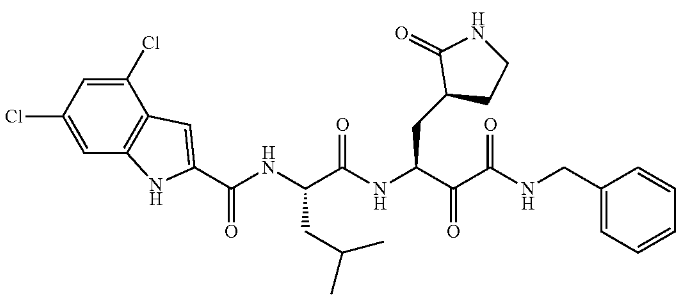 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-4,6-dichloro-1H-indole-2-carboxamide |
| A115 | 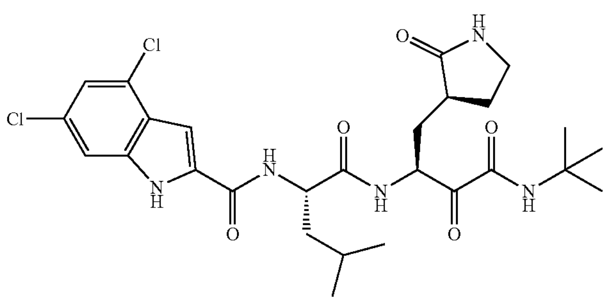 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-4,6-dichloro-1H-indole-2-carboxamide |
| A116 | 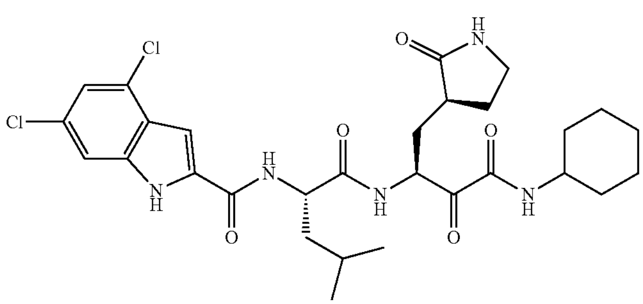 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-4,6-dichloro-1H-indole-2-carboxamide |

TABLE 1-continued

| number | structure | name |
|---|---|---|
| A117 | 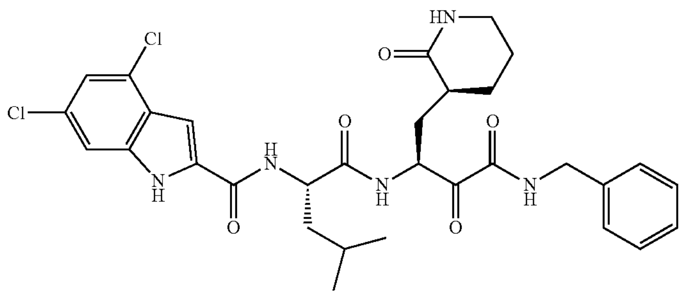 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-4,6-dichloro-1H-indole-2-carboxamide |
| A118 | 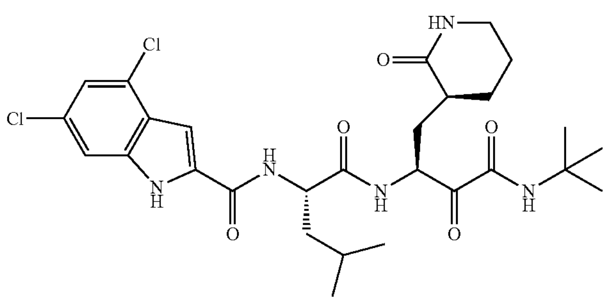 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-4,6-dichloro-1H-indole-2-carboxamide |
| A119 | 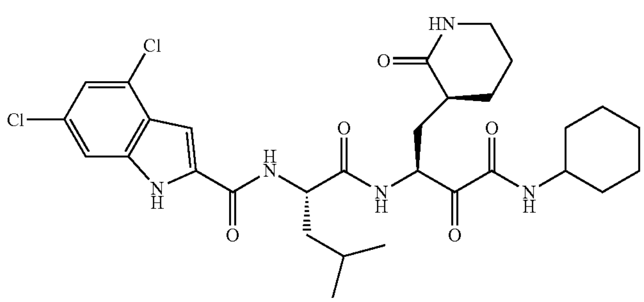 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-4,6-dichloro-1H-indole-2-carboxamide |
| A120 | 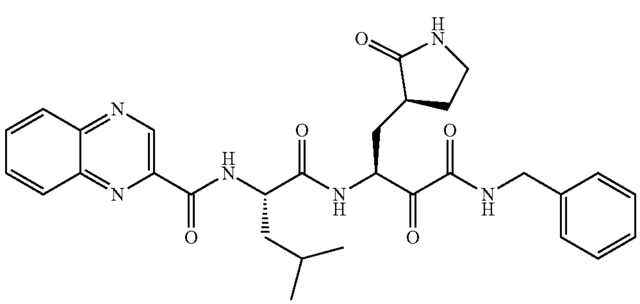 [SMILES: CC(C)C[C@H](NC(=O)c1cnc2ccccc2n1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-quinoxaline-2-carboxamide |

TABLE 1-continued

| number | structure | name |
| --- | --- | --- |
| A121 | 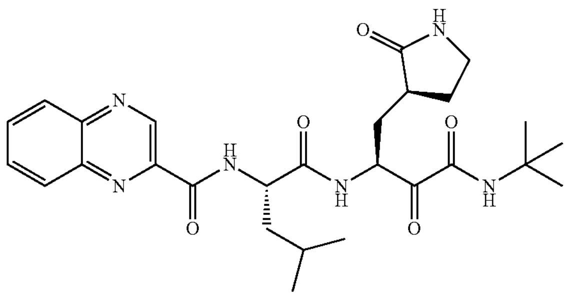 [SMILES: CC(C)C[C@H](NC(=O)c1cnc2ccccc2n1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-quinoxaline-2-carboxamide |
| A122 | 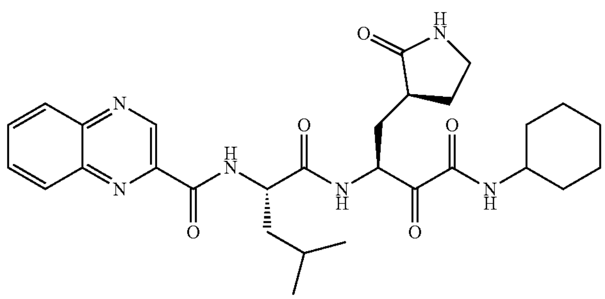 [SMILES: CC(C)C[C@H](NC(=O)c1cnc2ccccc2n1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-quinoxaline-2-carboxamide |
| A123 | 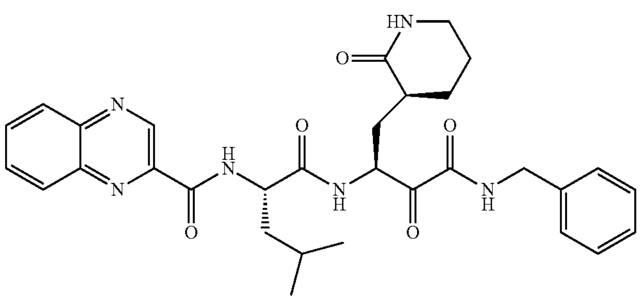 [SMILES: CC(C)C[C@H](NC(=O)c1cnc2ccccc2n1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-quinoxaline-2-carboxamide |
| A124 | 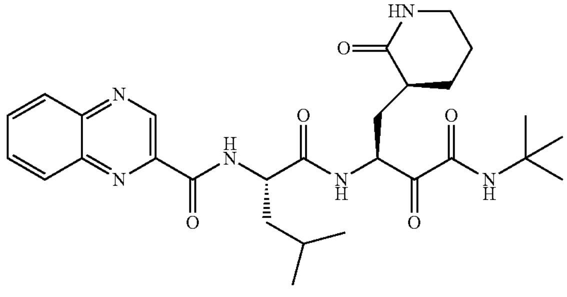 [SMILES: CC(C)C[C@H](NC(=O)c1cnc2ccccc2n1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-quinoxaline-2-carboxamide |

TABLE 1-continued

| number | structure | name |
| --- | --- | --- |
| A125 | 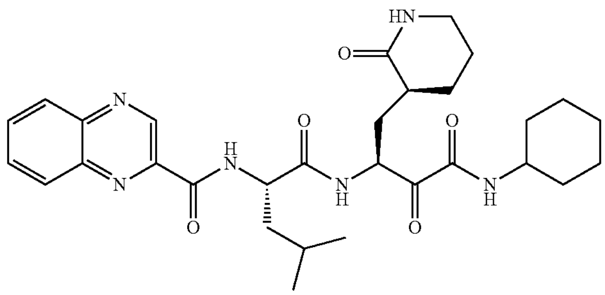 [SMILES: CC(C)C[C@H](NC(=O)c1cnc2ccccc2n1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-quinoxaline-2-carboxamide |
| A126 | 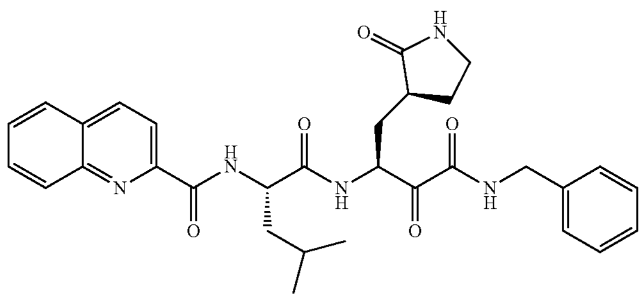 [SMILES: CC(C)C[C@H](NC(=O)c1ccc2ccccc2n1)C(=O)N[C@@H](C[C@@H]1CCNC1=O)C(=O)C(=O)NCc1ccccc1] | N-((S)-1-(((S)-4-(benzylamino)-3,4-dione-1-((S)-2-oxopyrrolidine-3-yl)but-2-yl)amino)-4-methyl-1-oxopentan-2-yl)-quinoline-2-carboxamide |
| A127 | 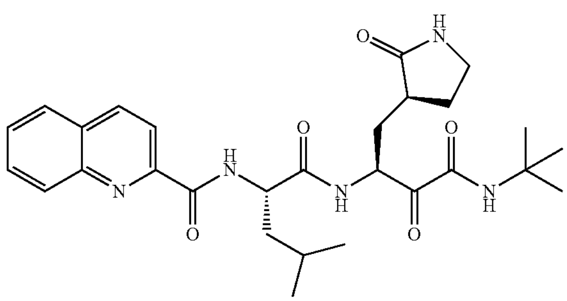 [SMILES: CC(C)C[C@H](NC(=O)c1ccc2ccccc2n1)C(=O)N[C@@H](C[C@@H]1CCNC1=O)C(=O)C(=O)NC(C)(C)C] | N-((S)-1-(((S)-4-(tert-butylamino)-3,4-dione-1-((S)-2-oxopyrrolidine-3-yl)but-2-yl)amino)-3-cyclohexyl-1-oxopentan-2-yl)-quinoline-2-carboxamide |
| A128 | 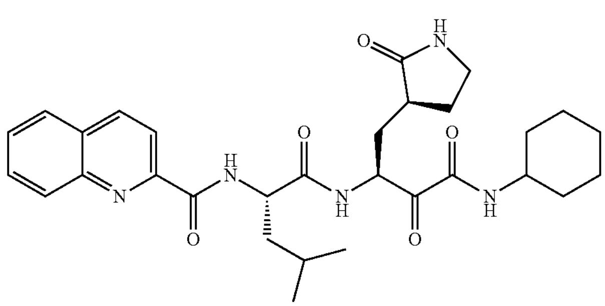 [SMILES: CC(C)C[C@H](NC(=O)c1ccc2ccccc2n1)C(=O)N[C@@H](C[C@@H]1CCNC1=O)C(=O)C(=O)NC1CCCCC1] | N-((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-quinoline-2-carboxamide |

TABLE 1-continued

| number | structure | name |
|---|---|---|
| A129 | 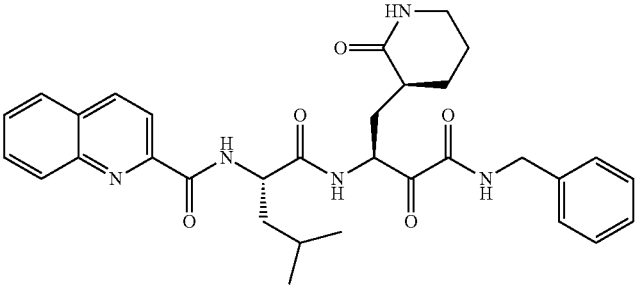 [SMILES: CC(C)C[C@H](NC(=O)c1ccc2ccccc2n1)C(=O)N[C@@H](C[C@@H]1CCCNC1=O)C(=O)C(=O)NCc1ccccc1] | N-((S)-1-(((S)-4-(benzylamino)-3,4-dione-1-((S)-2-oxopiperidine-3-yl)but-2-yl)amino)-4-methyl-1-oxopentan-2-yl)-quinoline-2-carboxamide |
| A130 | 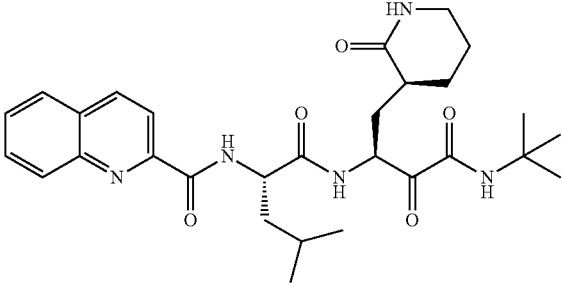 [SMILES: CC(C)C[C@H](NC(=O)c1ccc2ccccc2n1)C(=O)N[C@@H](C[C@@H]1CCCNC1=O)C(=O)C(=O)NC(C)(C)C] | N-((S)-1-(((S)-4-(tert-butylamino)-3,4-dione-1-((S)-2-oxopiperidine-3-yl)but-2-yl)amino)-3-cyclohexyl-1-oxopentan-2-yl)-quinoline-2-carboxamide |
| A131 | 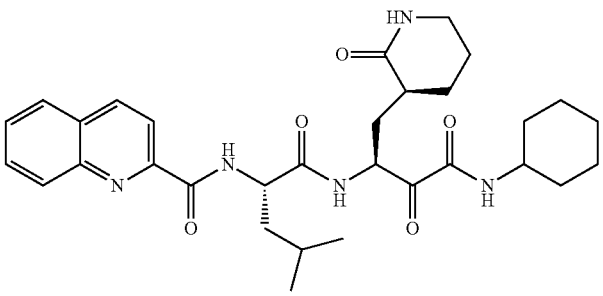 [SMILES: CC(C)C[C@H](NC(=O)c1ccc2ccccc2n1)C(=O)N[C@@H](C[C@@H]1CCCNC1=O)C(=O)C(=O)NC1CCCCC1] | N-((S)-3-cyclohexyl-1-(((S)-4-(cyclohexylamino)-3,4-dione-1-((S)-2-oxopiperidine-3-yl)but-2-yl)amino)-3-cyclohexyl-1-oxopentan-2-yl)-quinoline-2-carboxamide |
| A132 | 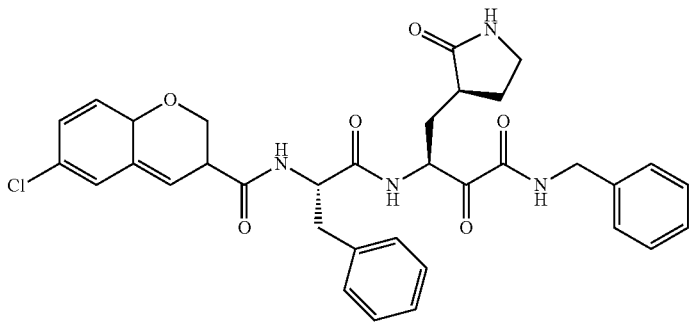 [SMILES: O=C(NCc1ccccc1)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(benzylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide |

TABLE 1-continued

| number | structure | name |
|---|---|---|
| A133 | 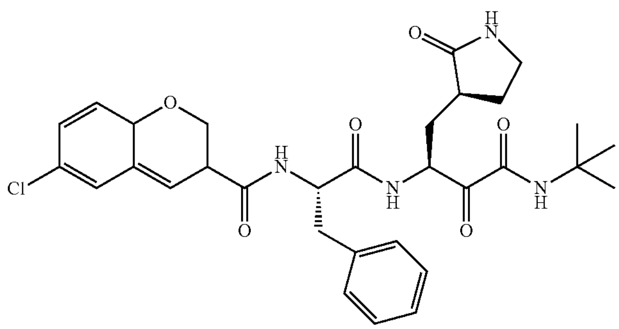 [SMILES: CC(C)(C)NC(=O)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide |
| A134 | 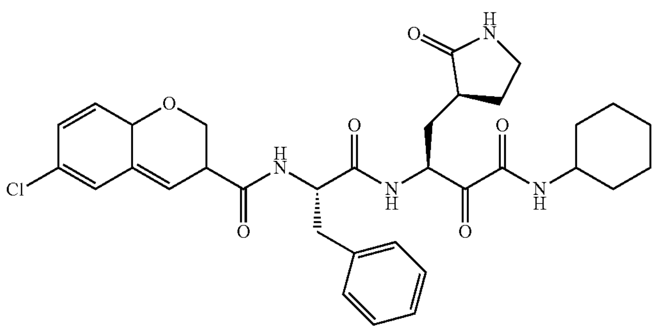 [SMILES: O=C(NC1CCCCC1)C(=O)[C@H](C[C@@H]1CCNC1=O)NC(=O)[C@H](Cc1ccccc1)NC(=O)C1C=C2C=C(Cl)C=CC2OC1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide |
| A135 | 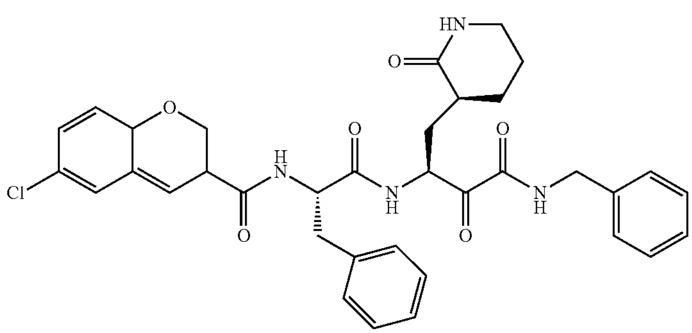 [SMILES: O=C(NCc1ccccc1)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(benzylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide |
| A136 | 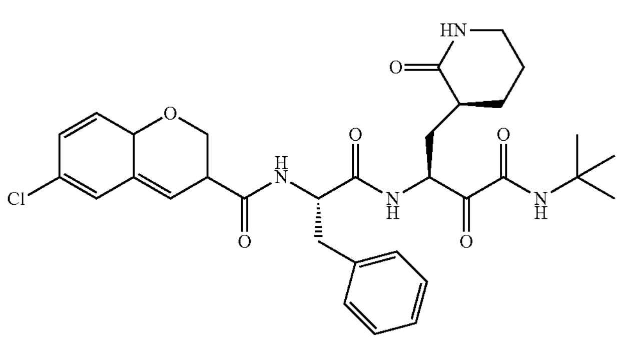 [SMILES: CC(C)(C)NC(=O)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(tert-butylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide |

TABLE 1-continued

| number | structure | name |
|---|---|---|
| A137 | 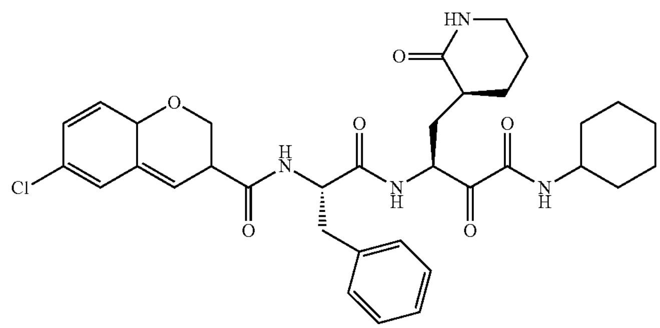 [SMILES: O=C(NC1CCCCC1)C(=O)[C@H](C[C@@H]1CCCNC1=O)NC(=O)[C@H](Cc1ccccc1)NC(=O)C1C=C2C=C(Cl)C=CC2OC1] | N-((S)-1-(((S)-4-(cyclohexylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide |
| A138 | 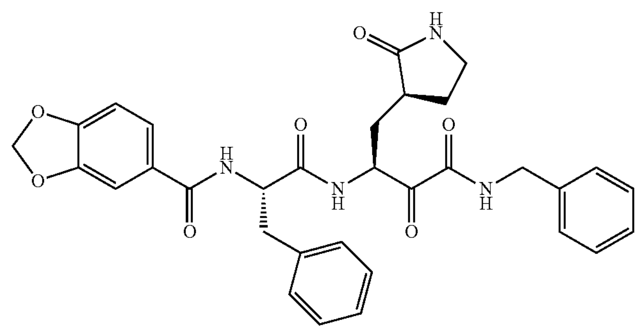 [SMILES: O=C(NCc1ccccc1)C(=O)[C@H](C[C@@H]1CCNC1=O)NC(=O)[C@H](Cc1ccccc1)NC(=O)c1ccc2c(c1)OCO2] | N-((S)-1-(((S)-4-(benzylamino)-3,4-dione-1-((S)-2-oxopyrrolidine-3-yl)but-2-yl)amino)-1-oxo-3-phenylpropan-2-yl)benzene[d][1,3] dioxol-5-carboxamide |
| A139 | 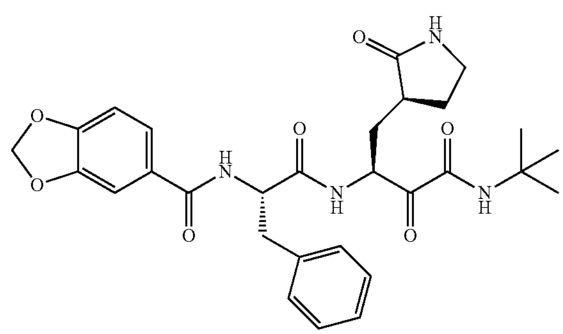 [SMILES: CC(C)(C)NC(=O)C(=O)[C@H](C[C@@H]1CCNC1=O)NC(=O)[C@H](Cc1ccccc1)NC(=O)c1ccc2c(c1)OCO2] | N-((S)-1-(((S)-4-(tert-butylamino)-3,4-dione-1-((S)-2-oxopyrrolidine-3-yl)but-2-yl)amino)-1-oxo-3-phenylpropan-2-yl)benzene[d][1,3] dioxol-5-carboxamide |
| A140 | 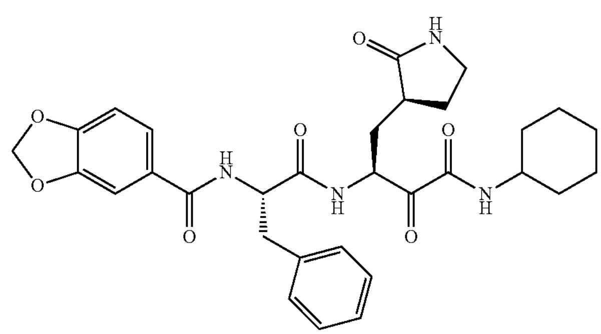 [SMILES: O=C(NC1CCCCC1)C(=O)[C@H](C[C@@H]1CCNC1=O)NC(=O)[C@H](Cc1ccccc1)NC(=O)c1ccc2c(c1)OCO2] | N-((S)-1-(((S)-4-(cyclohexylamino)-3,4-dione-1-((S)-2-oxopyrrolidine-3-yl)but-2-yl)amino)-1-oxo-3-phenylpropan-2-yl)benzene[d][1,3] dioxol-5-carboxamide |

TABLE 1-continued

| number | structure | name |
|---|---|---|
| A141 | 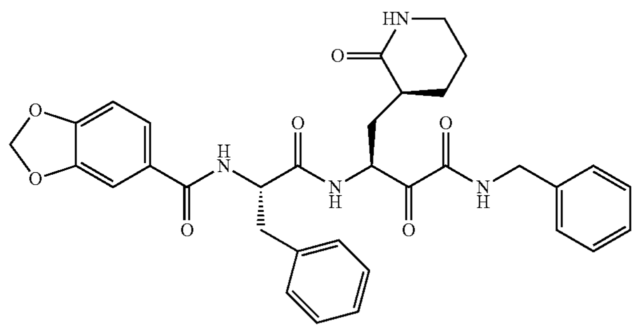 [SMILES: O=C(NCc1ccccc1)C(=O)[C@H](C[C@@H]1CCCNC1=O)NC(=O)[C@H](Cc1ccccc1)NC(=O)c1ccc2c(c1)OCO2] | N-((S)-1-(((S)-4-(benzylamino)-3,4-dione-1-((S)-2-oxopiperidine-3-yl)but-2-yl)amino)-1-oxo-3-phenylpropan-2-yl)benzene[d][1,3] dioxol-5-carboxamide |
| A142 | 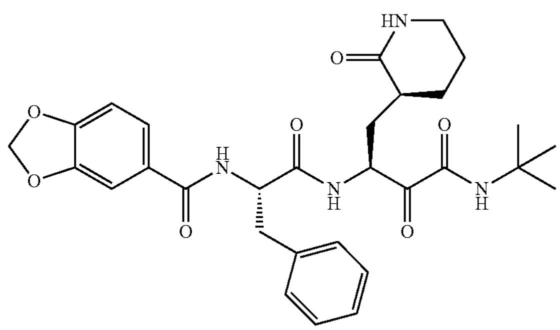 [SMILES: CC(C)(C)NC(=O)C(=O)[C@H](C[C@@H]1CCCNC1=O)NC(=O)[C@H](Cc1ccccc1)NC(=O)c1ccc2c(c1)OCO2] | N-((S)-1-(((S)-4-(tert-butylamino)-3,4-dione-1-((S)-2-oxopiperidine-3-yl)but-2-yl)amino)-1-oxo-3-phenylpropan-2-yl)benzene[d][1,3] dioxol-5-carboxamide |
| A143 | 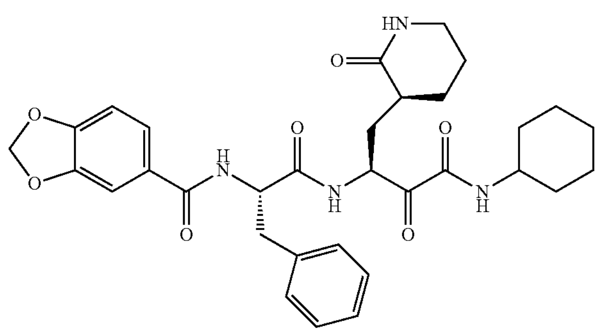 [SMILES: O=C(NC1CCCCC1)C(=O)[C@H](C[C@@H]1CCCNC1=O)NC(=O)[C@H](Cc1ccccc1)NC(=O)c1ccc2c(c1)OCO2] | N-((S)-1-(((S)-4-(cyclohexylamino)-3,4-dione-1-((S)-2-oxopiperidine-3-yl)but-2-yl)amino)-1-oxo-3-phenylpropan-2-yl)benzene[d][1,3] dioxol-5-carboxamide |
| A144 | 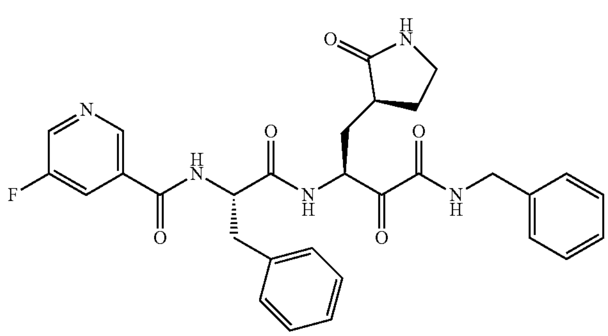 [SMILES: O=C(NCc1ccccc1)C(=O)[C@H](C[C@@H]1CCNC1=O)NC(=O)[C@H](Cc1ccccc1)NC(=O)c1cncc(F)c1] | N-((S)-1-(((S)-4-(benzylamino)-3,4-dione-1-((S)-2-oxopyrrolidine-3-yl)but-2-yl)amino)-1-oxo-3-phenylpropan-2-yl)-5-fluoronicotinamide |

TABLE 1-continued

| number | structure | name |
|---|---|---|
| A145 | 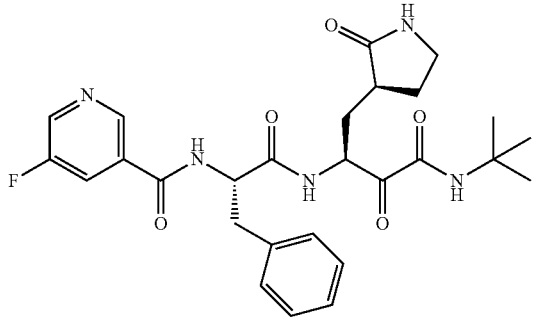 [SMILES: CC(C)(C)NC(=O)C(=O)[C@H](C[C@@H]1CCNC1=O)NC(=O)[C@H](Cc1ccccc1)NC(=O)c1cncc(F)c1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-5-fluoronicotinamide |
| A146 | 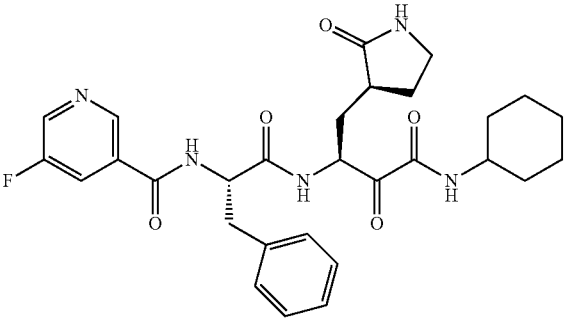 [SMILES: O=C(NC1CCCCC1)C(=O)[C@H](C[C@@H]1CCNC1=O)NC(=O)[C@H](Cc1ccccc1)NC(=O)c1cncc(F)c1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-5-fluoronicotinamide |
| A147 | 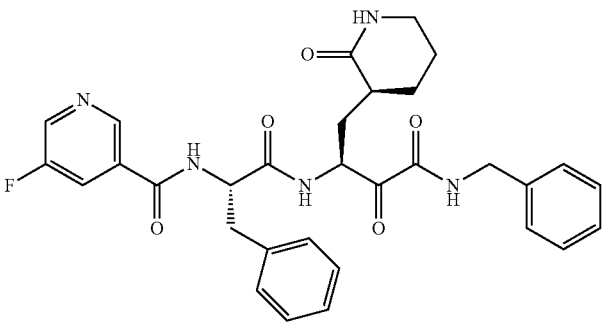 [SMILES: O=C(NCc1ccccc1)C(=O)[C@H](C[C@@H]1CCCNC1=O)NC(=O)[C@H](Cc1ccccc1)NC(=O)c1cncc(F)c1] | N-((S)-1-(((S)-4-(benzylamino)-3,4-dione-1-((S)-2-oxopiperidine-3-yl)but-2-yl)amino)-1-oxo-3-phenylpropan-2-yl)-5-fluoronicotinamide |
| A148 | 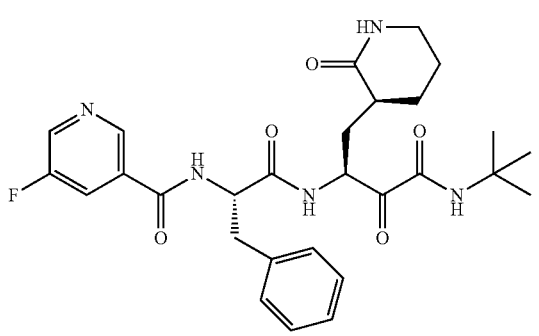 [SMILES: CC(C)(C)NC(=O)C(=O)[C@H](C[C@@H]1CCCNC1=O)NC(=O)[C@H](Cc1ccccc1)NC(=O)c1cncc(F)c1] | N-((S)-1-(((S)-4-(tert-butylamino)-3,4-dione-1-((S)-2-oxopiperidine-3-yl)but-2-yl)amino)-1-oxo-3-phenylpropan-2-yl)-5-fluoronicotinamide |

TABLE 1-continued

| number | structure | name |
|---|---|---|
| A149 | 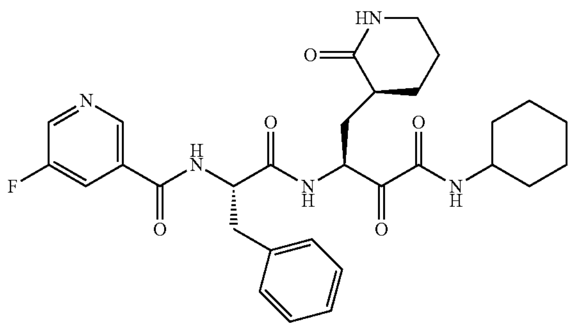 [SMILES: O=C(NC1CCCCC1)C(=O)[C@H](C[C@@H]1CCCNC1=O)NC(=O)[C@H](Cc1ccccc1)NC(=O)c1cncc(F)c1] | N-((S)-1-(((S)-4-(cyclohexylamino)-3,4-dione-1-((S)-2-oxopiperidine-3-yl)but-2-yl)amino)-1-oxo-3-phenylpropan-2-yl)-5-fluoronicotinamide |
| A150 | 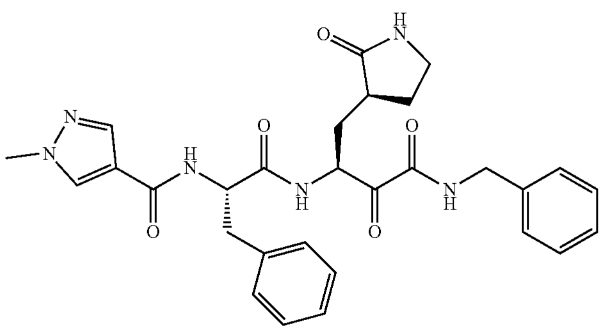 [SMILES: Cn1cc(C(=O)N[C@@H](Cc2ccccc2)C(=O)N[C@@H](C[C@@H]2CCNC2=O)C(=O)C(=O)NCc2ccccc2)cn1] | N-((S)-1-(((S)-4-(benzylamino)-3,4-dione-1-((S)-2-oxopyrrolidine-3-yl)but-2-yl)amino)-1-oxo-3-phenylpropan-2-yl)-1-methyl-1H-pyrazole-4-carboxamide |
| A151 | 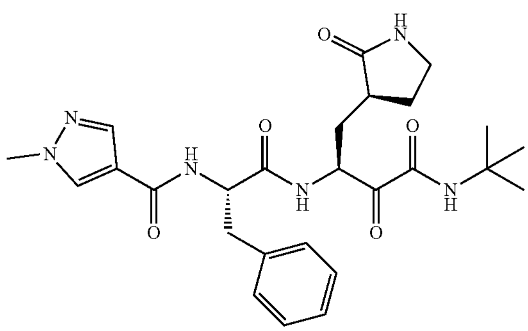 [SMILES: Cn1cc(C(=O)N[C@@H](Cc2ccccc2)C(=O)N[C@@H](C[C@@H]2CCNC2=O)C(=O)C(=O)NC(C)(C)C)cn1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-1-methyl-1H-pyrazole-4-carboxamide |
| A152 | 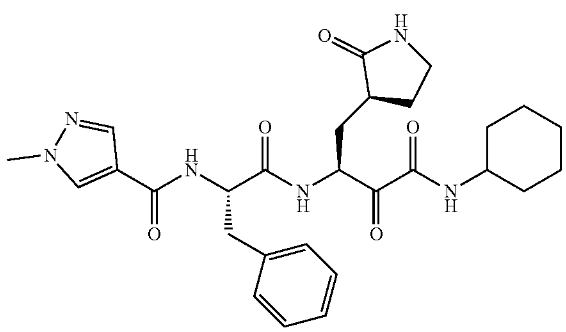 [SMILES: Cn1cc(C(=O)N[C@@H](Cc2ccccc2)C(=O)N[C@@H](C[C@@H]2CCNC2=O)C(=O)C(=O)NC2CCCCC2)cn1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-1-methyl-1H-pyrazole-4-carboxamide |

TABLE 1-continued

| number | structure | name |
|---|---|---|
| A153 | 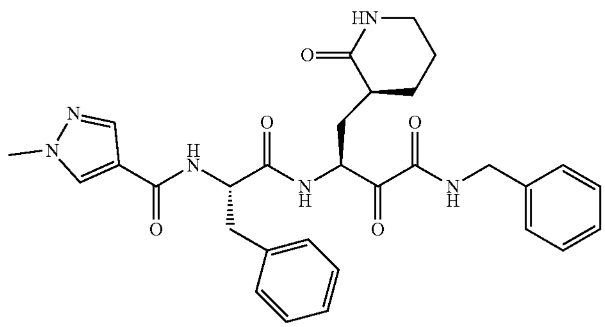 [SMILES: Cn1cc(C(=O)N[C@@H](Cc2ccccc2)C(=O)N[C@@H](C[C@@H]2CCCNC2=O)C(=O)C(=O)NCc2ccccc2)cn1] | N-((S)-1-(((S)-4-(benzylamino)-3,4-dione-1-((S)-2-oxopiperidine-3-yl)but-2-yl)amino)-1-oxo-3-phenylpropan-2-yl)-1-methyl-1H-pyrazole-4-carboxamide |
| A154 | 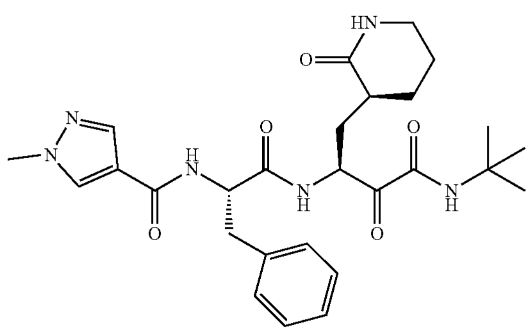 [SMILES: Cn1cc(C(=O)N[C@@H](Cc2ccccc2)C(=O)N[C@@H](C[C@@H]2CCCNC2=O)C(=O)C(=O)NC(C)(C)C)cn1] | N-((S)-1-(((S)-4-(tert-butylamino)-3,4-dione-1-((S)-2-oxopiperidine-3-yl)but-2-yl)amino)-1-oxo-3-phenylpropan-2-yl)-1-methyl-1H-pyrazole-4-carboxamide |
| A155 | 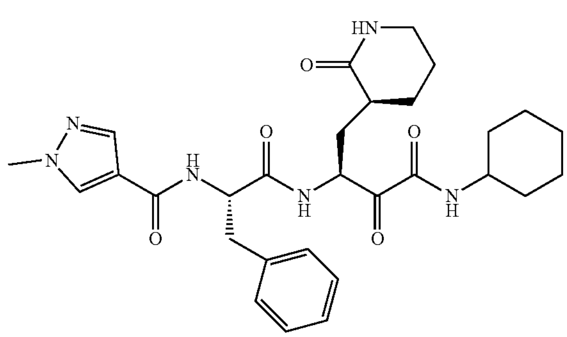 [SMILES: Cn1cc(C(=O)N[C@@H](Cc2ccccc2)C(=O)N[C@@H](C[C@@H]2CCCNC2=O)C(=O)C(=O)NC2CCCCC2)cn1] | N-((S)-1-(((S)-4-(cyclohexylamino)-3,4-dione-1-((S)-2-oxopiperidine-3-yl)but-2-yl)amino)-1-oxo-3-phenylpropan-2-yl)-1-methyl-1H-pyrazole-4-carboxamide |
| A156 | 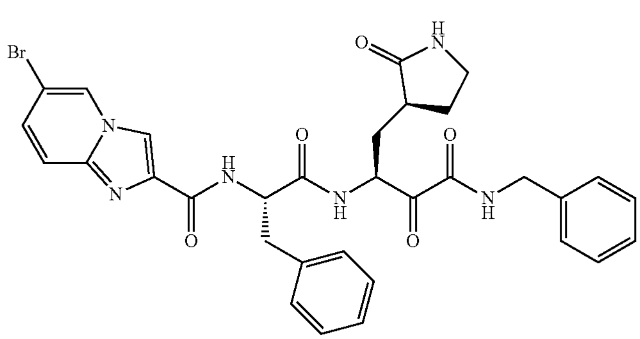 [SMILES: O=C(NCc1ccccc1)C(=O)[C@H](C[C@@H]1CCNC1=O)NC(=O)[C@H](Cc1ccccc1)NC(=O)c1cn2cc(Br)ccc2n1] | N-((S)-1-(((S)-4-(benzylamino)-3,4-dione-1-((S)-2-oxopyrrolidine-3-yl)but-2-yl)amino)-1-oxo-3-phenylpropan-2-yl)-6-bromo-imidazo[1,2-a]pyridine-2-carboxamide |

TABLE 1-continued

| number | structure | name |
|---|---|---|
| A157 | 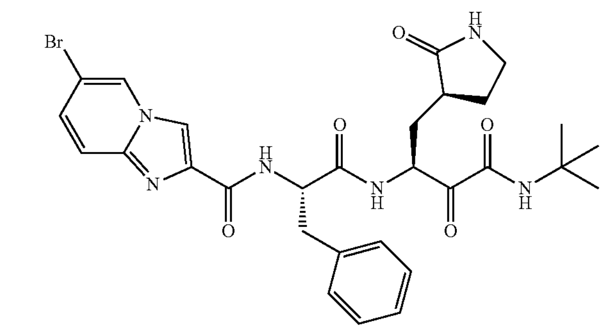 [SMILES: CC(C)(C)NC(=O)C(=O)[C@H](C[C@@H]1CCNC1=O)NC(=O)[C@H](Cc1ccccc1)NC(=O)c1cn2cc(Br)ccc2n1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-6-bromo-imidazo[1,2-a]pyridine-2-carboxamide |
| A158 | 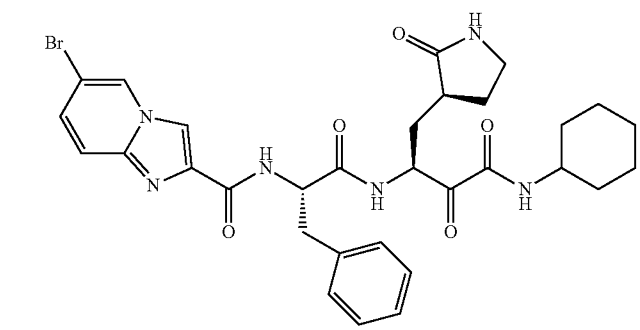 [SMILES: O=C(NC1CCCCC1)C(=O)[C@H](C[C@@H]1CCNC1=O)NC(=O)[C@H](Cc1ccccc1)NC(=O)c1cn2cc(Br)ccc2n1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-6-bromo-imidazo[1,2-a]pyridine-2-carboxamide |
| A159 | 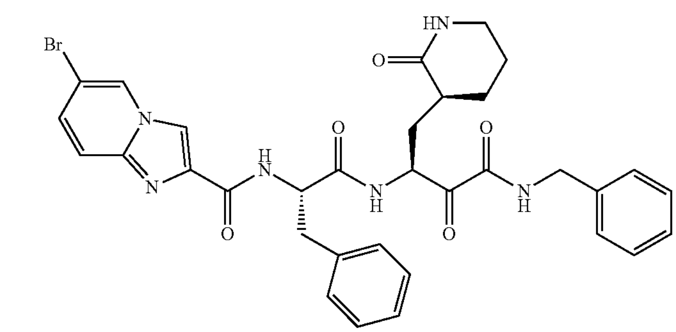 [SMILES: O=C(NCc1ccccc1)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(benzylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide |
| A160 | 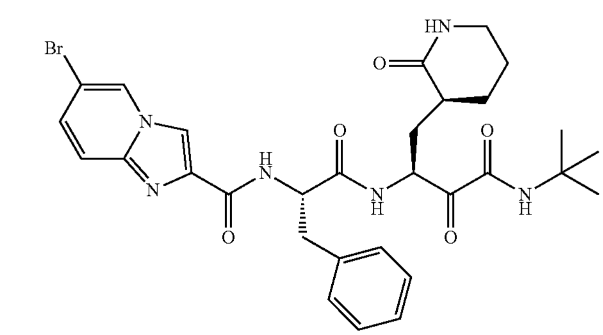 [SMILES: CC(C)(C)NC(=O)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(tert-butylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide |

TABLE 1-continued

| number | structure | name |
| --- | --- | --- |
| A161 | 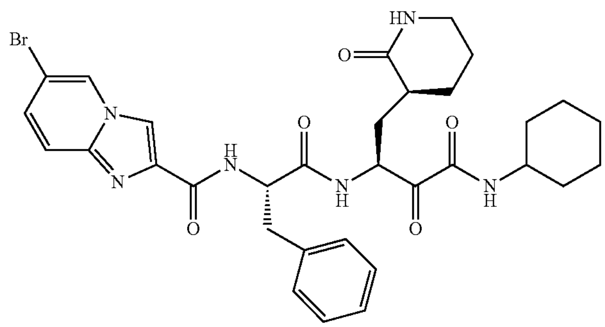 [SMILES: O=C(NC1CCCCC1)C(=O)[C@H](C[C@@H]1CCCNC1=O)NC(=O)[C@H](Cc1ccccc1)NC(=O)c1cn2cc(Br)ccc2n1] | N-((S)-1-(((S)-4-(cyclohexylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide |
| A162 | 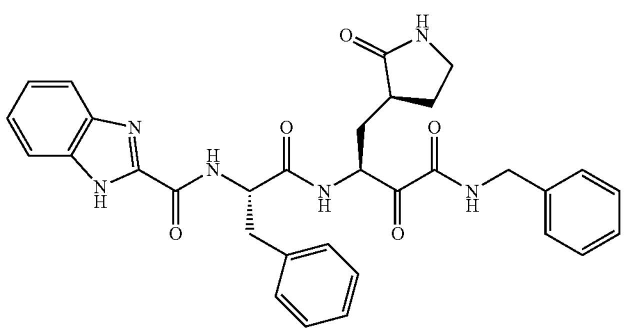 [SMILES: O=C(NCc1ccccc1)C(=O)[C@H](C[C@@H]1CCNC1=O)NC(=O)[C@H](Cc1ccccc1)NC(=O)c1nc2ccccc2[nH]1] | N-((S)-1-(((S)-4-(phenylamino)-3,4-dione-1-((S)-2-oxopyrrolidine-3-yl)but-2-yl)amino)-1-oxo-3-phenylpropan-2-yl)-1H-benzo[d]imidazole-2-carboxamide |
| A163 | 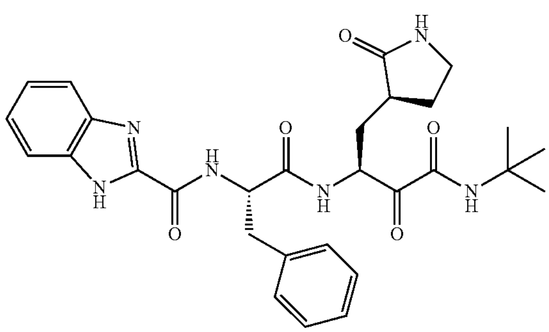 [SMILES: CC(C)(C)NC(=O)C(=O)[C@H](C[C@@H]1CCNC1=O)NC(=O)[C@H](Cc1ccccc1)NC(=O)c1nc2ccccc2[nH]1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-1H-benzo[d]imidazole-2-carboxamide |
| A164 | 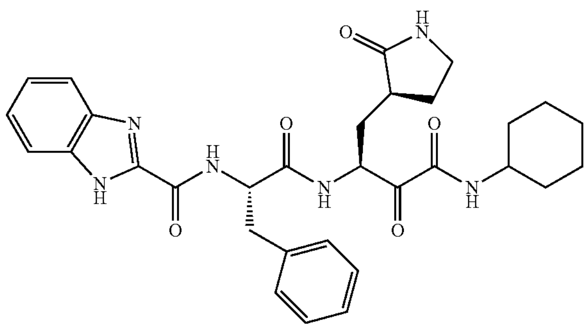 [SMILES: O=C(NC1CCCCC1)C(=O)[C@H](C[C@@H]1CCNC1=O)NC(=O)[C@H](Cc1ccccc1)NC(=O)c1nc2ccccc2[nH]1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-1H-benzo[d]imidazole-2-carboxamide |

TABLE 1-continued

| number | structure | name |
|---|---|---|
| A165 | 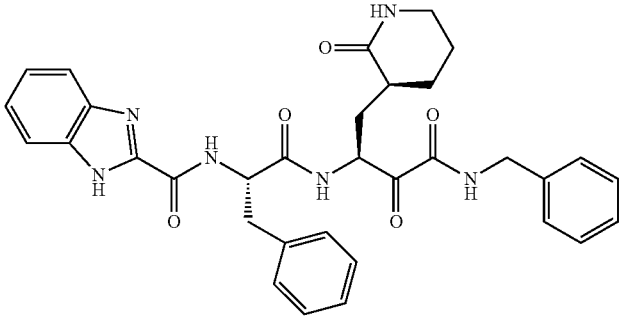 [SMILES: O=C(NCc1ccccc1)C(=O)[C@H](C[C@@H]1CCCNC1=O)NC(=O)[C@H](Cc1ccccc1)NC(=O)c1nc2ccccc2[nH]1] | N-((S)-1-(((S)-4-(phenylamino)-3,4-dione-1-((S)-2-oxopiperidine-3-yl)but-2-yl)amino)-1-oxo-3-phenylpropan-2-yl)-1H-benzo[d]imidazole-2-carboxamide |
| A166 | 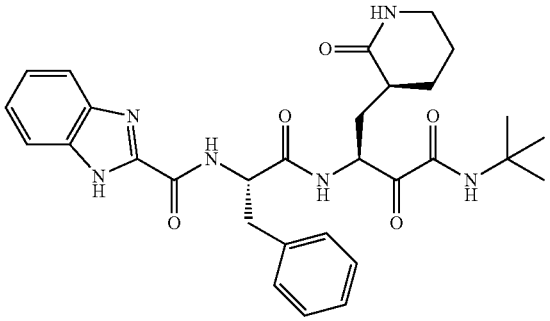 [SMILES: CC(C)(C)NC(=O)C(=O)[C@H](C[C@@H]1CCCNC1=O)NC(=O)[C@H](Cc1ccccc1)NC(=O)c1nc2ccccc2[nH]1] | N-((S)-1-(((S)-4-(tert-butylamino)-3,4-dione-1-((S)-2-oxopiperidine-3-yl)but-2-yl)amino)-1-oxo-3-phenylpropan-2-yl)-1H-benzo[d]imidazole-2-carboxamide |
| A167 | 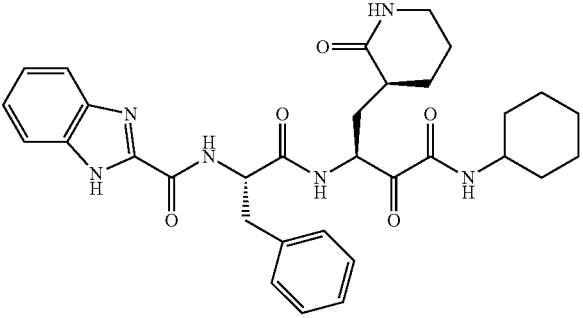 | N-((S)-1-(((S)-4-(cyclohexylamino)-3,4-dione-1-((S)-2-oxopiperidine-3-yl)but-2-yl)amino)-1-oxo-3-phenylpropan-2-yl)-1H-benzo[d]imidazole-2-carboxamide |
| A168 | 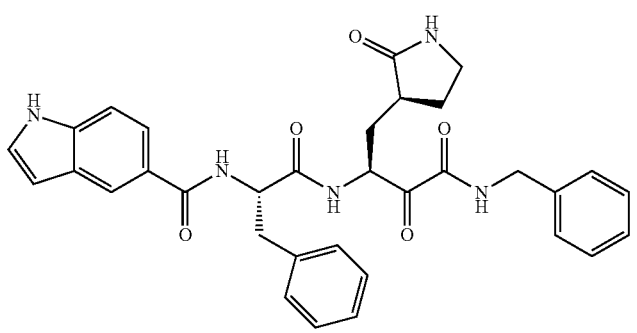 [SMILES: O=C(NCc1ccccc1)C(=O)[C@H](C[C@@H]1CCNC1=O)NC(=O)[C@H](Cc1ccccc1)NC(=O)c1ccc2[nH]ccc2c1] | N-((S)-1-(((S)-4-(benzylamino)-3,4-dione-1-((S)-2-oxopyrrolidine-3-yl)but-2-yl)amino)-1-oxo-3-phenylpropan-2-yl)-1H-indole-5-carboxamide |

TABLE 1-continued

| number | structure | name |
|---|---|---|
| A169 | 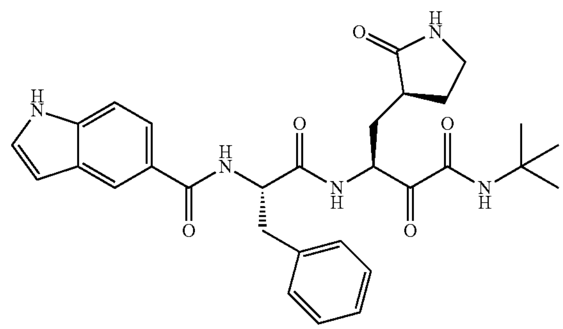 [SMILES: CC(C)(C)NC(=O)C(=O)[C@H](C[C@@H]1CCNC1=O)NC(=O)[C@H](Cc1ccccc1)NC(=O)c1ccc2[nH]ccc2c1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-1H-indole-5-carboxamide |
| A170 | 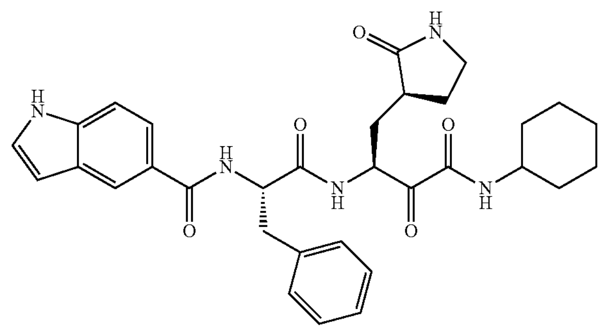 [SMILES: O=C(NC1CCCCC1)C(=O)[C@H](C[C@@H]1CCNC1=O)NC(=O)[C@H](Cc1ccccc1)NC(=O)c1ccc2[nH]ccc2c1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-1H-indole-5-carboxamide |
| A171 | 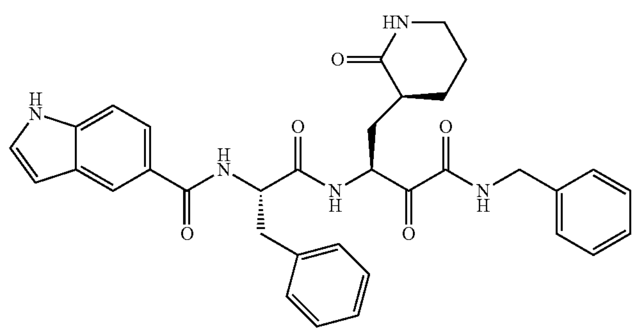 [SMILES: O=C(NCc1ccccc1)C(=O)[C@H](C[C@@H]1CCCNC1=O)NC(=O)[C@H](Cc1ccccc1)NC(=O)c1ccc2[nH]ccc2c1] | N-((S)-1-(((S)-4-(benzylamino)-3,4-dione-1-((S)-2-oxopiperidine-3-yl)but-2-yl)amino)-1-oxo-3-phenylpropan-2-yl)-1H-indole-5-carboxamide |
| A172 | 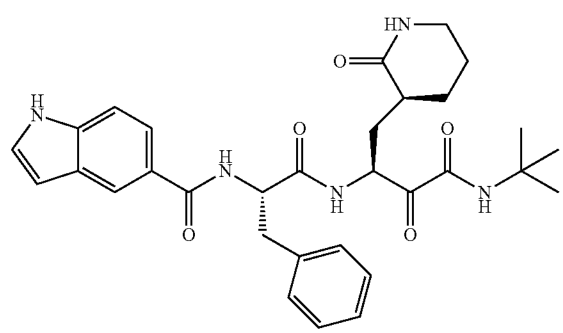 [SMILES: CC(C)(C)NC(=O)C(=O)[C@H](C[C@@H]1CCCNC1=O)NC(=O)[C@H](Cc1ccccc1)NC(=O)c1ccc2[nH]ccc2c1] | N-((S)-1-(((S)-4-(tert-butylamino)-3,4-dione-1-((S)-2-oxopiperidine-3-yl)but-2-yl)amino)-1-oxo-3-phenylpropan-2-yl)-1H-indole-5-carboxamide |

TABLE 1-continued

| number | structure | name |
|---|---|---|
| A173 | 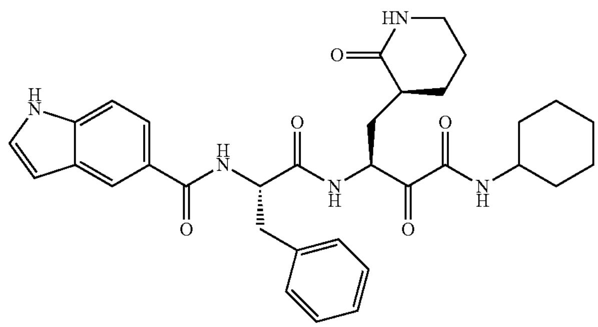 [SMILES: O=C(NC1CCCCC1)C(=O)[C@H](C[C@@H]1CCCNC1=O)NC(=O)[C@H](Cc1ccccc1)NC(=O)c1ccc2[nH]ccc2c1] | N-((S)-1-(((S)-4-(cyclohexylamino)-3,4-dione-1-((S)-2-oxopiperidine-3-yl)but-2-yl)amino)-1-oxo-3-phenylpropan-2-yl)-1H-indole-5-carboxamide |
| A174 | 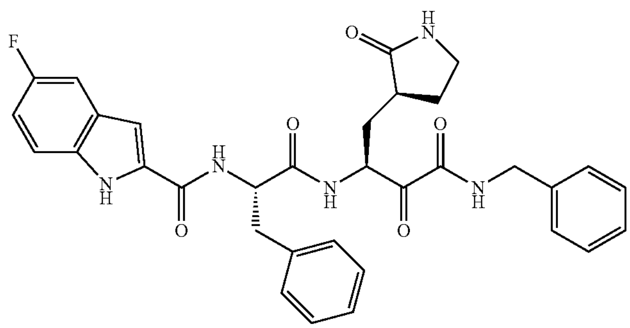 [SMILES: O=C(NCc1ccccc1)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(benzylamino)-3,4-dione-1-((S)-2-oxopyrrolidine-3-yl)but-2-yl)amino)-1-oxo-3-phenylpropan-2-yl)-5-fluoro-1H-indole-2-carboxamide |
| A175 | 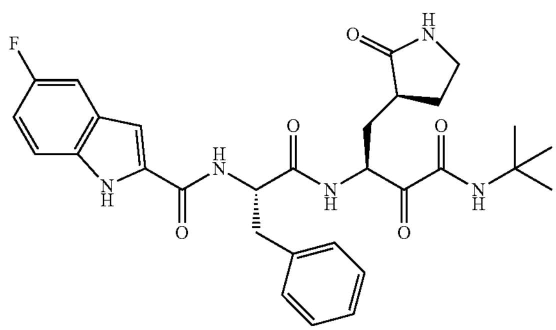 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-5-fluoro-1H-indole-2-carboxamide |
| A176 | 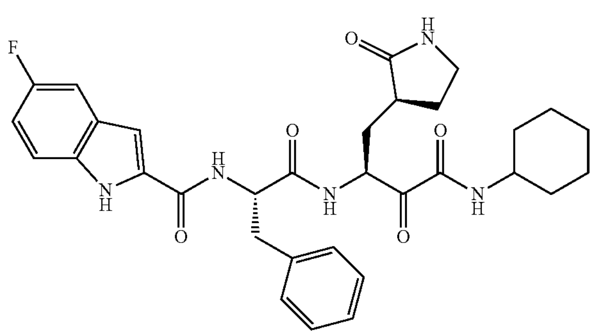 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-5-fluoro-1H-indole-2-carboxamide |

TABLE 1-continued

| number | structure | name |
|---|---|---|
| A177 | 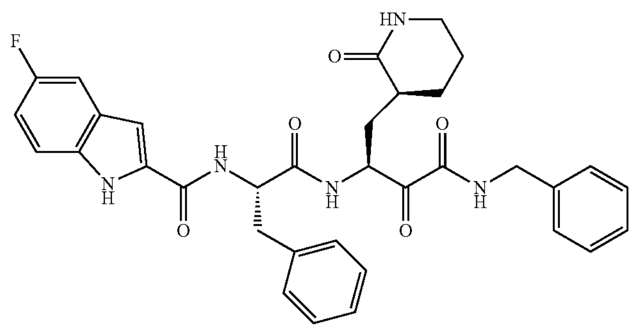 [SMILES: O=C(NCc1ccccc1)C(=O)[C@H](C[C@@H]1CCCNC1=O)NC(=O)[C@H](Cc1ccccc1)NC(=O)c1cc2cc(F)ccc2[nH]1] | N-((S)-1-(((S)-4-(benzylamino)-3,4-dione-1-((S)-2-oxopiperidine-3-yl)but-2-yl)amino)-1-oxo-3-phenylpropan-2-yl)-5-fluoro-1H-indole-2-carboxamide |
| A178 | 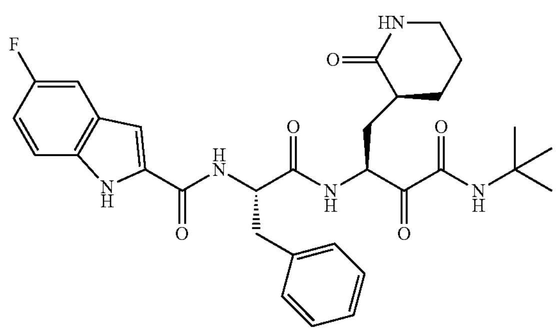 [SMILES: CC(C)(C)NC(=O)C(=O)[C@H](C[C@@H]1CCCNC1=O)NC(=O)[C@H](Cc1ccccc1)NC(=O)c1cc2cc(F)ccc2[nH]1] | N-((S)-1-(((S)-4-(tert-butylamino)-3,4-dione-1-((S)-2-oxopiperidine-3-yl)but-2-yl)amino)-1-oxo-3-phenylpropan-2-yl)-5-fluoro-1H-indole-2-carboxamide |
| A179 | 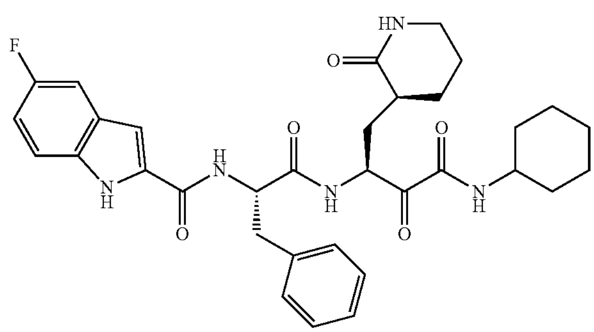 [SMILES: O=C(NC1CCCCC1)C(=O)[C@H](C[C@@H]1CCCNC1=O)NC(=O)[C@H](Cc1ccccc1)NC(=O)c1cc2cc(F)ccc2[nH]1] | N-((S)-1-(((S)-4-(cyclohexylamino)-3,4-dione-1-((S)-2-oxopiperidine-3-yl)but-2-yl)amino)-1-oxo-3-phenylpropan-2-yl)-5-fluoro-1H-indole-2-carboxamide |
| A180 | 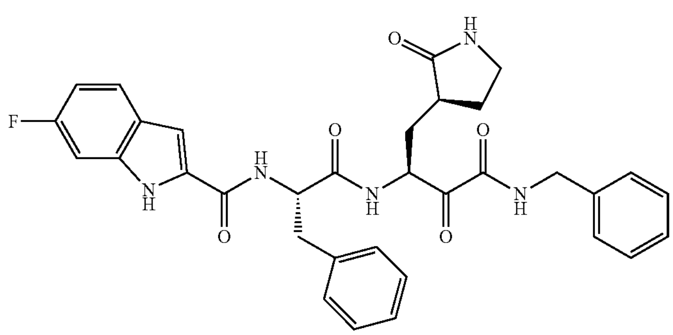 [SMILES: O=C(NCc1ccccc1)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(benzylamino)-3,4-dione-1-((S)-2-oxopyrrolidine-3-yl)but-2-yl)amino)-1-oxo-3-phenylpropan-2-yl)-6-fluoro-1H-indole-2-carboxamide |

TABLE 1-continued

| number | structure | name |
|---|---|---|
| A181 | 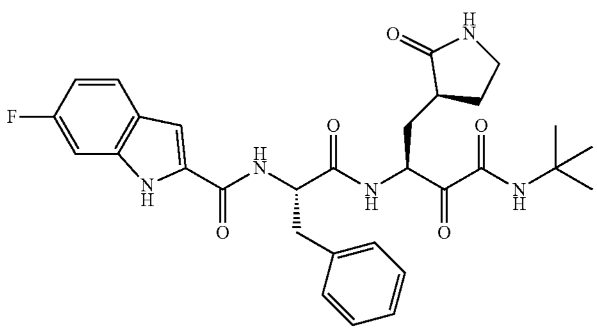 [SMILES: CC(C)(C)NC(=O)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-6-fluoro-1H-indole-2-carboxamide |
| A182 | 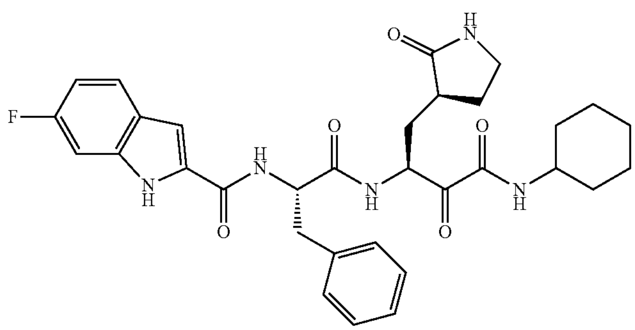 [SMILES: O=C(NC1CCCCC1)C(=O)[C@H](C[C@@H]1CCNC1=O)NC(=O)[C@H](Cc1ccccc1)NC(=O)c1cc2ccc(F)cc2[nH]1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-6-fluoro-1H-indole-2-carboxamide |
| A183 | 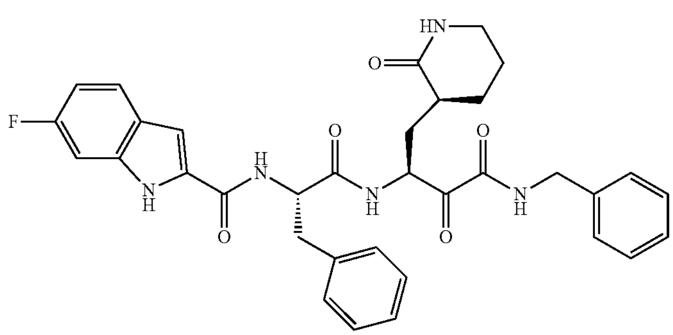 [SMILES: O=C(NCc1ccccc1)C(=O)[C@H](C[C@@H]1CCCNC1=O)NC(=O)[C@H](Cc1ccccc1)NC(=O)c1cc2ccc(F)cc2[nH]1] | N-((S)-1-(((S)-4-(benzylamino)-3,4-dione-1-((S)-2-oxopiperidine-3-yl)but-2-yl)amino)-1-oxo-3-phenylpropan-2-yl)-6-fluoro-1H-indole-2-carboxamide |
| A184 | 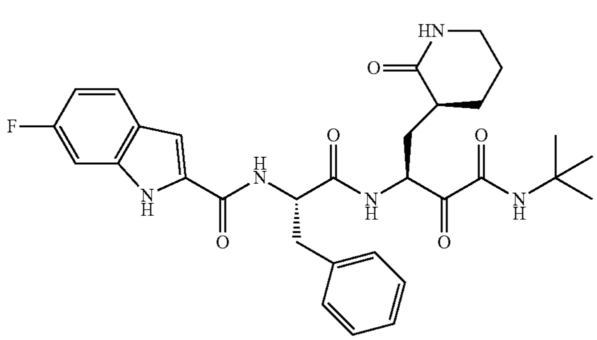 [SMILES: CC(C)(C)NC(=O)C(=O)[C@H](C[C@@H]1CCCNC1=O)NC(=O)[C@H](Cc1ccccc1)NC(=O)c1cc2ccc(F)cc2[nH]1] | N-((S)-1-(((S)-4-(tert-butylamino)-3,4-dione-1-((S)-2-oxopiperidine-3-yl)but-2-yl)amino)-1-oxo-3-phenylpropan-2-yl)-6-fluoro-1H-indole-2-carboxamide |

TABLE 1-continued

| number | structure | name |
| --- | --- | --- |
| A185 | 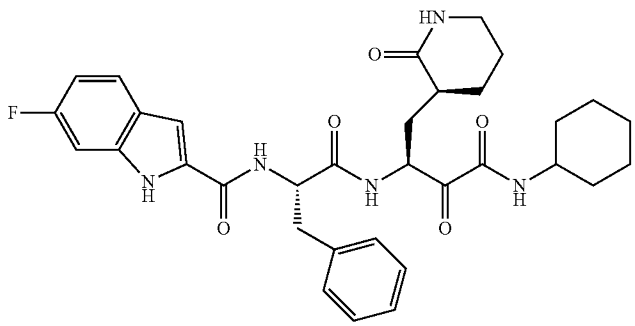 [SMILES: O=C(NC1CCCCC1)C(=O)[C@H](C[C@@H]1CCCNC1=O)NC(=O)[C@H](Cc1ccccc1)NC(=O)c1cc2ccc(F)cc2[nH]1] | N-((S)-1-(((S)-4-(cyclohexylamino)-3,4-dione-1-((S)-2-oxopiperidine-3-yl)but-2-yl)amino)-1-oxo-3-phenylpropan-2-yl)-6-fluoro-1H-indole-2-carboxamide |
| A186 | 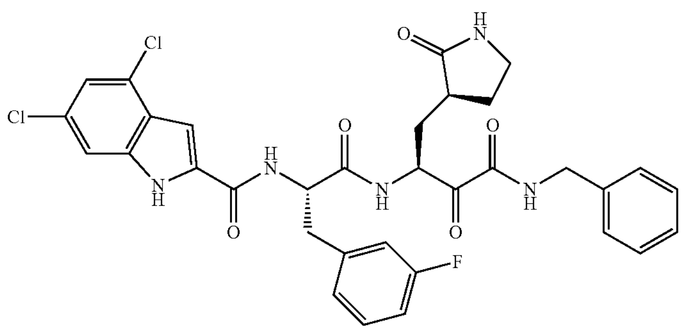 [SMILES: O=C(NCc1ccccc1)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(benzylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide |
| A187 | 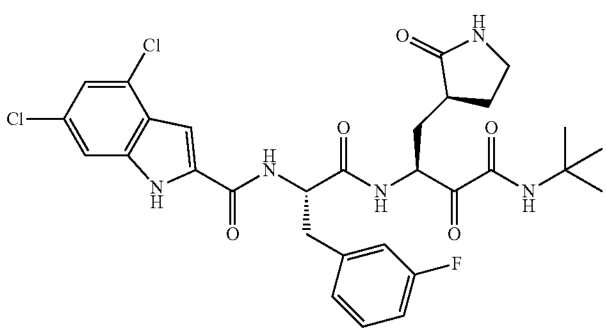 [SMILES: CC(C)(C)NC(=O)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(tert-butylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide |
| A188 | 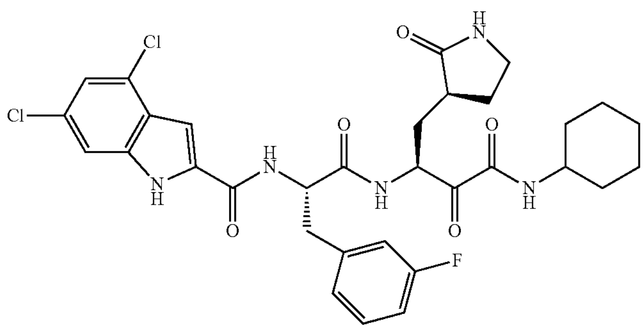 [SMILES: O=C(NC1CCCCC1)C(=O)[C@H](C[C@@H]1CCNC1=O)NC(=O)[C@H](Cc1cccc(F)c1)NC(=O)c1cc2c(Cl)cc(Cl)cc2[nH]1] | N-((S)-1-(((S)-4-(cyclohexylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide |

TABLE 1-continued

| number | structure | name |
|---|---|---|
| A189 | 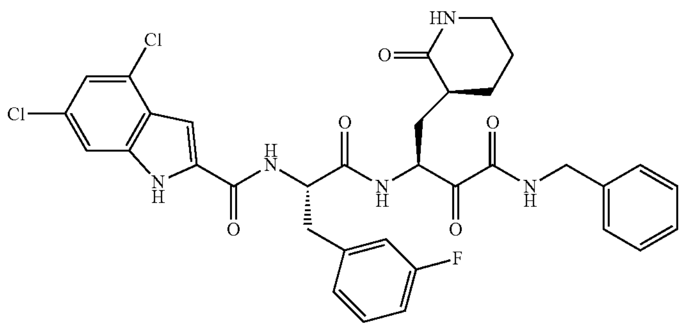 [SMILES: O=C(NCc1ccccc1)C(=O)[C@H](C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(benzylamino)-3,4-dione-1-((S)-2-oxopiperidine-3-yl)but-2-yl)amino)-3-(3-fluorophenyl)-1-oxopropan-2-yl)-4,6-dichloro-1H-indole-2-carboxamide |
| A190 | 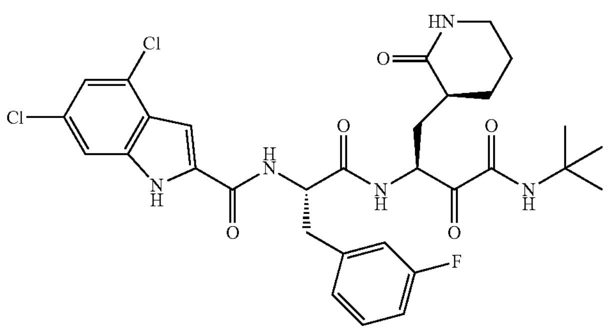 [SMILES: CC(C)(C)NC(=O)C(=O)[C@H](C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(tert-butylamino)-3,4-dione-1-((S)-2-oxopiperidine-3-yl)but-2-yl)amino)-3-(3-fluorophenyl)-1-oxopropan-2-yl)-4,6-dichloro-1H-indole-2-carboxamide |
| A191 | 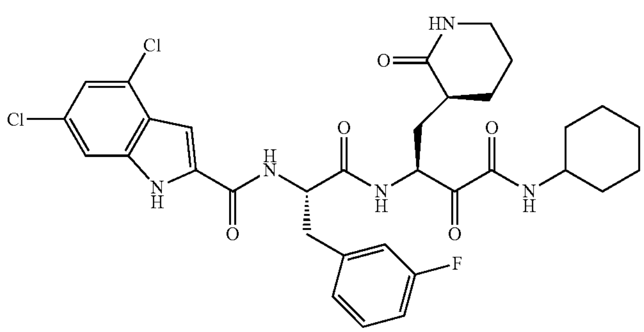 [SMILES: O=C(NC1CCCCC1)C(=O)[C@H](C[C@@H]1CCCNC1=O)NC(=O)[C@H](Cc1cccc(F)c1)NC(=O)c1cc2c(Cl)cc(Cl)cc2[nH]1] | N-((S)-1-(((S)-4-(cyclohexylamino)-3,4-dione-1-((S)-2-oxopiperidine-3-yl)but-2-yl)amino)-3-(3-fluorophenyl)-1-oxopropan-2-yl)-4,6-dichloro-1H-indole-2-carboxamide |
| A192 | 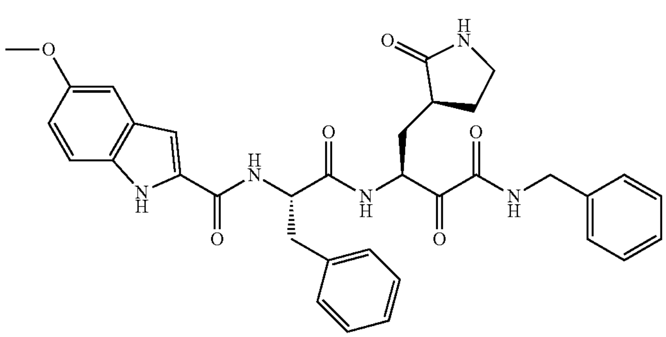 [SMILES: COc1ccc2[nH]c(C(=O)N[C@@H](Cc3ccccc3)C(=O)N[C@@H](C[C@@H]3CCNC3=O)C(=O)C(=O)NCc3ccccc3)cc2c1] | N-((S)-1-(((S)-4-(benzylamino)-3,4-dione-1-((S)-2-oxopyrrolidine-3-yl)but-2-yl)amino)-1-oxo-3-phenylpropan-2-yl)-5-methoxy-1H-indole-2-carboxamide |

TABLE 1-continued

| number | structure | name |
|---|---|---|
| A193 | 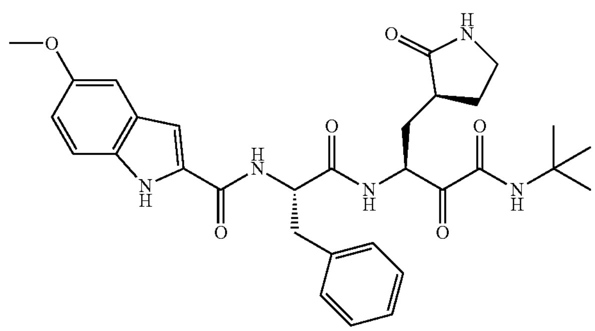 [SMILES: COc1ccc2[nH]c(C(=O)N[C@@H](Cc3ccccc3)C(=O)N[C@@H](C[C@@H]3CCNC3=O)C(=O)C(=O)NC(C)(C)C)cc2c1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-5-methoxy-1H-indole-2-carboxamide |
| A194 | 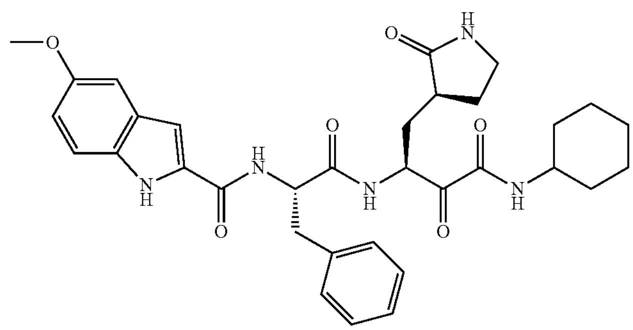 [SMILES: COc1ccc2[nH]c(C(=O)N[C@@H](Cc3ccccc3)C(=O)N[C@@H](C[C@@H]3CCNC3=O)C(=O)C(=O)NC3CCCCC3)cc2c1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-5-methoxy-1H-indole-2-carboxamide |
| A195 | 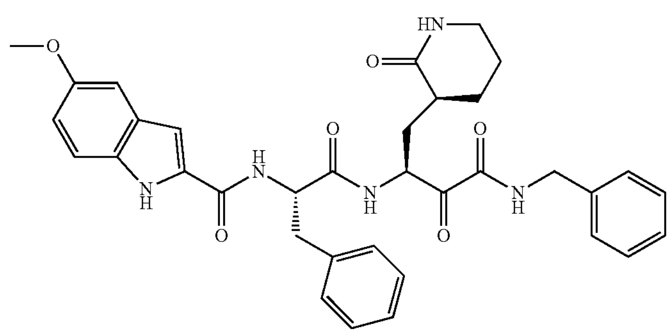 [SMILES: COc1ccc2[nH]c(C(=O)N[C@@H](Cc3ccccc3)C(=O)N[C@@H](C[C@@H]3CCCNC3=O)C(=O)C(=O)NCc3ccccc3)cc2c1] | N-((S)-1-(((S)-4-(benzylamino)-3,4-dione-1-((S)-2-oxopiperidine-3-yl)but-2-yl)amino)-1-oxo-3-phenylpropan-2-yl)-5-methoxy-1H-indole-2-carboxamide |
| A196 | 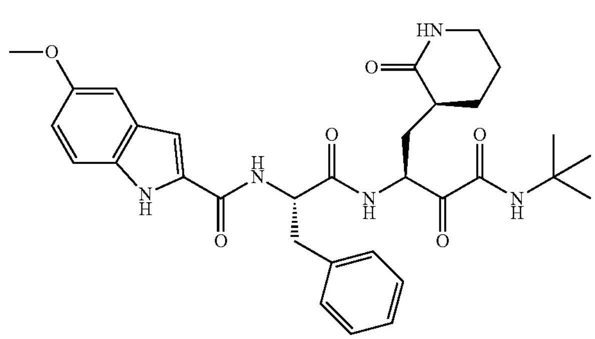 [SMILES: COc1ccc2[nH]c(C(=O)N[C@@H](Cc3ccccc3)C(=O)N[C@@H](C[C@@H]3CCCNC3=O)C(=O)C(=O)NC(C)(C)C)cc2c1] | N-((S)-1-(((S)-4-(tert-butylamino)-3,4-dione-1-((S)-2-oxopiperidine-3-yl)but-2-yl)amino)-1-oxo-3-phenylpropan-2-yl)-5-methoxy-1H-indole-2-carboxamide |

TABLE 1-continued

| number | structure | name |
|---|---|---|
| A197 | 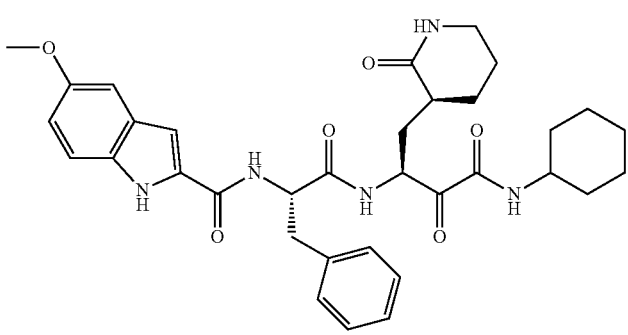 [SMILES: COc1ccc2[nH]c(C(=O)N[C@@H](Cc3ccccc3)C(=O)N[C@@H](C[C@@H]3CCCNC3=O)C(=O)C(=O)NC3CCCCC3)cc2c1] | N-((S)-1-(((S)-4-(cyclohexylamino)-3,4-dione-1-((S)-2-oxopiperidine-3-yl)but-2-yl)amino)-1-oxo-3-phenylpropan-2-yl)-5-methoxy-1H-indole-2-carboxamide |
| A198 | 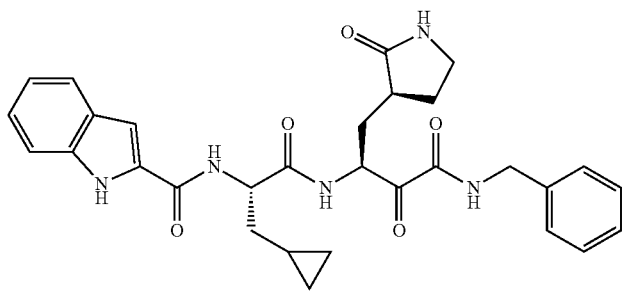 [SMILES: O=C(NCc1ccccc1)C(=O)[C@H](C[C@@H]1CCNC1=O)NC(=O)[C@H](CC1CC1)NC(=O)c1cc2ccccc2[nH]1] | N-((S)-1-(((S)-4-(benzylamino)-3,4-dione-1-((S)-2-oxopyrrolidine-3-yl)but-2-yl)amino)-3-cyclopropyl-1-oxopropan-2-yl)-1H-indole-2-carboxamide |
| A199 | 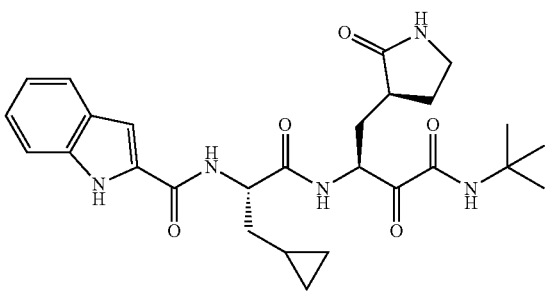 [SMILES: CC(C)(C)NC(=O)C(=O)[C@H](C[C@@H]1CCNC1=O)NC(=O)[C@H](CC1CC1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-3-cyclopropyl-1-oxopropan-2-yl)-1H-indole-2-carboxamide |
| A200 | 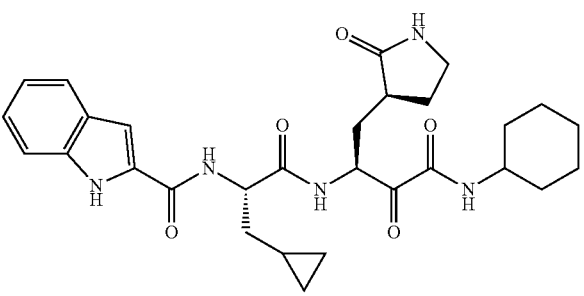 [SMILES: O=C(NC1CCCCC1)C(=O)[C@H](C[C@@H]1CCNC1=O)NC(=O)[C@H](CC1CC1)NC(=O)c1cc2ccccc2[nH]1] | N-((S)-1-(((S)-4-(cyclohexylamino)-3,4-dione-1-((S)-2-oxopyrrolidine-3-yl)but-2-yl)amino)-3-cyclopropyl-1-oxopropan-2-yl)-1H-indole-2-carboxamide |

TABLE 1-continued

| number | structure | name |
|---|---|---|
| A201 | 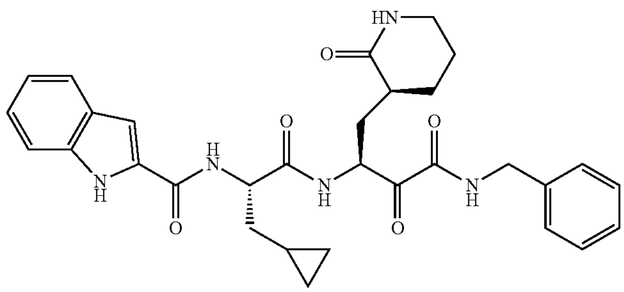 [SMILES: O=C(NCc1ccccc1)C(=O)[C@H](C[C@@H]1CCCNC1=O)NC(=O)[C@H](CC1CC1)NC(=O)c1cc2ccccc2[nH]1] | N-((S)-1-(((S)-4-(cyclohexylamino)-3,4-dione-1-((S)-2-oxopiperidine-3-yl)but-2-yl)amino)-3-cyclopropyl-1-oxopropan-2-yl)-1H-indole-2-carboxamide |
| A202 | 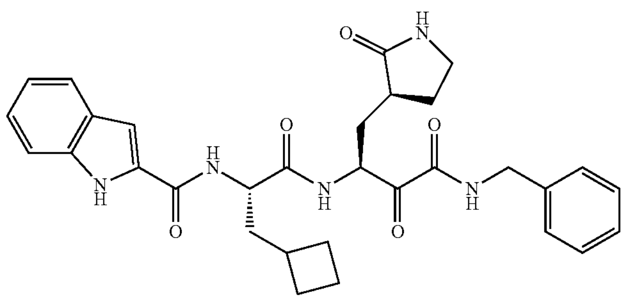 [SMILES: O=C(NCc1ccccc1)C(=O)[C@H](C[C@@H]1CCNC1=O)NC(=O)[C@H](CC1CCC1)NC(=O)c1cc2ccccc2[nH]1] | N-((S)-1-(((S)-4-(benzylamino)-3,4-dione-1-((S)-2-oxopyrrolidine-3-yl)but-2-yl)amino)-3-cyclobutyl-1-oxopropan-2-yl)-1H-indole-2-carboxamide |
| A203 | 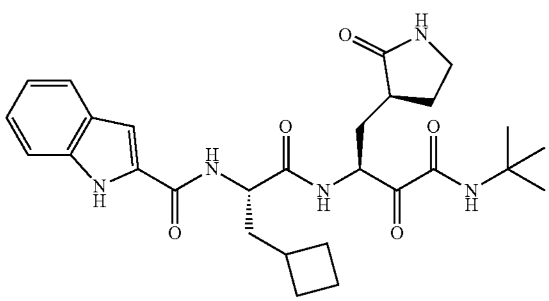 [SMILES: CC(C)(C)NC(=O)C(=O)[C@H](C[C@@H]1CCNC1=O)NC(=O)[C@H](CC1CCC1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-3-cyclobutyl-1-oxopropan-2-yl)-1H-indole-2-carboxamide |
| A204 | 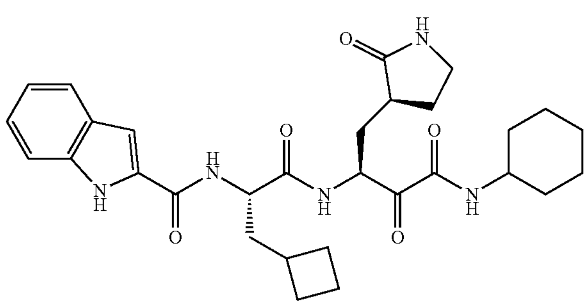 [SMILES: O=C(NC1CCCCC1)C(=O)[C@H](C[C@@H]1CCNC1=O)NC(=O)[C@H](CC1CCC1)NC(=O)c1cc2ccccc2[nH]1] | N-((S)-1-(((S)-4-(cyclohexylamino)-3,4-dione-1-((S)-2-oxopyrrolidine-3-yl)but-2-yl)amino)-3-cyclobutyl-1-oxopropan-2-yl)-1H-indole-2-carboxamide |

TABLE 1-continued

| number | structure | name |
|---|---|---|
| A205 | 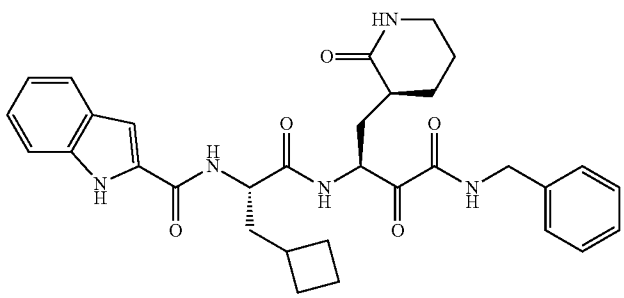 [SMILES: O=C(NCc1ccccc1)C(=O)[C@H](C[C@@H]1CCCNC1=O)NC(=O)[C@H](CC1CCC1)NC(=O)c1cc2ccccc2[nH]1] | N-((S)-1-(((S)-4-(benzylamino)-3,4-dione-1-((S)-2-oxopiperidine-3-yl)but-2-yl)amino)-3-cyclobutyl-1-oxopropan-2-yl)-1H-indole-2-carboxamide |
| A206 | 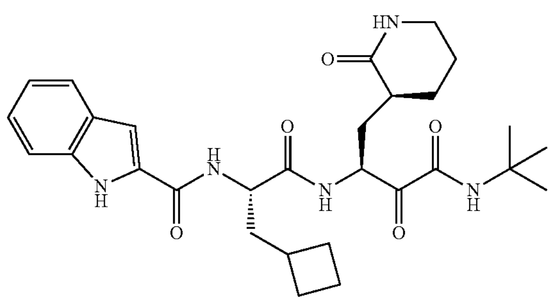 [SMILES: CC(C)(C)NC(=O)C(=O)[C@H](C[C@@H]1CCCNC1=O)NC(=O)[C@H](CC1CCC1)NC(=O)c1cc2ccccc2[nH]1] | N-((S)-1-(((S)-4-(tert-butylamino)-3,4-dione-1-((S)-2-oxopiperidine-3-yl)but-2-yl)amino)-3-cyclobutyl-1-oxopropan-2-yl)-1H-indole-2-carboxamide |
| A207 | 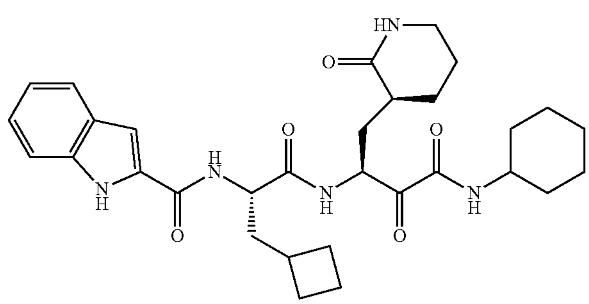 [SMILES: O=C(NC1CCCCC1)C(=O)[C@H](C[C@@H]1CCCNC1=O)NC(=O)[C@H](CC1CCC1)NC(=O)c1cc2ccccc2[nH]1] | N-((S)-1-(((S)-4-(cyclohexylamino)-3,4-dione-1-((S)-2-oxopiperidine-3-yl)but-2-yl)amino)-3-cyclobutyl-1-oxopropan-2-yl)-1H-indole-2-carboxamide |
| A208 | 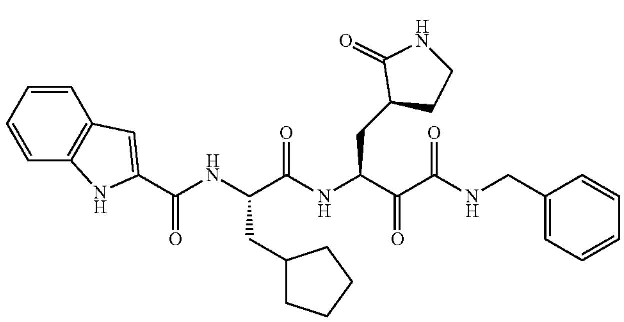 [SMILES: O=C(NCc1ccccc1)C(=O)[C@H](C[C@@H]1CCNC1=O)NC(=O)[C@H](CC1CCCC1)NC(=O)c1cc2ccccc2[nH]1] | N-((S)-1-(((S)-4-(benzylamino)-3,4-dione-1-((S)-2-oxopyrrolidine-3-yl)but-2-yl)amino)-3-cyclopentyl-1-oxopropan-2-yl)-1H-indole-2-carboxamide |

TABLE 1-continued

| number | structure | name |
|---|---|---|
| A209 | 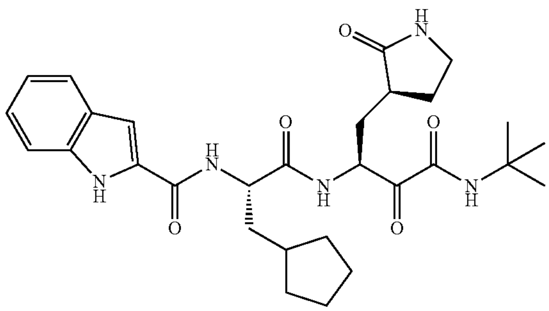 [SMILES: CC(C)(C)NC(=O)C(=O)[C@H](C[C@@H]1CCNC1=O)NC(=O)[C@H](CC1CCCC1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-3-cyclopentyl-1-oxopropan-2-yl)-1H-indole-2-carboxamide |
| A210 | 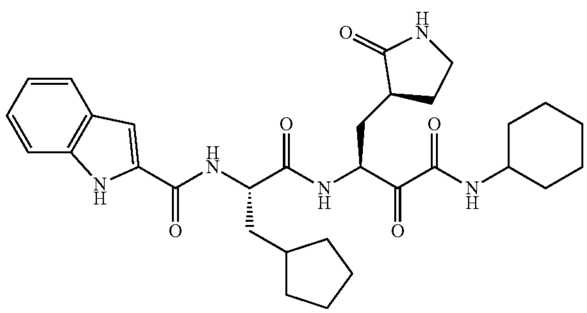 [SMILES: O=C(NC1CCCCC1)C(=O)[C@H](C[C@@H]1CCNC1=O)NC(=O)[C@H](CC1CCCC1)NC(=O)c1cc2ccccc2[nH]1] | N-((S)-1-(((S)-4-(cyclohexylamino)-3,4-dione-1-((S)-2-oxopyrrolidine-3-yl)but-2-yl)amino)-3-cyclopentyl-1-oxopropan-2-yl)-1H-indole-2-carboxamide |
| A211 | 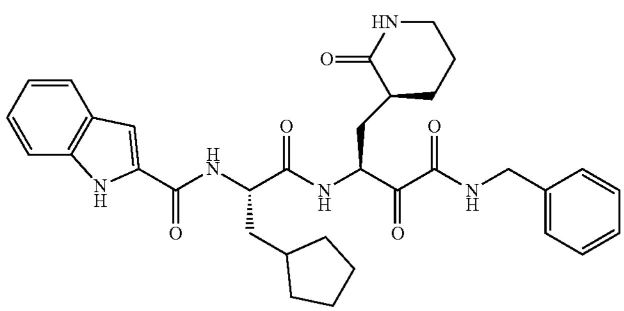 [SMILES: O=C(NCc1ccccc1)C(=O)[C@H](C[C@@H]1CCCNC1=O)NC(=O)[C@H](CC1CCCC1)NC(=O)c1cc2ccccc2[nH]1] | N-((S)-1-(((S)-4-(benzylamino)-3,4-dione-1-((S)-2-oxopiperidine-3-yl)but-2-yl)amino)-3-cyclopentyl-1-oxopropan-2-yl)-1H-indole-2-carboxamide |
| A212 | 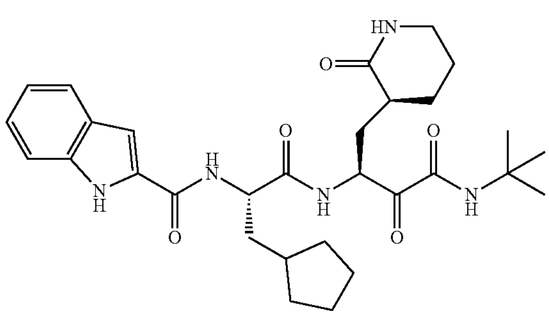 [SMILES: CC(C)(C)NC(=O)C(=O)[C@H](C[C@@H]1CCCNC1=O)NC(=O)[C@H](CC1CCCC1)NC(=O)c1cc2ccccc2[nH]1] | N-((S)-1-(((S)-4-(tert-butylamino)-3,4-dione-1-((S)-2-oxopiperidine-3-yl)but-2-yl)amino)-3-cyclopentyl-1-oxopropan-2-yl)-1H-indole-2-carboxamide |

TABLE 1-continued

| number | structure | name |
| --- | --- | --- |
| A213 | 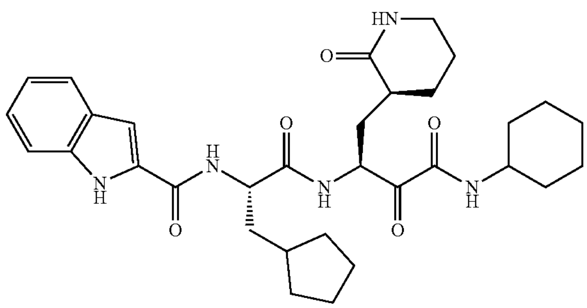 [SMILES: O=C(NC1CCCCC1)C(=O)[C@H](C[C@@H]1CCCNC1=O)NC(=O)[C@H](CC1CCCC1)NC(=O)c1cc2ccccc2[nH]1] | N-((S)-1-(((S)-4-(cyclohexylamino)-3,4-dione-1-((S)-2-oxopiperidine-3-yl)but-2-yl)amino)-3-cyclopentyl-1-oxopropan-2-yl)-1H-indole-2-carboxamide |
| A214 | 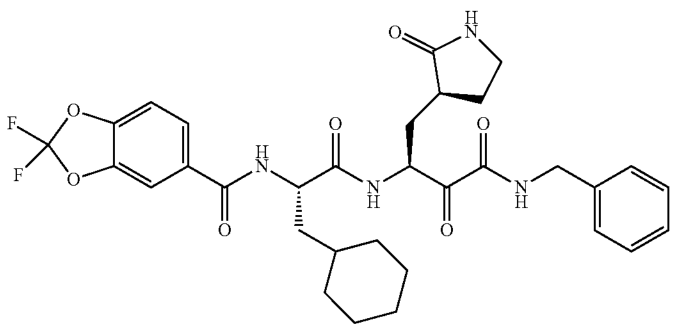 [SMILES: O=C(NCc1ccccc1)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-2,2-difluorobenzo[d][1,3]dioxol-5-carboxamide |
| A215 | 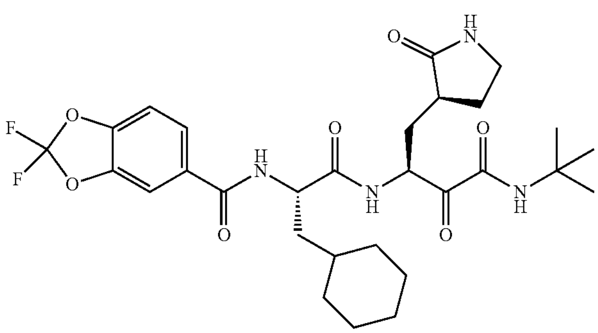 [SMILES: CC(C)(C)NC(=O)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(tert-butylamino)-3,4-dione-1-((S)-2-oxopyrrolidine-3-yl)but-2-yl)amino)-3-cyclohexyl-1-oxopropan-2-yl)-2,2-difluorobenzo[d][1,3]dioxol-5-carboxamide |
| A216 | 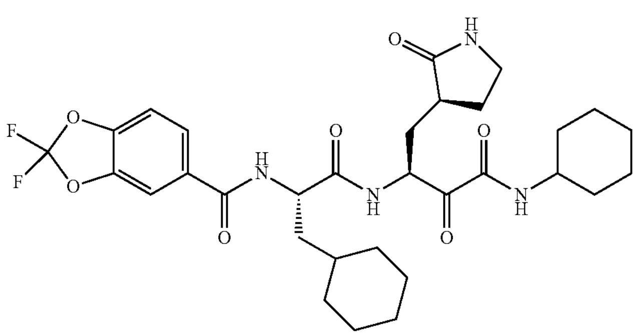 [SMILES: O=C(NC1CCCCC1)C(=O)[C@H](C[C@@H]1CCNC1=O)NC(=O)[C@H](CC1CCCCC1)NC(=O)c1ccc2c(c1)OC(F)(F)O2] | N-((S)-1-(((S)-4-(cyclohexylamino)-3,4-dione-1-((S)-2-oxopyrrolidine-3-yl)but-2-yl)amino)-3-cyclohexyl-1-oxopropan-2-yl)-2,2-difluorobenzo[d][1,3]dioxol-5-carboxamide |

TABLE 1-continued

| number | structure | name |
|---|---|---|
| A217 | 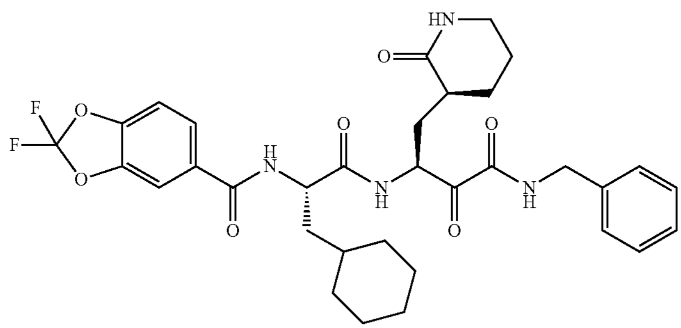 [SMILES: O=C(NCc1ccccc1)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(benzylamino)-3,4-dione-1-((S)-2-oxopiperidine-3-yl)but-2-yl)amino)-3-cyclohexyl-1-oxopropan-2-yl)-2,2-difluorobenzo[d][1,3]dioxol-5-carboxamide |
| A218 | 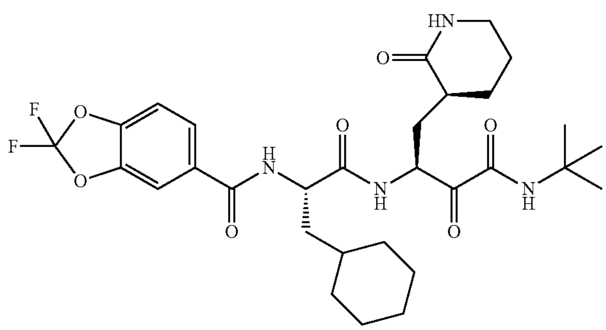 [SMILES: CC(C)(C)NC(=O)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(tert-butylamino)-3,4-dione-1-((S)-2-oxopiperidine-3-yl)but-2-yl)amino)-3-cyclohexyl-1-oxopropan-2-yl)-2,2-difluorobenzo[d][1,3]dioxol-5-carboxamide |
| A219 | 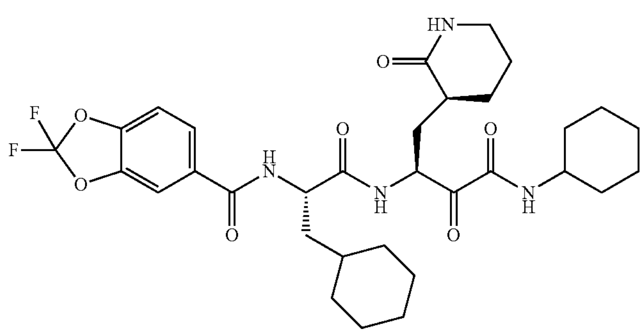 [SMILES: O=C(NC1CCCCC1)C(=O)[C@H](C[C@@H]1CCCNC1=O)NC(=O)[C@H](CC1CCCCC1)NC(=O)c1ccc2c(c1)OC(F)(F)O2] | N-((S)-1-(((S)-4-(cyclohexylamino)-3,4-dione-1-((S)-2-oxopiperidine-3-yl)but-2-yl)amino)-3-cyclohexyl-1-oxopropan-2-yl)-2,2-difluorobenzo[d][1,3]dioxol-5-carboxamide |
| A220 | 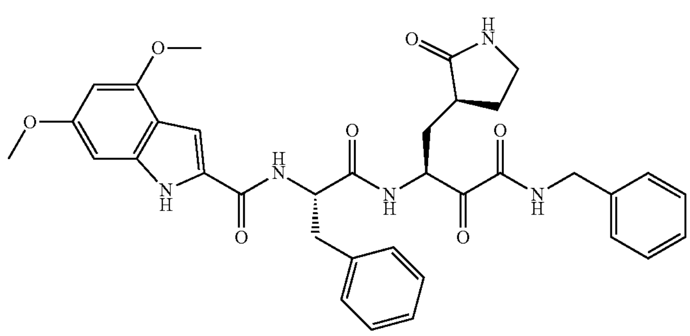 [SMILES: COc1cc(OC)c2cc(C(=O)N[C@@H](Cc3ccccc3)C(=O)N[C@@H](C[C@@H]3CCNC3=O)C(=O)C(=O)NCc3ccccc3)[nH]c2c1] | N-((S)-1-(((S)-4-(benzylamino)-3,4-dione-1-((S)-2-oxopyrrolidine-3-yl)but-2-yl)amino)-1-oxo-3-phenylpropan-2-yl)-4,6-dimethoxy-1H-indole-2-carboxamide |

TABLE 1-continued

| number | structure | name |
| --- | --- | --- |
| A221 | 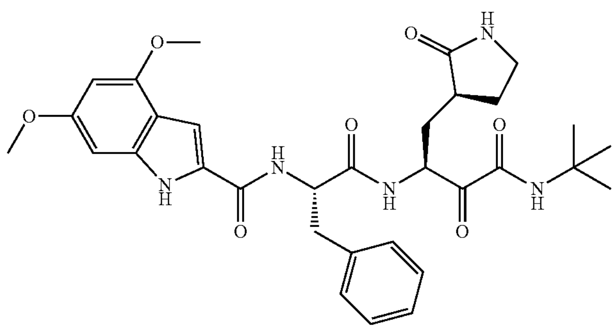 [SMILES: COc1cc(OC)c2cc(C(=O)N[C@@H](Cc3ccccc3)C(=O)N[C@@H](C[C@@H]3CCNC3=O)C(=O)C(=O)NC(C)(C)C)[nH]c2c1] | N-((S)-1-(((S)-4-(tert-butylamino)-3,4-dione-1-((S)-2-oxopyrrolidine-3-yl)but-2-yl)amino)-1-oxo-3-phenylpropan-2-yl)-4,6-dimethoxy-1H-indole-2-carboxamide |
| A222 | 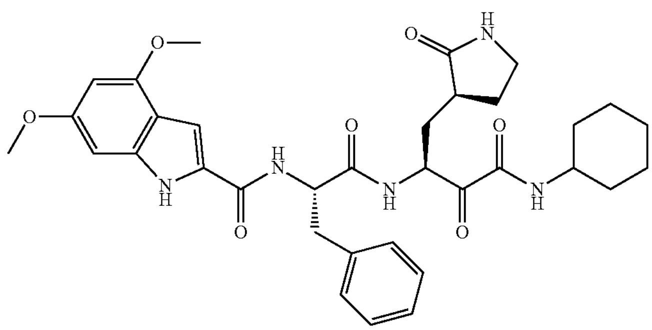 [SMILES: COc1cc(OC)c2cc(C(=O)N[C@@H](Cc3ccccc3)C(=O)N[C@@H](C[C@@H]3CCNC3=O)C(=O)C(=O)NC3CCCCC3)[nH]c2c1] | N-((S)-1-(((S)-4-(cyclohexylamino)-3,4-dione-1-((S)-2-oxopyrrolidine-3-yl)but-2-yl)amino)-1-oxo-3-phenylpropan-2-yl)-4,6-dimethoxy-1H-indole-2-carboxamide |
| A223 | 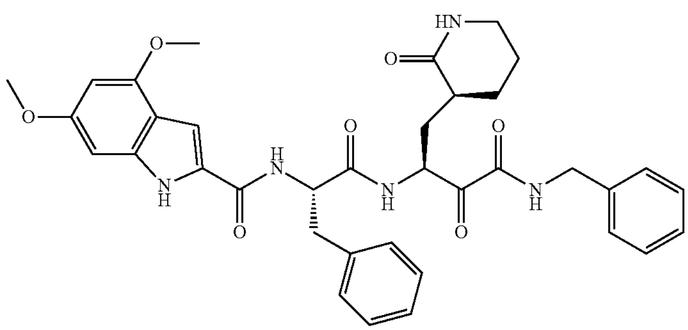 [SMILES: COc1cc(OC)c2cc(C(=O)N[C@@H](Cc3ccccc3)C(=O)N[C@@H](C[C@@H]3CCCNC3=O)C(=O)C(=O)NCc3ccccc3)[nH]c2c1] | N-((S)-1-(((S)-4-(benzylamino)-3,4-dione-1-((S)-2-oxopiperidine-3-yl)but-2-yl)amino)-1-oxo-3-phenylpropan-2-yl)-4,6-dimethoxy-1H-indole-2-carboxamide |
| A224 | 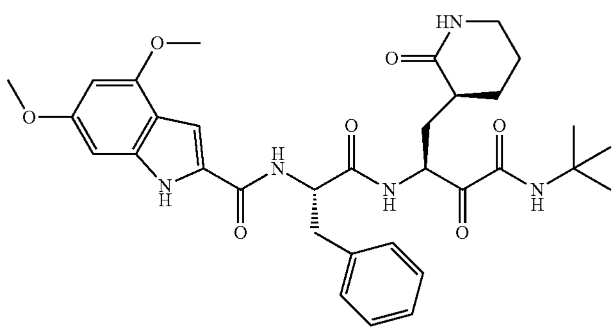 [SMILES: COc1cc(OC)c2cc(C(=O)N[C@@H](Cc3ccccc3)C(=O)N[C@@H](C[C@@H]3CCCNC3=O)C(=O)C(=O)NC(C)(C)C)[nH]c2c1] | N-((S)-1-(((S)-4-(tert-butylamino)-3,4-dione-1-((S)-2-oxopiperidine-3-yl)but-2-yl)amino)-1-oxo-3-phenylpropan-2-yl)-4,6-dimethoxy-1H-indole-2-carboxamide |

TABLE 1-continued

| number | structure | name |
|---|---|---|
| A225 | 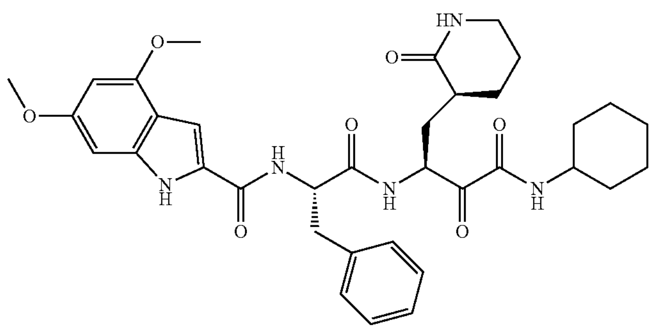 [SMILES: COc1cc(OC)c2cc(C(=O)N[C@@H](Cc3ccccc3)C(=O)N[C@@H](C[C@@H]3CCCNC3=O)C(=O)C(=O)NC3CCCCC3)[nH]c2c1] | N-((S)-1-(((S)-4-(cyclohexylamino)-3,4-dione-1-((S)-2-oxopiperidine-3-yl)but-2-yl)amino)-1-oxo-3-phenylpropan-2-yl)-4,6-dimethoxy-1H-indole-2-carboxamide |
| A226 | 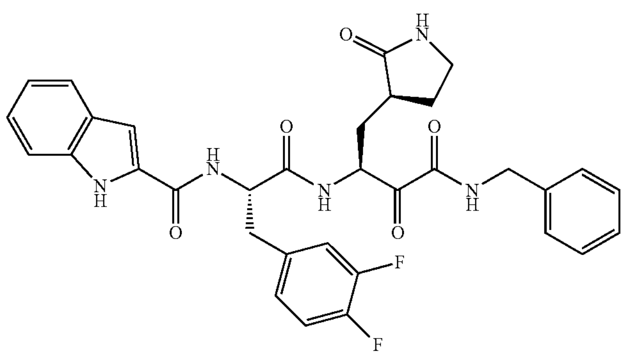 [SMILES: O=C(NCc1ccccc1)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(benzylamino)-3,4-dione-1-((S)-2-oxopyrrolidine-3-yl)but-2-yl)amino)-3-(3,4-difluorophenyl)-1-oxopropan-2-yl)-1H-indole-2-carboxamide |
| A227 | 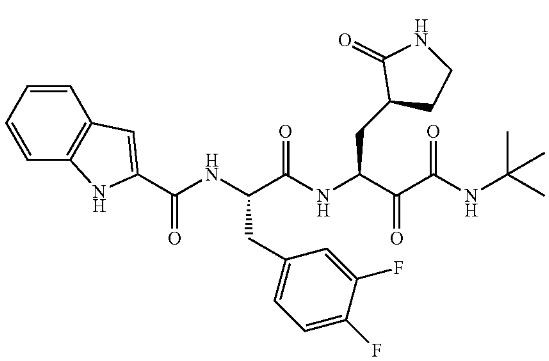 [SMILES: CC(C)(C)NC(=O)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(tert-butylamino)-3,4-dione-1-((S)-2-oxopyrrolidine-3-yl)but-2-yl)amino)-3-(3,4-difluorophenyl)-1-oxopropan-2-yl)-1H-indole-2-carboxamide |

TABLE 1-continued

| number | structure | name |
|---|---|---|
| A228 | 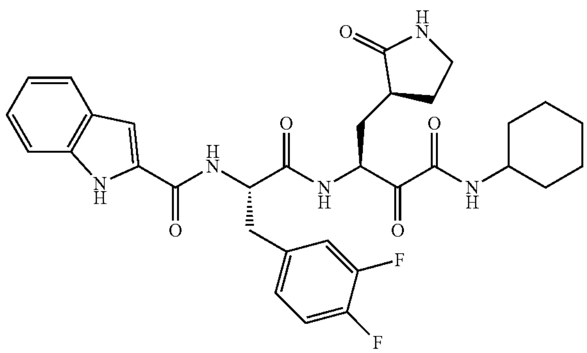 [SMILES: O=C(NC1CCCCC1)C(=O)[C@H](C[C@@H]1CCNC1=O)NC(=O)[C@H](Cc1ccc(F)c(F)c1)NC(=O)c1cc2ccccc2[nH]1] | N-((S)-1-(((S)-4-(cyclohexylamino)-3,4-dione-1-((S)-2-oxopyrrolidine-3-yl)but-2-yl)amino)-3-(3,4-difluorophenyl)-1-oxopropan-2-yl)-1H-indole-2-carboxamide |
| A229 | 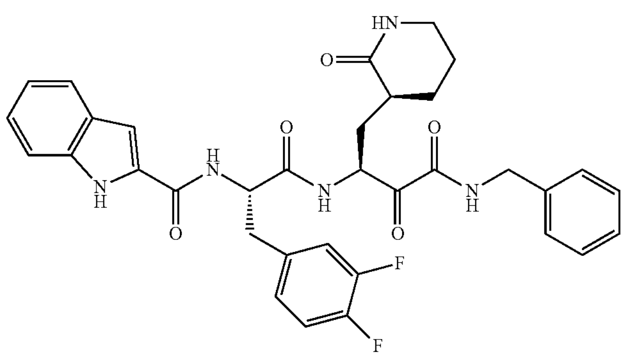 [SMILES: O=C(NCc1ccccc1)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(benzylamino)-3,4-dione-1-((S)-2-oxopiperidine-3-yl)but-2-yl)amino)-3-(3,4-difluorophenyl)-1-oxopropan-2-yl)-1H-indole-2-carboxamide |
| A230 | 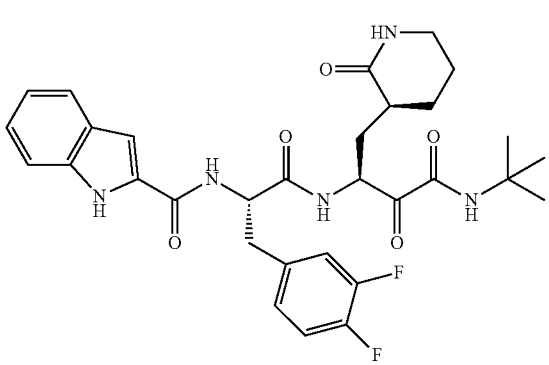 [SMILES: CC(C)(C)NC(=O)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(tert-butylamino)-3,4-dione-1-((S)-2-oxopiperidine-3-yl)but-2-yl)amino)-3-(3,4-difluorophenyl)-1-oxopropan-2-yl)-1H-indole-2-carboxamide |

TABLE 1-continued

| number | structure | name |
| --- | --- | --- |
| A231 | 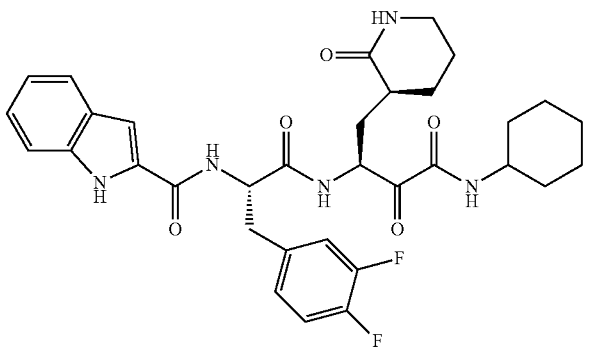 [SMILES: O=C(NC1CCCCC1)C(=O)[C@H](C[C@@H]1CCCNC1=O)NC(=O)[C@H](Cc1ccc(F)c(F)c1)NC(=O)c1cc2ccccc2[nH]1] | N-((S)-1-(((S)-4-(cyclohexylamino)-3,4-dione-1-((S)-2-oxopiperidine-3-yl)but-2-yl)amino)-3-(3,4-difluorophenyl)-1-oxopropan-2-yl)-1H-indole-2-carboxamide |
| A232 | 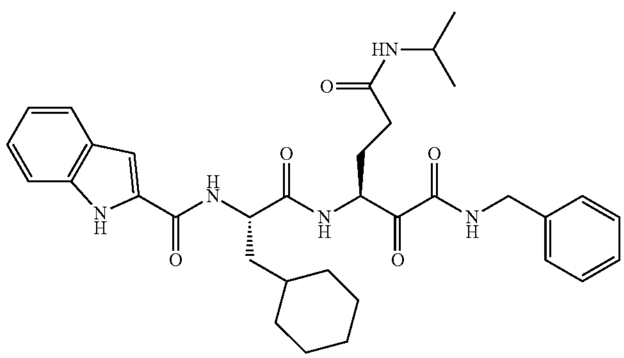 [SMILES: CC(C)NC(=O)CC[C@H](NC(=O)[C@H](CC1CCCCC1)NC(=O)c1cc2ccccc2[nH]1)C(=O)C(=O)NCc1ccccc1] | N-((S)-1-(((S)-4-(benzyl)-3,4-dione-1-(isopropylamino)-2-yl)amino)-3-(cyclohexyl)-1-oxopropan-2-yl)-1H-indole-2-carboxamide |
| A233 | 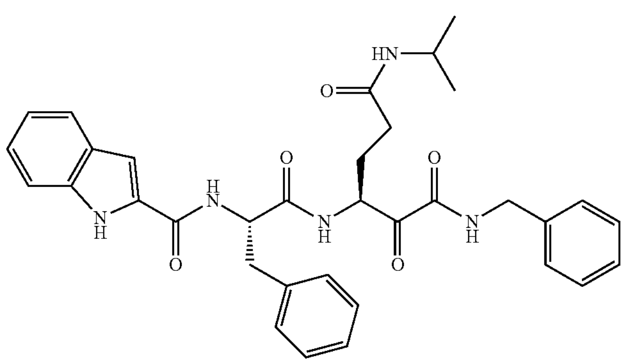 [SMILES: CC(C)NC(=O)CC[C@H](NC(=O)[C@H](Cc1ccccc1)NC(=O)c1cc2ccccc2[nH]1)C(=O)C(=O)NCc1ccccc1] | N-((S)-1-(((S)-4-(benzyl)-3,4-dione-1-(isopropylamino)-2-yl)amino)-3-(phenyl)-1-oxopropan-2-yl)-1H-indole-2-carboxamide |

TABLE 1-continued

| number | structure | name |
|---|---|---|
| A234 | 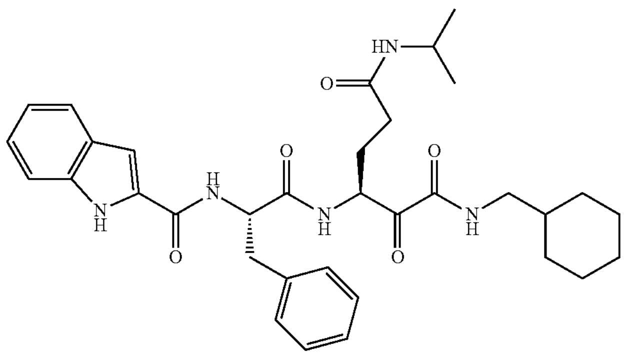 [SMILES: CC(C)NC(=O)CC[C@H](NC(=O)[C@H](Cc1ccccc1)NC(=O)c1cc2ccccc2[nH]1)C(=O)C(=O)NCC1CCCCC1] | N-((S)-1-(((S)-4-(cyclohexyl)-3,4-dione-1-(isopropylamino)-2-yl)amino)-3-(phenyl)-1-oxopropan-2-yl)-1H-indole-2-carboxamide |
| A235 | 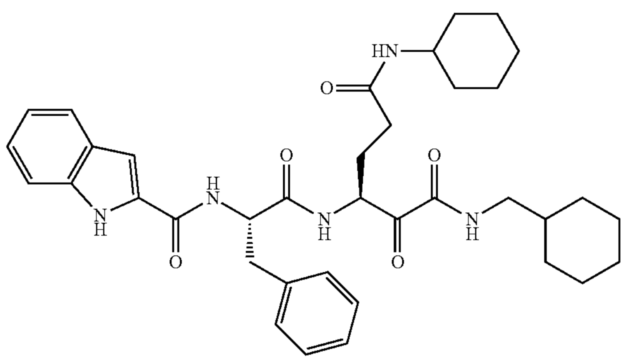 [SMILES: O=C(CC[C@H](NC(=O)[C@H](Cc1ccccc1)NC(=O)c1cc2ccccc2[nH]1)C(=O)C(=O)NCC1CCCCC1)NC1CCCCC1] | N-((S)-1-(((S)-4-(cyclohexyl)-3,4-dione-1-(cyclohexylamino)-2-yl)amino)-3-(phenyl)-1-oxopropan-2-yl)-1H-indole-2-carboxamide |
| A236 | 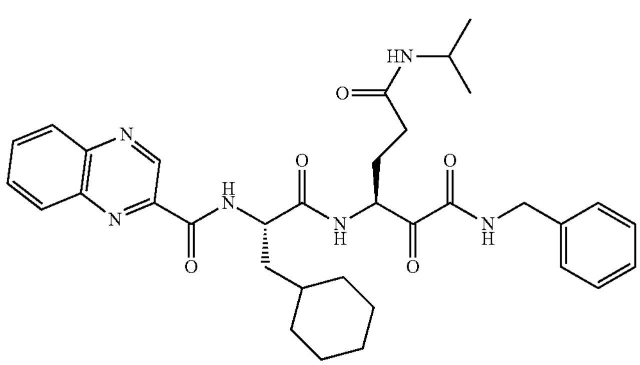 [SMILES: CC(C)NC(=O)CC[C@H](NC(=O)[C@H](CC1CCCCC1)NC(=O)c1cnc2ccccc2n1)C(=O)C(=O)NCc1ccccc1] | N-((S)-1-(((S)-4-(benzyl)-3,4-dione-1-(isopropylamino)-2-yl)amino)-3-(cyclohexyl)-1-oxopropan-2-yl)-quinoxaline-2-carboxamide |

TABLE 1-continued

| number | structure | name |
|---|---|---|
| A237 | 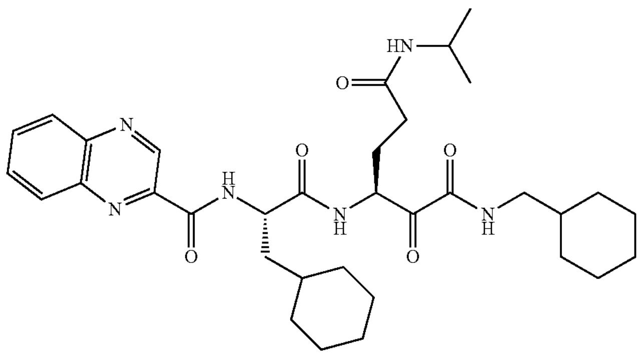 [SMILES: CC(C)NC(=O)CC[C@H](NC(=O)[C@H](CC1CCCCC1)NC(=O)c1cnc2ccccc2n1)C(=O)C(=O)NCC1CCCCC1] | N-((S)-1-(((S)-4-(cyclohexyl)-3,4-dione-1-(isopropylamino)-2-yl)amino)-3-(cyclohexyl)-1-oxopropan-2-yl)-quinoxaline-2-carboxamide |
| A238 | 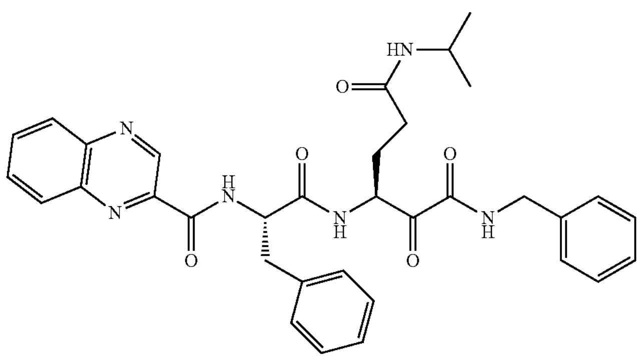 [SMILES: CC(C)NC(=O)CC[C@H](NC(=O)[C@H](Cc1ccccc1)NC(=O)c1cnc2ccccc2n1)C(=O)C(=O)NCc1ccccc1] | N-((S)-1-(((S)-4-(benzyl)-3,4-dione-1-(isopropylamino)-2-yl)amino)-3-(phenyl)-1-oxopropan-2-yl)-quinoxaline-2-carboxamide |
| A239 | 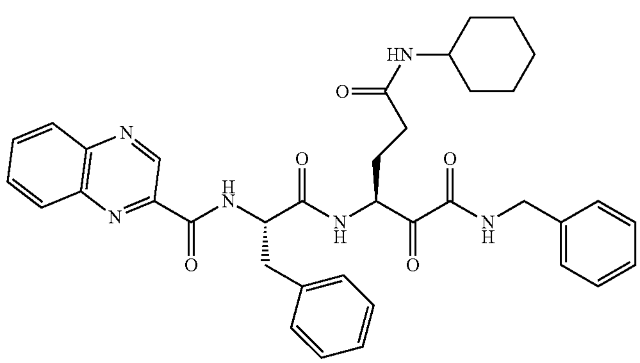 [SMILES: O=C(CC[C@H](NC(=O)[C@H](Cc1ccccc1)NC(=O)c1cnc2ccccc2n1)C(=O)C(=O)NCc1ccccc1)NC1CCCCC1] | N-((S)-1-(((S)-4-(benzyl)-3,4-dione-1-(cyclohexylamino)-2-yl)amino)-3-(phenyl)-1-oxopropan-2-yl)-quinoxaline-2-carboxamide |

TABLE 1-continued

| number | structure | name |
|---|---|---|
| A240 | 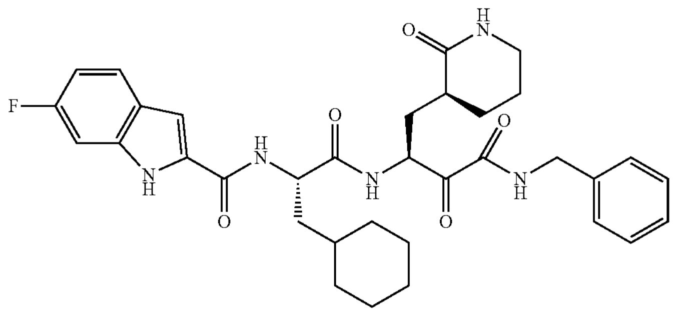 [SMILES: O=C(NCc1ccccc1)C(=O)[C@H](C[C@@H]1CCCNC1=O)NC(=O)[C@H](CC1CCCCC1)NC(=O)c1cc2ccc(F)cc2[nH]1] | N-((S)-1-(((S)-4-(benzylamino)-3,4-dione-1-((S)-2-oxopiperidine-3-yl)but-2-yl)amino)-3-cyclohexyl-1-oxopropan-2-yl)-1H-indole-6-fluoro-2-carboxamide |
| A241 | 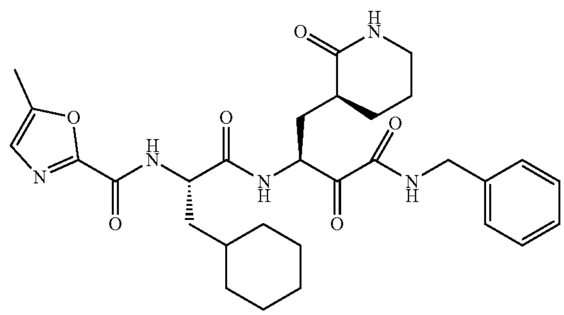 [SMILES: Cc1cnc(C(=O)N[C@@H](CC2CCCCC2)C(=O)N[C@@H](C[C@@H]2CCCNC2=O)C(=O)C(=O)NCc2ccccc2)o1] | N-((S)-1-(((S)-4-(benzylamino)-3,4-dione-1-((S)-2-oxopiperidine-3-yl)but-2-yl)amino)-3-cyclohexyl-1-oxopropan-2-yl)-5-methyloxazole-2-carboxamide |
| A242 | 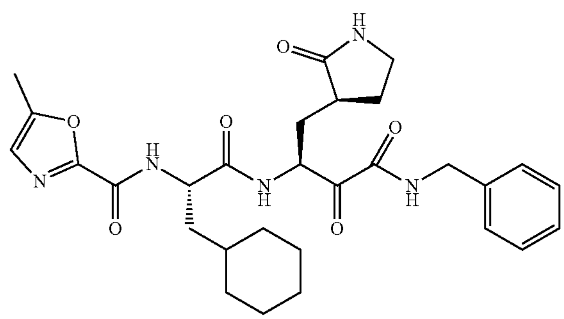 [SMILES: Cc1cnc(C(=O)N[C@@H](CC2CCCCC2)C(=O)N[C@@H](C[C@@H]2CCNC2=O)C(=O)C(=O)NCc2ccccc2)o1] | N-((S)-1-(((S)-4-(benzylamino)-3,4-dione-1-((S)-2-oxopyrrolidine-3-yl)but-2-yl)amino)-3-cyclohexyl-1-oxopropan-2-yl)-5-methyloxazole-2-carboxamide |
| A243 | 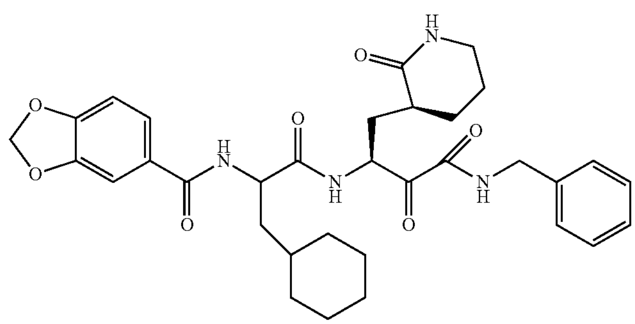 [SMILES: O=C(NCc1ccccc1)C(=O)[C@H](C[C@@H]1CCCNC1=O)NC(=O)C(CC1CCCCC1)NC(=O)c1ccc2c(c1)OCO2] | N-((S)-1-(((S)-4-(benzylamino)-3,4-dione-1-((S)-2-oxopiperidine-3-yl)but-2-yl)amino)-3-cyclohexyl-1-oxopropan-2-yl)-benzo[d]1,3-dioxole-5-carboxamide |

TABLE 1-continued

| number | structure | name |
| --- | --- | --- |
| A244 | 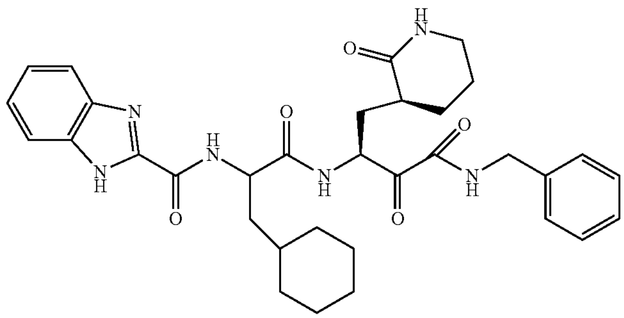 [SMILES: O=C(NCc1ccccc1)C(=O)[C@H](C[C@@H]1CCCNC1=O)NC(=O)C(CC1CCCCC1)NC(=O)c1nc2ccccc2[nH]1] | N-((S)-1-(((S)-4-(benzylamino)-3,4-dione-1-((S)-2-oxopiperidine-3-yl)but-2-yl)amino)-3-cyclohexyl-1-oxopropan-2-yl)-1H-benzo[d]imidazole-2-carboxamide |
| A245 | 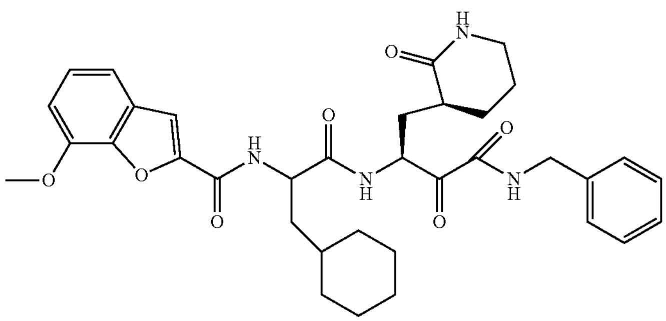 [SMILES: COc1cccc2cc(C(=O)NC(CC3CCCCC3)C(=O)N[C@@H](C[C@@H]3CCCNC3=O)C(=O)C(=O)NCc3ccccc3)oc12] | N-((S)-1-(((S)-4-(benzylamino)-3,4-dione-1-((S)-2-oxopiperidine-3-yl)but-2-yl)amino)-3-cyclohexyl-1-oxopropan-2-yl)-7-methoxy-benzofuran-2-carboxamide |
| A246 | 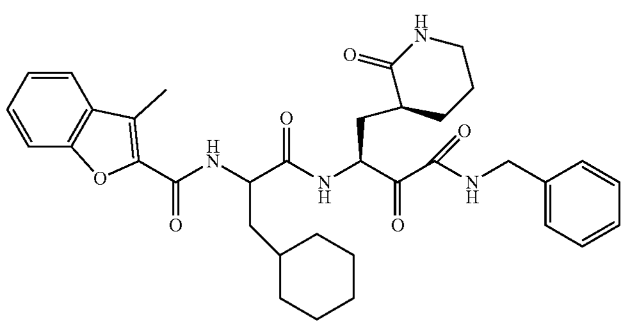 [SMILES: Cc1c(C(=O)NC(CC2CCCCC2)C(=O)N[C@@H](C[C@@H]2CCCNC2=O)C(=O)C(=O)NCc2ccccc2)oc2ccccc12] | N-((S)-1-(((S)-4-(benzylamino)-3,4-dione-1-((S)-2-oxopiperidine-3-yl)but-2-yl)amino)-3-cyclohexyl-1-oxopropan-2-yl)-3-methyl-benzofuran-2-carboxamide |
| A247 | 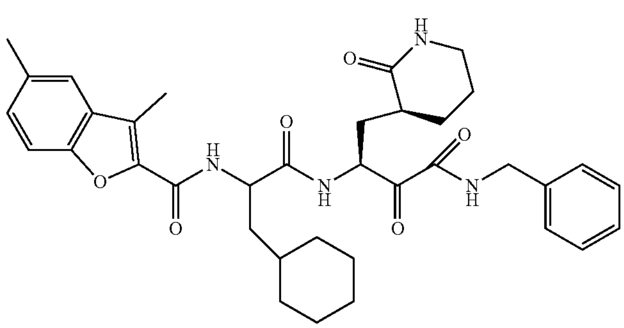 [SMILES: Cc1ccc2oc(C(=O)NC(CC3CCCCC3)C(=O)N[C@@H](C[C@@H]3CCCNC3=O)C(=O)C(=O)NCc3ccccc3)c(C)c2c1] | N-((S)-1-(((S)-4-(benzylamino)-3,4-dione-1-((S)-2-oxopiperidine-3-yl)but-2-yl)amino)-3-cyclohexyl-1-oxopropan-2-yl)-3,5-dimethyl-benzofuran-2-carboxamide |

TABLE 1-continued

| number | structure | name |
|---|---|---|
| A248 | 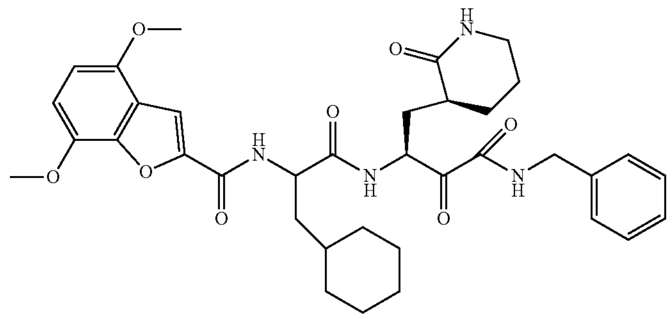 [SMILES: COc1ccc(OC)c2oc(C(=O)NC(CC3CCCCC3)C(=O)N[C@@H](C[C@@H]3CCCNC3=O)C(=O)C(=O)NCc3ccccc3)cc12] | N-((S)-1-(((S)-4-(benzylamino)-3,4-dione-1-((S)-2-oxopiperidine-3-yl)but-2-yl)amino)-3-cyclohexyl-1-oxopropan-2-yl)-4,7-dimethoxy-benzofuran-2-carboxamide |
| A249 | 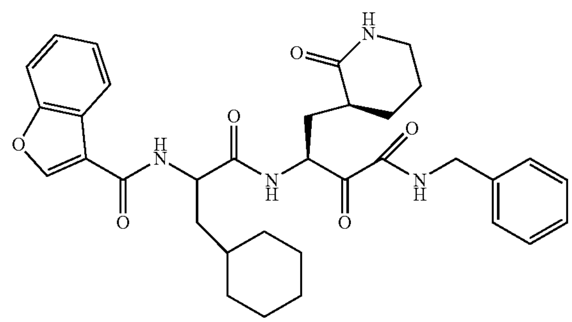 [SMILES: O=C(NCc1ccccc1)C(=O)[C@H](C[C@@H]1CCCNC1=O)NC(=O)C(CC1CCCCC1)NC(=O)c1coc2ccccc12] | N-((S)-1-(((S)-4-(benzylamino)-3,4-dione-1-((S)-2-oxopiperidine-3-yl)but-2-yl)amino)-3-cyclohexyl-1-oxopropan-2-yl)-benzofuran-3-carboxamide |
| A250 | 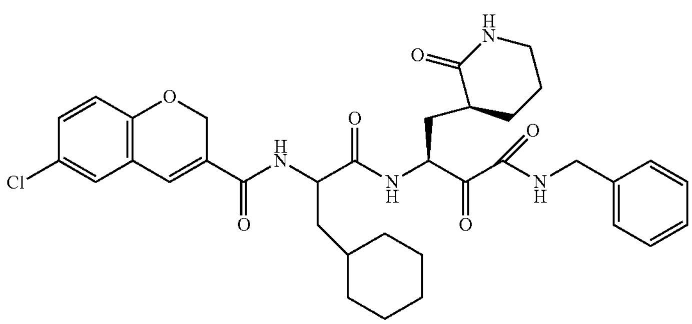 [SMILES: O=C(NCc1ccccc1)C(=O)[C@H](C[C@@H]1CCCNC1=O)NC(=O)C(CC1CCCCC1)NC(=O)C1=Cc2cc(Cl)ccc2OC1] | N-((S)-1-(((S)-4-(benzylamino)-3,4-dione-1-((S)-2-oxopiperidine-3-yl)but-2-yl)amino)-3-cyclohexyl-1-oxopropan-2-yl)-6-chloro-2H-chromene-3-carboxamide |
| A251 | 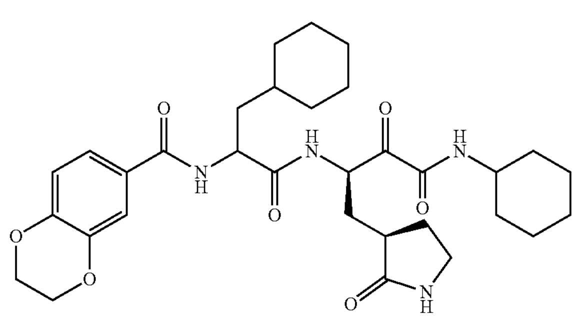 [SMILES: O=C(NC1CCCCC1)C(=O)[C@@H](C[C@H]1CCNC1=O)NC(=O)C(CC1CCCCC1)NC(=O)c1ccc2c(c1)OCCO2] | N-((S)-1-(((S)-4-(cyclohexylamino)-3,4-dione-1-((S)-2-oxopyrrolidine-3-yl)but-2-yl)amino)-3-cyclohexyl-1-oxopropan-2-yl)-2,3-dihydrobenzo[b]1,4-dioxin-6-carboxamide |

TABLE 1-continued

| number | structure | name |
|---|---|---|
| A252 | 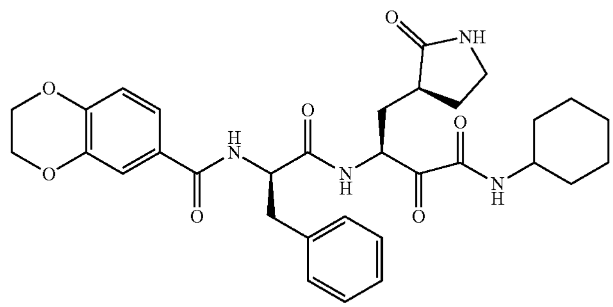 [SMILES: O=C(NC1CCCCC1)C(=O)[C@H](C[C@@H]1CCNC1=O)NC(=O)[C@@H](Cc1ccccc1)NC(=O)c1ccc2c(c1)OCCO2] | N-((S)-1-(((S)-4-(cyclohexylamino)-3,4-dione-1-((S)-2-oxopyrrolidine-3-yl)but-2-yl)amino)-3-phenyl-1-oxopropan-2-yl)-2,3-dihydrobenzo[b]1,4-dioxin-6-carboxamide |
| A253 | 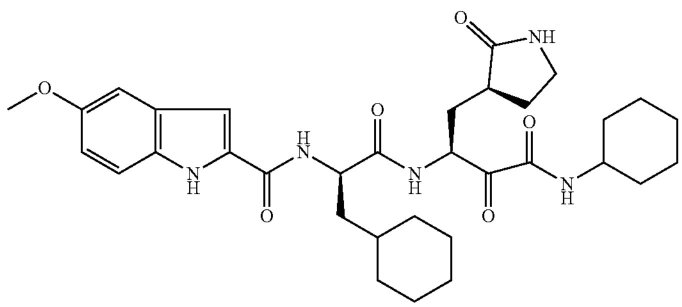 [SMILES: COc1ccc2[nH]c(C(=O)N[C@H](CC3CCCCC3)C(=O)N[C@@H](C[C@@H]3CCNC3=O)C(=O)C(=O)NC3CCCCC3)cc2c1] | N-((S)-1-(((S)-4-(cyclohexylamino)-3,4-dione-1-((S)-2-oxopyrrolidine-3-yl)but-2-yl)amino)-3-cyclohexyl-1-oxopropan-2-yl)-5-methoxyindole-6-carboxamide. |

The compound of the present invention can be used to inhibit enterovirus and coronavirus, especially MERS virus.

The compounds of the present invention may also have asymmetric centers, and may exist in the form of racemates, R-isomers or S-isomers or mixtures thereof. Those skilled in the art can use conventional technical means to obtain R-isomer and/or S-isomer from racemate.

Salt

As used herein, the term "pharmaceutically acceptable salt" refers to a salt formed by a compound of the present invention and an acid or base suitable for use as a medicine. Pharmaceutically acceptable salts include inorganic salts and organic salts. A preferred class of salts are the salts of the compounds of the invention formed with acids. Acids suitable for salt formation include but are not limited to: hydrochloric acid, hydrobromic acid, hydrofluoric acid, sulfuric acid, nitric acid, aminosulfonic acid, phosphoric acid and other inorganic acids; citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalenedisulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-aminobenzenesulfonic acid, 2-acetoxybenzoic acid, isethionic acid and other organic acids; and amino acids such as proline, phenylalanine, aspartic acid and glutamic acid.

Another preferred class of salts are salts of the compounds of the invention formed with bases, such as alkali metal salts (for example sodium or potassium salts), alkaline earth metal salts (for example magnesium or calcium salts), aluminum salt, ammonium salts (such as lower alkanol ammonium salts and other pharmaceutically acceptable amine salts), such as methylamine salt, ethylamine salt, ethanolamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, trishydroxyethylamine salt, and an amine salt formed with morpholine, piperazine, and lysine, respectively.

The term "solvate" refers to a complex in which the compound of the present invention coordinates with solvent molecules at a specific ratio.

The term "prodrug" includes a compound which is itself biologically active or inactive, when administered by an appropriate manner, which is metabolized or chemically reacted in the human body to form a compound of formula A, or salts or solution consisted of a compound of formula A. The prodrug includes, but is not limited to, a carboxylic acid ester, a carbonate, a phosphate, a nitrate, a sulfate, a sulfone ester, a sulfoxide ester, an amino compound, a carbamate, an azo compound, phosphoramide, glucoside, ether, acetal of the compound and the like.

Preparation Method

The preparation method of the formula A compound of the present invention is more specifically described below, but these specific methods do not constitute any limitation to the present invention. The compounds of the present invention may also be conveniently prepared by optionally combining various synthetic methods described in the specification or known in the art, and such combinations are readily made by those skilled in the art to which the present invention pertains.

Typically, the preparation process of the compounds of the present invention is as follows, wherein the starting materials and reagents used are commercially available unless otherwise specified.

step (2): in an inert solvent, compound III undergoes a reduction reaction under certain conditions to obtain compound IV; wherein the reducing agent is preferably a borohydride;

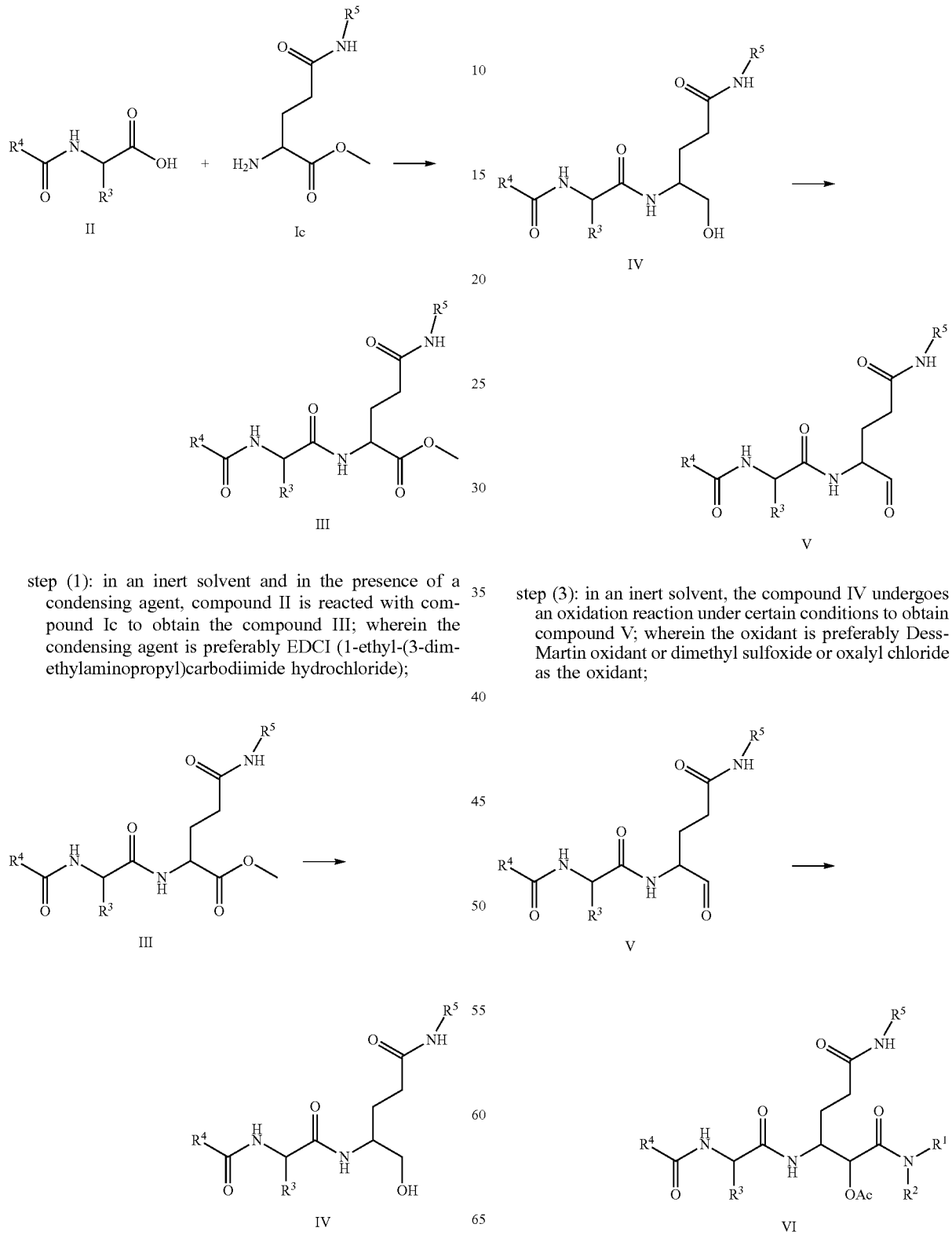

step (1): in an inert solvent and in the presence of a condensing agent, compound II is reacted with compound Ic to obtain the compound III; wherein the condensing agent is preferably EDCI (1-ethyl-(3-dimethylaminopropyl)carbodiimide hydrochloride);

step (3): in an inert solvent, the compound IV undergoes an oxidation reaction under certain conditions to obtain compound V; wherein the oxidant is preferably Dess-Martin oxidant or dimethyl sulfoxide or oxalyl chloride as the oxidant;

step (4): in an inert solvent, in the presence of acetic acid, reacting compound V with an isocyanide compound to obtain compound VI;

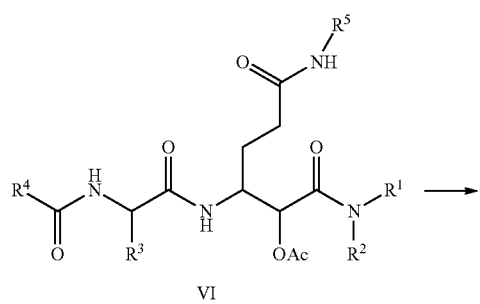

VI

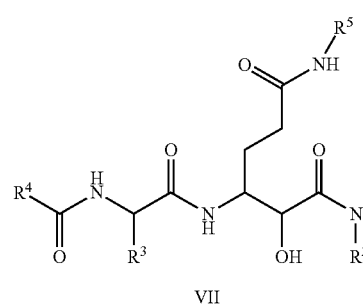

VII step (5): using methanol as the solvent, reacting compound VI with a base to obtain compound VII; wherein the base is preferably LiOH and potassium carbonate;

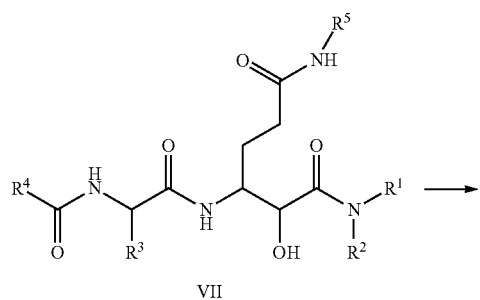

VII

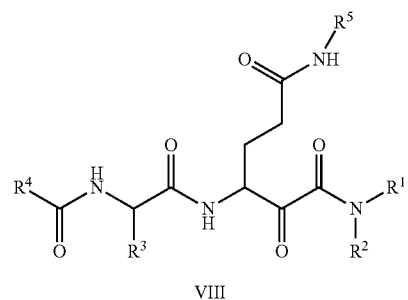

VIII step (6): in an inert solvent, compound VII is subjected to oxidation reaction under certain conditions to obtain compound VIII; wherein the oxidant is preferably Dess-Martin oxidant or dimethyl sulfoxide or oxalyl chloride as oxidant;

In the above formulas, the definition of each group is as described above.

Specifically, the present invention also provides a method for synthesizing the compound of formula A, which is prepared by the following process:

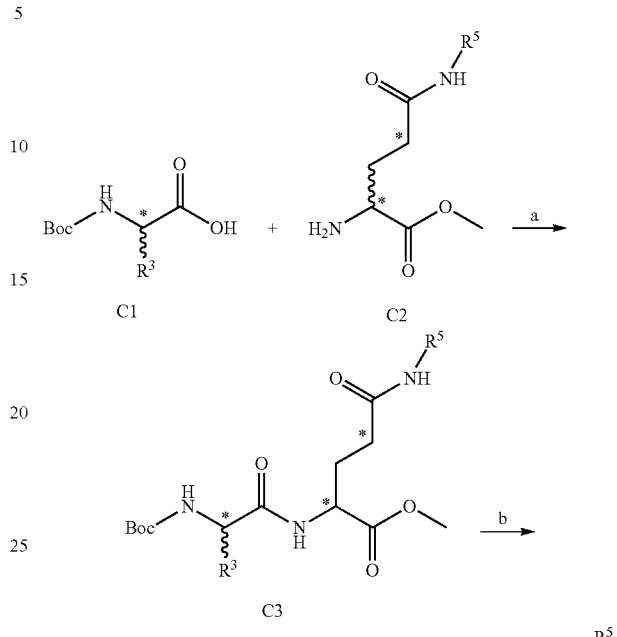

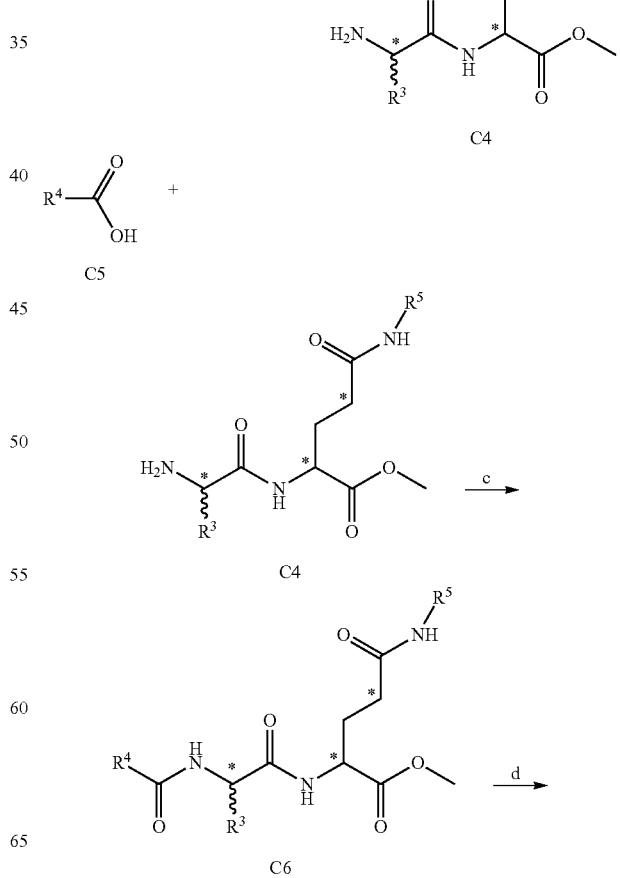

-continued

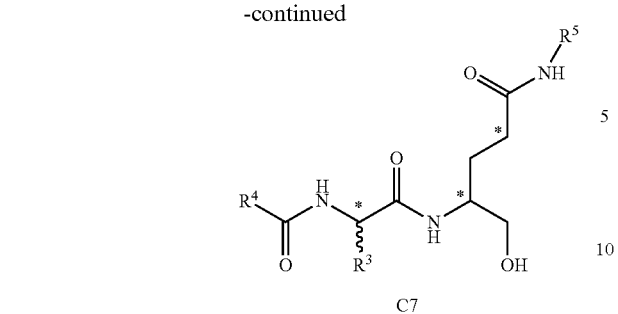

C7

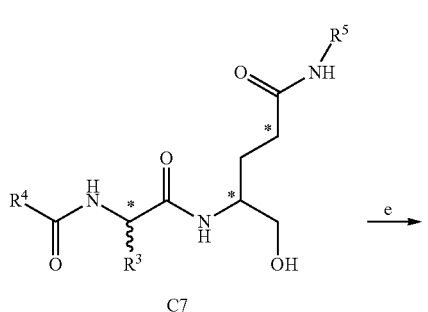

C7

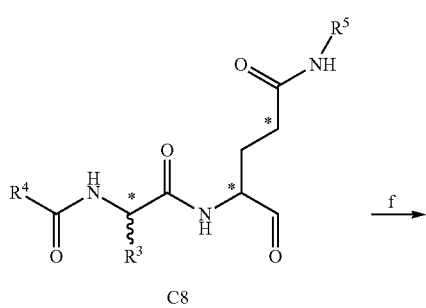

C8

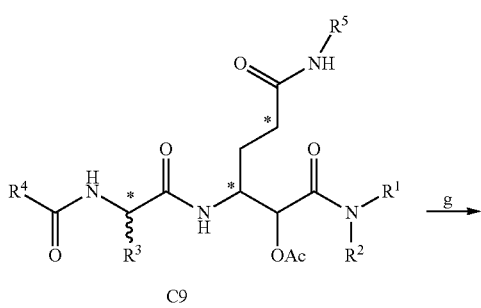

C9

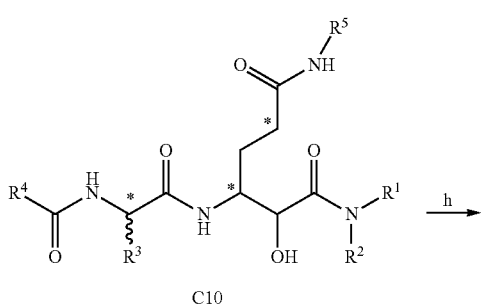

C10

-continued

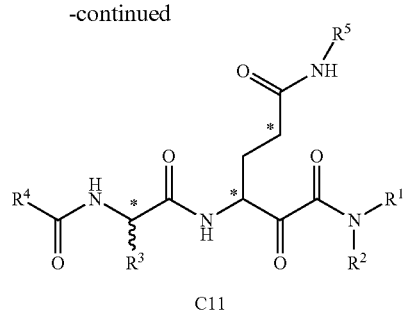

C11 step a: dissolving Boc-protected amino acids C1 and C2 in a solvent, and performing a condensation reaction with the aid of a condensing agent to obtain compound C3; wherein the solvent is dichloromethane or DMF;

step b: dissolving C3 in a solvent, stirring until the reaction is complete, and spin drying the reaction solvent to obtain compound C4; wherein the solvent is a mixed solvent of dichloromethane and trifluoroacetic acid;

step c: dissolving substituted carboxylic acids C5 and C4 in a solvent, and performing condensation reaction with the aid of a condensing agent to obtain compound C6; wherein the solvent is dichloromethane or DMF;

step d: dissolving compound C6 in a solvent, adding sodium borohydride, and stirring to obtain compound C7; wherein the solvent is methanol, tetrahydrofuran or ethanol;

step e: dissolving compound C7 in a solvent, adding an oxidant, adding base, and stirring to obtain compound C8; wherein the solvent is dichloromethane or tetrahydrofuran; the oxidant is Dess-Martin oxidant or dimethyl sulfoxide or oxalyl chloride; the base is sodium bicarbonate or triethylamine;

step f: dissolving compound C8 in a solvent, adding acetic acid and an isocyanide compound to react to obtain compound C9; wherein the solvent is dichloromethane;

step g: dissolving compound C9 in a solvent, adding base and stirring to obtain compound C10; wherein the base is preferably LiOH and potassium carbonate;

step h: dissolving compound C10 in a solvent, adding oxidant, adding base, and stirring to obtain compound C11;

wherein the solvent is dichloromethane or tetrahydrofuran; the oxidant is Dess-Martin oxidant or dimethyl sulfoxide or oxalyl chloride; the base is sodium bicarbonate or triethylamine;

$R^1$, $R^2$, $R^3$, $R^4$, $R^5$ and n are the same as defined above.

Pharmaceutical Composition

The present invention also relates to a pharmaceutical composition comprising a therapeutically effective amount of one or more of the ketoamide compound represented by formula A, its pharmaceutically acceptable salt, its prodrug, its hydrate and solvate, and optionally, a pharmaceutically acceptable carrier, which can be used to treat Coronavirus or Ebola virus related diseases. The pharmaceutical composition can be prepared into various forms according to different administration routes.

The pharmaceutical composition of the present invention comprises a safe and effective amount of a compound of the present invention or a pharmacologically acceptable salt thereof, and a pharmacologically acceptable excipient or carrier. The term "safe and effective amount" means that the amount of the compound is sufficient to significantly improve the condition without causing serious side effects. Generally, the pharmaceutical composition contains 1-2000 mg of the compound of the present invention/dosage, more preferably, 10-1000 mg of the compound of the present invention/dosage. Preferably, the "one dosage" is a capsule or a tablet.

"Pharmaceutically acceptable carrier" means one or more compatible solid or liquid fillers or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

According to the present invention, one or more of the ketoamide compounds represented by formula A, their pharmaceutically acceptable salts, their prodrugs and their hydrates and solvates, or the above-mentioned pharmaceutical composition containing a therapeutically effective amount of one or more of the ketoamide compounds represented by formula A, their pharmaceutically acceptable salts, their prodrugs and their hydrates and solvates can be used as MERS inhibitors, or are useful for the treatment of coronavirus infections or Ebola virus infection-related diseases.

The pharmaceutical composition provided by the present invention preferably contains active ingredients in a weight ratio of 1-99%, and the preferred ratio is that the compound represented by formula A as the active ingredient accounts for 65 wt %-99 wt % of the total weight, and the rest is a pharmaceutically acceptable carrier, diluent or solution or salt solution.

The compounds and pharmaceutical compositions provided by the present invention can be in various forms, such as tablets, capsules, powders, syrups, solutions, suspensions and aerosols, etc., and can be present in suitable solid or liquid carriers or diluents and sterilization equipment suitable for injection or drip.

Various dosage forms of the pharmaceutical composition of the present invention can be prepared according to conventional preparation methods in the pharmaceutical field. One unit of the preparation formula contains 1 mg-700 mg of the compound represented by general formula A, preferably, one unit of the preparation formula contains 25 mg-300 mg of the compound of general formula A.

The preparation of the medicinal salt of the compound of the present invention can be directly formed by the free base of the compound and inorganic or organic acid.

Inorganic or organic acids can be selected from hydrochloric acid, sulfuric acid, phosphoric acid, nitric acid, hydrofluoric acid, hydrobromic acid, formic acid, acetic acid, picric acid, citric acid, maleic acid, methanesulfonic acid, trifluoromethanesulfonic acid, ethanesulfonic acid and p-toluenesulfonic acid, etc.

The compound of the present invention has excellent inhibitory activity against Ebola and coronavirus replication. Therefore, the compound of the present invention and its various crystal forms, pharmaceutically acceptable inorganic or organic salts, hydrates or solvates, and the pharmaceutical composition in which the compound of the present invention is the main active ingredient can be used to treat, prevent and alleviate diseases related to Ebola virus and diseases related to coronavirus.

The administration mode of the compound or pharmaceutical composition of the present invention is not particularly limited, and the representative administration modes include, but are not limited to, oral, intratumoral, rectal, parenteral (intravenous, intramuscular or subcutaneous) and topical administration.

Solid dosage forms for oral administration include capsules, tablets, pills, powders and granules. In these solid dosage forms, the active compound is mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; (i) lubricants such as talc, calcium stearate, magnesium stearate, solid polyethylene glycol, sodium lauryl sulfate, or the mixture thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances. In addition to these inert diluents, the compositions may contain adjuvants such as wetting agents, emulsifying and suspending agents, sweetening agents, flavoring agents and spices.

In addition to the active compound, the suspension may contain suspending agent, for example, ethoxylated isooctadecanol, polyoxyethylene sorbitol and dehydrated sorbitan ester, microcrystalline cellulose, aluminum methoxide and agar, or the mixture thereof etc. The compositions for parenteral injection may comprise physiologically acceptable sterile aqueous or anhydrous solutions, dispersions, suspensions or emulsions and sterile powders which can be re-dissolved into sterile injectable solutions or dispersions. Suitable aqueous and non-aqueous carriers, diluents, solvents or excipients include water, ethanol, polyols and any suitable mixtures thereof. Dosage forms for the compounds of the invention for topical administration include ointments, powders, patches, propellants and inhalants. The active ingredient is mixed under sterile conditions with a physiologically acceptable carrier and any preservatives, buffers, or propellants which may be required if necessary.

The compound of the present invention can be administered alone or in combination with other pharmaceutically acceptable compounds (such as other antiviral drugs).

The treatment method of the present invention can be administered alone or in combination with other treatment means or therapeutic drugs.

The compound according to the present invention as described above can be used clinically on mammals, including humans and animals, and can be administered via oral, nasal, skin, lung, or gastrointestinal tract, and more preferably oral administration. The daily dose is preferably 0.01-200 mg/kg body weight, taken in one time, or 0.01-100 mg/kg body weight in divided doses. Regardless of the method of administration, the individual's optimal dosage should be determined based on the specific treatment. Normally, it starts with a small dose and gradually increase the dose until the most suitable dose is found. Of course, specific doses should also consider factors such as the administration route, the health of the patient, etc., which are within the skill of the skilled physician.

The Main Advantages of the Present Invention are as Follows:

Compared with the existing coronavirus inhibitors, the compound has higher inhibitory activity and lower toxicity.

The present invention will be further illustrated below with reference to the specific examples. It should be understood that these examples are only to illustrate the invention but not to limit the scope of the invention. Experimental methods in which the specific conditions are not specified in the following examples are usually in accordance with conventional conditions such as the conditions described in Sambrook et al., Molecular Cloning: Laboratory Manual (New York:Cold Spring Harbor Laboratory Press, 1989), or in accordance with the conditions recommended by the manufacturer. Unless indicated otherwise, parts and percentage are calculated by weight.

Unless otherwise defined, all professional and scientific terminology used in the text have the same meanings as known to the skilled in the art. In addition, any methods and materials similar or equal with the record content can apply to the methods of the invention. The method of the preferred embodiment described herein and the material are only for demonstration purposes.

The analytical data of the samples were measured by the following instruments: NMR was measured by GEMINI-300, Bruker AMX-400 and INVOA-600 NMR instruments, TMS (tetramethylsilane) was internal standard, chemical shift unit was ppm, unit of the coupling constant was Hz; the mass spectrum was measured by Finnigan MAT-711, MAT-95 and LCQ-DECA mass spectrometers and IonSpec 4.7 Tesla mass spectrometer.

200-300 mesh silica gel (produced by Qingdao Ocean Chemical Plant) was used for column chromatography; TLC silica gel plate was HSGF-254 thin layer chromatography prefabricated plate produced by Yantai Chemical Plant; petroleum ether boiling range was 60-90° C.; UV lamp was used, the iodine cylinder was used for developing color. Unless otherwise stated, the conventional reagents and medicines used in the following examples were purchased from Sinopharm Group. The reagents and solvents used in the experiment were processed according to the specific conditions of the reaction.

Example 1 Compound A1

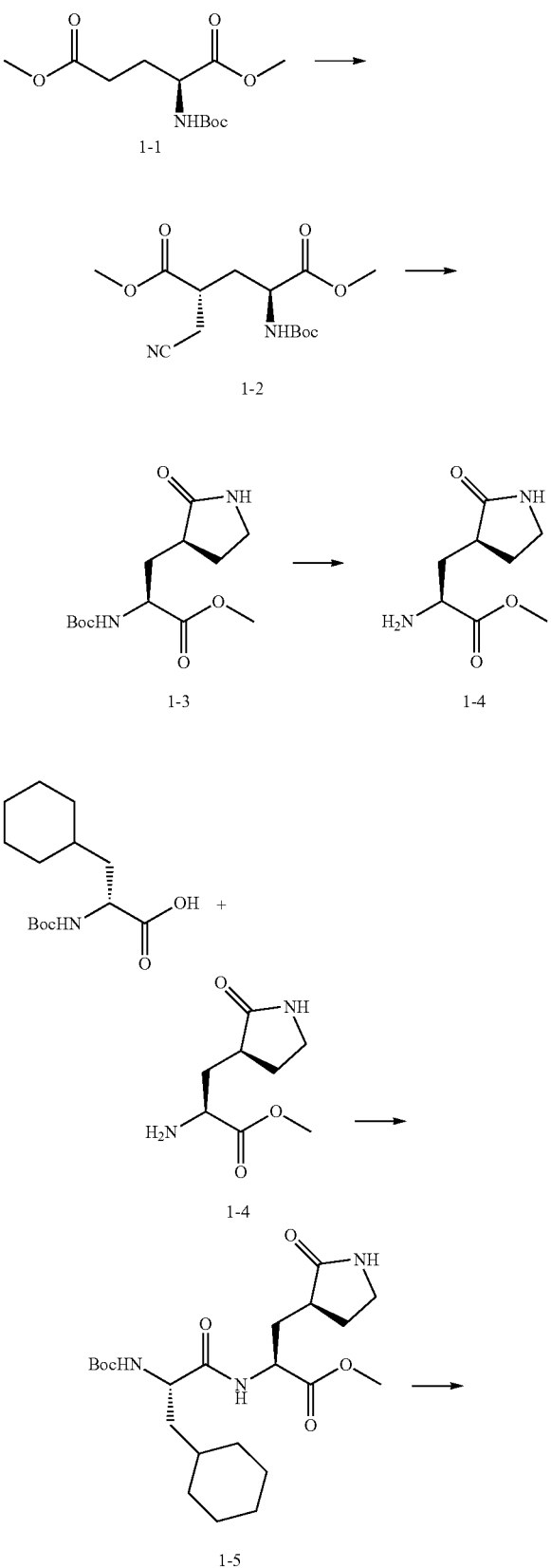

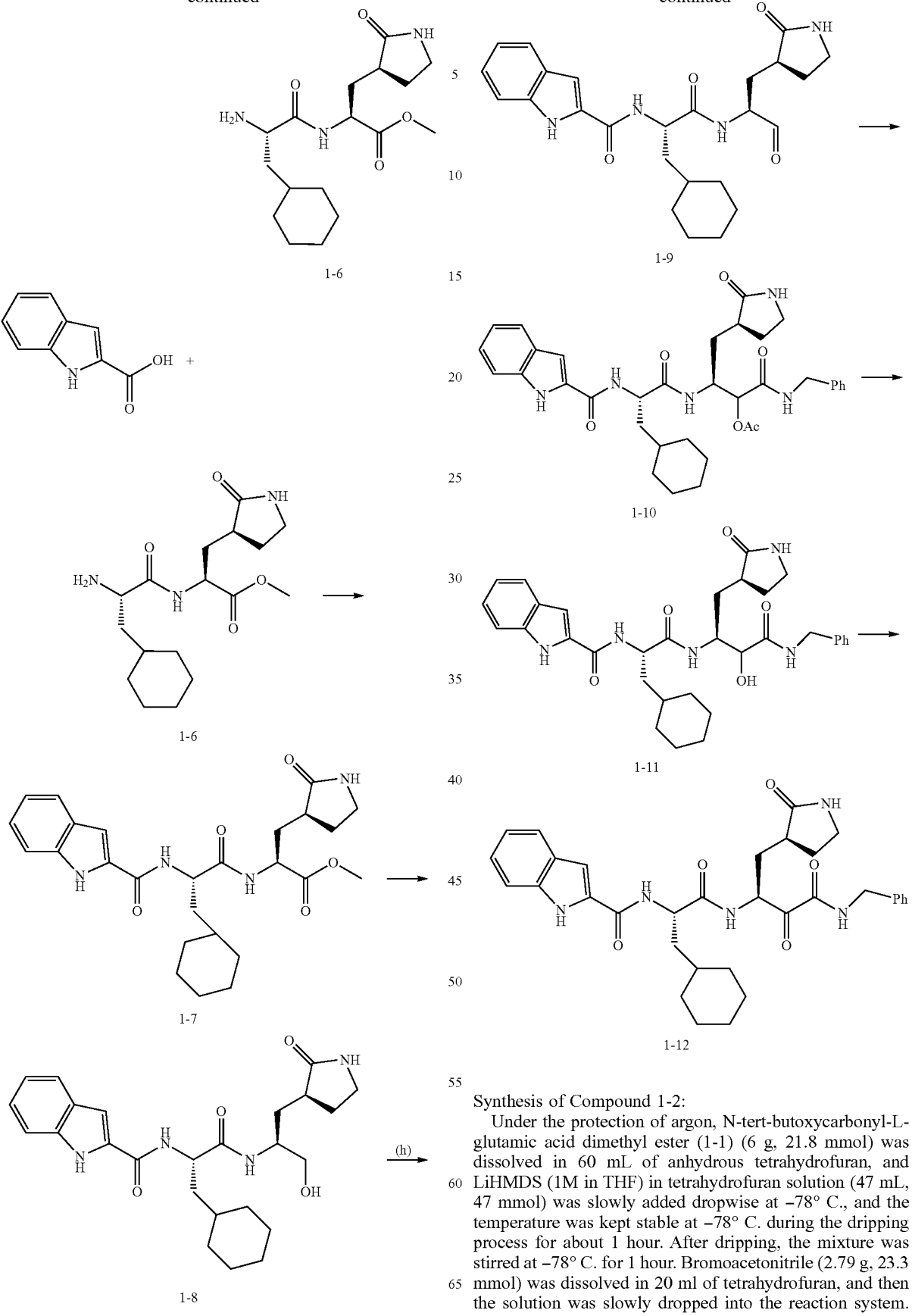

Synthesis of Compound 1-2:

Under the protection of argon, N-tert-butoxycarbonyl-L-glutamic acid dimethyl ester (1-1) (6 g, 21.8 mmol) was dissolved in 60 mL of anhydrous tetrahydrofuran, and LiHMDS (1M in THF) in tetrahydrofuran solution (47 mL, 47 mmol) was slowly added dropwise at −78° C., and the temperature was kept stable at −78° C. during the dripping process for about 1 hour. After dripping, the mixture was stirred at −78° C. for 1 hour. Bromoacetonitrile (2.79 g, 23.3 mmol) was dissolved in 20 ml of tetrahydrofuran, and then the solution was slowly dropped into the reaction system. The dropping process was lasted for 1 to 2 hours. The temperature was controlled at −78° C. and the reaction was continued for 3 hours. When TLC monitoring (alkaline potassium permanganate color development) indicated the reaction was completed, NH₄Cl solution was added into the reaction solution to quench the reaction, the reaction mixture was stirred for 10 min, and then warmed to room temperature. 40 mL of saturated sodium chloride solution was poured in and stirred well, and the reaction system appeared to separate into layers. The organic layer was separated, and the aqueous phase was extracted with ethyl acetate (EA). The organic layers were combined and dried over anhydrous sodium sulfate, concentrated, and purified with column chromatography (Flash, PE:EA=1:5) to obtain a pale yellow oil (1-2 3.9 g, the yield was 58%).

Synthesis of Compound 1-3:

Compound 1-2 (1 g, 3.15 mmol) was dissolved in 25 mL of anhydrous methanol, the mixture was stirred under an ice bath to 0° C., and cobalt dichloride hexahydrate (450 mg, 1.89 mmol) was added. After 10 min, sodium borohydride (715 mg, 18.9 mmol) was added in small portions, and the reaction solution continued to react in an ice bath for 1 h before turning to room temperature. After 15 h, 5 mL saturated NH₄Cl solution was used to quench the reaction and the mixture was continuously stirred for 10 min. After filtering off the solid, the filtrate was evaporated to dryness, extracted with 20 mL of water and 30×3 mL of ethyl acetate. the organic phases were combined, and dried with anhydrous Na₂SO₄ for 1 h, concentrated under reduced pressure and separated by column chromatography [PE:EA=1:2] to obtain 460 mg of a white powdery solid with a yield of 51%.

Synthesis of Compound 1-4:

Compound 1-3 (2.6 g) was dissolved in trifluoroacetic acid in dichloromethane solution (1/1, v/v), stirred at room temperature for 1 hour, and 100 ml of dichloromethane was added after concentration. The saturated sodium carbonate solution was used for washing and the organic layer was dried with anhydrous sodium sulfate and concentrated to obtain oily substance 1-4 (2.7 g) with a yield of 99%.

Synthesis of Compound 1-5:

Boc-cyclohexylalanine (1.26 g, 5 mmol), EDCI (1.36 g, 6 mmol) and HOBt (0.822 g, 6 mmol) were added into 80 ml dichloromethane solution, and the mixture was stirred at room temperature for 30 min. Subsequently, compound 1-4 (0.896 g, 5 mmol) was added, 1.2 equivalent of triethylamine was added dropwise, and the mixture was stirred at room temperature. When TLC monitoring (UV) indicated the reaction was complete, the mixture was extracted with dichloromethane, washed with dilute hydrochloric acid, saturated sodium bicarbonate solution and saturated sodium chloride. The organic layers were combined and dried with anhydrous sodium sulfate, and concentrated to obtain 1.2 g of white viscous solid with a yield of 60%.

Synthesis of Compound 1-6:

Compound 1-5 (2.5 g) was dissolved in trifluoroacetic acid in dichloromethane solution (1/1, v/v), and mixture was stirred at room temperature for 1 hour. 100 ml of dichloromethane was added after concentration, and saturated sodium carbonate solution was used for washing. The organic layer was dried with anhydrous sodium sulfate and concentrated to obtain oily substance 1-6 (2.61 g) with a yield of 99%.

Synthesis of Compound 1-7:

Indole 2-formic acid (0.795 g, 5 mmol), EDCI (1.36 g, 6 mmol), and HOBt (0.822 g, 6 mmol) were added into 80 ml of dichloromethane solution, and the mixture was stirred at room temperature for 30 min. Subsequently, compound 1-6 (2.2 g, 5 mmol) was added, 1.2 equivalent of triethylamine was added dropwise, and the mixture was stirred at room temperature. When TLC monitoring (UV) indicated the reaction was complete, the mixture was extracted with dichloromethane, washed with dilute hydrochloric acid, saturated sodium bicarbonate solution and saturated sodium chloride, and the organic layers were combined and dried with anhydrous sodium sulfate, and concentrated to obtain 1.3 g of white viscous solid with a yield of 60%.

Synthesis of Compound 1-8:

Compound 1-7 (243 mg, 0.51 mmol) was dissolved in 20 ml of methanol, sodium borohydride (107 mg, 2.9 mmol) was slowly added in batches, and mixture was stirred at room temperature for about 2 hours to complete the reaction. After the reaction was complete, about 20 ml of saturated brine was added to quench the reaction, the reaction system was concentrated to remove methanol, and dichloromethane was added for extraction. The organic phase was washed with saturated brine, dried with anhydrous sodium sulfate, and concentrated to obtain a white solid substance 1-8, which was directly used in the next reaction.

Synthesis of Compound 1-9:

Intermediate 1-8 (129 mg, 0.29 mmol) was dissolved in 20 ml of dichloromethane, and Dess-Martin oxidant (147 mg, 0.35 mmol) and sodium bicarbonate solid (29 mg, 0.35 mmol) were added, and mixture was stirred at room temperature. When TLC monitoring (UV) indicated the reaction was complete, the reaction system was suction filtered, the filtrate obtained was extracted with saturated sodium bicarbonate, and the organic layer was subjected to wash with saturated saline, dried with anhydrous sodium sulfate and concentrated. After separation and purification by flash column chromatography ($CH_2Cl_2$:MeOH=20:1), 77 mg of white solid powder compound was obtained, with a yield of 60%.

Synthesis of Compound 1-10:

Compound 1-9 (129 mg, 0.29 mmol) was dissolved in dichloromethane solvent, acetic acid (19.2 mg, 0.32 mmol) and benzyl isocyanide (37.6 mg, 0.32 mmol) were added to react to obtain compound 1-10. Column chromatography ($CH_2Cl_2$:MeOH=20:1) was used to separate and purify, thereby obtaining 126 mg of white solid powder compound 1-10 with a yield of 70%.

Synthesis of Compound 1-11:

Compound 1-10 (187 mg, 0.3 mmol) was dissolved in methanol solvent, LiOH (0.6 mmol) was added and the mixture was stirred to obtain compound 1-11, which was separated and purified by flash column chromatography ($CH_2Cl_2$:MeOH=20:1) to obtain a total of 148 mg of white solid powder compound 1-11, with a yield of 85%.

Synthesis of Compound 1-12:

Compound 1-11 (174 mg, 0.3 mmol) was dissolved in dichloromethane solvent, Dess-Martin oxidant (152 mg, 0.36 mmol) was added, sodium bicarbonate (30 mg, 0.36 mmol) was added, and mixture was stirred to obtain the compound 1-12, as a white solid powder (140 mg in total, yield 80%).

¹H NMR (500 MHz, Chloroform) δ 9.76 (s, 1H), 7.73 (s, 1H), 7.39 (s, 1H), 7.32-7.26 (m, 2H), 7.22 (s, 1H), 7.20-7.10 (m, 3H), 7.01 (s, 1H), 6.82 (s, 1H), 6.68 (s, 1H), 6.14 (s, 1H), 5.57 (s, 1H), 5.43 (s, 1H), 4.38 (s, 1H), 4.32 (d, J=19.2 Hz, 2H), 3.45 (s, 1H), 3.35 (s, 1H), 3.06 (s, 1H), 2.20 (dd, J=15.4, 2.3 Hz, 4H), 2.12-2.03 (m, 2H), 1.92 (s, 1H), 1.77 (s, 1H), 1.73-1.67 (m, 3H), 1.66-1.53 (m, 6H), 1.37 (s, 1H).

Example 2

N—((S)-1-((((S)-4-(tert-butylamino)-3,4-dione-1-((S)-2-oxopyrrolidine-3-yl)but-2-yl)amino)-3-cyclohexyl-1-oxopropan-2-yl)-1H-indole-2-carboxamide (A2)

$^1$H NMR (500 MHz, Chloroform) δ 8.38 (s, 1H), 7.51 (d, J=18.0 Hz, 2H), 7.38 (s, 1H), 7.12 (s, 1H), 7.06 (s, 1H), 6.26 (s, 1H), 6.04 (s, 1H), 5.80 (s, 1H), 5.25 (s, 1H), 4.81 (s, 1H), 4.67 (s, 1H), 3.45 (s, 1H), 3.35 (s, 1H), 2.55 (s, 1H), 2.18 (s, 1H), 2.09-2.05 (m, 2H), 1.96-1.91 (m, 3H), 1.73-1.52 (m, 5H), 1.40-1.36 (m, 2H), 1.35-1.29 (m, 10H), 1.20-1.09 (m, 3H).

Example 3 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-1H-indole-2-carboxamide (A3)

$^1$H NMR (500 MHz, Chloroform) δ 8.28 (s, 1H), 7.48 (d, J=1.2 Hz, 2H), 7.34 (s, 1H), 7.10 (d, J=1.0 Hz, 2H), 7.03 (s, 1H), 6.05 (s, 1H), 5.59 (s, 1H), 5.30 (s, 1H), 4.63 (s, 1H), 4.45 (s, 1H), 3.58 (s, 1H), 3.45 (s, 1H), 3.35 (s, 1H), 2.95 (s, 1H), 2.18 (s, 1H), 2.09-2.05 (m, 2H), 1.98-1.90 (m, 3H), 1.73-1.67 (m, 3H), 1.65-1.61 (m, 2H), 1.51 (dtd, J=12.9, 8.9, 1.3 Hz, 13H), 1.45-1.39 (m, 3H), 1.38-1.34 (m, 2H).

Example 4 N—((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-1H-indole-2-carboxamide (A4)

$^1$H NMR (500 MHz, Chloroform) δ 8.46 (s, 1H), 7.53 (d, J=3.4 Hz, 2H), 7.40 (d, J=17.1 Hz, 2H), 7.12 (s, 1H), 7.06 (s, 1H), 6.16 (d, J=14.3 Hz, 2H), 5.65 (s, 1H), 5.23 (s, 1H), 4.44 (s, 1H), 3.44 (d, J=11.4 Hz, 2H), 3.35 (s, 1H), 3.09 (s, 1H), 2.97 (s, 1H), 2.19 (s, 1H), 2.09-2.05 (m, 2H), 1.92 (s, 1H), 1.75-1.68 (m, 4H), 1.62 (s, 1H), 1.48 (dt, J=16.0, 8.0 Hz, 5H), 1.37-1.31 (m, 2H), 1.28 (s, 1H), 1.09-1.05 (m, 9H).

Example 5 N—((S)-1-((((S)-4-(benzylamino)-3,4-dione-1-((S)-2-oxopiperidine-3-yl)but-2-yl)amino)-3-cyclohexyl-1-oxopropan-2-yl)-1H-indole-2-carboxamide (A5)

$^1$H NMR (500 MHz, Chloroform) δ 8.22 (s, 1H), 7.96 (s, 1H), 7.53 (s, 1H), 7.42 (s, 1H), 7.38 (s, 1H), 7.29-7.24 (m, 4H), 7.17 (d, J=29.6 Hz, 2H), 7.07 (s, 1H), 6.54 (s, 1H), 5.74 (s, 1H), 5.27 (s, 1H), 5.06 (s, 1H)), 4.49 (s, 1H), 4.41 (s, 1H), 4.31 (s, 1H), 3.24 (d, J=17.4 Hz, 2H), 2.56 (s, 1H), 2.08-2.04 (m, 2H), 1.95-1.88 (m, 2H), 1.78 (d, J=6.9 Hz, 2H), 1.69 (dt, J=6.3, 3.5 Hz, 7H), 1.51 (s, 1H), 1.40-1.36 (m, 2H), 1.32 (s, 1H), 1.15-1.11 (m, 2H), 1.08 (s, 1H).

Example 6 N—((S)-1-(((S)-4-(tert-butylamino)-3,4-dione-1-((S)-2-oxopiperidine-3-yl)but-2-yl)amino)-3-cyclohexyl-1-oxopropan-2-yl)-1H-indole-2-carboxamide (A6)

$^1$H NMR (500 MHz, Chloroform) δ 8.30 (s, 2H), 7.48 (s, 2H), 7.43 (s, 2H), 7.35 (s, 2H), 7.10 (s, 2H), 7.03 (s, 2H), 6.45 (s, 2H), 5.99 (s, 2H), 5.76 (s, 2H), 5.25 (s, 2H), 4.81 (s, 2H), 4.29 (s, 2H), 3.24 (d, J=17.1 Hz, 4H), 2.75 (s, 2H), 2.05 (t, J=8.9 Hz, 6H), 1.79 (s, 2H), 1.71 (t, J=2.5 Hz, 7H), 1.58-1.54 (m, 3H), 1.51-1.33 (m, 10H), 1.33-1.29 (m, 20H), 1.23 (s, 2H), 1.15-1.11 (m, 3H), 0.94-0.90 (m, 31-1).

Example 7 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-1H-indole-2-carboxamide (A7)

1H NMR (500 MHz, Chloroform) δ 9.29 (s, 1H), 8.69 (s, 1H), 7.52 (s, 1H), 7.43 (d, J=15.1 Hz, 2H), 7.13 (s, 1H), 7.06 (s, 1H), 5.93 (s, 1H), 5.59 (d, J=3.5 Hz, 2H), 5.11 (s, 1H), 4.51 (s, 1H), 3.41 (s, 1H), 3.24 (d, J=16.6 Hz, 2H), 2.66 (s, 1H), 2.54 (s, 1H), 2.08-2.04 (m, 2H), 2.01-1.89 (m, 2H), 1.89-1.77 (m, 4H), 1.73-1.61 (m, 7H), 1.55-1.50 (m, 3H), 1.48 (s, 1H), 1.44-1.39 (m, 2H), 1.39-1.35 (m, 2H), 1.31 (s, 1H), 1.09-0.99 (m, 3H).

Example 8 N—((S)-3-cyclohexyl-1-(((S)-4-(neopentylamino)-3,4-dione-1-((S)-2-oxopiperidine-3-yl)but-2-yl)amino)-3-cyclohexyl-1-oxopropan-2-yl)-1H-indole-2-carboxamide (A8)

1H NMR (500 MHz, Chloroform) δ 8.45 (s, 4H), 7.50 (d, J=31.7 Hz, 8H), 7.46-7.46 (m, 1H), 7.39 (s, 5H), 7.13 (s, 4H), 7.06 (s, 4H), 6.01 (s, 4H), 5.44 (s, 4H), 5.40 (s, 4H), 5.23 (s, 4H), 4.89 (s, 4H), 4.47 (s, 4H), 3.30-3.20 (m, 12H), 3.13 (s, 4H), 2.30 (s, 4H), 2.10-2.02 (m, 8H), 1.97 (s, 3H), 1.81-1.76 (m, 11H), 1.71 (t, J=1.6 Hz, 11H), 1.69-1.63 (m, 13H), 1.50 (s, 3H), 1.39-1.35 (m, 7H), 1.31 (s, 4H), 1.14-1.05 (m, 44H), 1.02 (s, 3H).

Example 9 N—((S)-1-(((S)-4-(benzylamino)-3,4-dione-1-((S)-2-oxopyrrolidine-3-yl)but-2-yl)amino)-3-cyclohexyl-1-oxopropan-2-yl)-benzofuran-2-carboxamide (A9)

1H NMR (500 MHz, Chloroform) δ 7.66 (s, 1H), 7.34-7.28 (m, 5H), 7.22 (d, J=7.1 Hz, 2H), 7.10 (s, 1H), 6.72 (s, 1H), 6.17 (s, 1H), 5.97 (s, 1H), 5.84 (s, 1H), 5.47 (s, 1H), 4.42 (s, 1H), 4.34 (d, J=9.3 Hz, 2H), 3.45 (s, 1H), 3.35 (s, 1H), 3.22 (s, 1H), 2.64 (s, 1H), 2.18 (s, 1H), 2.09-2.05 (m, 2H), 2.05-1.98 (m, 2H), 1.92 (s, 1H), 1.75-1.66 (m, 4H), 1.66-1.55 (m, 6H), 1.36 (s, 1H).

Example 10 N—((S)-1-(((((S)-4-(tert-butylamino)-3,4-dione-1-((S)-2-oxopyrrolidine-3-yl)but-2-yl) amino)-3-cyclohexyl-1-oxopropan-2-yl)-benzofuran-2-carboxamide (A10)

1H NMR (500 MHz, Chloroform) δ 9.59 (s, 1H), 8.31 (s, 1H), 7.63 (s, 1H), 7.50 (s, 1H), 7.41 (s, 1H), 7.22 (s, 1H), 7.16 (s, 1H), 6.40 (s, 1H), 5.82 (s, 1H), 4.81 (s, 1H), 4.64 (s, 1H), 3.97 (s, 1H), 3.35 (s, 1H), 2.69 (s, 1H), 2.19 (s, 1H), 2.09-2.05 (m, 2H), 1.94-1.88 (m, 3H), 1.76-1.66 (m, 2H), 1.66-1.48 (m, 3H), 1.36-1.32 (m, 11H), 1.28 (s, 1H), 1.20 (s, 1H), 0.99-0.95 (m, 2H).

Example 11 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-benzofuran-2-carboxamide (A11)

1H NMR (500 MHz, Chloroform) δ 7.63 (s, 4H), 7.47 (s, 4H), 7.36 (s, 4H), 7.26 (s, 4H), 7.21 (s, 4H), 7.14 (s, 4H), 5.98 (s, 4H), 5.77 (s, 4H), 5.16 (s, 4H), 4.60 (s, 4H), 4.32 (s, 4H), 3.53 (s, 3H), 3.45 (s, 4H), 3.35 (s, 3H), 2.58 (s, 3H), 2.19 (s, 3H), 2.09-2.05 (m, 8H), 1.95-1.88 (m, 11H), 1.74-1.68 (m, 27H), 1.65-1.61 (m, 6H), 1.61-1.47 (m, 31H), 1.44-1.39 (m, 8H), 1.35-1.31 (m, 6H), 1.24 (s, 3H).

Example 12 N—((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-benzofuran-2-carboxamide (A12)

1H NMR (500 MHz, Chloroform) δ 8.31 (s, 4H), 7.60 (s, 4H), 7.49 (s, 4H), 7.40 (s, 4H), 7.21 (s, 4H), 7.15 (s, 4H), 6.18 (s, 4H), 5.46 (s, 4H), 5.25 (s, 4H), 5.12 (s, 4H), 4.63 (s, 4H), 3.43 (d, J=18.9 Hz, 8H), 3.35 (s, 3H), 3.11 (s, 4H), 2.76 (s, 4H), 2.17 (s, 3H), 2.13-2.01 (m, 8H), 1.93 (s, 4H), 1.85-1.81 (m, 6H), 1.73-1.69 (m, 7H), 1.69-1.62 (m, 7H), 1.61-1.42 (m, 16H), 1.33-1.29 (m, 6H), 1.26 (s, 3H), 1.14-1.10 (m, 3H).

Example 13 N—((S)-1-((((S)-4-(benzylamino)-3,4-dione-1-((S)-2-oxopiperidine-3-yl)but-2-yl)amino)-3-cyclohexyl-1-oxopropan-2-yl)-benzofuran-2-carboxamide (A13)

1H NMR (500 MHz, Chloroform) δ 7.59 (s, 4H), 7.51 (d, J=1.4 Hz, 1H), 7.46 (d, J=36.6 Hz, 7H), 7.32-7.14 (m, 29H), 6.56 (s, 4H), 5.75 (s, 4H), 5.66 (s, 4H), 5.09 (s, 4H), 4.56 (s, 4H), 4.41 (s, 4H), 4.32 (s, 4H), 3.24 (d, J=17.0 Hz, 8H), 2.32 (s, 4H), 2.10-2.02 (m, 9H), 1.99 (s, 4H), 1.97-1.89 (m, 8H), 1.79 (s, 4H), 1.75-1.52 (m, 28H), 1.40-1.36 (m, 7H), 1.32 (s, 4H), 1.23-1.19 (m, 8H), 1.16 (s, 3H).

Example 14 N—((S)-1-((((S)-4-(tert-butylamino)-3,4-dione-1-((S)-2-oxopiperidine-3-yl)but-2-yl)amino)-3-cyclohexyl-1-oxopropan-2-yl)-benzofuran-2-carboxamide (A14)

1H NMR (500 MHz, Chloroform) δ 7.63 (s, 1H), 7.50 (s, 1H), 7.37 (s, 1H), 7.22 (s, 1H), 7.16 (s, 1H), 6.25 (s, 1H), 6.08 (s, 1H), 5.76 (s, 1H), 4.70 (d, J=19.7 Hz, 2H), 3.24 (d, J=14.7 Hz, 2H), 2.83 (s, 1H), 2.08-2.04 (m, 2H), 2.01 (s, 1H), 1.90 (s, 1H), 1.85-1.78 (m, 3H), 1.75-1.64 (m, 5H), 1.56-1.41 (m, 6H), 1.32 (s, 1H), 1.25-1.21 (m, 9H).

Example 15 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-benzofuran-2-carboxamide (A15)

1H NMR (500 MHz, Chloroform) δ 9.45 (s, 1H), 8.16 (s, 1H), 7.51 (s, 1H), 7.42 (s, 1H), 7.22 (s, 1H), 7.16 (s, 1H), 6.16 (s, 1H), 6.07 (s, 1H), 5.85 (s, 1H), 5.08 (s, 1H), 4.48 (s, 1H), 3.32 (s, 1H), 3.24 (d, J=16.1 Hz, 2H), 2.92 (s, 1H), 2.16-2.08 (m, 2H), 2.08-2.04 (m, 2H), 2.02 (s, 1H), 1.80 (s, 1H), 1.76-1.66 (m, 8H), 1.65 (s, 1H), 1.57 (s, 1H), 1.55-1.40 (m, 8H), 1.40-1.37 (m, 1H), 1.31 (s, 1H), 1.12 (s, 1H), 0.90-0.82 (m, 2H).

Example 16 N—((S)-3-cyclohexyl-1-((((S)-4-(neopentylamino)-3,4-dione-1-((S)-2-oxopiperidine-3-yl)but-2-yl)amino)-3-cyclohexyl-1-oxopropan-2-yl)-benzofuran-2-carboxamide (A16)

1 1H NMR (500 MHz, Chloroform) δ 7.60 (s, 1H), 7.49 (s, 1H), 7.40 (s, 1H), 7.21 (s, 1H), 7.15 (s, 1H), 6.20 (s, 1H)), 5.99 (s, 1H), 5.91 (s, 1H), 5.65 (s, 1H), 4.86 (s, 1H), 4.76 (s, 1H), 3.30 (s, 1H), 3.24 (d, J=17.4 Hz, 2H), 2.92 (s, 1H), 2.65 (s, 1H), 2.08-2.04 (m, 2H), 2.01 (s, 1H), 1.90-1.84 (m, 2H), 1.82 (s, 1H)), 1.77-1.65 (m, 5H), 1.60-1.53 (m, 4H), 1.52-1.48 (m, 2H), 1.40 (s, 1H), 1.34 (s, 1H), 1.07-1.03 (m, 9H).

Example 17 N—((S)-1-((((S)-4-(benzylamino)-3,4-dione-1-((S)-2-oxopyrrolidine-3-yl)but-2-yl)amino)-3-cyclohexyl-1-oxopropan-2-yl)-benzothiophene-2-carboxamide (A17)

1H NMR (500 MHz, Chloroform) δ 8.13 (s, 5H), 7.89 (s, 5H), 7.65 (s, 5H), 7.28 (dd, J=7.5, 4.2 Hz, 20H), 7.21 (dd, J=4.2, 2.6 Hz, 2H), 7.20-7.08 (m, 13H), 6.14 (s, 5H), 5.53 (s, 5H), 5.37 (s, 5H), 4.39-4.32 (m, 15H), 4.24 (s, 5H), 3.45 (s, 5H), 3.35 (s, 4H), 3.24 (s, 5H), 2.94 (s, 4H), 2.19 (s, 4H), 2.09-2.05 (m, 10H), 1.92 (s, 4H), 1.80-1.67 (m, 25H), 1.59-1.49 (m, 15H), 1.46-1.38 (m, 19H), 1.23 (s, 5H).

Example 18 N—((S)-1-((((S)-4-(tert-butylamino)-3,4-dione-1-((S)-2-oxopyrrolidine-3-yl)but-2-yl)amino)-3-cyclohexyl-1-oxopropan-2-yl)-benzothiophene-2-carboxamide (A18)

1H NMR (500 MHz, Chloroform) δ 8.37 (s, 1H), 7.89 (s, 1H), 7.73 (s, 1H), 7.31 (d, J=1.5 Hz, 2H), 6.28 (s, 1H), 6.05 (s, 1H), 5.80 (s, 1H), 5.25 (s, 1H), 4.82 (s, 1H), 4.68 (s, 1H), 3.45 (s, 1H), 3.35 (s, 1H), 2.56 (s, 1H), 2.18 (s, 1H), 2.09-2.05 (m, 2H), 1.95-1.88 (m, 3H), 1.73-1.52 (m, 5H), 1.41-1.37 (m, 2H), 1.35-1.29 (m, 10H), 1.18-1.09 (m, 3H).

Example 19 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-benzothiophene-2-carboxamide (A19)

1H NMR (500 MHz, Chloroform) δ 8.95 (s, 1H), 8.43 (s, 1H), 8.26 (s, 1H), 7.90 (s, 1H), 7.74 (s, 1H), 7.61 (s, 1H), 7.31 (d, J=2.0 Hz, 2H), 5.94 (s, 1H), 4.69 (s, 1H), 4.53 (s, 1H), 3.44 (d, J=9.6 Hz, 2H), 3.35 (s, 1H), 2.95 (s, 1H), 2.19 (s, 1H), 2.09-2.05 (m, 2H), 1.91 (t, J=7.7 Hz, 3H), 1.75-1.68 (m, 5H), 1.68-1.63 (m, 2H), 1.62-1.58 (m, 2H), 1.58-1.46 (m, 8H), 1.45-1.40 (m, 2H), 1.22-1.14 (m, 2H), 1.07 (s, 1H).

Example 20 N—((S)-3-cyclohexyl-1-(((S)-4-(neopentylamino)-3,4-dione-1-((S)-2-oxopyrrolidine-3-yl)but-2-yl)amino)-3-cyclohexyl-1-oxopropan-2-yl)-benzothiophene-2-carboxamide (A20)

1H NMR (500 MHz, Chloroform) δ 8.36 (s, 1H), 7.88 (s, 1H), 7.73 (s, 1H), 7.30 (d, J=2.5 Hz, 2H), 6.53 (s, 1H), 6.04 (s, 1H), 5.82 (s, 1H), 5.52 (s, 1H), 4.68 (d, J=6.4 Hz, 2H), 3.45 (s, 1H), 3.35 (d, J=3.1 Hz, 2H), 2.90 (s, 1H), 2.43 (s, 1H), 2.19 (s, 1H), 2.09-2.05 (m, 2H), 1.91 (t, J=5.9 Hz, 3H), 1.74-1.65 (m, 4H), 1.60-1.51 (m, 6H), 1.34 (s, 1H), 1.08-1.04 (m, 9H).

Example 21 N—((S)-1-((((S)-4-(benzylamino)-3,4-dione-1-((S)-2-oxopiperidine-3-yl)but-2-yl)amino)-3-cyclohexyl-1-oxopropan-2-yl)-benzothiophene-2-carboxamide (A21)

1H NMR (500 MHz, Chloroform) δ 8.31 (s, 1H), 7.92 (s, 1H), 7.74 (s, 1H), 7.34-7.23 (m, 6H), 7.20 (s, 1H), 6.76 (s, 1H), 5.59 (s, 1H), 5.49 (s, 1H), 5.08 (s, 1H), 4.52 (s, 1H), 4.42 (s, 1H), 4.34 (s, 1H), 3.24 (d, J=17.6 Hz, 2H), 2.68 (s, 1H), 2.08-2.04 (m, 2H), 1.74-1.67 (m, 5H), 1.64 (dd, J=2.9, 1.7 Hz, 4H), 1.36-1.32 (m, 2H), 1.30 (s, 1H), 1.26 (s, 1H), 1.17 (s, 1H), 1.13-1.05 (m, 2H), 0.98 (s, 1H).

Example 22 N—((S)-1-((((S)-4-(tert-butylamino)-3,4-dione-1-((S)-2-oxopiperidine-3-yl)but-2-yl)amino)-3-cyclohexyl-1-oxopropan-2-yl)-benzothiophene-2-carboxamide (A22)

1H NMR (500 MHz, Chloroform) δ 8.34 (s, 1H), 8.22 (s, 1H), 7.88 (s, 1H), 7.72 (s, 1H), 7.30 (d, J=1.5 Hz, 2H), 6.15 (s, 1H), 6.10 (s, 1H), 5.41 (s, 1H), 4.64 (d, J=11.7 Hz, 2H), 3.24 (d, J=14.8 Hz, 2H), 2.90 (s, 1H), 2.11-2.01 (m, 2H), 1.89-1.81 (m, 4H), 1.77 (s, 1H), 1.73-1.68 (m, 4H), 1.66-1.59 (m, 5H), 1.55-1.49 (m, 2H), 1.35 (s, 1H), 1.32-1.28 (m, 9H).

Example 23 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-benzothiophene-2-carboxamide (A23)

1H NMR (500 MHz, Chloroform) δ 8.93 (s, 1H), 8.55 (s, 1H), 7.91 (s, 1H), 7.72 (s, 1H), 7.30 (d, J=2.6 Hz, 2H), 6.05 (s, 1H), 5.83 (s, 1H), 5.68 (s, 1H), 5.13 (s, 1H), 4.34 (s, 1H), 3.33 (s, 1H), 3.24 (d, J=15.0 Hz, 2H), 2.73 (s, 1H), 2.43 (s, 1H), 2.08-2.04 (m, 5H), 1.85 (s, 1H), 1.78 (s, 1H), 1.73-1.67 (m, 5H), 1.66-1.52 (m, 7H), 1.51 (s, 2H), 1.44-1.39 (m, 3H), 1.34-1.30 (m, 2H), 1.27 (s, 1H), 0.83-0.72 (m, 2H).

Example 24 N—((S)-1-(((S)-4-(benzylamino)-3,4-dione-1-((S)-2-oxopyrrolidine-3-yl)but-2-yl)amino)-3-cyclohexyl-1-oxopropan-2-yl)-1-methyl-1H-indole-2-carboxamide (A24)

1H NMR (500 MHz, Chloroform) δ 7.61 (s, 2H), 7.40-7.26 (m, 10H), 7.18 (dd, J=24.7, 8.9 Hz, 9H), 6.51 (s, 2H), 6.14 (s, 2H), 5.17 (s, 2H), 4.61 (s, 2H), 4.40 (s, 2H), 4.27 (s, 2H), 4.19 (s, 2H), 3.60-3.56 (m, 6H), 3.52 (s, 2H), 3.45 (s, 2H), 3.35 (s, 2H), 2.87 (s, 2H), 2.18 (s, 2H), 2.09-2.05 (m, 4H), 1.92 (s, 2H), 1.73-1.69 (m, 4H), 1.60-1.50 (m, 11H), 1.36-1.32 (m, 3H), 1.18 (s, 2H), 1.07-1.03 (m, 3H).

Example 25 N—((S)-1-((((S)-4-(tert-butylamino)-3,4-dione-1-((S)-2-oxopyrrolidine-3-yl)but-2-yl)amino)-3-cyclohexyl-1-oxopropan-2-yl)-1-methyl-1H-indole-2-carboxamide (A25)

1H NMR (500 MHz, Chloroform) δ 7.40 (s, 1H), 7.27 (d, J=5.4 Hz, 2H), 7.18 (d, J=11.2 Hz, 2H), 6.05 (d, J=0.5 Hz, 2H), 5.79 (s, 1H), 5.25 (s, 1H), 4.80 (s, 1H), 4.65 (s, 1H), 3.88-3.84 (m, 3H), 3.45 (s, 1H), 3.35 (s, 1H), 2.58 (s, 1H), 2.18 (s, 1H), 2.09-2.05 (m, 2H), 1.95-1.91 (m, 3H), 1.73-1.52 (m, 5H), 1.41-1.37 (m, 2H), 1.35-1.29 (m, 10H), 1.19-1.09 (m, 3H).

Example 26 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-1-methyl-1H-indole-2-carboxamide (A26)

1H NMR (500 MHz, Chloroform) δ 7.24 (s, 1H), 7.17 (s, 1H), 7.12 (d, J=0.8 Hz, 2H), 7.05 (s, 1H), 6.01 (s, 1H), 5.68 (d, J=17.0 Hz, 2H), 4.92 (s, 1H), 4.81 (s, 1H), 3.98 (s, 1H), 3.81 (s, 1H), 3.74-3.70 (m, 3H), 3.35 (s, 1H), 2.62 (s, 1H), 2.19 (s, 1H), 2.09-2.05 (m, 2H), 1.95-1.91 (m, 3H), 1.90-1.77 (m, 4H), 1.73-1.69 (m, 2H), 1.66-1.54 (m, 13H), 1.39-1.35 (m, 2H), 1.33 (s, 1H).

Example 27 N—((S)-1-((((S)-4-(benzylamino)-3,4-dione-1-((S)-2-oxopiperidine-3-yl)but-2-yl)amino)-3-cyclohexyl-1-oxopropan-2-yl)-1-methyl-1H-indole-2-carboxamide (A27)

1H NMR (500 MHz, Chloroform) δ 7.43 (s, 1H), 7.38-7.24 (m, 7H), 7.20 (d, J=8.0 Hz, 2H), 5.93 (s, 1H), 5.87 (s, 1H), 5.57 (s, 1H), 5.47 (s, 1H), 4.73 (s, 1H), 4.55 (s, 1H), 4.39 (d, J=18.9 Hz, 2H), 3.61-3.57 (m, 3H), 3.23 (d, J=15.5 Hz, 2H), 2.08-2.04 (m, 2H), 1.96-1.92 (m, 3H), 1.85 (s, 1H), 1.73-1.64 (m, 6H), 1.61 (s, 1H), 1.41 (t, J=7.7 Hz, 3H), 1.32 (s, 1H), 1.24 (s, 1H), 1.14-1.07 (m, 2H).

Example 28 N—((S)-1-((((S)-4-(tert-butylamino)-3,4-dione-1-((S)-2-oxopiperidine-3-yl)but-2-yl)amino)-3-cyclohexyl-1-oxopropan-2-yl)-1-methyl-1H-indole-2-carboxamide (A28)

1H NMR (500 MHz, Chloroform) δ 7.46 (s, 47H), 7.26 (d, J=19.3 Hz, 98H), 7.17 (d, J=7.3 Hz, 95H), 6.39 (s, 47H), 5.92 (d, J=11.5 Hz, 95H), 5.44 (s, 47H), 4.71 (s, 46H), 4.53 (s, 46H), 3.74-3.70 (m, 141H), 3.24 (d, J=18.1 Hz, 90H), 2.77 (s, 44H), 2.11-2.01 (m, 97H), 1.91 (s, 34H), 1.81 (s, 43H), 1.77-1.69 (m, 222H), 1.66-1.62 (m, 70H), 1.61-1.42 (m, 241H), 1.49-1.42 (m, 10H), 1.40-1.36 (m, 70H), 1.32-1.22 (m, 478H).

Example 29 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-1-methyl-1H-indole-2-carboxamide (A29)

1H NMR (500 MHz, Chloroform) δ 7.41 (s, 1H), 7.35-7.22 (m, 2H), 7.19 (d, J=7.5 Hz, 2H), 5.92 (s, 1H), 5.54 (s, 1H), 5.38 (s, 1H), 5.23 (s, 1H), 5.04 (s, 1H), 4.34 (s, 1H), 3.99-3.95 (m, 3H), 3.86 (s, 1H), 3.24 (d, J=15.7 Hz, 2H), 2.86 (s, 1H), 2.08-2.02 (m, 4H), 1.99 (s, 1H), 1.81 (s, 1H), 1.78-1.67 (m, 7H), 1.66-1.51 (m, 10H), 1.43 (s, 1H), 1.41-1.37 (m, 2H), 1.30 (s, 1H), 0.77-0.70 (m, 2H).

Example 30 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-1-methyl-1H-indole-2-carboxamide (A30)

1H NMR (500 MHz, Chloroform) δ 7.87 (s, 1H), 7.29 (t, J=9.9 Hz, 3H), 7.22-7.11 (m, 2H), 6.98 (s, 1H), 6.61 (s, 1H), 6.43 (s, 1H), 6.20 (s, 1H), 5.62 (s, 1H), 4.55 (s, 1H), 4.43 (d, J=15.9 Hz, 2H), 4.32 (s, 1H), 3.45 (s, 1H), 3.35 (s, 1H), 3.12 (s, 1H), 2.33 (s, 1H), 2.18 (s, 1H), 2.09-2.05 (m, 2H), 1.94-1.88 (m, 3H), 1.74-1.66 (m, 4H), 1.63-1.55 (m, 6H), 1.35 (s, 1H).

Example 31 N—((S)-1-((((S)-4-(benzylamino)-3,4-dione-1-((S)-2-oxopyrrolidine-3-yl)but-2-yl)amino)-3-cyclohexyl-1-oxopropan-2-yl)-4,6-dichloro-1H-indole-2-carboxamide (A31)

1H NMR (500 MHz, Chloroform) δ 9.04 (s, 1H), 8.68 (s, 1H), 8.53 (s, 1H), 7.42 (s, 1H), 7.38 (s, 1H), 7.06 (s, 1H), 6.78 (s, 1H), 5.77 (s, 1H), 4.93 (s, 1H), 4.55 (s, 1H), 3.99 (s, 1H), 3.35 (s, 1H), 2.63 (s, 1H), 2.19 (s, 1H), 2.10-2.04 (m, 4H), 1.93 (s, 1H), 1.69 (dt, J=18.2, 9.1 Hz, 5H), 1.41-1.37 (m, 2H), 1.35-1.27 (m, 11H), 1.24 (s, 1H), 1.05-1.01 (m, 2H).

Example 32 N—((S)-1-(((S)-4-(tert-butylamino)-3, 4-dione-1-((S)-2-oxopyrrolidine-3-yl)but-2-yl) amino)-3-cyclohexyl-1-oxopropan-2-yl)-4,6-dichloro-1H-indole-2-carboxamide (A32)

1H NMR (500 MHz, Chloroform) δ 8.86 (s, 1H), 8.48 (s, 1H), 7.54 (s, 1H), 7.41 (s, 1H), 7.06 (s, 1H), 6.01 (s, 1H), 5.47 (s, 1H), 5.20 (s, 1H), 5.05 (s, 1H), 4.55 (s, 1H), 4.00 (s, 1H), 3.58 (s, 1H), 3.51 (s, 1H), 3.35 (s, 1H), 2.19 (s, 1H), 2.12-2.02 (m, 2H), 2.00-1.96 (m, 2H), 1.94-1.87 (m, 3H), 1.73-1.46 (m, 14H), 1.40-1.36 (m, 2H), 1.32 (s, 1H), 1.12-1.06 (m, 3H).

Example 33 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-4,6-dichloro-1H-indole-2-carboxamide (A33)

1H NMR (500 MHz, Chloroform) δ 8.68 (s, 11H), 7.45 (s, 11H), 7.38 (s, 11H), 7.31-7.23 (m, 34H), 7.23-7.17 (m, 26H), 7.16 (s, 8H), 7.11 (s, 11H), 5.89 (s, 11H), 5.79 (s, 11H), 4.76 (s, 11H), 4.51 (s, 11H), 4.35 (s, 11H), 4.29 (s, 11H), 3.24 (d, J=17.5 Hz, 21H), 2.73 (s, 11H), 2.10-2.04 (m, 23H), 2.02 (s, 9H), 1.83 (s, 10H), 1.81-1.74 (m, 33H), 1.73-1.65 (m, 23H), 1.65-1.50 (m, 45H), 1.52 (d, J=5.6 Hz, 2H), 1.34-1.30 (m, 19H), 1.28 (s, 11H), 0.99-0.93 (m, 32H).

Example 34 N—((S)-1-((((S)-4-(benzylamino)-3,4-dione-1-((S)-2-oxopiperidine-3-yl)but-2-yl)amino)-3-cyclohexyl-1-oxopropan-2-yl)-4,6-dichloro-1H-indole-2-carboxamide (A34)

1H NMR (500 MHz, Chloroform) δ 8.35 (s, 1H), 7.62 (s, 1H), 7.39 (s, 1H), 7.05 (s, 1H), 6.43 (s, 1H), 5.97 (s, 1H), 5.59 (s, 1H), 5.50 (d, J=15.7 Hz, 2H), 4.67 (s, 1H), 3.24 (d, J=17.3 Hz, 2H), 2.48 (s, 1H), 2.08-2.04 (m, 2H), 1.87 (t, J=9.6 Hz, 3H), 1.78 (s, 1H), 1.72 (dd, J=8.3, 4.2 Hz, 4H), 1.67 (s, 1H), 1.65-1.50 (m, 6H), 1.45 (s, 1H), 1.36-1.28 (m, 10H).

Example 35 N—((S)-1-((((S)-4-(tert-butylamino)-3, 4-dione-1-((S)-2-oxopiperidine-3-yl)but-2-yl) amino)-3-cyclohexyl-1-oxopropan-2-yl)-4,6-dichloro-1H-indole-2-carboxamide (A35)

1H NMR (500 MHz, Chloroform) δ 8.51 (s, 1H), 8.33 (s, 1H), 8.28 (s, 1H), 7.42 (s, 1H), 7.07 (s, 1H), 6.66 (s, 1H), 6.41 (s, 1H), 5.86 (s, 1H), 5.04 (s, 1H), 4.52 (s, 1H), 3.32 (s, 1H), 3.24 (d, J=16.6 Hz, 2H), 2.97 (s, 1H), 2.16-2.01 (m, 5H), 2.01-1.92 (m, 2H), 1.82 (s, 1H), 1.78-1.69 (m, 8H), 1.65 (d, J=15.4 Hz, 2H), 1.56-1.46 (m, 3H), 1.44-1.40 (m, 4H), 1.32 (s, 1H), 1.17 (s, 1H), 1.07-1.00 (m, 2H).

Example 36 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-4,6-dichloro-1H-indole-2-carboxamide (A36)

1H NMR (500 MHz, Chloroform) δ 8.98 (s, 1H), 8.03 (d, J=1.1 Hz, 2H), 7.63 (d, J=5.1 Hz, 2H), 7.37-7.27 (m, 4H), 7.21 (s, 1H), 6.95 (s, 1H), 6.43 (s, 1H), 6.01 (s, 1H), 4.94 (s, 1H), 4.85 (s, 1H), 4.67 (s, 1H), 4.41 (s, 1H), 4.32 (s, 1H), 3.45 (s, 1H), 3.35 (s, 1H), 2.77 (s, 1H), 2.19 (s, 1H), 2.13-2.01 (m, 2H), 1.89 (s, 1H), 1.83-1.74 (m, 2H), 1.74-1.69 (m, 2H), 1.66 (d, J=5.7 Hz, 2H), 1.58-1.49 (m, 6H), 1.31 (s, 1H).

Example 37 N—((S)-1-(((S)-4-(benzylamino)-3,4-dione-1-((S)-2-oxopyrrolidine-3-yl)but-2-yl)amino)-3-cyclohexyl-1-oxopropan-2-yl)-quinoxaline-2-carboxamide (A37)

1H NMR (500 MHz, Chloroform) δ 9.39 (s, 1H), 8.47 (s, 1H), 8.11 (s, 1H), 7.62 (d, J=3.2 Hz, 2H), 6.17 (d, J=6.0 Hz, 2H), 5.59 (s, 1H), 5.27 (s, 1H), 4.98 (s, 1H), 4.91 (s, 1H), 3.45 (s, 1H), 3.35 (s, 1H), 2.51 (s, 1H), 2.19 (s, 1H), 2.09-2.05 (m, 2H), 1.98-1.95 (m, 2H), 1.92 (s, 1H), 1.73-1.61 (m, 5H), 1.41-1.37 (m, 2H), 1.34-1.28 (m, 10H), 1.21-1.11 (m, 3H).

Example 38 N—((S)-1-(((S)-4-(tert-butylamino)-3, 4-dione-1-((S)-2-oxopyrrolidine-3-yl)but-2-yl) amino)-3-cyclohexyl-1-oxopropan-2-yl)-quinoxaline-2-carboxamide (A38)

1H NMR (500 MHz, Chloroform) δ 9.09 (s, 1H), 8.31 (s, 1H), 8.03 (d, J=4.8 Hz, 2H), 7.61 (d, J=2.2 Hz, 2H), 6.41 (s, 1H), 6.06 (s, 1H), 5.27 (s, 1H), 5.20 (s, 1H), 4.45 (s, 1H), 3.72 (s, 1H), 3.45 (s, 1H), 3.35 (s, 1H), 2.73 (s, 1H), 2.39-2.31 (m, 2H), 2.19 (s, 1H), 2.09-2.05 (m, 2H), 1.92 (s, 1H), 1.76-1.56 (m, 15H), 1.55-1.45 (m, 6H), 1.30 (s, 1H).

Example 39 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-quinoxaline-2-carboxamide (A39)

1H NMR (500 MHz, Chloroform) δ 9.55 (s, 1H), 9.32 (s, 1H), 8.12 (s, 1H), 7.96 (s, 1H), 7.64 (d, J=11.6 Hz, 2H), 7.29-7.22 (m, 4H), 7.19 (s, 1H), 6.56 (s, 1H), 6.06 (s, 1H), 5.63 (s, 1H), 5.02 (s, 1H), 4.71 (s, 1H), 4.41 (s, 1H), 4.31 (s, 1H), 3.24 (d, J=17.3 Hz, 2H), 2.37 (s, 1H), 2.10-2.02 (m, 2H), 2.02-1.96 (m, 3H), 1.82 (s, 1H), 1.72 (t, J=9.8 Hz, 3H), 1.69-1.57 (m, 3H), 1.53 (s, 1H), 1.38-1.34 (m, 2H), 1.31 (s, 1H), 1.13-1.04 (m, 3H).

Example 40 N—((S)-1-(((S)-4-(benzylamino)-3,4-dione-1-((S)-2-oxopiperidine-3-yl)but-2-yl)amino)-3-cyclohexyl-1-oxopropan-2-yl)-quinoxaline-2-carboxamide (A40)

1H NMR (500 MHz, Chloroform) δ 9.29 (s, 1H), 8.16 (s, 1H), 8.11 (s, 1H), 7.65 (d, J=4.6 Hz, 2H), 7.22 (s, 1H), 5.87 (d, J=8.3 Hz, 2H), 5.65 (s, 1H), 4.94 (s, 1H), 4.46 (s, 1H), 3.24 (d, J=14.8 Hz, 2H), 2.72 (s, 1H), 2.11-2.01 (m, 2H), 1.79 (d, J=1.0 Hz, 2H), 1.76-1.62 (m, 5H), 1.59 (s, 1H), 1.49-1.42 (m, 4H), 1.35-1.28 (m, 11H), 1.25 (s, 1H), 1.21-1.15 (m, 2H).

Example 41 N—((S)-1-((((S)-4-(tert-butylamino)-3, 4-dione-1-((S)-2-oxopiperidine-3-yl)but-2-yl) amino)-3-cyclohexyl-1-oxopropan-2-yl)-quinoxaline-2-carboxamide (A41)

1H NMR (500 MHz, Chloroform) δ 9.64 (s, 4H), 8.11 (d, J=10.4 Hz, 8H), 7.65 (d, J=1.9 Hz, 8H), 6.00 (s, 4H), 5.76 (s, 4H), 5.70 (s, 4H), 5.64 (s, 4H), 5.04 (s, 4H), 4.45 (s, 4H), 3.86 (s, 4H), 3.24 (d, J=17.3 Hz, 8H), 2.85 (s, 4H), 2.11-2.01 (m, 9H), 1.99-1.91 (m, 12H), 1.91-1.80 (m, 9H), 1.75 (s, 2H), 1.75-1.53 (m, 62H), 1.55-1.53 (m, 1H), 1.51 (s, 3H), 1.38-1.34 (m, 7H), 1.30 (s, 4H), 1.06 (s, 3H), 1.03-0.99 (m, 8H).

Example 42 N—((S)-1-(((S)-4-(benzylamino)-3,4-dione-1-((S)-2-oxopyrrolidine-3-yl)but-2-yl)amino)-3-cyclohexyl-1-oxopropan-2-yl)-quinoline-2-carboxamide (A42)

1H NMR (500 MHz, Chloroform) δ 8.56 (s, 1H), 8.19 (s, 1H), 7.82 (s, 1H), 7.58 (s, 1H), 7.42 (s, 1H), 7.42-7.28 (m, 5H), 7.21 (s, 1H), 6.00 (d, J=2.7 Hz, 2H), 4.43 (s, 1H), 4.33 (s, 1H), 4.11 (s, 1H), 3.83 (d, J=3.7 Hz, 2H), 3.45 (s, 1H), 3.35 (s, 1H), 3.25 (s, 1H), 2.15 (s, 1H), 2.09-2.05 (m, 2H), 1.91 (s, 1H), 1.73-1.69 (m, 2H), 1.62-1.55 (m, 3H), 1.36-1.27 (m, 6H), 1.23 (s, 1H), 1.20-1.14 (m, 2H).

Example 43 N—((S)-1-((((S)-4-(tert-butylamino)-3,4-dione-1-((S)-2-oxopyrrolidine-3-yl)but-2-yl)amino)-3-cyclohexyl-1-oxopropan-2-yl)-quinoline-2-carboxamide (A43)

1H NMR (500 MHz, Chloroform) δ 9.34 (s, 1H), 8.46 (s, 1H), 8.17 (s, 1H), 7.82 (s, 1H), 7.72 (s, 1H), 7.55 (s, 1H), 7.50 (s, 1H), 5.96 (s, 1H), 5.84 (s, 1H), 5.40 (s, 1H), 5.22 (s, 1H), 4.77 (s, 1H), 3.45 (s, 1H), 3.35 (s, 1H), 2.83 (s, 1H), 2.18 (s, 1H), 2.09-2.05 (m, 2H), 1.94-1.81 (m, 3H), 1.73-1.63 (m, 5H), 1.40-1.36 (m, 2H), 1.36-1.27 (m, 10H), 1.18 (s, 1H), 1.14-1.10 (m, 2H).

Example 44 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopropan-2-yl)-quinoline-2-carboxamide (A44)

1H NMR (500 MHz, Chloroform) δ 8.47 (s, 1H), 8.24 (s, 1H), 8.06 (s, 1H), 7.73 (s, 1H), 7.65 (s, 1H), 7.43 (d, J=13.7 Hz, 2H), 6.58 (s, 1H), 6.06 (s, 1H), 5.40 (s, 1H), 5.20 (s, 1H), 4.45 (s, 1H), 3.73 (s, 1H), 3.45 (s, 1H), 3.35 (s, 1H), 2.72 (s, 1H), 2.34-2.30 (m, 2H), 2.19 (s, 1H), 2.09-2.05 (m, 2H), 1.92 (s, 1H), 1.77-1.56 (m, 15H), 1.55-1.46 (m, 6H), 1.30 (s, 1H).

Example 45 N—((S)-1-((((S)-4-(benzylamino)-3,4-dione-1-((S)-2-oxopiperidine-3-yl)but-2-yl)amino)-3-cyclohexyl-1-oxopropan-2-yl)-quinoline-2-carboxamide (A45)

1H NMR (500 MHz, Chloroform) δ 8.42 (s, 1H), 8.15 (s, 1H), 7.79 (s, 1H), 7.69 (s, 1H), 7.47 (s, 1H), 7.42 (s, 1H), 7.34-7.25 (m, 4H), 7.20 (s, 1H), 6.77 (s, 1H), 5.89 (s, 1H), 5.82 (s, 1H), 5.57 (d, J=7.5 Hz, 2H), 4.42 (d, J=5.7 Hz, 2H), 4.34 (s, 1H), 3.24 (d, J=19.0 Hz, 2H), 2.81 (s, 1H), 2.43 (s, 1H), 2.11-2.01 (m, 2H), 1.95 (s, 1H), 1.86 (s, 1H), 1.81-1.74 (m, 3H), 1.69 (dt, J=17.1, 8.6 Hz, 5H), 1.47 (s, 1H), 1.41-1.37 (m, 2H), 1.31 (s, 1H), 0.84-0.77 (m, 2H).

Example 46 N—((S)-1-((((S)-4-(tert-butylamino)-3,4-dione-1-((S)-2-oxopiperidine-3-yl)but-2-yl)amino)-3-cyclohexyl-1-oxopropan-2-yl)-quinoline-2-carboxamide (A46)

1H NMR (500 MHz, Chloroform) δ 8.46 (s, 3H), 8.13 (s, 3H), 7.79 (s, 3H), 7.69 (d, J=0.8 Hz, 6H), 7.44 (d, J=32.8 Hz, 6H), 6.55 (s, 3H), 6.05 (s, 3H), 5.75 (s, 3H), 4.77 (d, J=2.1 Hz, 6H), 3.25 (s, 3H), 3.21 (s, 3H), 2.70 (s, 3H), 2.11-2.01 (m, 6H), 1.96-1.87 (m, 6H), 1.79 (d, J=13.1 Hz, 5H), 1.70 (dt, J=19.3, 3.5 Hz, 19H), 1.60-1.51 (m, 18H), 1.35-1.30 (m, 30H).

Example 47 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopropan-2-yl)-quinoline-2-carboxamide (A47)

1H NMR (500 MHz, Chloroform) δ 9.06 (s, 3H), 8.44 (s, 3H), 8.15 (s, 3H), 7.79 (s, 3H), 7.75 (s, 3H), 7.70 (s, 3H), 7.48 (d, J=8.2 Hz, 6H), 7.38 (s, 3H), 5.73 (s, 3H), 4.96 (s, 3H), 4.57 (s, 3H), 3.90 (s, 3H), 3.24 (d, J=14.7 Hz, 6H), 2.92 (s, 3H), 2.15-2.11 (m, 5H), 2.11-2.01 (m, 9H), 1.99 (t, J=7.9 Hz, 7H), 1.80 (s, 2H), 1.76-1.65 (m, 18H), 1.65-1.58 (m, 24H), 1.45 (t, J=13.5 Hz, 10H), 1.36 (dd, J=21.5, 15.7 Hz, 2H), 1.33 (s, 3H), 1.20 (s, 2H), 1.11-1.04 (m, 6H).

Example 48 N—((S)-1-(((S)-4-(benzylamino)-3,4-dione-1-((S)-2-oxopyrrolidine-3-yl)but-2-yl)amino)-1-oxo-3-phenylpropan-2-yl)-1H-indole-2-carboxamide (A48)

1H NMR (500 MHz, Chloroform) δ 8.36 (s, 1H), 7.55 (d, J=12.3 Hz, 2H), 7.34 (t, J=21.8 Hz, 3H), 7.30-7.17 (m, 9H), 7.15 (d, J=2.2 Hz, 2H), 7.09 (s, 1H), 6.35 (s, 1H), 6.01 (s, 1H), 5.67 (s, 1H), 5.03 (s, 1H), 4.88 (s, 1H), 4.37 (s, 1H), 4.30 (s, 1H), 3.45 (s, 1H), 3.35 (s, 1H), 3.15 (d, J=18.6 Hz, 2H), 2.94 (s, 1H), 2.19 (s, 1H), 2.10-2.04 (m, 2H), 1.92 (s, 1H).

Example 49 N—((S)-1-((((S)-4-(tert-butylamino)-3,4-dione-1-((S)-2-oxopyrrolidine-3-yl)but-2-yl)amino)-1-oxo-3-phenylpropan-2-yl)-1H-indole-2-carboxamide (A49)

1H NMR (500 MHz, Chloroform) δ 8.26 (s, 1H), 7.46 (s, 1H), 7.32 (t, J=17.0 Hz, 3H), 7.20 (dd, J=7.8, 5.2 Hz, 4H), 7.12 (s, 1H), 7.06 (s, 1H), 6.01 (s, 1H), 5.57 (s, 1H), 4.84 (s, 1H), 4.69 (s, 1H), 4.53 (s, 1H), 3.45 (s, 1H), 3.41 (s, 1H), 3.35 (s, 1H), 3.30 (s, 1H), 3.19 (s, 1H), 2.96 (s, 1H), 2.16 (s, 1H), 2.13-2.01 (m, 2H), 1.89 (s, 1H), 1.30-1.26 (m, 9H).

Example 50 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-1H-indole-2-carboxamide (A50)

1H NMR (500 MHz, Chloroform) δ 8.35 (s, 1H), 7.90 (s, 1H), 7.52 (d, J=25.5 Hz, 2H), 7.39 (s, 1H), 7.29-7.21 (m, 4H), 7.14 (d, J=3.6 Hz, 2H), 7.08 (s, 1H), 6.52 (s, 1H), 6.16 (s, 1H), 5.70 (s, 1H), 4.92 (s, 1H), 4.78 (s, 1H), 3.46 (d, J=5.2 Hz, 2H), 3.35 (s, 1H), 3.21 (s, 1H), 2.85 (d, J=4.0 Hz, 2H), 2.17 (s, 1H), 2.13-2.02 (m, 2H), 2.00-1.90 (m, 3H), 1.68 (s, 1H), 1.56-1.50 (m, 2H), 1.49-1.45 (m, 3H), 1.44-1.40 (m, 2H).

Example 51 N—((S)-1-(((S)-4-(benzylamino)-3,4-dione-1-((S)-2-oxopiperidine-3-yl)but-2-yl)amino)-1-oxo-3-phenylpropan-2-yl)-1H-indole-2-carboxamide (A51)

1H NMR (500 MHz, Chloroform) δ 8.70 (s, 1H), 7.50 (s, 1H), 7.39-7.20 (m, 5H), 7.20-7.11 (m, 4H), 7.09 (d, J=4.4 Hz, 2H), 7.06-6.94 (m, 2H), 6.90 (s, 1H), 6.19 (s, 1H), 5.93 (s, 1H), 5.51 (s, 1H), 4.70 (s, 1H), 4.25 (d, J=17.1 Hz, 2H), 3.79 (d, J=9.5 Hz, 2H), 3.24 (t, J=8.3 Hz, 3H), 3.04 (s, 1H), 2.16 (s, 1H), 2.12-2.04 (m, 3H), 1.78 (s, 1H), 1.72 (s, 1H), 1.62 (s, 1H).

Example 52 N—((S)-1-((((S)-4-(tert-butylamino)-3,4-dione-1-((S)-2-oxopiperidine-3-yl)but-2-yl)amino)-1-oxo-3-phenylpropan-2-yl)-1H-indole-2-carboxamide (A52)

1H NMR (500 MHz, Chloroform) δ 8.64 (d, J=17.0 Hz, 2H), 8.19 (s, 1H), 7.56 (s, 1H), 7.43 (s, 1H), 7.36-7.27 (m, 2H), 7.27-7.22 (m, 2H), 7.14 (d, J=12.9 Hz, 2H), 7.08 (s, 1H), 5.63 (s, 1H), 5.01 (d, J=14.2 Hz, 2H), 4.78 (d, J=1.3 Hz, 2H), 3.24 (d, J=18.2 Hz, 2H), 3.18 (s, 1H), 3.03 (s, 1H), 2.97 (s, 1H), 2.06 (t, J=3.5 Hz, 3H), 1.94 (s, 1H), 1.88 (s, 1H), 1.81 (s, 1H), 1.21-1.17 (m, 9H).

Example 53 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-1H-indole-2-carboxamide (A53)

1H NMR (500 MHz, Chloroform) δ 8.76 (s, 1H), 7.53 (s, 1H), 7.41 (d, J=25.5 Hz, 2H), 7.27-7.21 (m, 2H), 7.21-7.18 (m, 2H), 7.15 (d, J=7.6 Hz, 2H), 7.08 (s, 1H), 5.95 (s, 1H), 5.61 (s, 1H), 5.25 (s, 1H), 5.14 (s, 1H), 4.78 (s, 1H), 3.42 (s, 1H), 3.25 (t, J=12.6 Hz, 3H), 2.87 (s, 1H), 2.70 (s, 1H), 2.56 (s, 1H), 2.08-2.04 (m, 2H), 2.02-1.90 (m, 2H), 1.87 (s, 1H), 1.80 (s, 1H), 1.68 (d, J=3.3 Hz, 2H), 1.55-1.51 (m, 4H), 1.48 (s, 1H), 1.45-1.39 (m, 2H).

Example 54 N—((S)-1-((((S)-4-(benzylamino)-3,4-dione-1-((S)-2-oxopyrrolidine-3-yl)but-2-yl)amino)-1-oxo-3-phenylpropan-2-yl)-benzofuran-2-carboxamide (A54)

1H NMR (500 MHz, Chloroform) δ 7.51 (d, J=8.2 Hz, 2H), 7.41 (s, 1H), 7.30-7.12 (m, 12H), 6.67 (s, 1H), 5.69-5.61 (m, 3H), 5.09 (s, 1H), 4.88 (s, 1H), 4.41 (s, 1H), 4.33 (s, 1H), 3.45 (s, 1H), 3.35 (s, 1H), 3.26 (s, 1H)), 3.16 (s, 1H), 3.07 (s, 1H), 2.19 (s, 1H), 2.09-2.05 (m, 2H), 1.92 (s, 1H).

Example 55 N—((S)-1-((((S)-4-(tert-butylamino)-3,4-dione-1-((S)-2-oxopyrrolidine-3-yl)but-2-yl)amino)-1-oxo-3-phenylpropan-2-yl)-benzofuran-2-carboxamide (A55)

1H NMR (500 MHz, Chloroform) δ 7.54 (s, 1H), 7.47 (d, J=17.7 Hz, 2H), 7.28-7.22 (m, 3H), 7.18 (dd, J=20.8, 5.2 Hz, 4H), 6.42 (s, 1H), 6.05 (s, 1H), 5.83 (s, 1H), 5.27 (s, 1H), 4.98 (s, 1H), 4.85 (s, 1H), 3.45 (s, 1H), 3.35 (s, 1H), 3.19 (s, 1H), 2.96 (s, 1H), 2.61 (s, 1H), 2.18 (s, 1H), 2.09-2.05 (m, 2H), 1.93 (s, 1H), 1.34-1.30 (m, 9H).

Example 56 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-benzofuran-2-carboxamide (A56)

1H NMR (500 MHz, Chloroform) δ 8.77 (s, 2H), 8.67 (s, 2H), 7.56 (s, 1H), 7.50 (s, 3H), 7.41 (s, 2H), 7.28-7.19 (m, 6H), 7.16 (d, J=4.9 Hz, 4H), 7.13-7.04 (m, 4H), 6.04 (s, 2H), 5.93 (s, 2H), 5.05 (s, 2H), 4.66 (s, 2H)), 3.70 (s, 2H), 3.45 (s, 2H), 3.35 (s, 1H), 3.25 (s, 2H), 3.05 (s, 2H), 2.88 (s, 2H), 2.19 (s, 2H), 2.09-2.05 (m, 4H), 1.97-1.91 (m, 5H), 1.68-1.64 (m, 3H), 1.64-1.43 (m, 13H).

Example 57 N—((S)-1-(((S)-4-(benzylamino)-3,4-dione-1-((S)-2-oxopiperidine-3-yl)but-2-yl)amino)-1-oxo-3-phenylpropan-2-yl)-benzofuran-2-carboxamide (A57)

1H NMR (500 MHz, Chloroform) δ 7.48 (s, 1H), 7.29 (d, J=38.0 Hz, 2H), 7.25 (s, 1H), 7.27-7.19 (m, 3H), 7.19-7.05 (m, 10H), 6.97 (s, 1H), 6.43 (s, 1H), 6.07 (s, 1H), 5.18 (d, J=3.4 Hz, 2H), 4.73 (s, 1H), 4.63 (s, 1H), 4.36 (s, 1H), 4.29 (s, 1H), 3.24 (d, J=16.8 Hz, 2H), 3.10 (s, 1H), 2.86 (d, J=21.8 Hz, 2H), 2.43 (s, 1H), 2.08-2.04 (m, 2H), 1.85 (s, 1H), 1.79 (s, 1H), 1.64 (s, 1H).

Example 58 N—((S)-1-((((S)-4-(tert-butylamino)-3,4-dione-1-((S)-2-oxopiperidine-3-yl)but-2-yl)amino)-1-oxo-3-phenylpropan-2-yl)-benzofuran-2-carboxamide (A58)

1H NMR (500 MHz, Chloroform) δ 9.35 (s, 5H), 7.60 (s, 5H), 7.48 (d, J=29.1 Hz, 10H), 7.28-7.18 (m, 27H), 7.16 (d, J=17.5 Hz, 8H), 5.86 (s, 5H), 5.55 (s, 5H), 4.94 (s, 5H), 4.69 (s, 5H), 3.24 (t, J=10.0 Hz, 14H), 2.90 (s, 5H), 2.66 (s, 5H), 2.09-2.02 (m, 10H), 1.92 (s, 4H), 1.84-1.80 (m, 8H), 1.76 (s, 4H), 1.30-1.26 (m, 44H).

Example 59 N—((S)-1-((((S)-4-(tert-butylamino)-3,4-dione-1-((S)-2-oxopiperidine-3-yl)but-2-yl)amino)-1-oxo-3-phenylpropan-2-yl)-benzofuran-2-carboxamide (A59)

1H NMR (500 MHz, Chloroform) δ 9.35 (s, 5H), 7.60 (s, 5H), 7.48 (d, J=29.1 Hz, 10H), 7.28-7.18 (m, 27H), 7.16 (d, J=17.5 Hz, 8H), 5.86 (s, 5H), 5.55 (s, 5H), 4.94 (s, 5H), 4.69 (s, 5H), 3.24 (t, J=10.0 Hz, 14H), 2.90 (s, 5H), 2.66 (s, 5H), 2.09-2.02 (m, 10H), 1.92 (s, 4H), 1.84-1.80 (m, 8H), 1.76 (s, 4H), 1.30-1.26 (m, 44H).

Example 60 N—((S)-1-(((S)-4-(benzylamino)-3,4-dione-1-((S)-2-oxopyrrolidine-3-yl)but-2-yl)amino)-1-oxo-3-phenylpropan-2-yl)-benzothiophene-2-carboxamide (A60)

1H NMR (500 MHz, Chloroform) δ 8.40 (s, 1H), 7.91 (s, 1H), 7.76 (s, 1H), 7.33 (d, J=3.7 Hz, 2H), 7.32-7.16 (m, 10H), 7.13 (d, J=16.7 Hz, 2H), 6.27 (s, 1H), 5.97 (s, 1H), 5.64 (s, 1H), 5.03 (s, 1H), 4.89 (s, 1H), 4.34 (d, J=4.2 Hz, 2H), 3.45 (s, 1H), 3.35 (s, 1H), 3.15-3.11 (m, 2H), 2.94 (s, 1H), 2.19 (s, 1H), 2.09-2.05 (m, 2H), 1.92 (s, 1H).

Example 61 N—((S)-1-(((S)-4-(tert-butylamino)-3,4-dione-1-((S)-2-oxopyrrolidine-3-yl)but-2-yl)amino)-1-oxo-3-phenylpropan-2-yl)-benzothiophene-2-carboxamide (A61)

1H NMR (500 MHz, Chloroform) δ 8.93 (s, 1H), 7.82 (d, J=4.4 Hz, 2H), 7.28 (dd, J=20.7, 7.2 Hz, 4H), 7.22-7.11 (m, 3H), 6.05 (s, 1H), 4.70 (s, 1H), 4.64 (s, 1H), 4.59 (s, 1H), 4.39 (s, 1H), 3.99 (s, 1H), 3.55 (s, 1H), 3.45 (s, 1H), 3.35 (s, 1H), 3.15 (s, 1H), 2.95 (s, 1H), 2.17 (s, 1H), 2.13-2.02 (m, 2H), 1.89 (s, 1H), 1.21-1.17 (m, 9H).

Example 62 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-benzothiophene-2-carboxamide (A62)

1H NMR (500 MHz, Chloroform) δ 8.73 (s, 1H), 8.54 (s, 1H), 8.35 (s, 1H), 7.91 (s, 1H), 7.74 (s, 1H), 7.32 (d, J=1.5 Hz, 2H), 7.28-7.23 (m, 2H), 7.15 (s, 1H), 7.12-7.05 (m, 2H), 6.14 (s, 1H), 5.94 (s, 1H), 5.04 (s, 1H)), 4.66 (s, 1H), 3.45 (d, J=3.2 Hz, 2H), 3.35 (s, 1H), 3.26 (s, 1H), 3.05 (s, 1H), 2.89 (s, 1H), 2.19 (s, 1H), 2.09-2.05 (m, 2H), 1.95-1.91 (m, 3H), 1.73-1.64 (m, 3H), 1.56-1.52 (m, 2H), 1.50 (s, 1H), 1.46-1.40 (m, 2H).

Example 63 N—((S)-1-(((S)-4-(benzylamino)-3,4-dione-1-((S)-2-oxopiperidine-3-yl)but-2-yl)amino)-1-oxo-3-phenylpropan-2-yl)-benzothiophene-2-carboxamide (A63)

1H NMR (500 MHz, Chloroform) δ 8.49 (s, 1H), 8.30 (s, 1H), 8.00 (s, 1H), 7.63 (s, 1H), 7.29 (dd, J=19.0, 2.9 Hz, 4H), 7.18-7.07 (m, 5H), 7.07-6.97 (m, 3H), 6.33 (s, 1H), 6.11 (s, 1H), 4.93-4.89 (m, 2H), 4.36 (d, J=9.1 Hz, 2H), 4.29 (s, 1H), 3.28-3.20 (m, 3H), 2.92 (s, 1H), 2.58 (s, 1H), 2.16 (s, 1H), 2.08-2.04 (m, 2H), 1.83 (s, 1H), 1.77 (s, 1H), 1.73 (s, 1H).

Example 64 N—((S)-1-((((S)-4-(tert-butylamino)-3,4-dione-1-((S)-2-oxopiperidine-3-yl)but-2-yl)amino)-1-oxo-3-phenylpropan-2-yl)-benzothiophene-2-carboxamide (A64)

1H NMR (500 MHz, Chloroform) δ 8.38 (s, 1H), 7.90 (s, 1H), 7.75 (s, 1H), 7.30 (dd, J=17.5, 1.0 Hz, 4H), 7.26-7.19 (m, 2H), 7.17 (s, 1H), 7.02 (s, 1H), 6.45 (s, 1H), 6.10 (s, 1H), 5.93 (s, 1H), 4.93 (s, 1H), 4.86 (s, 1H)), 3.27-3.11 (m, 3H), 2.95 (s, 1H), 2.83 (s, 1H), 2.11-2.01 (m, 2H), 1.95 (s, 1H), 1.83 (s, 1H), 1.76 (s, 1H), 1.56 (s, 1H), 1.35-1.31 (m, 9H).

Example 65 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-benzothiophene-2-carboxamide (A65)

1H NMR (500 MHz, Chloroform) δ 8.28 (s, 6H), 7.86 (s, 6H), 7.60 (s, 6H), 7.27 (dd, J=17.2, 1.6 Hz, 20H), 7.24-7.12 (m, 22H), 5.78 (s, 6H), 5.41 (s, 6H), 5.09 (s, 6H), 4.97 (s, 6H), 4.85 (s, 6H), 3.31-3.10 (m, 30H), 2.97 (s, 6H), 2.60 (s, 4H), 2.51 (s, 5H), 2.12-2.00 (m, 12H), 1.97-1.86 (m, 12H), 1.71 (t, J=16.5 Hz, 17H), 1.58-1.45 (m, 30H), 1.45-1.36 (m, 12H), 1.12 (s, 4H).

Example 66 N—((S)-1-(((S)-4-(benzylamino)-3,4-dione-1-((S)-2-oxopyrrolidine-3-yl)but-2-yl)amino)-1-oxo-3-phenylpropan-2-yl)-1-methyl-1H-indole-2-carboxamide (A66)

1H NMR (500 MHz, Chloroform) δ 8.78 (s, 1H), 7.69 (s, 1H), 7.49 (s, 1H), 7.34-7.13 (m, 12H), 7.13-7.05 (m, 2H), 6.10 (s, 1H), 5.99 (s, 1H), 5.07 (s, 1H), 4.69 (s, 1H), 4.36 (d, J=3.5 Hz, 2H), 3.78-3.74 (m, 3H), 3.45 (s, 1H), 3.35 (s, 1H), 3.24 (s, 1H), 3.06 (s, 1H), 2.88 (s, 1H), 2.19 (s, 1H), 2.09-2.05 (m, 2H), 1.93 (s, 1H).

Example 67 N—((S)-1-((((S)-4-(tert-butylamino)-3,4-dione-1-((S)-2-oxopyrrolidine-3-yl)but-2-yl)amino)-1-oxo-3-phenylpropan-2-yl)-1-methyl-1H-indole-2-carboxamide (A67)

1H NMR (500 MHz, Chloroform) δ 7.38 (s, 1H), 7.29-7.13 (m, 9H), 6.07 (s, 1H), 5.82 (d, J=4.8 Hz, 2H), 5.28 (s, 1H), 4.94 (s, 1H), 4.87 (s, 1H), 3.67-3.63 (m, 3H), 3.45 (s, 1H), 3.35 (s, 1H), 3.19 (s, 1H), 2.93 (s, 1H)), 2.68 (s, 1H), 2.18 (s, 1H), 2.09-2.05 (m, 2H), 1.94 (s, 1H), 1.34-1.30 (m, 9H).

Example 68 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-1-methyl-1H-indole-2-carboxamide (A68)

1H NMR (500 MHz, Chloroform) δ 7.49 (s, 3H), 7.34-7.20 (m, 23H), 7.20 (s, 3H), 7.15 (s, 2H), 6.73 (s, 3H), 6.27 (s, 3H), 5.73 (s, 3H), 5.11 (s, 3H), 4.83 (s, 3H), 3.98 (s, 2H), 3.76 (s, 3H), 3.58-3.54 (m, 9H), 3.35 (s, 2H), 3.22 (s, 3H), 2.88 (s, 3H), 2.63 (s, 3H), 2.19 (s, 2H), 2.09-2.05 (m, 6H), 1.95-1.91 (m, 7H), 1.76-1.66 (m, 7H), 1.66-1.55 (m, 20H).

Example 69 N—((S)-1-(((S)-4-(benzylamino)-3,4-dione-1-((S)-2-oxopiperidine-3-yl)but-2-yl)amino)-1-oxo-3-phenylpropan-2-yl)-1-methyl-1H-indole-2-carboxamide (A69)

1H NMR (500 MHz, Chloroform) δ 7.35-7.29 (m, 2H), 7.29-7.26 (m, 1H), 7.26-7.06 (m, 11H), 6.67 (s, 1H), 6.05 (d, J=11.7 Hz, 2H), 5.74 (s, 1H), 4.95 (s, 1H), 4.77 (s, 1H), 4.39 (s, 1H), 4.34 (s, 1H), 3.86-3.82 (m, 3H), 3.29-3.17 (m, 3H), 2.95 (s, 1H), 2.56 (s, 1H), 2.44 (s, 1H), 2.12-2.00 (m, 2H), 1.85 (s, 1H), 1.78 (s, 1H)), 1.41 (s, 1H), 1.15 (s, 1H).

Example 70 N—((S)-1-((((S)-4-(tert-butylamino)-3,4-dione-1-((S)-2-oxopiperidine-3-yl)but-2-yl)amino)-1-oxo-3-phenylpropan-2-yl)-1-methyl-1H-indole-2-carboxamide (A70)

1H NMR (500 MHz, Chloroform) δ 7.51 (s, 1H), 7.31 (s, 1H), 7.22 (ddd, J=42.8, 13.4, 8.7 Hz, 8H), 6.91 (s, 1H), 6.06 (s, 1H), 5.93 (s, 1H), 5.54 (s, 1H), 4.80 (s, 1H), 4.71 (s, 1H), 3.73-3.69 (m, 3H), 3.26 (t, J=14.0 Hz, 3H), 2.82 (d, J=27.3 Hz, 2H), 2.11-2.01 (m, 2H), 1.92 (s, 1H), 1.82 (s, 1H), 1.75 (s, 1H), 1.54 (s, 1H), 1.32-1.28 (m, 9H).

Example 71 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-1-methyl-1H-indole-2-carboxamide (A71)

1H NMR (500 MHz, Chloroform) δ 8.25 (s, 1H), 7.38 (s, 1H), 7.28 (dd, J=15.9, 3.4 Hz, 4H), 7.24-7.12 (m, 5H), 5.93 (s, 1H), 5.32 (s, 1H), 5.07 (s, 1H), 4.75 (s, 1H), 4.41 (s, 1H), 3.85-3.77 (m, 4H), 3.27-3.20 (m, 3H), 3.04 (s, 1H), 2.84 (s, 1H), 2.49 (s, 1H), 2.17-2.10 (m, 2H), 2.10-2.02 (m, 2H), 1.86-1.75 (m, 6H), 1.65 (s, 1H), 1.58-1.52 (m, 4H).

Example 72 N—((S)-1-(((S)-4-(benzylamino)-3,4-dione-1-((S)-2-oxopyrrolidine-3-yl)but-2-yl)amino)-1-oxo-3-phenylpropan-2-yl)-4,6-dichloro-1H-indole-2-carboxamide (A72)

1H NMR (500 MHz, Chloroform) δ 8.55 (s, 1H), 7.52 (s, 1H), 7.44 (s, 1H), 7.38 (s, 1H), 7.32-7.27 (m, 4H), 7.27-7.12 (m, 8H), 7.10 (s, 1H), 6.00 (s, 1H), 5.04 (s, 1H), 4.92 (s, 1H), 4.77 (s, 1H), 4.38 (s, 1H), 4.30 (s, 1H), 3.45 (s, 1H), 3.35 (s, 1H), 3.27 (s, 1H), 3.12 (s, 1H), 2.87 (s, 1H), 2.19 (s, 1H), 2.09-2.05 (m, 2H), 1.92 (s, 1H).

Example 73 N—((S)-1-((((S)-4-(tert-butylamino)-3,4-dione-1-((S)-2-oxopyrrolidine-3-yl)but-2-yl)amino)-1-oxo-3-phenylpropan-2-yl)-4,6-dichloro-1H-indole-2-carboxamide (A73)

1H NMR (500 MHz, Chloroform) δ 8.55 (s, 1H), 8.14 (s, 1H), 7.52 (s, 1H), 7.44 (s, 1H), 7.28-7.22 (m, 2H), 7.22-7.11 (m, 3H), 7.09 (s, 1H), 6.01 (s, 1H), 5.55 (s, 1H), 5.12 (s, 1H), 4.74 (s, 1H), 4.31 (s, 1H), 3.45 (s, 1H), 3.35 (s, 1H), 3.30 (s, 1H), 3.08 (s, 1H), 2.92 (s, 1H), 2.18 (s, 1H), 2.09-2.05 (m, 2H), 1.92 (s, 1H), 1.39-1.35 (m, 9H).

Example 74 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-4,6-dichloro-1H-indole-2-carboxamide (A74)

1H NMR (500 MHz, Chloroform) δ 8.85 (s, 1H), 8.44 (s, 1H), 8.39 (s, 1H), 7.58 (s, 1H), 7.42 (s, 1H), 7.28-7.23 (m, 2H), 7.15 (s, 1H), 7.12-7.06 (m, 3H), 6.10 (s, 1H), 5.94 (s, 1H), 5.03 (s, 1H), 4.66 (s, 1H), 3.45 (d, J=5.0 Hz, 2H), 3.35 (s, 1H), 3.27 (s, 1H), 3.06 (s, 1H), 2.90 (s, 1H), 2.19 (s, 1H), 2.09-2.05 (m, 2H), 1.95-1.91 (m, 3H), 1.72-1.68 (m, 3H), 1.56-1.52 (m, 2H), 1.50 (s, 1H), 1.46-1.41 (m, 2H).

Example 75 N—((S)-1-(((S)-4-(benzylamino)-3,4-dione-1-((S)-2-oxopiperidine-3-yl)but-2-yl)amino)-1-oxo-3-phenylpropan-2-yl)-4,6-dichloro-1H-indole-2-carboxamide (A75)

1H NMR (500 MHz, Chloroform) δ 8.67 (s, 13H), 7.46 (s, 13H), 7.30-7.24 (m, 28H), 7.24-7.14 (m, 80H), 7.12-7.00 (m, 30H), 7.00 (s, 11H), 6.93 (d, J=12.0 Hz, 26H), 6.07 (s, 13H), 4.91 (s, 13H), 4.80 (s, 13H), 4.36 (s, 13H), 4.31 (s, 13H), 4.27 (s, 13H), 4.04 (s, 13H), 3.31 (d, J=52.2 Hz, 35H), 3.22 (s, 5H), 3.01 (s, 14H), 2.86 (s, 11H), 2.31 (s, 9H), 2.08-2.04 (m, 25H), 1.83 (s, 12H), 1.77 (s, 10H), 1.54 (s, 9H).

Example 76 N—((S)-1-(((S)-4-(tert-butylamino)-3,4-dione-1-((S)-2-oxopiperidine-3-yl)but-2-yl)amino)-1-oxo-3-phenylpropan-2-yl)-4,6-dichloro-1H-indole-2-carboxamide (A76)

1H NMR (500 MHz, Chloroform) δ 8.53 (s, 8H), 7.62 (s, 8H), 7.43 (s, 8H), 7.38 (s, 8H), 7.26-7.21 (m, 16H), 7.21-7.14 (m, 21H), 7.14-7.11 (m, 4H), 7.09 (s, 8H), 5.81 (s, 8H), 5.66 (s, 8H), 5.34 (s, 8H), 4.92 (s, 8H), 4.75 (s, 8H), 3.33-3.20 (m, 24H), 2.87 (s, 7H), 2.59 (s, 7H), 2.08-2.04 (m, 16H), 1.86 (s, 6H), 1.80 (s, 7H), 1.73 (s, 6H), 1.48 (s, 6H), 1.34-1.30 (m, 72H).

Example 77 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-4,6-dichloro-1H-indole-2-carboxamide (A77)

1H NMR (500 MHz, Chloroform) δ 9.14 (s, 1H), 9.09 (s, 1H), 7.58 (s, 1H), 7.47 (s, 1H), 7.33-7.27 (m, 2H), 7.27-7.14 (m, 3H), 7.10 (s, 1H), 6.82 (s, 1H), 5.96 (s, 1H), 5.80 (s, 1H), 4.98 (s, 1H), 4.82 (s, 1H), 3.35 (s, 1H), 3.24 (d, J=14.7 Hz, 2H), 3.16 (s, 1H), 2.96 (s, 1H), 2.83 (s, 1H), 2.16-2.04 (m, 5H), 1.82 (s, 1H), 1.75 (dd, J=19.9, 8.6 Hz, 4H), 1.59-1.49 (m, 4H), 1.44-1.40 (m, 2H).

Example 78 N—((S)-1-((((S)-4-(benzylamino)-3,4-dione-1-((S)-2-oxopyrrolidine-3-yl)but-2-yl)amino)-1-oxo-3-phenylpropan-2-yl)-quinoxaline-2-carboxamide (A78)

1H NMR (500 MHz, Chloroform) δ 9.21 (s, 1H), 8.80 (s, 1H), 8.10 (d, J=21.9 Hz, 2H), 7.71 (s, 1H), 7.63 (d, J=6.0 Hz, 2H), 7.30-7.11 (m, 10H), 6.38 (s, 1H), 5.97 (s, 1H), 4.90 (s, 1H), 4.69 (s, 1H), 4.36 (d, J=4.9 Hz, 1H), 3.45 (s, 1H), 3.35 (s, 1H), 3.16 (s, 1H), 2.95 (s, 1H), 2.86 (s, 1H), 2.19 (s, 1H), 2.09-2.05 (m, 2H), 1.93 (s, 1H).

Example 79 N—((S)-1-((((S)-4-(tert-butylamino)-3,4-dione-1-((S)-2-oxopyrrolidine-3-yl)but-2-yl)amino)-1-oxo-3-phenylpropan-2-yl)-quinoxaline-2-carboxamide (A79)

1H NMR (500 MHz, Chloroform) δ 9.43 (s, 1H), 9.01 (s, 1H), 8.10 (d, J=11.8 Hz, 2H), 7.68-7.64 (m, 2H), 7.25-7.19 (m, 1H), 7.19-7.09 (m, 4H), 6.12 (s, 1H), 6.04 (s, 1H), 5.51 (s, 1H), 5.09 (s, 1H), 4.74 (s, 1H), 3.45 (s, 1H), 3.35 (d, J=2.3 Hz, 2H), 3.11 (s, 1H), 2.89 (s, 1H), 2.19 (s, 1H), 2.09-2.05 (m, 2H), 1.92 (s, 1H), 1.39-1.35 (m, 9H).

Example 80 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-quinoxaline-2-carboxamide (A80)

1H NMR (500 MHz, Chloroform) δ 9.46 (s, 1H), 8.10 (d, J=1.3 Hz, 2H), 7.64 (d, J=1.4 Hz, 2H), 7.29-7.21 (m, 4H), 7.15 (s, 1H), 6.17 (s, 1H), 5.60 (s, 1H), 5.41 (s, 1H), 5.16 (s, 1H), 4.42 (s, 1H), 3.77 (s, 1H), 3.45 (s, 1H), 3.35 (d, J=2.0 Hz, 2H), 2.94 (s, 1H), 2.49 (s, 1H), 2.19 (s, 1H), 2.09-2.05 (m, 2H), 1.93 (s, 1H), 1.81-1.74 (m, 6H), 1.74-1.70 (m, 2H), 1.57-1.51 (m, 2H).

Example 81 N—((S)-1-(((S)-4-(benzylamino)-3,4-dione-1-((S)-2-oxopiperidine-3-yl)but-2-yl)amino)-1-oxo-3-phenylpropan-2-yl)-quinoxaline-2-carboxamide (A81)

1H NMR (500 MHz, Chloroform) δ 9.04 (s, 1H), 8.07 (d, J=5.3 Hz, 2H), 7.62 (d, J=0.9 Hz, 2H), 7.30-7.20 (m, 5H), 7.20-7.12 (m, 5H), 7.10 (s, 1H), 6.69 (s, 1H), 5.68 (d, J=19.5 Hz, 2H), 5.14 (s, 1H), 5.08 (s, 1H), 4.42 (s, 1H), 4.34 (s, 1H), 3.37 (s, 1H), 3.24 (d, J=17.2 Hz, 2H), 2.95 (s, 1H), 2.15 (s, 1H), 2.09-2.03 (m, 2H), 1.76 (s, 1H), 1.70 (s, 1H), 1.63 (s, 1H), 1.43 (s, 1H).

Example 82 N—((S)-1-((((S)-4-(tert-butylamino)-3,4-dione-1-((S)-2-oxopiperidine-3-yl)but-2-yl)amino)-1-oxo-3-phenylpropan-2-yl)-quinoxaline-2-carboxamide (A82)

1H NMR (500 MHz, Chloroform) δ 9.37 (s, 1H), 8.11 (d, J=1.9 Hz, 2H), 7.64 (d, J=1.0 Hz, 2H), 7.32-7.26 (m, 2H), 7.26-7.13 (m, 3H), 6.08 (s, 1H), 5.93 (d, J=13.8 Hz, 2H), 5.60 (s, 1H), 4.97 (s, 1H), 4.83 (s, 1H), 3.24 (d, J=16.7 Hz, 2H), 3.18 (s, 1H), 2.93 (s, 1H), 2.70 (s, 1H), 2.11-2.01 (m, 2H), 1.98 (s, 1H), 1.78 (s, 1H), 1.71 (s, 1H), 1.42 (s, 1H), 1.35-1.31 (m, 9H).

Example 83 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-quinoxaline-2-carboxamide (A83)

1H NMR (500 MHz, Chloroform) δ 9.67 (s, 6H), 8.12 (d, J=8.3 Hz, 12H), 7.66 (d, J=1.4 Hz, 12H), 7.26-7.16 (m, 25H), 7.14 (s, 6H), 6.12 (s, 6H), 5.79 (s, 6H), 5.56 (s, 6H), 5.33 (s, 6H), 5.10 (s, 6H), 4.95 (s, 6H), 3.84 (s, 6H), 3.27 (t, J=34.6 Hz, 16H), 3.21 (d, J=6.1 Hz, 2H), 3.02 (s, 6H), 2.83 (s, 6H), 2.11-2.01 (m, 13H), 2.01-1.94 (m, 18H), 1.75 (s, 4H), 1.71-1.55 (m, 59H).

Example 84 N—((S)-1-(((S)-4-(benzylamino)-3,4-dione-1-((S)-2-oxopyrrolidine-3-yl)but-2-yl)amino)-1-oxo-3-phenylpropan-2-yl)-quinoline-2-carboxamide (A84)

1H NMR (500 MHz, Chloroform) δ 8.46 (s, 1H), 8.12 (s, 1H), 7.78 (s, 1H), 7.65 (s, 1H), 7.54 (s, 1H), 7.44 (s, 1H), 7.31-7.24 (m, 4H), 7.24-7.14 (m, 4H), 7.12 (s, 2H), 5.72 (s, 1H), 5.54 (s, 1H), 5.14 (s, 1H), 4.70 (s, 1H), 4.59 (s, 1H), 4.29 (d, J=9.5 Hz, 2H), 3.74 (s, 1H), 3.35 (s, 1H), 3.31 (s, 1H), 3.08 (s, 1H), 2.72 (s, 1H), 2.17 (s, 1H), 2.10-2.05 (m, 2H), 1.89 (s, 1H).

Example 85 N—((S)-1-((((S)-4-(tert-butylamino)-3,4-dione-1-((S)-2-oxopyrrolidine-3-yl)but-2-yl)amino)-1-oxo-3-phenylpropan-2-yl)-quinoline-2-carboxamide (A85)

1H NMR (500 MHz, Chloroform) δ 8.40 (d, J=39.3 Hz, 11H), 8.36-8.34 (m, 1H), 8.19 (s, 6H), 7.80 (s, 6H), 7.71 (s, 6H), 7.49 (d, J=5.7 Hz, 12H), 7.30-7.25 (m, 12H), 7.25-7.15 (m, 14H), 7.14 (s, 4H), 6.20 (s, 6H), 5.92 (s, 6H)), 5.07 (s, 6H), 4.75 (s, 6H), 3.45 (s, 6H), 3.38 (d, J=25.1 Hz, 12H), 3.32 (s, 1H), 3.02 (s, 6H), 2.35 (s, 5H), 2.19 (s, 4H), 2.09-2.05 (m, 12H), 1.92 (s, 5H), 1.36-1.32 (m, 53H).

Example 86 N—((S)-3-cyclohexyl-1-(((S)-4-(cyclohexylamino)-3,4-dione-1-((S)-2-oxopyrrolidine-3-yl)but-2-yl)amino)-1-oxo-3-phenylpropan-2-yl)-quinoline-2-carboxamide (A86)

1H NMR (500 MHz, Chloroform) δ 8.46 (s, 1H), 8.12 (s, 1H), 7.81 (s, 1H), 7.69 (s, 1H), 7.49 (d, J=7.1 Hz, 2H), 7.26-7.20 (m, 2H), 7.20-7.09 (m, 3H), 5.94 (d, J=1.5 Hz, 2H), 5.63 (s, 1H), 5.44 (s, 1H), 4.91 (s, 1H), 4.76 (s, 1H), 3.89 (s, 1H), 3.45 (s, 1H), 3.34 (d, J=11.1 Hz, 2H), 3.01 (s, 1H), 2.19 (d, J=10.9 Hz, 2H), 2.14-2.04 (m, 4H), 1.92 (s, 1H), 1.65-1.49 (m, 8H).

Example 87 N—((S)-1-(((S)-4-(benzylamino)-3,4-dione-1-((S)-2-oxopiperidine-3-yl)but-2-yl)amino)-1-oxo-3-phenylpropan-2-yl)-quinoline-2-carboxamide (A87)

1H NMR (500 MHz, Chloroform) δ 8.46 (s, 1H), 8.10 (s, 1H), 7.78 (s, 1H), 7.66 (s, 1H), 7.55 (s, 1H), 7.45 (s, 1H), 7.26-7.11 (m, 10H), 6.86 (s, 1H), 5.98 (s, 1H), 5.89 (s, 1H), 5.56 (d, J=16.8 Hz, 2H), 4.75 (s, 1H), 4.44 (s, 1H), 4.32 (s, 1H), 3.44 (s, 1H), 3.23 (d, J=18.1 Hz, 2H), 2.84 (s, 1H), 2.72 (s, 1H), 2.11-2.01 (m, 2H), 1.98 (s, 1H), 1.63 (s, 1H), 1.56 (s, 1H), 1.25 (s, 1H).

Example 88 N—((S)-1-((((S)-4-(tert-butylamino)-3,4-dione-1-((S)-2-oxopiperidine-3-yl)but-2-yl)amino)-1-oxo-3-phenylpropan-2-yl)-quinoline-2-carboxamide (A88)

1H NMR (500 MHz, Chloroform) δ 8.50 (d, J=13.8 Hz, 2H), 8.17 (s, 1H), 7.81 (s, 1H), 7.69 (s, 1H), 7.65 (s, 1H), 7.48 (s, 1H), 7.28-7.24 (m, 1H), 7.24-7.11 (m, 4H), 6.95 (s, 1H), 6.17 (s, 1H), 5.50 (s, 1H), 5.00 (s, 1H)), 4.79 (s, 1H), 3.24 (d, J=15.4 Hz, 2H), 3.08 (s, 1H), 2.90 (s, 1H), 2.69 (s, 1H), 2.11-2.01 (m, 2H), 1.90 (s, 1H), 1.84 (d, J=3.8 Hz, 2H), 1.78 (s, 1H), 1.29-1.25 (m, 9H).

Example 89 N—((S)-3-cyclohexyl-1-((((S)-4-(cyclohexylamino)-3,4-dione-1-((S)-2-oxopiperidine-3-yl)but-2-yl)amino)-1-oxo-3-phenylpropan-2-yl)-quinoline-2-carboxamide (A89)

1H NMR (500 MHz, Chloroform) δ 9.70 (s, 4H), 8.44 (s, 4H), 8.18 (s, 4H), 7.80 (s, 4H), 7.69 (d, J=18.4 Hz, 8H), 7.48 (d, J=4.0 Hz, 8H), 7.32-7.26 (m, 8H), 7.23-7.13 (m, 12H), 6.67 (s, 4H), 5.84 (s, 4H), 4.95 (s, 4H), 4.88 (s, 4H), 3.90 (s, 4H), 3.31 (d, J=56.1 Hz, 10H), 3.22 (s, 2H), 2.99 (s, 4H), 2.86 (s, 4H), 2.11-2.04 (m, 8H), 2.01 (t, J=7.0 Hz, 12H), 1.81 (s, 3H), 1.74 (s, 3H), 1.67-1.60 (m, 35H), 1.45 (s, 3H).

Example 90 N—((S)-1-(((S)-4-(benzylamino)-3,4-dione-1-((S)-2-oxopyrrolidine-3-yl)but-2-yl)amino)-4-methyl-1-oxopentan-2-yl)-1H-indole-2-carboxamide (A90)

1H NMR (500 MHz, Chloroform) δ 8.36 (s, 1H), 7.52 (d, J=19.2 Hz, 2H), 7.39 (s, 1H), 7.26-7.19 (m, 4H), 7.18 (s, 1H), 7.13 (s, 1H), 7.07 (s, 1H), 6.32 (s, 1H), 6.24 (s, 1H), 6.05 (s, 1H), 5.47 (s, 1H), 5.27 (s, 1H), 4.61 (s, 1H), 4.41 (s, 1H), 4.32 (s, 1H), 3.59 (s, 1H), 3.45 (s, 1H), 2.17 (s, 1H), 2.09-2.05 (m, 2H), 1.92 (s, 1H), 1.73 (d, J=11.4 Hz, 2H), 1.63 (s, 1H), 1.55 (s, 1H), 1.12-0.99 (m, 6H).

Example 91 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-1H-indole-2-carboxamide (A91)

1H NMR (500 MHz, Chloroform) δ 9.33 (s, 1H), 8.28 (s, 1H), 7.46 (d, J=15.1 Hz, 2H), 7.35 (s, 1H), 7.10 (s, 1H), 7.03 (s, 1H), 6.79 (s, 1H), 6.12 (s, 1H), 5.28 (s, 1H), 4.95 (s, 1H), 4.31 (s, 1H), 3.45 (s, 1H), 3.35 (s, 1H), 2.75 (s, 1H), 2.19 (s, 1H), 2.09-2.05 (m, 2H), 1.92 (s, 1H), 1.70 (d, J=19.2 Hz, 2H), 1.44 (s, 1H), 1.36-1.32 (m, 9H), 0.99-0.85 (m, 6H).

Example 92 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-1H-indole-2-carboxamide (A92)

1H NMR (500 MHz, Chloroform) δ 8.38 (s, 1H), 7.51 (d, J=17.6 Hz, 2H), 7.37 (s, 1H), 7.12 (s, 1H), 7.06 (s, 1H), 6.50 (s, 1H), 6.00 (s, 1H), 5.60 (s, 1H), 5.50 (s, 1H), 5.00 (s, 1H), 4.68 (s, 1H), 3.45 (s, 1H), 3.35 (s, 1H), 3.29 (s, 1H), 2.71 (s, 1H), 2.19 (s, 1H), 2.09-2.05 (m, 2H), 1.97-1.91 (m, 3H), 1.70 (t, J=9.1 Hz, 3H), 1.59-1.55 (m, 2H), 1.50 (dd, J=10.4, 1.1 Hz, 4H), 1.43-1.38 (m, 2H), 1.13-1.00 (m, 6H).

Example 93 N—((S)-1-(((S)-4-(benzylamino)-3,4-dione-1-((S)-2-oxopiperidine-3-yl)but-2-yl)amino)-4-methyl-1-oxopentan-2-yl)-1H-indole-2-carboxamide (A93)

1H NMR (500 MHz, Chloroform) δ 8.63 (s, 1H), 7.56 (s, 1H), 7.46 (d, J=25.5 Hz, 2H), 7.29-7.24 (m, 2H), 7.24-7.17 (m, 3H), 7.17-7.06 (m, 3H), 6.14 (s, 1H), 5.63 (s, 1H), 5.02 (d, J=15.0 Hz, 2H), 4.43 (s, 1H), 4.37 (s, 1H), 4.30 (s, 1H), 3.24 (d, J=17.4 Hz, 2H), 2.81 (s, 1H), 2.21 (s, 1H), 2.08-2.04 (m, 2H), 1.85 (s, 1H), 1.77 (t, J=13.2 Hz, 3H), 1.51 (s, 1H), 1.41 (s, 1H), 1.04-0.90 (m, 6H).

Example 94 N—((S)-1-((((S)-4-(tert-butylamino)-3,4-dione-1-((S)-2-oxopiperidine-3-yl)but-2-yl)amino)-3-cyclohexyl-1-oxopentan-2-yl)-1H-indole-2-carboxamide (A94)

1H NMR (500 MHz, Chloroform) δ 8.38 (s, 1H), 8.13 (s, 1H), 7.49 (s, 1H), 7.41 (s, 1H), 7.37 (s, 1H), 7.12 (s, 1H), 7.04 (s, 1H), 5.95 (s, 1H), 5.30 (d, J=18.0 Hz, 2H), 4.86 (s, 1H), 4.51 (s, 1H), 3.23 (d, J=15.7 Hz, 2H), 2.45 (s, 1H), 2.19 (s, 1H), 2.08-2.04 (m, 2H), 1.96 (s, 1H), 1.75 (s, 1H), 1.69 (d, J=8.0 Hz, 2H), 1.51 (s, 1H), 1.36-1.27 (m, 10H), 1.12-0.99 (m, 6H).

Example 95 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-1H-indole-2-carboxamide (A95)

1H NMR (500 MHz, Chloroform) δ 9.04 (s, 1H), 8.28 (s, 1H), 7.50 (d, J=31.2 Hz, 2H), 7.38 (s, 1H), 7.13 (s, 1H), 7.06 (s, 1H), 6.19 (s, 1H), 5.81 (s, 1H), 5.63 (s, 1H), 4.78 (s, 1H), 4.59 (s, 1H), 3.94 (s, 1H), 3.24 (d, J=18.2 Hz, 2H), 2.35 (s, 1H), 2.13-2.04 (m, 4H), 2.00 (s, 1H), 1.83-1.60 (m, 8H), 1.57 (s, 1H), 1.52-1.46 (m, 2H), 1.45-1.41 (m, 2H), 1.33 (s, 1H), 1.13-1.01 (m, 6H).

Example 96 N—((S)-1-(((S)-4-(benzylamino)-3,4-dione-1-((S)-2-oxopyrrolidine-3-yl)but-2-yl)amino)-4-methyl-1-oxopentan-2-yl)-benzofuran-2-carboxamide (A96)

1H NMR (500 MHz, Chloroform) δ 7.74 (s, 1H), 7.42 (s, 1H), 7.36-7.26 (m, 4H), 7.23 (s, 1H), 7.17 (s, 1H), 7.07 (s, 1H), 6.96 (s, 1H), 6.46 (s, 1H), 6.22 (s, 1H), 5.75 (s, 1H), 5.06 (s, 1H), 4.63 (s, 1H), 4.46 (d, J=17.5 Hz, 2H), 4.34 (s, 1H), 3.45 (s, 1H), 3.35 (s, 1H), 3.28 (s, 1H), 2.19 (s, 1H), 2.09-2.05 (m, 2H), 1.93 (s, 1H), 1.67 (s, 1H), 1.55 (s, 1H), 1.19 (s, 1H), 1.07-0.94 (m, 6H).

Example 97 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-benzofuran-2-carboxamide (A97)

1H NMR (500 MHz, Chloroform) δ 8.17 (s, 1H), 7.45 (d, J=28.3 Hz, 2H), 7.22 (s, 1H), 7.15 (s, 1H), 6.41 (s, 1H), 6.00 (s, 1H), 5.96 (s, 1H), 4.94 (s, 1H), 4.55 (s, 1H), 3.45 (s, 1H), 3.35 (s, 1H), 2.53 (s, 1H), 2.18 (s, 1H), 2.13-2.02 (m, 2H), 1.93 (s, 1H), 1.76 (s, 1H), 1.65 (s, 1H), 1.35-1.31 (m, 9H), 1.25 (s, 1H), 1.07-0.94 (m, 6H).

Example 98 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-benzofuran-2-carboxamide (A98)

1H NMR (500 MHz, Chloroform) δ 7.59 (s, 4H), 7.55-7.39 (m, 12H), 7.22 (s, 4H), 7.15 (s, 4H), 6.04 (s, 4H), 5.94 (s, 4H), 5.89 (s, 4H), 4.87 (s, 4H), 4.48 (s, 4H), 3.80 (s, 4H), 3.45 (s, 4H), 3.35 (s, 3H), 2.58 (s, 4H)), 2.18 (s, 4H), 2.11-2.04 (m, 8H), 1.95-1.88 (m, 19H), 1.87 (t, J=3.1 Hz, 4H), 1.75 (d, J=29.9 Hz, 6H), 1.71 (d, J=3.3 Hz, 2H), 1.69-1.64 (m, 8H), 1.62 (s, 3H), 1.59-1.51 (m, 8H), 1.06-0.93 (m, 24H).

Example 99 N—((S)-1-(((S)-4-(benzylamino)-3,4-dione-1-((S)-2-oxopiperidine-3-yl)but-2-yl)amino)-4-methyl-1-oxopentan-2-yl)-benzofuran-2-carboxamide (A99)

1H NMR (500 MHz, Chloroform) δ 7.58 (s, 1H), 7.52 (d, J=13.8 Hz, 2H), 7.38-7.32 (m, 2H), 7.30 (s, 1H), 7.26 (s, 1H), 7.23-7.16 (m, 3H), 6.21 (s, 1H), 5.77 (s, 1H), 5.68 (s, 1H), 4.86 (s, 1H), 4.82 (s, 1H), 4.56 (s, 1H)), 4.37 (s, 1H), 4.33 (s, 1H), 3.24 (d, J=17.0 Hz, 2H), 2.63 (s, 1H), 2.05 (t, J=5.4 Hz, 3H), 1.82 (s, 1H), 1.75 (s, 1H), 1.60 (d, J=3.4 Hz, 2H), 1.48 (s, 1H), 1.39 (s, 1H), 1.09-1.00 (m, 6H).

Example 100 N—((S)-1-(((S)-4-(benzylamino)-3,4-dione-1-((S)-2-oxopiperidine-3-yl)but-2-yl)amino)-4-methyl-1-oxopentan-2-yl)-benzofuran-2-carboxamide (A100)

1H NMR (500 MHz, Chloroform) δ 7.58 (s, 1H), 7.52 (d, J=13.8 Hz, 2H), 7.38-7.32 (m, 2H), 7.30 (s, 1H), 7.26 (s, 1H), 7.23-7.16 (m, 3H), 6.21 (s, 1H), 5.77 (s, 1H), 5.68 (s, 1H), 4.86 (s, 1H), 4.82 (s, 1H), 4.56 (s, 1H)), 4.37 (s, 1H), 4.33 (s, 1H), 3.24 (d, J=17.0 Hz, 2H), 2.63 (s, 1H), 2.05 (t, J=5.4 Hz, 3H), 1.82 (s, 1H), 1.75 (s, 1H), 1.60 (d, J=3.4 Hz, 2H), 1.48 (s, 1H), 1.39 (s, 1H), 1.09-1.00 (m, 6H).

Example 101 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-benzofuran-2-carboxamide (A101)

1H NMR (500 MHz, Chloroform) δ 7.59 (s, 1H), 7.48 (d, J=9.6 Hz, 2H), 7.20 (s, 1H), 7.14 (s, 1H), 5.80 (s, 1H), 5.26 (s, 1H), 5.11 (d, J=5.2 Hz, 2H), 4.91 (s, 1H), 3.81 (s, 1H), 3.24 (d, J=17.3 Hz, 2H), 2.61 (s, 1H), 2.09-2.02 (m, 4H), 1.95-1.87 (m, 2H), 1.84 (s, 1H), 1.77 (s, 1H), 1.69 (s, 1H), 1.58 (d, J=5.5 Hz, 2H), 1.51-1.44 (m, 4H), 1.26-1.22 (m, 4H), 1.08-0.95 (m, 6H).

Example 102 N—((S)-1-((((S)-4-(benzylamino)-3,4-dione-1-((S)-2-oxopyrrolidine-3-yl)but-2-yl)amino)-4-methyl-1-oxopentan-2-yl)-benzothiophene-2-carboxamide (A102)

1H NMR (500 MHz, Chloroform) δ 8.47 (s, 1H), 7.91 (s, 1H), 7.78 (s, 1H), 7.33 (d, J=6.1 Hz, 2H), 7.28-7.17 (m, 5H), 6.42 (s, 1H), 6.05 (s, 1H), 5.73 (s, 1H), 5.38 (s, 1H), 5.27 (s, 1H), 4.46 (s, 1H), 4.36 (d, J=16.9 Hz, 2H), 3.45 (s, 1H), 3.35 (s, 1H), 2.67 (s, 1H), 2.18 (s, 1H), 2.09-2.05 (m, 2H), 1.92 (s, 1H), 1.82 (s, 1H), 1.70 (s, 1H), 1.52 (s, 1H), 1.10-0.96 (m, 6H).

Example 103 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-benzothiophene-2-carboxamide (A103)

1H NMR (500 MHz, Chloroform) δ 8.37 (s, 1H), 7.89 (s, 1H), 7.73 (s, 1H), 7.30 (d, J=2.2 Hz, 2H), 6.58 (s, 1H), 6.03 (s, 1H), 5.61 (s, 1H), 5.53 (s, 1H), 5.02 (s, 1H), 4.70 (s, 1H), 3.45 (s, 1H), 3.35 (s, 1H), 2.69 (s, 1H), 2.19 (s, 1H), 2.09-2.05 (m, 2H), 1.93 (s, 1H), 1.69 (d, J=8.4 Hz, 2H), 1.49 (s, 1H), 1.32-1.28 (m, 9H), 1.10-1.02 (m, 6H).

Example 104 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-benzothiophene-2-carboxamide (A104)

1H NMR (500 MHz, Chloroform) δ 8.63 (s, 1H), 7.91 (s, 1H), 7.74 (s, 1H), 7.34-7.30 (m, 2H), 6.18 (d, J=11.5 Hz, 2H), 6.02 (s, 1H), 4.62 (s, 1H), 4.48 (s, 1H), 3.45 (s, 1H), 3.35 (s, 1H), 3.27 (s, 1H), 2.56 (s, 1H), 2.19 (s, 1H), 2.11-2.05 (m, 3H), 1.92 (s, 1H), 1.83-1.70 (m, 3H), 1.69 (s, 1H), 1.59-1.54 (m, 3H), 1.50 (t, J=6.7 Hz, 3H), 1.42-1.37 (m, 2H), 1.12-0.98 (m, 6H).

Example 105 N—((S)-1-(((S)-4-(benzylamino)-3,4-dione-1-((S)-2-oxopiperidine-3-yl)but-2-yl)amino)-4-methyl-1-oxopentan-2-yl)-benzothiophene-2-carboxamide (A105)

1H NMR (500 MHz, Chloroform) δ 8.43 (s, 1H), 7.93 (d, J=0.7 Hz, 2H), 7.74 (s, 1H), 7.33 (d, J=2.2 Hz, 2H), 7.30-7.25 (m, 4H), 7.20 (s, 1H), 6.65 (s, 1H), 6.05 (s, 1H), 5.58 (s, 1H), 4.71 (s, 1H), 4.52 (s, 1H), 4.40 (s, 1H), 4.30 (s, 1H), 3.23 (d, J=15.8 Hz, 2H), 2.73 (s, 1H), 2.16 (s, 1H), 2.08-2.04 (m, 2H), 1.80 (s, 1H), 1.69 (d, J=6.6 Hz, 2H), 1.63 (s, 1H), 1.44 (s, 1H), 1.35 (s, 1H), 1.12-0.99 (m, 6H).

Example 106 N—((S)-1-((((S)-4-(tert-butylamino)-3,4-dione-1-((S)-2-oxopiperidine-3-yl)but-2-yl)amino)-3-cyclohexyl-1-oxopentan-2-yl)-benzothiophene-2-carboxamide (A106)

1H NMR (500 MHz, Chloroform) δ 8.39 (s, 1H), 7.91 (s, 1H), 7.71 (s, 1H), 7.31 (d, J=2.6 Hz, 2H), 6.50 (s, 1H), 5.87 (s, 1H), 5.71 (s, 1H), 5.57 (s, 1H), 4.80 (s, 1H), 4.75 (s, 1H), 3.23 (d, J=15.7 Hz, 2H), 2.64 (s, 1H), 2.08-2.04 (m, 2H), 1.87 (d, J=17.5 Hz, 2H), 1.68 (d, J=6.0 Hz, 2H), 1.61 (d, J=2.0 Hz, 2H), 1.37 (s, 1H), 1.32-1.28 (m, 9H), 1.10-0.97 (m, 6H).

Example 107 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-benzothiophene-2-carboxamide (A107)

1H NMR (500 MHz, Chloroform) δ 8.30 (s, 15H), 8.25 (s, 15H), 7.87 (s, 15H), 7.71 (s, 15H), 7.30 (d, J=1.3 Hz, 30H), 6.03 (s, 15H), 5.58 (s, 15H), 5.39 (s, 15H), 5.03 (s, 15H), 4.37 (s, 15H), 3.85 (s, 15H), 3.24 (d, J=16.7 Hz, 29H), 2.67 (s, 11H), 2.57 (s, 13H), 2.08-2.04 (m, 30H), 1.96-1.90 (m, 46H), 1.86 (s, 15H), 1.79 (s, 12H), 1.76-1.53 (m, 169H), 1.58 (d, J=5.6 Hz, 3H), 1.05-0.92 (m, 93H).

Example 108 N—((S)-1-((((S)-4-(benzylamino)-3,4-dione-1-((S)-2-oxopyrrolidine-3-yl)but-2-yl)amino)-4-methyl-1-oxopentan-2-yl)-1-methyl-1H-indole-2-carboxamide (A108)

1H NMR (500 MHz, Chloroform) δ 7.39 (d, J=5.1 Hz, 10H), 7.31-7.22 (m, 12H), 7.22-7.06 (m, 35H), 5.99 (s, 5H), 5.29 (s, 5H), 4.40 (d, J=4.6 Hz, 10H), 4.30 (d, J=5.3 Hz, 1H), 4.24 (d, J=52.5 Hz, 9H), 3.68-3.64 (m, 15H), 3.58 (s, 5H), 3.45 (s, 5H), 2.78 (s, 5H), 2.17 (s, 3H), 2.15-1.95 (m, 17H), 1.89 (s, 4H), 1.81 (s, 5H), 1.62 (s, 5H), 1.48 (s, 4H), 1.07-0.94 (m, 31H).

Example 109 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-1-methyl-1H-indole-2-carboxamide (A109)

1H NMR (500 MHz, Chloroform) δ 8.20 (s, 1H), 7.48 (s, 1H), 7.27 (d, J=17.1 Hz, 2H), 7.18 (d, J=7.0 Hz, 2H), 6.13 (s, 1H), 5.90 (s, 1H), 5.38 (s, 1H), 5.08 (s, 1H), 4.65 (s, 1H), 3.79-3.75 (m, 3H), 3.45 (s, 1H), 3.35 (s, 1H), 2.81 (s, 1H), 2.17 (s, 1H), 2.13-2.02 (m, 2H), 1.93 (s, 1H), 1.67 (s, 1H), 1.60 (s, 1H), 1.55 (s, 1H), 1.34-1.30 (m, 9H), 1.13-1.00 (m, 6H).

Example 110 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-1-methyl-1H-indole-2-carboxamide (A110)

1H NMR (500 MHz, Chloroform) δ 7.37 (s, 3H), 7.28 (d, J=4.7 Hz, 6H), 7.19 (d, J=11.4 Hz, 6H), 6.24 (s, 3H), 5.90 (s, 3H), 5.81 (s, 3H), 5.30 (s, 3H), 4.90 (s, 3H), 4.68 (s, 3H), 3.90-3.86 (m, 9H), 3.45 (s, 3H), 3.37-3.33 (m, 5H), 2.70 (s, 3H), 2.19 (s, 3H), 2.12-2.04 (m, 6H), 1.93 (s, 3H), 1.86-1.76 (m, 9H), 1.71-1.60 (m, 11H), 1.60-1.54 (m, 1H), 1.51 (dd, J=18.4, 1.5 Hz, 11H), 1.44-1.38 (m, 6H), 1.08-0.95 (m, 18H).

Example 111 N—((S)-1-(((S)-4-(benzylamino)-3,4-dione-1-((S)-2-oxopiperidine-3-yl)but-2-yl)amino)-4-methyl-1-oxopentan-2-yl)-1-methyl-1H-indole-2-carboxamide (A111)

1H NMR (500 MHz, Chloroform) δ 7.62 (s, 1H), 7.34 (s, 1H), 7.30-7.17 (m, 8H), 6.58 (s, 1H), 6.10 (s, 1H), 5.61 (s, 1H), 5.41 (s, 1H), 4.83 (s, 1H), 4.48 (s, 1H), 4.37 (s, 1H), 4.32 (s, 1H), 3.76-3.72 (m, 3H), 3.24 (d, J=17.6 Hz, 2H), 2.57 (s, 1H), 2.08-2.04 (m, 2H), 1.80 (s, 1H), 1.76 (s, 1H), 1.71-1.65 (m, 2H), 1.56 (d, J=15.2 Hz, 2H), 1.21 (s, 1H), 1.10-0.97 (m, 6H).

Example 112 N—((S)-1-((((S)-4-(tert-butylamino)-3,4-dione-1-((S)-2-oxopiperidine-3-yl)but-2-yl)amino)-3-cyclohexyl-1-oxopentan-2-yl)-1-methyl-1H-indole-2-carboxamide (A112)

1H NMR (500 MHz, Chloroform) δ 7.57 (s, 1H), 7.51 (s, 1H), 7.31 (s, 1H), 7.25 (s, 1H), 7.18 (d, J=5.1 Hz, 2H), 5.92 (s, 1H), 5.59 (s, 1H), 5.43 (s, 1H), 4.99 (s, 1H), 4.47 (s, 1H), 3.74-3.70 (m, 3H), 3.24 (d, J=16.8 Hz, 2H), 2.71 (s, 1H), 2.41 (s, 1H), 2.08-2.04 (m, 2H), 1.76 (dd, J=34.2, 16.8 Hz, 4H), 1.55 (s, 1H), 1.45 (s, 1H), 1.30-1.26 (m, 9H), 1.09-0.96 (m, 6H).

Example 113 N—((S)-1-((((S)-4-(tert-butylamino)-3,4-dione-1-((S)-2-oxopiperidine-3-yl)but-2-yl)amino)-3-cyclohexyl-1-oxopentan-2-yl)-1-methyl-1H-indole-2-carboxamide (A113)

1H NMR (500 MHz, Chloroform) δ 7.57 (s, 1H), 7.51 (s, 1H), 7.31 (s, 1H), 7.25 (s, 1H), 7.18 (d, J=5.1 Hz, 2H), 5.92 (s, 1H), 5.59 (s, 1H), 5.43 (s, 1H), 4.99 (s, 1H), 4.47 (s, 1H), 3.74-3.70 (m, 3H), 3.24 (d, J=16.8 Hz, 2H), 2.71 (s, 1H), 2.41 (s, 1H), 2.08-2.04 (m, 2H), 1.76 (dd, J=34.2, 16.8 Hz, 4H), 1.55 (s, 1H), 1.45 (s, 1H), 1.30-1.26 (m, 9H), 1.09-0.96 (m, 6H).

Example 114 N—((S)-1-(((S)-4-(benzylamino)-3,4-dione-1-((S)-2-oxopyrrolidine-3-yl)but-2-yl)amino)-4-methyl-1-oxopentan-2-yl)-4,6-dichloro-1H-indole-2-carboxamide (A114)

1H NMR (500 MHz, Chloroform) δ 9.48 (s, 5H), 7.69 (s, 5H), 7.37 (s, 5H), 7.29 (d, J=6.5 Hz, 3H), 7.28-7.15 (m, 23H), 7.06 (s, 5H), 6.19 (s, 5H), 5.64 (s, 5H), 5.49 (s, 5H), 5.18 (s, 5H), 4.42 (s, 5H), 4.35 (d, J=14.2 Hz, 10H), 3.45 (s, 5H), 3.35 (d, J=1.5 Hz, 9H), 3.05 (s, 5H), 2.19 (s, 4H), 2.09-2.05 (m, 10H), 1.92 (s, 4H), 1.68 (s, 5H), 1.58 (s, 5H), 1.52 (s, 5H), 1.02-0.89 (m, 31H).

Example 115 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-4,6-dichloro-1H-indole-2-carboxamide (A115)

1H NMR (500 MHz, Chloroform) δ 8.36 (s, 1H), 7.60 (s, 1H), 7.40 (s, 1H), 7.06 (s, 1H), 6.45 (s, 1H), 6.04 (s, 1H), 5.52 (d, J=2.2 Hz, 2H), 4.99 (s, 1H), 4.68 (s, 1H), 3.45 (s, 1H), 3.35 (s, 1H), 2.72 (s, 1H), 2.19 (s, 1H), 2.09-2.05 (m, 2H), 1.93 (s, 1H), 1.70 (d, J=9.3 Hz, 2H), 1.49 (s, 1H), 1.32-1.28 (m, 9H), 1.11-1.02 (m, 6H).

Example 116 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-4,6-dichloro-1H-indole-2-carboxamide (A116)

1H NMR (500 MHz, Chloroform) δ 9.33 (s, 1H), 8.27 (s, 1H), 7.54 (s, 1H), 7.37 (s, 1H), 7.03 (s, 1H), 6.84 (s, 1H), 6.14 (s, 1H), 5.29 (s, 1H), 4.95 (s, 1H), 4.31 (s, 1H), 3.83 (s, 1H), 3.45 (s, 1H), 3.35 (s, 1H), 2.73 (s, 1H), 2.19 (s, 1H), 2.09-2.05 (m, 2H), 2.05-1.90 (m, 3H), 1.72 (s, 1H), 1.70-1.44 (m, 9H), 1.44 (d, J=5.3 Hz, 1H), 0.98-0.85 (m, 6H).

Example 117 N—((S)-1-(((S)-4-(benzylamino)-3,4-dione-1-((S)-2-oxopiperidine-3-yl)but-2-yl)amino)-4-methyl-1-oxopentan-2-yl)-4,6-dichloro-1H-indole-2-carboxamide (A117)

1H NMR (500 MHz, Chloroform) δ 8.38 (s, 1H), 7.67 (s, 1H), 7.42 (s, 1H), 7.29-7.22 (m, 4H), 7.19 (s, 1H), 7.10 (d, J=11.4 Hz, 2H), 6.65 (s, 1H), 5.62 (s, 1H), 5.55 (s, 1H), 4.99 (s, 1H), 4.48 (s, 1H), 4.37 (s, 1H), 4.33 (s, 1H), 3.24 (d, J=16.8 Hz, 2H), 2.56 (s, 1H), 2.45 (s, 1H), 2.08-2.04 (m, 2H), 1.80 (d, J=3.6 Hz, 2H), 1.72 (d, J=14.6 Hz, 2H), 1.55 (s, 1H), 1.46 (s, 1H), 1.10-0.97 (m, 6H).

Example 118 N—((S)-1-((((S)-4-(tert-butylamino)-3,4-dione-1-((S)-2-oxopiperidine-3-yl)but-2-yl)amino)-3-cyclohexyl-1-oxopentan-2-yl)-4,6-dichloro-1H-indole-2-carboxamide (A118)

1H NMR (500 MHz, Chloroform) δ 8.59 (s, 1H), 7.55 (s, 1H), 7.41 (s, 1H), 7.05 (s, 1H), 6.20 (s, 1H), 5.74 (s, 1H), 5.41 (s, 1H), 4.71 (s, 1H), 4.48 (s, 1H), 3.24 (d, J=17.3 Hz, 2H), 2.48 (s, 1H), 2.06 (t, J=2.1 Hz, 3H), 1.86-1.74 (m, 3H), 1.68 (s, 1H), 1.58 (s, 1H), 1.53 (s, 1H), 1.32-1.28 (m, 9H), 1.15-1.01 (m, 6H).

Example 119 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-4,6-dichloro-1H-indole-2-carboxamide (A119)

1H NMR (500 MHz, Chloroform) δ 8.63 (s, 1H), 8.33 (s, 1H), 7.58 (s, 1H), 7.40 (s, 1H), 7.07 (s, 1H), 6.32 (s, 1H), 5.80 (s, 1H), 5.52 (s, 1H), 4.79 (s, 1H), 4.59 (s, 1H), 3.96 (s, 1H), 3.24 (d, J=17.9 Hz, 2H), 2.36 (s, 1H), 2.15-2.08 (m, 2H), 2.08-2.04 (m, 2H), 2.00 (s, 1H), 1.74-1.68 (m, 5H), 1.68-1.60 (m, 3H), 1.60-1.50 (m, 5H), 1.33 (s, 1H), 1.13-1.01 (m, 6H).

Example 120 N—((S)-1-((((S)-4-(benzylamino)-3,4-dione-1-((S)-2-oxopyrrolidine-3-yl)but-2-yl)amino)-4-methyl-1-oxopentan-2-yl)-quinoxaline-2-carboxamide (A120)

1H NMR (500 MHz, Chloroform) δ 8.79 (s, 1H), 8.05 (s, 1H), 8.01 (s, 1H), 7.64 (d, J=1.5 Hz, 2H), 7.36-7.25 (m, 4H), 7.20 (s, 1H), 5.82 (s, 1H), 5.78 (s, 1H), 5.24 (s, 1H), 4.97 (s, 1H), 4.68 (s, 1H), 4.36 (s, 1H), 4.23 (s, 1H), 3.68 (s, 1H), 3.45 (s, 1H), 3.35 (s, 1H), 2.21 (s, 1H), 2.09-2.05 (m, 2H), 1.90 (d, J=15.7 Hz, 1H), 1.76 (s, 1H), 1.65 (s, 1H), 1.45 (s, 1H), 1.10-0.97 (m, 6H).

Example 121 N—((S)-1-((((S)-4-(tert-butylamino)-3,4-dione-1-((S)-2-oxopyrrolidine-3-yl)but-2-yl)amino)-3-cyclohexyl-1-oxopentan-2-yl)-quinoxaline-2-carboxamide (A121)

1H NMR (500 MHz, Chloroform) δ 9.24 (s, 1H), 8.11 (d, J=7.7 Hz, 2H), 7.85 (s, 1H), 7.65 (d, J=1.9 Hz, 2H), 6.22 (s, 1H), 6.11 (s, 1H), 5.66 (s, 1H), 4.77 (s, 1H), 4.62 (s, 1H), 3.45 (s, 1H), 3.35 (s, 1H), 2.79 (s, 1H), 2.17 (s, 1H), 2.13-2.02 (m, 2H), 1.92 (s, 1H), 1.67 (d, J=2.5 Hz, 2H), 1.51 (s, 1H), 1.34-1.30 (m, 9H), 1.11-1.02 (m, 6H).

Example 122 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-quinoxaline-2-carboxamide (A122)

1H NMR (500 MHz, Chloroform) δ 9.29 (s, 1H), 8.09 (d, J=18.4 Hz, 2H), 7.60 (d, J=2.0 Hz, 2H), 6.27 (s, 1H), 6.23 (s, 1H), 5.90 (s, 1H), 5.24 (s, 1H), 4.80 (s, 1H), 4.70 (s, 1H), 3.45 (s, 1H), 3.35 (d, J=1.2 Hz, 2H), 2.58 (s, 1H), 2.18 (s, 1H), 2.11-2.03 (m, 2H), 1.93 (s, 1H), 1.86-1.71 (m, 3H), 1.71-1.60 (m, 4H), 1.55-1.46 (m, 4H), 1.44-1.39 (m, 2H), 1.09-0.96 (m, 6H).

Example 123 N—((S)-1-(((S)-4-(benzylamino)-3,4-dione-1-((S)-2-oxopiperidine-3-yl)but-2-yl)amino)-4-methyl-1-oxopentan-2-yl)-quinoxaline-2-carboxamide (A123)

1H NMR (500 MHz, Chloroform) δ 9.35 (s, 1H), 8.12 (s, 1H), 7.95 (s, 1H), 7.64 (d, J=15.8 Hz, 2H), 7.33-7.26 (m, 3H), 7.26-7.21 (m, 2H), 6.55 (s, 1H), 6.29 (s, 1H), 5.62 (d, J=10.0 Hz, 2H), 4.84 (s, 1H), 4.54 (s, 1H), 4.16 (d, J=16.2 Hz, 2H), 3.24 (d, J=17.4 Hz, 2H), 2.98 (s, 1H), 2.32 (s, 1H), 2.10-2.04 (m, 3H), 1.85 (s, 1H), 1.78 (s, 1H), 1.71 (s, 1H), 1.59 (s, 1H), 1.45 (s, 1H), 1.13-1.00 (m, 6H).

Example 124 N—((S)-1-((((S)-4-(tert-butylamino)-3,4-dione-1-((S)-2-oxopiperidine-3-yl)but-2-yl)amino)-3-cyclohexyl-1-oxopentan-2-yl)-quinoxaline-2-carboxamide (A124)

1H NMR (500 MHz, Chloroform) δ 9.23 (s, 1H), 8.12 (d, J=11.8 Hz, 2H), 7.65 (d, J=2.9 Hz, 2H), 6.31 (s, 1H), 6.08 (s, 1H), 5.70 (s, 1H), 5.63 (s, 1H), 4.89 (s, 1H), 4.62 (s, 1H), 3.24 (d, J=17.3 Hz, 2H), 2.62 (s, 1H), 2.04 (t, J=12.6 Hz, 3H), 1.80 (s, 1H), 1.76-1.69 (m, 3H), 1.51 (s, 1H), 1.40 (s, 1H), 1.33-1.29 (m, 9H), 1.12-0.99 (m, 6H).

Example 125 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-quinoxaline-2-carboxamide (A125)

1H NMR (500 MHz, Chloroform) δ 9.32 (s, 1H), 8.97 (s, 1H), 8.11 (d, J=3.7 Hz, 2H), 7.65 (d, J=2.2 Hz, 2H), 5.73 (s, 1H), 5.60 (s, 1H), 5.56 (s, 1H), 4.72 (s, 1H), 4.51 (s, 1H), 3.31-3.20 (m, 3H), 2.59 (s, 1H), 2.08-2.00 (m, 5H), 1.81 (s, 1H), 1.69 (d, J=9.0 Hz, 2H), 1.62 (s, 1H), 1.60-1.54 (m, 3H), 1.53-1.42 (m, 3H), 1.39 (dd, J=11.3, 3.2 Hz, 4H), 1.09-0.96 (m, 6H).

Example 126 N—((S)-1-((((S)-4-(benzylamino)-3,4-dione-1-((S)-2-oxopyrrolidine-3-yl)but-2-yl)amino)-4-methyl-1-oxopentan-2-yl)-quinoline-2-carboxamide (A126)

1H NMR (500 MHz, Chloroform) δ 8.47 (s, 1H), 8.14 (s, 1H), 7.80 (s, 1H), 7.68 (s, 1H), 7.52 (s, 1H), 7.47 (s, 1H), 7.30-7.26 (m, 1H), 7.26-7.17 (m, 5H), 6.50 (s, 1H), 6.42 (s, 1H), 6.10 (s, 1H), 5.27 (s, 1H), 4.65 (d, J=5.3 Hz, 2H), 4.40 (s, 1H), 4.32 (s, 1H), 3.45 (s, 1H), 3.35 (s, 1H), 2.65 (s, 1H), 2.19 (s, 1H), 2.09-2.05 (m, 2H), 1.93 (s, 1H), 1.69 (s, 1H), 1.59 (d, J=10.7 Hz, 2H), 1.13-1.00 (m, 7H).

Example 127 N—((S)-1-(((S)-4-(tert-butylamino)-3,4-dione-1-((S)-2-oxopyrrolidine-3-yl)but-2-yl)amino)-3-cyclohexyl-1-oxopentan-2-yl)-quinoline-2-carboxamide (A127)

1H NMR (500 MHz, Chloroform) δ 8.36 (s, 1H), 8.14 (s, 1H), 7.77 (s, 1H), 7.69 (s, 1H), 7.46 (s, 1H), 7.40 (s, 1H), 6.36 (s, 1H), 6.13 (s, 1H), 6.02 (s, 1H), 5.67 (s, 1H), 4.93 (s, 1H), 4.61 (s, 1H), 3.45 (s, 1H), 3.35 (s, 1H), 2.63 (s, 1H), 2.18 (s, 1H), 2.09-2.05 (m, 2H), 1.92 (s, 1H), 1.73 (d, J=1.3 Hz, 2H), 1.52 (s, 1H), 1.33-1.29 (m, 9H), 1.09-1.03 (m, 6H).

Example 128 N—((S)-3-cyclohexyl-1-(((S)-4-(cyclohexylamino)-3,4-dione-1-((S)-2-oxopyrrolidine-3-yl)but-2-yl)amino)-3-cyclohexyl-1-oxopentan-2-yl)-quinoline-2-carboxamide (A128)

1H NMR (500 MHz, Chloroform) δ 9.46 (s, 1H), 8.44 (s, 1H), 8.17 (s, 1H), 7.80 (s, 1H), 7.71 (s, 1H), 7.47 (d, J=10.8 Hz, 2H), 5.88 (s, 1H), 5.82 (s, 1H), 5.18 (s, 1H), 4.96 (s, 1H), 4.52 (s, 1H), 3.74 (s, 1H), 3.45 (s, 1H), 3.35 (s, 1H), 2.64 (s, 1H), 2.19 (s, 1H), 2.09-2.05 (m, 2H), 1.95 (t, J=7.9 Hz, 3H), 1.71 (s, 1H), 1.57 (tt, J=16.6, 2.2 Hz, 9H), 1.44 (s, 1H), 1.11-0.98 (m, 6H).

Example 129 N—((S)-1-(((S)-4-(benzylamino)-3,4-dione-1-((S)-2-oxopiperidine-3-yl)but-2-yl)amino)-4-methyl-1-oxopentan-2-yl)-quinoline-2-carboxamide (A129)

1H NMR (500 MHz, Chloroform) δ 8.45 (s, 1H), 8.18 (s, 1H), 7.81 (s, 1H), 7.72 (s, 1H), 7.47 (d, J=14.9 Hz, 2H), 7.29-7.21 (m, 4H), 7.19 (s, 1H), 6.66 (s, 1H), 6.36 (s, 1H), 5.90 (s, 1H), 5.60 (s, 1H), 5.00 (s, 1H), 4.50 (s, 1H), 4.34 (d, J=14.6 Hz, 2H), 3.24 (d, J=16.9 Hz, 2H), 2.47 (d, J=1.9 Hz, 2H), 2.08-2.04 (m, 2H), 1.80 (s, 1H), 1.77-1.69 (m, 3H), 1.55 (s, 1H), 1.46 (s, 1H), 1.09-0.96 (m, 6H).

Example 130 N—((S)-1-((((S)-4-(tert-butylamino)-3,4-dione-1-((S)-2-oxopiperidine-3-yl)but-2-yl)amino)-3-cyclohexyl-1-oxopentan-2-yl)-quinoline-2-carboxamide (A130)

1H NMR (500 MHz, Chloroform) δ 8.45 (s, 1H), 8.17 (s, 1H), 7.81 (s, 1H), 7.71 (s, 1H), 7.48 (d, J=2.3 Hz, 2H), 5.90 (s, 1H), 5.74 (s, 1H), 5.54 (s, 1H), 5.27 (s, 1H), 5.13 (s, 1H), 4.51 (s, 1H), 3.24 (d, J=17.6 Hz, 2H), 2.61 (s, 1H), 2.08-2.04 (m, 2H), 1.89-1.64 (m, 5H), 1.48 (d, J=18.1 Hz, 2H), 1.33-1.29 (m, 9H), 1.09-0.96 (m, 6H).

Example 131 N—((S)-3-cyclohexyl-1-((((S)-4-(cyclohexylamino)-3,4-dione-1-((S)-2-oxopiperidine-3-yl)but-2-yl)amino)-3-cyclohexyl-1-oxopentan-2-yl)-quinoline-2-carboxamide (A131)

1H NMR (500 MHz, Chloroform) δ 8.45 (s, 1H), 8.17 (s, 1H), 7.81 (s, 1H), 7.71 (s, 1H), 7.49 (d, J=4.2 Hz, 2H), 6.05 (s, 1H), 5.83 (s, 1H), 5.54 (s, 1H), 5.39 (s, 1H), 5.11 (s, 1H), 4.52 (s, 1H), 3.30-3.20 (m, 3H), 2.61 (s, 1H), 2.08-2.04 (m, 2H), 2.02-1.90 (m, 2H), 1.87-1.77 (m, 3H), 1.75-1.68 (m, 5H), 1.55-1.44 (m, 5H), 1.44-1.39 (m, 2H), 1.09-0.96 (m, 6H).

Example 132 N—((S)-1-((((S)-4-(benzylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide (A132)

1H NMR (500 MHz, Chloroform) δ 7.39-7.29 (m, 2H), 7.29-7.20 (m, 7H), 7.18 (s, 1H), 6.65 (s, 1H), 6.45 (d, J=4.2 Hz, 2H), 6.24 (s, 1H), 6.13 (d, J=3.8 Hz, 2H), 6.03 (s, 1H), 5.47 (s, 1H), 4.93 (d, J=16.9 Hz, 2H), 4.66 (s, 1H), 4.42 (s, 1H), 4.33 (s, 1H), 3.66 (s, 1H), 3.45 (s, 1H), 3.40-3.30 (m, 3H), 3.18 (s, 1H), 2.96 (d, J=11.1 Hz, 2H), 2.18 (s, 1H), 2.12-2.02 (m, 2H), 1.93 (s, 1H).

Example 133 N—((S)-1-((((S)-4-(tert-butylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide (A133)

1H NMR (500 MHz, Chloroform) δ 7.27-7.21 (m, 2H), 7.21-7.11 (m, 3H), 7.10 (s, 1H), 6.49 (s, 1H), 6.31 (s, 1H), 6.20 (s, 1H), 6.13 (s, 1H), 5.96 (d, J=15.6 Hz, 2H), 5.67 (s, 1H), 4.90 (s, 1H), 4.85 (s, 1H), 4.66 (s, 1H)), 4.14 (s, 1H), 3.69 (s, 1H), 3.42 (d, J=26.2 Hz, 2H), 3.33 (d, J=15.0 Hz, 2H), 3.23 (s, 1H), 2.83 (s, 1H), 2.68 (s, 1H), 2.17 (s, 1H), 2.09-2.05 (m, 2H), 1.91 (s, 1H), 1.36-1.32 (m, 10H).

Example 134 N—((S)-1-((((S)-4-(tert-butylamino)-3,4-dione-1-((S)-2-oxopyrrolidine-3-yl)but-2-yl)amino)-1-oxo-3-phenylpropan-2-yl)-6-chloro-3,8a-dihydro-2H-benzopyran-3-carboxamide (A134)

1H NMR (500 MHz, Chloroform) δ 8.76 (s, 5H), 8.45 (s, 5H), 7.29-7.23 (m, 10H), 7.16 (s, 5H), 7.14-7.05 (m, 10H), 6.44 (s, 5H), 6.29 (s, 5H), 6.03 (s, 5H), 5.93 (d, J=10.5 Hz, 10H), 5.21 (s, 5H), 5.05 (s, 5H), 4.64 (d, J=18.2 Hz, 10H), 3.67 (s, 4H), 3.48-3.46 (m, 2H), 3.43 (t, J=11.4 Hz, 14H), 3.37 (dt, J=43.5, 18.6 Hz, 29H), 3.05 (s, 5H), 2.86 (s, 5H), 2.19 (s, 5H), 2.09-2.05 (m, 10H), 1.95-1.86 (m, 15H), 1.72-1.64 (m, 15H), 1.56-1.52 (m, 9H), 1.50 (s, 6H), 1.45-1.40 (m, 10H).

Example 135 N—((S)-1-((((S)-4-(benzylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide (A135)

1H NMR (500 MHz, Chloroform) δ 7.82 (s, 1H), 7.30-7.22 (m, 4H), 7.21-7.07 (m, 6H), 6.48 (s, 1H), 6.29 (s, 1H), 6.16 (s, 1H), 6.09 (s, 1H), 5.96 (d, J=19.6 Hz, 2H), 5.31 (s, 1H), 4.94 (s, 1H), 4.66 (s, 1H), 4.61 (s, 1H)), 4.41 (s, 1H), 4.33 (s, 1H), 3.72 (s, 1H), 3.51-3.12 (m, 5H), 3.24 (d, J=16.9 Hz, 2H), 3.24 (d, J=16.9 Hz, 2H), 2.96 (s, 1H), 2.43 (s, 1H), 2.19 (s, 1H), 2.08-2.03 (m, 2H), 1.80 (s, 1H), 1.73 (s, 1H), 1.55 (s, 1H).

Example 136 N—((S)-1-((((S)-4-(tert-butylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide (A136)

1H NMR (500 MHz, Chloroform) δ 7.32-7.26 (m, 2H), 7.18 (s, 1H), 7.15-7.08 (m, 2H), 6.45 (s, 1H), 6.28 (s, 1H), 6.02 (s, 1H), 5.94 (d, J=3.0 Hz, 2H), 5.80 (s, 1H), 5.63 (s, 1H), 5.14 (s, 1H), 4.66 (s, 1H), 4.55 (s, 1H)), 3.91 (s, 1H), 3.65 (s, 1H), 3.49-3.10 (m, 5H), 3.25 (t, J=14.8 Hz, 3H), 3.25 (t, J=14.8 Hz, 3H), 3.01 (s, 1H), 2.53 (s, 1H), 2.08-2.04 (m, 2H), 1.94 (s, 1H), 1.80 (d, J=1.0 Hz, 2H), 1.73 (s, 1H), 1.34-1.30 (m, 9H).

Example 137 N—((S)-1-((((S)-4-(tert-butylamino)-3,4-dione-1-((S)-2-oxopiperidine-3-yl)but-2-yl)amino)-1-oxo-3-phenylpropan-2-yl)-6-chloro-3,8a-dihydro-2H-benzopyran-3-carboxamide (A137)

1H NMR (500 MHz, Chloroform) δ 7.30-7.26 (m, 1H), 7.26-7.14 (m, 4H), 6.52 (s, 1H), 6.47 (s, 1H), 6.14 (s, 1H), 6.04 (s, 1H), 5.96 (s, 1H), 5.87 (d, J=16.5 Hz, 2H), 5.02 (d, J=1.5 Hz, 2H), 4.66 (s, 1H), 4.48 (s, 1H), 3.68 (s, 1H), 3.51 (s, 1H), 3.40 (s, 1H), 3.31 (d, J=10.7 Hz, 2H), 3.24 (d, J=17.3 Hz, 2H), 3.01 (d, J=17.6 Hz, 2H), 2.12-2.04 (m, 5H), 1.96 (s, 1H), 1.82 (s, 1H), 1.75 (s, 1H), 1.71-1.64 (m, 3H), 1.56-1.52 (m, 2H), 1.48 (s, 1H), 1.45-1.40 (m, 2H).

Example 138 N—((S)-1-((((S)-4-(benzylamino)-3,4-dione-1-((S)-2-oxopyrrolidine-3-yl)but-2-yl)amino)-1-oxo-3-phenylpropan-2-yl)benzene[d][1,3]dioxol-5-carboxamide (A138)

1H NMR (500 MHz, Chloroform) δ 7.52 (s, 1H), 7.43-7.23 (m, 8H), 7.23-7.19 (m, 3H), 7.16 (s, 1H), 6.92 (s, 1H), 6.04 (s, 1H), 5.92-5.88 (m, 2H), 5.21 (s, 1H), 4.83 (s, 1H), 4.75 (s, 1H), 4.44 (s, 1H), 4.38 (s, 1H), 3.45 (s, 1H), 3.36 (d, J=13.2 Hz, 2H), 2.95 (s, 1H), 2.80 (s, 1H), 2.18 (s, 1H), 2.09-2.05 (m, 2H), 1.92 (s, 1H).

Example 139 N—((S)-1-((((S)-4-(tert-butylamino)-3,4-dione-1-((S)-2-oxopyrrolidine-3-yl)but-2-yl)amino)-1-oxo-3-phenylpropan-2-yl)benzene[d][1,3]dioxol-5-carboxamide (A139)

1H NMR (500 MHz, Chloroform) δ 7.48 (s, 1H), 7.32 (s, 1H), 7.29-7.23 (m, 2H), 7.23-7.14 (m, 3H), 6.91 (s, 1H), 5.95 (s, 1H), 5.92-5.88 (m, 2H), 4.76 (d, J=1.1 Hz, 2H), 4.71 (s, 1H), 3.46 (d, J=12.3 Hz, 2H), 3.35 (s, 1H), 3.08 (s, 1H), 2.99 (s, 1H), 2.19 (s, 1H), 2.09-2.05 (m, 2H), 1.93 (s, 1H), 1.40-1.36 (m, 9H).

Example 140 N—((S)-1-(((S)-4-(cyclohexylamino)-3,4-dione-1-((S)-2-oxopyrrolidine-3-yl)but-2-yl)amino)-1-oxo-3-phenylpropan-2-yl)benzene[d][1,3]dioxol-5-carboxamide (A140)

1H NMR (500 MHz, Chloroform) δ 7.30 (dd, J=21.6, 15.7 Hz, 4H), 7.28-7.23 (m, 1H), 7.28-7.14 (m, 4H), 6.89 (s, 1H), 6.05 (s, 1H), 5.92-5.88 (m, 2H), 5.08 (s, 1H), 4.75 (d, J=16.1 Hz, 2H), 3.59 (s, 1H), 3.45 (d, J=2.5 Hz, 2H), 3.35 (s, 1H), 3.12 (s, 1H), 2.99 (s, 1H), 2.19 (s, 1H), 2.10-2.04 (m, 4H), 1.93 (s, 1H), 1.81-1.70 (m, 3H), 1.58-1.54 (m, 2H), 1.51 (s, 1H), 1.47-1.42 (m, 2H).

Example 141 N—((S)-1-(((S)-4-(benzylamino)-3,4-dione-1-((S)-2-oxopiperidine-3-yl)but-2-yl)amino)-1-oxo-3-phenylpropan-2-yl)benzene[d][1,3]dioxol-5-carboxamide (A141)

1H NMR (500 MHz, Chloroform) δ 7.41 (s, 1H), 7.36 (s, 1H), 10.00-7.08 (m, 14H), 6.54 (s, 1H), 6.07 (s, 1H), 5.92-5.88 (m, 2H), 5.10 (s, 1H), 4.42 (s, 1H), 4.37 (d, J=6.5 Hz, 2H), 4.30 (s, 1H), 3.60 (s, 1H), 3.25 (t, J=13.9 Hz, 3H), 3.03 (s, 1H), 2.73 (s, 1H), 2.09-2.03 (m, 2H), 1.79 (d, J=5.2 Hz, 2H), 1.73 (s, 1H), 1.57 (s, 1H).

Example 142 N—((S)-1-((((S)-4-(tert-butylamino)-3,4-dione-1-((S)-2-oxopiperidine-3-yl)but-2-yl)amino)-1-oxo-3-phenylpropan-2-yl)benzene[d][1,3]dioxol-5-carboxamide (A142)

1H NMR (500 MHz, Chloroform) δ 8.38 (s, 28H), 7.44 (s, 29H), 7.30-7.23 (m, 86H), 7.23-7.15 (m, 82H), 7.15 (d, J=1.8 Hz, 4H), 6.98 (s, 29H), 5.92-5.85 (m, 85H), 5.21 (s, 28H), 5.00 (s, 27H), 4.81 (s, 28H), 4.66 (s, 28H), 3.26 (t, J=21.5 Hz, 87H), 2.91 (s, 30H), 2.78 (s, 26H), 2.21 (s, 20H), 2.11-2.02 (m, 61H), 2.00 (s, 21H), 1.83 (s, 25H), 1.77 (s, 21H), 1.32-1.28 (m, 251H).

Example 143 N—((S)-1-((((S)-4-(cyclohexylamino)-3,4-dione-1-((S)-2-oxopiperidine-3-yl)but-2-yl)amino)-1-oxo-3-phenylpropan-2-yl)benzene[d][1,3]dioxol-5-carboxamide (A143)

1H NMR (500 MHz, Chloroform) δ 8.29 (s, 1H), 7.48 (s, 1H), 7.38 (s, 1H), 7.28-7.23 (m, 2H), 7.23-7.11 (m, 3H), 6.94 (s, 1H), 6.09 (s, 1H), 5.92-5.88 (m, 2H), 5.06 (s, 1H), 4.91 (s, 1H), 4.73 (s, 1H), 4.38 (s, 1H), 3.36 (s, 1H), 3.31-3.20 (m, 3H), 3.07 (s, 1H), 2.85 (s, 1H), 2.08-2.03 (m, 4H), 1.88 (s, 1H), 1.81 (s, 1H)), 1.78-1.69 (m, 3H), 1.67 (s, 1H), 1.58 (s, 1H), 1.51 (t, J=7.6 Hz, 3H), 1.43-1.39 (m, 2H).

Example 144 N—((S)-1-((((S)-4-(cyclohexylamino)-3,4-dione-1-((S)-2-oxopiperidine-3-yl)but-2-yl)amino)-1-oxo-3-phenylpropan-2-yl)benzene[d][1,3]dioxol-5-carboxamide (A144)

1H NMR (500 MHz, Chloroform) δ 8.29 (s, 1H), 7.48 (s, 1H), 7.38 (s, 1H), 7.28-7.23 (m, 2H), 7.23-7.11 (m, 3H), 6.94 (s, 1H), 6.09 (s, 1H), 5.92-5.88 (m, 2H), 5.06 (s, 1H), 4.91 (s, 1H), 4.73 (s, 1H), 4.38 (s, 1H), 3.36 (s, 1H), 3.31-3.20 (m, 3H), 3.07 (s, 1H), 2.85 (s, 1H), 2.08-2.03 (m, 4H), 1.88 (s, 1H), 1.81 (s, 1H)), 1.78-1.69 (m, 3H), 1.67 (s, 1H), 1.58 (s, 1H), 1.51 (t, J=7.6 Hz, 3H), 1.43-1.39 (m, 2H).

Example 145 N—((S)-1-((((S)-4-(tert-butylamino)-3,4-dione-1-((S)-2-oxopyrrolidine-3-yl)but-2-yl)amino)-1-oxo-3-phenylpropan-2-yl)-5-fluoronicotinamide (A145)

1H NMR (500 MHz, Chloroform) δ 8.60 (d, J=2.3 Hz, 2H), 7.83 (s, 1H), 7.23 (d, J=6.4 Hz, 1H), 7.22-7.08 (m, 5H), 5.97 (s, 1H), 5.48 (s, 1H), 4.88 (s, 1H), 4.38 (s, 1H), 4.01 (s, 1H), 3.45 (s, 1H), 3.35 (s, 1H), 3.26 (s, 1H), 2.96 (s, 1H), 2.69 (s, 1H), 2.40 (s, 1H), 2.16 (s, 1H), 2.09-2.05 (m, 2H), 1.92 (s, 1H), 1.32-1.28 (m, 10H).

Example 146 N—((S)-1-((((S)-4-(cyclohexylamino)-3,4-dione-1-((S)-2-oxopyrrolidine-3-yl)but-2-yl)amino)-1-oxo-3-phenylpropan-2-yl)-5-fluoronicotinamide (A146)

1H NMR (500 MHz, Chloroform) δ 8.82 (s, 1H), 8.50 (s, 1H), 7.89 (s, 1H), 7.31-7.24 (m, 4H), 7.17 (s, 1H), 6.22 (s, 1H), 5.95 (s, 1H), 5.47 (s, 1H), 5.14 (s, 1H), 4.38 (s, 1H), 3.45 (s, 1H), 3.37 (d, J=16.6 Hz, 2H), 3.29 (s, 1H), 2.86 (s, 1H), 2.47 (s, 1H), 2.19 (s, 1H), 2.09-2.05 (m, 2H), 1.93 (s, 1H), 1.91-1.79 (m, 2H), 1.70 (s, 1H), 1.58-1.51 (m, 4H), 1.50 (s, 1H), 1.45-1.40 (m, 2H).

Example 147 N—((S)-1-((((S)-4-(benzylamino)-3,4-dione-1-((S)-2-oxopiperidine-3-yl)but-2-yl)amino)-1-oxo-3-phenylpropan-2-yl)-5-fluoronicotinamide (A147)

1H NMR (500 MHz, Chloroform) δ 8.80 (s, 1H), 8.58 (s, 1H), 7.99 (s, 1H), 7.41-7.32 (m, 2H), 7.32-7.18 (m, 6H), 7.16 (s, 1H), 7.09 (s, 1H), 6.51 (s, 1H), 6.23 (s, 1H), 5.85 (s, 1H), 4.87 (s, 1H), 4.36 (s, 1H), 4.30 (d, J=5.9 Hz, 2H), 3.24 (d, J=15.2 Hz, 2H), 3.09 (s, 1H), 2.82 (s, 1H), 2.57 (s, 1H), 2.08-2.04 (m, 2H), 1.98 (s, 1H), 1.82 (s, 1H), 1.76 (s, 1H), 1.65 (s, 1H).

Example 148 N—((S)-1-((((S)-4-(tert-butylamino)-3,4-dione-1-((S)-2-oxopiperidine-3-yl)but-2-yl)amino)-1-oxo-3-phenylpropan-2-yl)-5-fluoronicotinamide (A148)

1H NMR (500 MHz, Chloroform) δ 8.82 (s, 1H), 8.52 (s, 1H), 8.05 (s, 1H), 7.30-7.22 (m, 4H), 7.15 (s, 1H), 6.03 (s, 1H), 5.79 (s, 1H), 5.01 (s, 1H), 4.84 (s, 1H), 4.27 (s, 1H), 3.36 (s, 1H), 3.24 (d, J=14.9 Hz, 2H), 2.95 (s, 1H), 2.72 (s, 1H), 2.07 (t, J=5.5 Hz, 3H), 1.85 (s, 1H), 1.78 (s, 1H), 1.70 (s, 1H), 1.32-1.28 (m, 9H).

Example 149 N—((S)-1-((((S)-4-(cyclohexylamino)-3,4-dione-1-((S)-2-oxopiperidine-3-yl)but-2-yl)amino)-1-oxo-3-phenylpropan-2-yl)-5-fluoronicotinamide (A149)

1H NMR (500 MHz, Chloroform) δ 8.86 (s, 7H), 8.52 (s, 7H), 7.93 (s, 7H), 7.42 (s, 7H), 7.24-7.19 (m, 14H), 7.14 (s, 7H), 7.12-7.04 (m, 14H), 6.15 (d, J=16.5 Hz, 14H), 5.79 (s, 7H), 4.89 (s, 7H), 4.62 (s, 7H), 3.87 (s, 7H)), 3.27 (t, J=22.0 Hz, 22H), 3.17 (t, J=12.5 Hz, 1H), 3.11 (d, J=17.0 Hz, 14H), 2.12 (s, 5H), 2.10-2.01 (m, 16H), 2.01-1.94 (m, 14H), 1.87 (s, 5H), 1.80 (s, 5H), 1.67-1.58 (m, 67H).

Example 150 N—((S)-1-((((S)-4-(benzylamino)-3,4-dione-1-((S)-2-oxopyrrolidine-3-yl)but-2-yl)amino)-1-oxo-3-phenylpropan-2-yl)-1-methyl-1H-pyrazole-4-carboxamide (A150)

1H NMR (500 MHz, Chloroform) δ 7.52 (s, 5H), 7.32-7.14 (m, 55H), 7.13 (t, J=1.5 Hz, 1H), 7.07 (s, 5H), 6.09 (s, 5H), 6.01 (s, 5H), 5.64 (s, 5H), 5.02 (s, 5H), 4.84 (s, 5H), 4.36 (s, 5H), 4.29 (s, 5H), 3.89-3.85 (m, 15H), 3.45 (s, 5H), 3.35 (s, 4H), 3.17 (s, 4H), 3.11 (s, 5H), 2.93 (s, 5H), 2.19 (s, 4H), 2.10-2.04 (m, 10H), 1.92 (s, 4H).

Example 151 N—((S)-1-((((S)-4-(tert-butylamino)-3,4-dione-1-((S)-2-oxopyrrolidine-3-yl)but-2-yl)amino)-1-oxo-3-phenylpropan-2-yl)-1-methyl-1H-pyrazole-4-carboxamide (A151)

1H NMR (500 MHz, Chloroform) δ 7.86 (s, 1H), 7.42 (s, 1H), 10.00-7.19 (m, 6H), 7.17 (s, 1H), 7.05 (s, 1H), 5.92 (d, J=15.2 Hz, 2H), 5.77 (s, 1H), 5.06 (s, 1H), 4.87 (s, 1H), 3.89-3.85 (m, 3H), 3.45 (s, 1H), 3.35 (s, 1H)), 3.18 (s, 1H), 2.88 (d, J=18.2 Hz, 2H), 2.17 (s, 1H), 2.13-2.02 (m, 2H), 1.92 (s, 1H), 1.34-1.30 (m, 9H).

Example 152 N—((S)-1-((((S)-4-(cyclohexylamino)-3,4-dione-1-((S)-2-oxopyrrolidine-3-yl)but-2-yl)amino)-1-oxo-3-phenylpropan-2-yl)-1-methyl-1H-pyrazole-4-carboxamide (A152)

1H NMR (500 MHz, Chloroform) δ 7.28-7.17 (m, 5H), 7.15 (s, 1H), 7.08 (s, 1H), 6.04 (s, 1H), 5.89 (s, 1H), 4.77 (s, 1H), 4.30 (s, 1H), 4.02-3.98 (m, 3H), 3.83 (s, 1H), 3.71 (s, 1H), 3.45 (s, 1H), 3.35 (s, 1H), 3.30 (s, 1H), 3.05 (s, 1H), 2.97 (s, 1H), 2.65 (s, 1H), 2.20 (s, 1H), 2.09-2.05 (m, 2H), 2.04-2.00 (m, 1H), 1.91 (s, 1H), 1.67-1.55 (m, 7H).

Example 153 N—((S)-1-((((S)-4-(benzylamino)-3,4-dione-1-((S)-2-oxopiperidine-3-yl)but-2-yl)amino)-1-oxo-3-phenylpropan-2-yl)-1-methyl-1H-pyrazole-4-carboxamide (A153)

1H NMR (500 MHz, Chloroform) δ 8.58 (s, 7H), 8.29 (s, 7H), 7.42 (s, 7H), 7.32-7.24 (m, 28H), 7.18 (dt, J=57.0, 25.2 Hz, 40H), 7.08-7.07 (m, 2H), 6.51 (s, 7H), 6.01 (s, 7H), 5.10 (s, 7H), 4.81 (s, 7H), 4.38 (s, 7H), 4.32 (s, 7H), 3.93-3.89 (m, 21H), 3.30 (d, J=53.3 Hz, 17H), 3.21 (s, 3H), 3.21 (s, 6H), 2.99 (s, 7H), 2.17 (s, 6H), 2.11-2.01 (m, 14H), 1.76 (d, J=12.9 Hz, 12H), 1.68 (s, 5H), 1.42 (s, 6H).

Example 154 N—((S)-1-((((S)-4-(tert-butylamino)-3,4-dione-1-((S)-2-oxopiperidine-3-yl)but-2-yl)amino)-1-oxo-3-phenylpropan-2-yl)-1-methyl-1H-pyrazole-4-carboxamide (A154)

1H NMR (500 MHz, Chloroform) δ 9.02 (s, 1H), 7.53 (s, 1H), 7.31-7.25 (m, 2H), 7.17 (dd, J=16.8, 9.4 Hz, 4H), 6.20 (s, 1H), 6.11 (s, 1H), 5.60 (s, 1H), 5.16 (s, 1H), 4.76 (s, 1H), 3.90-3.86 (m, 3H), 3.24 (d, J=15.4 Hz, 2H), 3.12 (s, 1H), 2.92 (d, J=17.7 Hz, 2H), 2.05 (t, J=4.4 Hz, 3H), 1.82 (s, 1H), 1.76 (s, 1H), 1.56 (s, 1H), 1.31-1.27 (m, 9H).

Example 155 N—((S)-1-((((S)-4-(cyclohexylamino)-3,4-dione-1-((S)-2-oxopiperidine-3-yl)but-2-yl)amino)-1-oxo-3-phenylpropan-2-yl)-1-methyl-1H-pyrazole-4-carboxamide (A155)

1H NMR (500 MHz, Chloroform) δ 8.38 (s, 1H), 7.28-7.22 (m, 2H), 7.22-7.11 (m, 3H), 7.04 (s, 1H), 6.62 (s, 1H), 5.99 (s, 1H), 4.76 (s, 1H), 4.62 (s, 1H), 4.30 (s, 1H), 3.83-3.79 (m, 3H), 3.26 (dd, J=17.5, 12.1 Hz, 4H), 3.05 (s, 1H), 3.01 (s, 1H), 2.72 (s, 1H), 2.20-2.13 (m, 3H), 2.09-2.03 (m, 2H), 1.86 (s, 1H), 1.80 (s, 1H), 1.72-1.66 (m, 3H), 1.56 (t, J=5.2 Hz, 3H), 1.49 (s, 1H), 1.46-1.41 (m, 2H).

Example 156 N—((S)-1-((((S)-4-(benzylamino)-3,4-dione-1-((S)-2-oxopyrrolidine-3-yl)but-2-yl)amino)-1-oxo-3-phenylpropan-2-yl)-6-bromo-imidazo[1,2-a]pyridine-2-carboxamide (A156)

1H NMR (500 MHz, Chloroform) δ 8.45 (s, 1H), 7.77 (s, 1H), 7.68 (s, 1H), 7.58 (s, 1H), 7.40 (s, 1H), 7.32-7.26 (m, 4H), 7.26-7.11 (m, 7H), 6.00 (s, 1H), 5.04 (s, 1H), 4.92 (s, 1H), 4.77 (s, 1H), 4.38 (s, 1H), 4.30 (s, 1H), 3.45 (s, 1H), 3.35 (s, 1H), 3.27 (s, 1H), 3.11 (s, 1H), 2.85 (s, 1H), 2.19 (s, 1H), 2.09-2.05 (m, 2H), 1.92 (s, 1H).

Example 157 N—((S)-1-((((S)-4-(tert-butylamino)-3,4-dione-1-((S)-2-oxopyrrolidine-3-yl)but-2-yl)amino)-1-oxo-3-phenylpropan-2-yl)-6-bromo-imidazo[1,2-a]pyridine-2-carboxamide (A157)

1H NMR (500 MHz, Chloroform) δ 8.80 (s, 1H), 8.37 (s, 1H), 7.69 (d, J=2.2 Hz, 2H), 7.59 (s, 1H), 7.28-7.21 (m, 2H), 7.21-7.11 (m, 3H), 6.78 (s, 1H), 5.98 (s, 1H), 5.45 (s, 1H), 4.93 (s, 1H), 4.66 (s, 1H), 3.45 (s, 1H)), 3.35 (s, 1H), 3.22 (s, 1H), 2.96 (d, J=29.5 Hz, 2H), 2.19 (s, 1H), 2.09-2.05 (m, 2H), 1.92 (s, 1H), 1.34-1.30 (m, 9H).

Example 158 N—((S)-1-(((S)-4-(benzylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide (A158)

1H NMR (500 MHz, Chloroform) δ 8.39 (s, 1H), 7.69 (d, J=16.1 Hz, 2H), 7.60 (s, 1H), 7.36-7.20 (m, 9H), 7.19 (d, J=13.6 Hz, 2H), 6.50 (s, 1H), 6.28 (s, 1H), 6.16 (s, 1H), 6.10 (s, 1H), 4.75 (d, J=4.7 Hz, 2H), 4.39 (s, 1H), 4.30 (s, 1H), 3.24 (t, J=8.9 Hz, 3H), 3.01 (s, 1H), 2.72 (s, 1H), 2.11-2.01 (m, 2H), 1.84 (s, 1H)), 1.80 (s, 1H), 1.73 (s, 1H), 1.36 (s, 1H).

Example 159 N—((S)-1-((((S)-4-(tert-butylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide (A159)

1H NMR (500 MHz, Chloroform) δ 8.41 (s, 1H), 8.18 (s, 1H), 7.79-7.57 (m, 3H), 7.27-7.21 (m, 2H), 7.21-7.10 (m, 3H), 6.09 (s, 1H), 5.52 (s, 1H), 5.08 (s, 1H), 4.74 (s, 1H), 4.45 (s, 1H), 3.25 (t, J=9.9 Hz, 3H), 3.01 (s, 1H), 2.85 (s, 1H), 2.10-2.02 (m, 2H), 1.88 (s, 1H), 1.81 (s, 1H), 1.68 (s, 1H), 1.60 (s, 1H), 1.35-1.31 (m, 9H).

Example 160 N—((S)-1-((((S)-4-(cyclohexylamino)-3,4-dione-1-((S)-2-oxopiperidine-3-yl)but-2-yl)amino)-1-oxo-3-phenylpropan-2-yl)-6-bromo-imidazo[1,2-a]pyridine-2-carboxamide (A160)

1H NMR (500 MHz, Chloroform) δ 9.87 (s, 1H), 8.26 (s, 1H), 7.68 (s, 1H), 7.57 (d, J=11.2 Hz, 2H), 7.27-7.21 (m, 2H), 7.21-7.10 (m, 3H), 6.07 (s, 1H), 4.94 (s, 1H), 4.78 (s, 1H), 4.51 (s, 1H), 3.54 (s, 1H), 3.45 (s, 1H)), 3.24 (d, J=16.2 Hz, 2H), 3.17 (s, 1H), 2.97 (s, 1H), 2.92 (s, 1H), 2.28 (s, 1H), 2.09-2.04 (m, 4H), 1.81 (s, 1H), 1.74 (s, 1H), 1.70 (s, 1H), 1.59-1.52 (m, 4H), 1.49 (d, J=1.6 Hz, 2H), 1.47-1.41 (m, 2H).

Example 161 N—((S)-1-(((S)-4-(phenylamino)-3,4-dione-1-((S)-2-oxopyrrolidine-3-yl)but-2-yl)amino)-1-oxo-3-phenylpropan-2-yl)-1H-benzo[d]imidazole-2-carboxamide (A161)

1H NMR (500 MHz, Chloroform) δ 7.62 (d, J=18.9 Hz, 2H), 7.34-7.23 (m, 9H), 7.23-7.12 (m, 3H), 6.92 (s, 1H), 6.17 (s, 1H), 5.35 (s, 1H), 5.03 (s, 1H), 4.70 (d, J=4.7 Hz, 2H), 4.38 (s, 1H), 4.33 (s, 1H), 4.03 (s, 1H), 3.35 (s, 1H), 3.27 (s, 1H), 3.04 (s, 1H), 2.82 (s, 1H), 2.17 (s, 1H), 2.12-2.03 (m, 2H), 1.93 (s, 1H).

Example 162 N—((S)-1-(((S)-4-(tert-butylamino)-3,4-dione-1-((S)-2-oxopyrrolidine-3-yl)but-2-yl)amino)-1-oxo-3-phenylpropan-2-yl)-1H-benzo[d]imidazole-2-carboxamide (A162)

1H NMR (500 MHz, Chloroform) δ 7.68 (s, 1H), 7.59 (s, 1H), 7.30-7.25 (m, 2H), 7.22-7.16 (m, 2H), 7.16-7.06 (m, 3H), 6.17 (s, 1H), 5.89 (s, 1H), 5.84 (s, 1H), 5.11 (s, 1H), 4.98 (s, 1H), 3.45 (s, 1H), 3.35 (s, 1H), 3.25 (s, 1H), 3.04 (s, 1H), 2.28 (s, 1H), 2.19 (s, 1H), 2.11-2.03 (m, 2H), 1.92 (s, 1H), 1.35-1.31 (m, 9H).

Example 163 N—((S)-1-((((S)-4-(cyclohexylamino)-3,4-dione-1-((S)-2-oxopyrrolidine-3-yl)but-2-yl)amino)-1-oxo-3-phenylpropan-2-yl)-1H-benzo[d]imidazole-2-carboxamide (A163)

1H NMR (500 MHz, Chloroform) δ 7.70 (s, 1H), 7.57 (d, J=4.5 Hz, 2H), 7.22 (dd, J=17.6, 7.1 Hz, 4H), 7.18-7.07 (m, 3H), 5.97 (s, 1H), 5.74 (s, 1H), 5.03 (s, 1H), 4.50 (d, J=11.0 Hz, 2H), 4.41 (s, 1H), 3.61 (s, 1H), 3.45 (s, 1H), 3.35 (s, 1H), 3.21 (s, 1H), 3.03 (s, 1H), 2.80 (s, 1H), 2.17 (s, 1H), 2.09-2.05 (m, 2H), 1.93-1.78 (m, 3H), 1.71 (s, 1H), 1.64-1.60 (m, 2H), 1.58-1.54 (m, 2H), 1.50 (s, 1H), 1.48-1.42 (m, 2H).

Example 164 N—((S)-1-(((S)-4-(phenylamino)-3,4-dione-1-((S)-2-oxopiperidine-3-yl)but-2-yl)amino)-1-oxo-3-phenylpropan-2-yl)-1H-benzo[d]imidazole-2-carboxamide (A164)

1H NMR (500 MHz, Chloroform) δ 7.73 (s, 1H), 7.67 (s, 1H), 7.38 (t, J=17.9 Hz, 3H), 7.27-7.13 (m, 9H), 7.11 (s, 1H), 6.99 (s, 1H), 6.45 (s, 1H), 5.48 (s, 1H), 4.94 (d, J=7.2 Hz, 2H), 4.89 (s, 1H), 4.32 (s, 1H), 4.26 (s, 1H), 3.42 (s, 1H), 3.24 (d, J=18.2 Hz, 2H), 3.06 (s, 1H), 2.92 (s, 1H), 2.13 (s, 1H), 2.11-2.00 (m, 2H), 1.92 (s, 1H), 1.86 (s, 1H), 1.79 (s, 1H).

Example 165 N—((S)-1-((((S)-4-(tert-butylamino)-3,4-dione-1-((S)-2-oxopiperidine-3-yl)but-2-yl)amino)-1-oxo-3-phenylpropan-2-yl)-1H-benzo[d]imidazole-2-carboxamide (A165)

1H NMR (500 MHz, Chloroform) δ 9.34 (s, 4H), 7.98 (s, 4H), 7.79 (s, 4H), 7.62 (s, 4H), 7.54 (s, 4H), 7.42-7.28 (m, 23H), 7.28-7.26 (m, 2H), 7.16 (s, 4H), 5.87 (s, 4H), 5.43 (s, 4H), 5.16 (s, 4H), 4.27 (s, 4H), 3.33-3.20 (m, 12H), 2.94 (s, 4H), 2.82 (s, 4H), 2.08-2.04 (m, 8H), 1.96 (s, 3H), 1.82 (s, 3H), 1.76 (s, 3H), 1.63 (s, 3H), 1.33-1.29 (m, 36H).

Example 166 N—((S)-1-((((S)-4-(cyclohexylamino)-3,4-dione-1-((S)-2-oxopiperidine-3-yl)but-2-yl)amino)-1-oxo-3-phenylpropan-2-yl)-1H-benzo[d]imidazole-2-carboxamide (A166)

1H NMR (500 MHz, Chloroform) δ 8.45 (s, 1H), 8.24 (s, 1H), 7.65 (s, 1H), 7.60 (s, 1H), 7.53 (s, 1H), 7.24 (dd, J=20.9, 2.1 Hz, 4H), 7.16-7.04 (m, 3H), 5.61 (s, 1H), 5.36 (s, 1H), 5.09 (s, 1H), 4.63 (s, 1H), 3.50 (s, 1H)), 3.41 (s, 1H), 3.24 (d, J=15.7 Hz, 2H), 2.98 (s, 1H), 2.66 (s, 1H), 2.57 (s, 1H), 2.27-2.16 (m, 2H), 2.08-2.04 (m, 2H), 1.98 (s, 1H), 1.85 (s, 1H), 1.78 (s, 1H), 1.72 (s, 1H), 1.63-1.55 (m, 4H), 1.55-1.44 (m, 3H).

Example 167 N—((S)-1-(((S)-4-(benzylamino)-3,4-dione-1-((S)-2-oxopyrrolidine-3-yl)but-2-yl)amino)-1-oxo-3-phenylpropan-2-yl)-1H-indole-5-carboxamide (A167)

1H NMR (500 MHz, Chloroform) δ 9.78 (s, 1H), 8.99 (s, 1H), 8.23 (s, 1H), 7.81 (s, 1H), 7.49 (d, J=90.0 Hz, 2H), 7.40-7.38 (m, 4H), 7.30 (d, J=15.0 Hz, 5H), 7.19 (s, 34H), 7.14 (s, 4H), 7.07 (s, 1H), 6.56 (s, 1H)), 6.10 (s, 1H), 5.29 (s, 1H), 5.09 (s, 1H), 4.85 (s, 1H), 4.34 (s, 2H), 3.63 (s, 21H), 3.51 (s, 1H), 3.33 (s, 1H), 3.08 (s, 1H), 2.65 (s, 1H), 2.20 (s, 1H), 2.02 (s, 1H), 1.90 (s, 1H).

Example 168 N—((S)-1-((((S)-4-(tert-butylamino)-3,4-dione-1-((S)-2-oxopyrrolidine-3-yl)but-2-yl)amino)-1-oxo-3-phenylpropan-2-yl)-1H-indole-5-carboxamide (A168)

1H NMR (500 MHz, Chloroform) δ 8.95 (s, 1H), 8.26 (d, J=60.3 Hz, 2H), 7.78 (s, 1H), 7.55 (s, 1H), 7.31-7.18 (m, 4H), 7.16 (s, 1H), 7.31-6.84 (m, 7H), 6.55 (d, J=16.4 Hz, 2H), 5.97 (s, 1H), 5.15 (s, 1H), 4.79 (s, 1H), 3.63 (s, 1H), 3.51 (s, 1H), 3.32 (s, 1H), 3.07 (s, 1H), 2.54 (s, 1H), 2.21 (s, 1H), 2.02 (s, 1H), 1.91 (s, 1H), 1.26 (s, 9H).

Example 169 N—((S)-1-((((S)-4-(cyclohexylamino)-3,4-dione-1-((S)-2-oxopyrrolidine-3-yl)but-2-yl)amino)-1-oxo-3-phenylpropan-2-yl)-1H-indole-5-carboxamide (A169)

1H NMR (500 MHz, Chloroform) δ 8.98 (s, 13H), 8.34 (s, 13H), 8.22 (s, 14H), 7.80 (s, 13H), 7.57 (s, 14H), 7.37-7.20 (m, 2H), 7.18 (s, 14H), 7.37-6.87 (m, 82H), 6.56 (s, 13H), 6.49 (s, 13H), 5.99 (s, 13H), 5.17 (s, 7H), 4.95 (s, 5H), 4.79 (s, 7H), 3.64 (s, 6H), 3.52 (s, 6H), 3.33 (s, 15H), 3.08 (s, 14H), 2.55 (s, 5H), 2.20 (d, J=14.4 Hz, 31H), 2.02 (s, 14H), 1.88 (d, J=38.0 Hz, 37H), 1.80 (s, 5H), 1.62 (s, 9H), 1.37 (s, 27H), 1.31 (s, 11H), 1.20 (s, 23H).

Example 170 N—((S)-1-(((S)-4-(benzylamino)-3,4-dione-1-((S)-2-oxopiperidine-3-yl)but-2-yl)amino)-1-oxo-3-phenylpropan-2-yl)-1H-indole-5-carboxamide (A170)

¹H NMR (500 MHz, Chloroform) δ 8.99 (s, 2H), 8.23 (s, 2H), 8.06 (s, 2H), 7.81 (s, 2H), 7.58 (s, 2H), 7.29 (d, J=15.0 Hz, 9H), 7.19 (s, 1H), 7.14 (s, 9H), 7.05 (d, J=24.0 Hz, 3H), 6.56 (s, 2H), 6.06 (s, 2H), 5.05 (s, 2H), 4.76 (s, 1H), 4.34 (s, 4H), 3.55-2.80 (m, 10H), 3.48-2.77 (m, 10H), 3.28-2.80 (m, 8H), 2.87-2.77 (m, 1H), 2.70 (s, 1H), 2.34 (s, 1H), 2.01 (s, 1H), 1.91 (d, J=2.6 Hz, 2H), 1.60 (s, 1H).

Example 171 N—((S)-1-((((S)-4-(tert-butylamino)-3,4-dione-1-((S)-2-oxopiperidine-3-yl)but-2-yl)amino)-1-oxo-3-phenylpropan-2-yl)-1H-indole-5-carboxamide (A171)

1H NMR (500 MHz, Chloroform) δ 8.99 (s, 1H), 8.23 (s, 1H), 7.91 (s, 1H), 7.81 (s, 1H), 7.58 (s, 1H), 7.26-7.21 (m, 4H), 7.19 (s, 1H), 7.26-6.88 (m, 6H), 6.57 (d, J=15.1 Hz, 2H), 6.06 (s, 1H), 5.06 (s, 1H), 4.71 (s, 1H), 3.33 (s, 1H), 3.21 (d, J=15.0 Hz, 2H), 3.08 (s, 1H), 2.93 (s, 1H), 2.43 (s, 1H), 2.39 (s, 1H), 2.01 (s, 1H), 1.91 (d, J=1.1 Hz, 1H), 1.58 (s, 13H), 1.27 (s, 9H).

Example 172 N—((S)-1-((((S)-4-(cyclohexylamino)-3,4-dione-1-((S)-2-oxopiperidine-3-yl)but-2-yl)amino)-1-oxo-3-phenylpropan-2-yl)-1H-indole-5-carboxamide (A172)

¹H NMR (500 MHz, Chloroform) δ 8.99 (s, 1H), 8.23 (s, 1H), 7.81 (s, 1H), 7.68 (s, 1H), 7.58 (s, 1H), 7.26-7.21 (m, 7H), 7.19 (s, 1H), 7.26-6.88 (m, 6H), 6.53 (d, J=28.7 Hz, 2H), 6.50-6.48 (m, 5H), 6.08 (s, 1H), 5.06 (s, 1H), 4.95 (s, 1H), 4.70 (s, 1H), 3.33 (s, 1H), 3.21 (d, J=15.0 Hz, 2H), 3.08 (s, 1H), 2.94 (s, 1H), 2.44 (d, J=13.0 Hz, 2H), 2.19 (s, 2H), 2.03-1.73 (m, 5H), 1.84 (s, 3H), 1.84 (s, 2H), 1.60 (d, J=15.4 Hz, 2H), 1.37 (s, 2H), 1.31 (s, 1H), 1.20 (s, 2H).

Example 173 N—((S)-1-(((S)-4-(benzylamino)-3,4-dione-1-((S)-2-oxopyrrolidine-3-yl)but-2-yl)amino)-1-oxo-3-phenylpropan-2-yl)-5-fluoro-1H-indole-2-carboxamide (A173)

¹H NMR (500 MHz, Chloroform) δ 8.75 (s, 2H), 8.14 (s, 2H), 7.54 (d, J=24.9 Hz, 4H), 7.37-7.24 (m, 13H), 7.17 (s, 1H), 7.11 (d, J=10.0 Hz, 11H), 6.85 (s, 2H), 6.14 (s, 2H), 5.18 (s, 2H), 4.86 (s, 1H), 4.33 (s, 4H)), 3.65 (s, 1H), 3.53 (s, 1H), 3.28 (s, 4H), 3.03 (s, 1H), 2.54 (s, 2H), 2.22 (s, 2H), 2.02 (s, 2H), 1.93 (s, 1H).

Example 174 N—((S)-1-((((S)-4-(tert-butylamino)-3,4-dione-1-((S)-2-oxopyrrolidine-3-yl)but-2-yl)amino)-1-oxo-3-phenylpropan-2-yl)-5-fluoro-1H-indole-2-carboxamide (A174)

¹H NMR (500 MHz, Chloroform) δ 8.73 (s, 1H), 8.12 (s, 1H), 7.55 (d, J=25.0 Hz, 2H), 7.51 (s, 3H), 7.16 (dd, J=31.6, 6.6 Hz, 7H), 6.56 (s, 1H), 6.10 (s, 1H), 5.19 (s, 1H), 4.83 (s, 1H), 3.65 (s, 1H), 3.54 (s, 1H)), 3.29 (s, 1H), 3.04 (s, 1H), 2.58 (s, 1H), 2.22 (s, 1H), 2.02 (s, 1H), 1.92 (s, 5H), 1.27 (s, 9H).

Example 175 N—((S)-1-((((S)-4-(cyclohexylamino)-3,4-dione-1-((S)-2-oxopyrrolidine-3-yl)but-2-yl)amino)-1-oxo-3-phenylpropan-2-yl)-5-fluoro-1H-indole-2-carboxamide (A175)

1H NMR (500 MHz, Chloroform) δ 8.74 (s, 1H), 8.08 (s, 1H), 7.55 (d, J=25.0 Hz, 2H), 7.51 (s, 3H), 7.19 (d, J=2.2 Hz, 2H), 7.13 (d, J=10.0 Hz, 5H), 6.44 (s, 1H), 6.11 (s, 1H), 5.19 (s, 1H), 4.83 (s, 1H), 3.67 (d, J=15.7 Hz, 1H), 3.54 (s, 1H), 3.29 (s, 1H), 3.04 (s, 1H), 2.58 (s, 1H), 2.22 (s, 1H), 2.02 (s, 1H), 1.92 (s, 1H), 1.74 (s, 1H), 1.46 (t, J=12.5 Hz, 3H), 1.21 (s, 1H), 1.11 (s, 1H).

Example 176 N—((S)-1-(((S)-4-(benzylamino)-3,4-dione-1-((S)-2-oxopiperidine-3-yl)but-2-yl)amino)-1-oxo-3-phenylpropan-2-yl)-5-fluoro-1H-indole-2-carboxamide (A176)

¹H NMR (500 MHz, Chloroform) δ 8.71 (s, 2H), 8.61 (s, 2H), 7.69 (s, 2H), 7.58 (s, 2H), 7.53 (s, 1H), 7.33-7.20 (m, 12H), 7.19 (s, 1H), 7.13 (d, J=10.0 Hz, 10H), 5.84 (s, 2H), 5.09 (s, 1H), 4.57 (s, 1H), 4.34 (s, 4H)), 3.29 (s, 1H), 3.21 (d, J=15.0 Hz, 4H), 3.04 (s, 2H), 2.73 (s, 1H), 2.41 (s, 1H), 2.28 (s, 1H), 2.01 (s, 1H), 1.91 (d, J=4.5 Hz, 2H), 1.53 (s, 1H).

Example 177 N—((S)-1-((((S)-4-(tert-butylamino)-3,4-dione-1-((S)-2-oxopiperidine-3-yl)but-2-yl)amino)-1-oxo-3-phenylpropan-2-yl)-5-fluoro-1H-indole-2-carboxamide (A177)

¹H NMR (500 MHz, Chloroform) δ 8.68 (s, 1H), 8.29 (s, 1H), 7.54 (d, J=25.0 Hz, 2H), 7.49 (s, 3H), 7.24 (s, 1H), 7.17 (s, 1H), 7.11 (d, J=10.0 Hz, 5H), 6.61 (s, 1H), 5.90 (s, 1H), 5.05 (s, 1H), 4.68 (s, 1H), 3.28 (s, 1H), 3.22 (s, 1H), 3.11 (d, J=77.9 Hz, 2H), 2.85 (s, 1H), 2.33 (s, 1H), 2.13 (s, 1H), 2.01 (s, 1H), 1.89 (d, J=13.2 Hz, 11H), 1.53 (s, 5H), 1.27 (s, 9H).

Example 178 N—((S)-1-(((S)-4-(cyclohexylamino)-3,4-dione-1-((S)-2-oxopiperidine-3-yl)but-2-yl)amino)-1-oxo-3-phenylpropan-2-yl)-5-fluoro-1H-indole-2-carboxamide (A178)

¹H NMR (500 MHz, Chloroform) δ 8.69 (s, 1H), 8.21 (s, 1H), 7.58 (s, 1H), 7.53 (s, 1H), 7.23 (s, 1H), 7.19 (s, 1H), 7.13 (d, J=10.0 Hz, 5H), 6.53 (s, 1H), 5.93 (s, 1H), 5.07 (s, 1H), 4.95 (s, 1H), 4.67 (s, 1H), 3.29 (s, 1H), 3.25-2.88 (m, 3H), 2.85 (s, 1H), 2.36 (s, 1H), 2.17 (d, J=18.2 Hz, 3H), 2.01 (s, 1H), 1.90 (d, J=11.3 Hz, 1H), 1.84 (s, 2H), 1.62 (s, 1H), 1.53 (s, 1H), 1.37 (s, 2H), 1.31 (s, 1H), 1.20 (s, 2H).

Example 179 N—((S)-1-((((S)-4-(benzylamino)-3,4-dione-1-((S)-2-oxopyrrolidine-3-yl)but-2-yl)amino)-1-oxo-3-phenylpropan-2-yl)-6-fluoro-1H-indole-2-carboxamide (A179)

$^1$H NMR (500 MHz, Chloroform) δ 8.73 (s, 1H), 8.13 (s, 1H), 7.95 (s, 1H), 7.32-7.18 (m, 7H), 7.08 (d, J=49.9 Hz, 6H), 7.03 (s, 1H), 7.03 (s, 1H), 6.74 (s, 1H), 6.16 (s, 1H), 5.20 (s, 1H), 4.86 (s, 1H), 4.33 (s, 2H), 3.66 (s, 1H), 3.54 (s, 1H), 3.16 (d, J=124.8 Hz, 2H), 3.01 (d, J=6.4 Hz, 1H), 2.57 (s, 1H), 2.22 (s, 1H), 2.02 (s, 1H), 1.93 (s, 1H).

Example 180 N—((S)-1-((((S)-4-(tert-butylamino)-3,4-dione-1-((S)-2-oxopyrrolidine-3-yl)but-2-yl)amino)-1-oxo-3-phenylpropan-2-yl)-6-fluoro-1H-indole-2-carboxamide (A180)

$^1$H NMR (500 MHz, Chloroform) δ 8.71 (s, 1H), 8.11 (s, 1H), 7.96 (s, 1H), 7.46-6.88 (m, 8H), 7.04 (s, 1H), 7.04 (s, 1H), 6.57 (s, 1H), 6.10 (s, 1H), 5.19 (s, 1H), 4.83 (s, 1H), 3.65 (s, 1H), 3.54 (s, 1H), 3.29 (s, 1H)), 3.04 (s, 1H), 2.58 (s, 1H), 2.22 (s, 1H), 2.02 (s, 1H), 1.92 (s, 1H), 1.27 (s, 9H).

Example 181 N—((S)-1-(((S)-4-(cyclohexylamino)-3,4-dione-1-((S)-2-oxopyrrolidine-3-yl)but-2-yl)amino)-1-oxo-3-phenylpropan-2-yl)-6-fluoro-1H-indole-2-carboxamide (A181)

$^1$H NMR (500 MHz, Chloroform) δ 8.71 (s, 2H), 8.04 (s, 2H), 7.96 (s, 2H), 7.46-6.88 (m, 16H), 7.04 (s, 2H), 7.04 (s, 2H), 6.46 (s, 2H), 6.12 (s, 2H), 5.20 (s, 2H), 4.83 (s, 1H), 3.67 (d, J=17.5 Hz, 3H), 3.54 (s, 1H)), 3.29 (s, 3H), 3.04 (s, 1H), 2.58 (s, 1H), 2.22 (s, 1H), 2.02 (s, 2H), 1.93 (s, 1H), 1.74 (s, 2H), 1.46 (t, J=12.5 Hz, 6H), 1.21 (s, 3H), 1.11 (s, 2H).

Example 182 N—((S)-1-((((S)-4-(cyclohexylamino)-3,4-dione-1-((S)-2-oxopyrrolidine-3-yl)but-2-yl)amino)-1-oxo-3-phenylpropan-2-yl)-6-fluoro-1H-indole-2-carboxamide (A182)

$^1$H NMR (500 MHz, Chloroform) δ 8.68 (s, 2H), 8.30 (s, 2H), 7.96 (s, 2H), 7.40 (s, 2H), 7.28 (t, J=11.5 Hz, 12H), 7.15 (dd, J=57.0, 32.0 Hz, 15H), 7.04 (s, 2H), 7.04 (s, 2H), 5.92 (s, 2H), 5.05 (s, 1H), 4.71 (s, 1H)), 4.34 (s, 4H), 3.29 (s, 1H), 3.21 (d, J=15.0 Hz, 4H), 3.04 (s, 2H), 2.86 (s, 1H), 2.39 (s, 1H), 2.18 (s, 1H), 2.01 (s, 1H), 1.90 (d, J=6.3 Hz, 4H), 1.54 (s, 1H).

Example 183 N—((S)-1-((((S)-4-(tert-butylamino)-3,4-dione-1-((S)-2-oxopiperidine-3-yl)but-2-yl)amino)-1-oxo-3-phenylpropan-2-yl)-6-fluoro-1H-indole-2-carboxamide (A183)

$^1$H NMR (500 MHz, Chloroform) δ 8.68 (s, 1H), 8.30 (s, 11H), 7.96 (s, 1H), 7.45-6.97 (m, 8H), 7.04 (s, 1H), 7.04 (s, 1H), 6.62 (s, 1H), 5.92 (s, 1H), 5.06 (s, 1H), 4.69 (s, 1H), 3.29 (s, 1H), 3.21 (d, J=15.0 Hz, 2H), 3.04 (s, 1H), 2.85 (s, 1H), 2.33 (s, 1H), 2.13 (s, 1H), 2.01 (s, 1H), 1.90 (d, J=13.5 Hz, 1H), 1.53 (s, 1H), 1.27 (s, 9H).

Example 184 N—((S)-1-((((S)-4-(cyclohexylamino)-3,4-dione-1-((S)-2-oxopiperidine-3-yl)but-2-yl)amino)-1-oxo-3-phenylpropan-2-yl)-6-fluoro-1H-indole-2-carboxamide (A184)

$^1$H NMR (500 MHz, Chloroform) δ 8.67 (s, 1H), 8.20 (s, 1H), 7.96 (s, 1H), 7.45-6.89 (m, 8H), 7.14 (s, 4H), 7.09 (d, J=50.0 Hz, 5H), 7.04 (s, 1H), 6.53 (s, 1H), 5.93 (s, 1H), 5.07 (s, 1H), 4.95 (s, 1H), 4.67 (s, 1H)), 3.29 (s, 1H), 3.25-2.88 (m, 3H), 2.85 (s, 1H), 2.35 (s, 1H), 2.17 (d, J=17.6 Hz, 3H), 2.01 (s, 1H), 1.90 (d, J=11.7 Hz, 1H), 1.84 (s, 1H), 1.62 (s, 1H), 1.53 (s, 1H), 1.37 (s, 2H), 1.31 (s, 1H)), 1.20 (s, 2H).

Example 185 N—((S)-1-(((S)-4-(benzylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide (A185)

$^1$H NMR (500 MHz, Chloroform) δ 8.92 (s, 2H), 8.83 (s, 2H), 7.84 (s, 2H), 7.49 (s, 2H), 7.33-7.26 (m, 11H), 7.22 (s, 2H), 7.02 (d, J=21.6 Hz, 6H), 6.97 (dd, J=5.6, 2.6 Hz, 1H), 6.77 (s, 2H), 6.28 (s, 2H), 5.16 (s, 2H), 4.91 (s, 1H), 4.34 (s, 4H), 3.67 (s, 1H), 3.55 (s, 1H), 3.29 (s, 3H), 3.04 (s, 1H), 2.61 (s, 1H), 2.23 (s, 2H), 2.02 (s, 2H), 1.93 (s, 1H).

Example 186 N—((S)-1-((((S)-4-(tert-butylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide (A186)

$^1$H NMR (500 MHz, Chloroform) δ 8.75 (s, 1H), 7.97 (s, 1H), 7.45 (s, 1H), 7.31-7.15 (m, 3H), 6.97 (d, J=7.1 Hz, 5H), 6.50 (s, 1H), 6.15 (s, 1H), 5.18 (s, 1H), 4.82 (s, 1H), 3.65 (s, 1H), 3.53 (s, 1H), 3.27 (s, 1H)), 3.03 (s, 3H), 2.60 (s, 1H), 2.22 (s, 1H), 2.01 (s, 1H), 1.92 (s, 1H), 1.26 (s, 9H).

Example 187 N—((S)-1-((((S)-4-(cyclohexylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carboxamide (A187)

$^1$H NMR (500 MHz, Chloroform) δ 8.79 (s, 2H), 8.00 (s, 2H), 7.48 (s, 2H), 7.31 (d, J=14.5 Hz, 4H), 7.19 (s, 2H), 7.01 (d, J=5.2 Hz, 5H), 6.40 (s, 2H), 6.18 (s, 2H), 5.20 (s, 2H), 4.85 (s, 1H), 3.68 (d, J=15.6 Hz, 3H), 3.55 (s, 1H), 3.29 (s, 1H), 3.04 (s, 3H), 2.61 (s, 2H), 2.23 (s, 1H), 2.02 (s, 2H), 1.93 (s, 1H), 1.74 (s, 2H), 1.46 (t, J=12.5 Hz, 6H), 1.21 (s, 3H), 1.11 (s, 2H).

Example 188 N—((S)-1-((((S)-4-(cyclohexylamino)-3,4-dione-1-((S)-2-oxopyrrolidine-3-yl)but-2-yl)amino)-3-(3-fluorophenyl)-1-oxopropan-2-yl)-4,6-dichloro-1H-indole-2-carb oxamide (A188)

$^1$H NMR (500 MHz, Chloroform) δ 9.00 (s, 4H), 8.91 (s, 4H), 7.70 (s, 4H), 7.49 (d, J=3.7 Hz, 8H), 7.29 (dd, J=9.6, 5.4 Hz, 26H), 7.21 (s, 5H), 7.00 (d, J=5.1 Hz, 11H), 6.69 (s, 4H), 4.96 (d, J=17.8 Hz, 6H), 4.33 (s, 8H), 3.29 (s, 3H), 3.21 (d, J=15.0 Hz, 8H), 2.96 (d, J=80.6 Hz, 8H), 2.85-2.81 (m, 1H), 2.48 (s, 4H), 2.27 (s, 4H), 2.00 (d, J=2.8 Hz, 4H), 1.91 (s, 6H), 1.53 (s, 2H).

Example 189 N—((S)-1-((((S)-4-(tert-butylamino)-3,4-dione-1-((S)-2-oxopiperidine-3-yl)but-2-yl)amino)-3-(3-fluorophenyl)-1-oxopropan-2-yl)-4,6-dichloro-1H-indole-2-carboxamide (A189)

$^1$H NMR (500 MHz, Chloroform) δ 8.57 (s, 1H), 7.45 (s, 1H), 7.32 (d, J=18.3 Hz, 2H), 7.20 (d, J=6.7 Hz, 2H), 7.04 (s, 1H), 7.00 (s, 1H), 6.57 (s, 1H), 5.75 (s, 1H), 5.11 (s, 1H), 4.79 (s, 1H), 3.29 (s, 1H), 3.21 (d, J=15.0 Hz, 2H), 3.04 (s, 1H), 2.75 (s, 1H), 2.47 (s, 1H), 2.36 (s, 1H), 2.01 (s, 1H), 1.95 (s, 1H), 1.91 (s, 1H), 1.51 (s, 1H), 1.27 (s, 9H).

Example 190 N—((S)-1-(((S)-4-(cyclohexylamino)-3,4-dione-1-((S)-2-oxopiperidine-3-yl)but-2-yl)amino)-3-(3-fluorophenyl)-1-oxopropan-2-yl)-4,6-dichloro-1H-indole-2-carboxamide (A190)

$^1$H NMR (500 MHz, Chloroform) δ 8.77 (s, 1H), 7.93 (s, 1H), 7.48 (s, 41H), 7.34-7.15 (m, 3H), 7.00 (s, 1H), 6.83 (s, 2H), 6.56 (s, 1H), 6.15 (s, 1H), 5.71 (s, 1H), 5.05 (s, 2H), 4.95 (s, 2H), 4.90 (s, 1H), 3.36-3.12 (m, 4H), 3.20 (s, 1H), 3.12 (d, J=78.0 Hz, 2H), 2.32 (s, 2H), 2.31-2.17 (m, 3H), 2.03-1.86 (m, 3H), 1.84 (s, 2H), 1.62 (s, 1H), 1.49 (s, 2H), 1.37 (s, 2H), 1.31 (s, 1H), 1.20 (s, 2H).

Example 191 N—((S)-1-((((S)-4-(benzylamino)-3,4-dione-1-((S)-2-oxopyrrolidine-3-yl)but-2-yl)amino)-1-oxo-3-phenylpropan-2-yl)-5-methoxy-1H-indole-2-carboxamide (A191)

$^1$H NMR (500 MHz, Chloroform) δ 8.78 (s, 1H), 8.27 (s, 1H), 7.75-7.37 (m, 3H), 7.38 (s, 1H), 7.38 (s, 1H), 7.28 (d, J=15.0 Hz, 5H), 7.20-6.87 (m, 6H), 6.90 (s, 1H), 6.90 (s, 1H), 6.78 (s, 1H), 5.71 (s, 1H), 5.15 (s, 1H), 5.06 (s, 1H), 4.33 (s, 2H), 3.80 (s, 3H), 3.63 (s, 1H), 3.50 (s, 1H), 3.29 (s, 2H), 3.04 (s, 1H), 2.54 (s, 1H), 2.22 (s, 1H), 2.02 (s, 2H), 1.91 (s, 1H).

Example 192 N—((S)-1-((((S)-4-(tert-butylamino)-3,4-dione-1-((S)-2-oxopyrrolidine-3-yl)but-2-yl)amino)-1-oxo-3-phenylpropan-2-yl)-5-methoxy-1H-indole-2-carboxamide (A192)

$^1$H NMR (500 MHz, Chloroform) δ 8.78 (s, 1H), 8.27 (s, 1H), 7.75-7.37 (m, 3H), 7.38 (s, 1H), 7.38 (s, 1H), 7.28 (d, J=15.0 Hz, 5H), 7.20-6.87 (m, 6H), 6.90 (s, 1H), 6.90 (s, 1H), 6.78 (s, 1H), 5.71 (s, 1H), 5.15 (s, 1H), 5.06 (s, 1H), 4.33 (s, 2H), 3.80 (s, 3H), 3.63 (s, 1H), 3.50 (s, 1H), 3.29 (s, 2H), 3.04 (s, 1H), 2.54 (s, 1H), 2.22 (s, 1H), 2.02 (s, 2H), 1.91 (s, 1H), 1.27 (s, 9H).

Example 193 N—((S)-1-((((S)-4-(cyclohexylamino)-3,4-dione-1-((S)-2-oxopyrrolidine-3-yl)but-2-yl)amino)-1-oxo-3-phenylpropan-2-yl)-5-methoxy-1H-indole-2-carboxamide (A193)

$^1$H NMR (500 MHz, Chloroform) δ 8.68 (s, 1H), 8.12 (s, 1H), 7.59 (s, 1H), 7.45 (s, 1H), 7.16 (t, J=12.5 Hz, 6H), 6.79 (s, 1H), 6.44 (s, 1H), 6.10 (s, 1H), 5.19 (s, 1H), 4.95 (s, 1H), 4.82 (s, 2H), 3.81 (s, 3H), 3.65 (s, 1H), 3.54 (s, 1H), 3.29 (s, 1H), 3.04 (s, 1H), 2.58 (s, 2H), 2.21 (d, J=16.4 Hz, 2H), 2.02 (s, 1H), 1.88 (d, J=41.9 Hz, 3H), 1.80 (s, 1H), 1.62 (s, 2H), 1.37 (s, 2H), 1.31 (s, 1H), 1.20 (s, 2H).

Example 194 N—((S)-1-(((S)-4-(benzylamino)-3,4-dione-1-((S)-2-oxopiperidine-3-yl)but-2-yl)amino)-1-oxo-3-phenylpropan-2-yl)-5-methoxy-1H-indole-2-carboxamide (A194)

$^1$H NMR (500 MHz, Chloroform) δ 8.66 (s, 1H), 8.34 (s, 1H), 7.59 (s, 1H), 7.45 (s, 1H), 7.29 (d, J=15.0 Hz, 5H), 7.24-6.99 (m, 7H), 6.79 (s, 1H), 5.90 (s, 1H), 5.04 (s, 1H), 4.72 (s, 1H), 4.34 (s, 2H), 3.81 (s, 3H), 3.29 (s, 1H), 3.21 (d, J=15.0 Hz, 2H), 3.04 (s, 1H), 2.86 (s, 1H), 2.29 (s, 1H), 2.11 (s, 1H), 2.01 (s, 21H), 1.90 (d, J=11.7 Hz, 1H), 1.52 (s, 1H).

Example 195 N—((S)-1-((((S)-4-(tert-butylamino)-3,4-dione-1-((S)-2-oxopiperidine-3-yl)but-2-yl)amino)-1-oxo-3-phenylpropan-2-yl)-5-methoxy-1H-indole-2-carboxamide (A195)

$^1$H NMR (500 MHz, Chloroform) δ 8.46 (s, 1H), 7.57 (s, 1H), 7.43 (s, 1H), 7.17 (s, 1H), 7.12 (s, 4H), 7.00 (s, 1H), 6.92 (s, 1H), 6.77 (s, 1H), 6.49 (s, 1H), 5.75 (s, 1H), 5.20 (s, 1H), 4.67 (s, 1H), 3.80 (s, 3H), 3.28 (s, 1H), 3.20 (d, J=15.0 Hz, 2H), 3.03 (s, 1H), 2.77 (s, 1H), 2.40 (s, 1H), 2.30 (s, 1H), 2.00 (s, 1H), 1.94 (s, 41H), 1.90 (s, 1H), 1.51 (s, 1H), 1.27 (s, 9H).

Example 196 N—((S)-1-((((S)-4-(cyclohexylamino)-3,4-dione-1-((S)-2-oxopiperidine-3-yl)but-2-yl)amino)-1-oxo-3-phenylpropan-2-yl)-5-methoxy-1H-indole-2-carboxamide (A196)

$^1$H NMR (500 MHz, Chloroform) δ 8.61 (s, 1H), 8.10 (s, 1H), 7.59 (s, 1H), 7.45 (s, 1H), 7.19 (d, J=2.6 Hz, 2H), 7.14 (s, 4H), 6.72 (d, J=66.4 Hz, 2H), 5.95 (s, 1H), 5.05 (s, 1H), 4.95 (s, 1H), 4.71 (s, 1H), 3.81 (s, 3H), 3.29 (s, 1H), 3.21 (d, J=15.0 Hz, 2H), 3.04 (s, 1H), 2.86 (s, 1H), 2.37 (s, 61H), 2.21-2.17 (m, 2H), 2.01 (s, 1H), 1.90 (d, J=11.5 Hz, 1H), 1.84 (s, 2H), 1.62 (s, 1H), 1.54 (s, 1H), 1.37 (s, 2H), 1.31 (s, 1H), 1.20 (s, 2H).

Example 197 N—((S)-1-(((S)-4-(benzylamino)-3,4-dione-1-((S)-2-oxopyrrolidine-3-yl)but-2-yl)amino)-3-cyclopropyl-1-oxopropan-2-yl)-1H-indole-2-carboxamide (A197)

$^1$H NMR (500 MHz, Chloroform) δ 8.60 (s, 1H), 7.97 (s, 1H), 7.59 (s, 1H), 7.38 (s, 1H), 7.29 (d, J=15.0 Hz, 5H), 7.16 (s, 1H), 7.10 (d, J=9.2 Hz, 2H), 6.97 (s, 1H), 6.16 (s, 1H), 4.87 (s, 1H), 4.67 (s, 1H), 4.34 (s, 2H), 3.65 (s, 1H), 3.54 (s, 1H), 2.61 (s, 1H), 2.22 (s, 1H), 2.02 (s, 1H), 1.92 (s, 1H), 1.76 (s, 1H), 1.11 (s, 1H), 0.60 (s, 1H), 0.35 (s, 1H).

Example 198 N—((S)-1-((((S)-4-(tert-butylamino)-3,4-dione-1-((S)-2-oxopyrrolidine-3-yl)but-2-yl)amino)-3-cyclopropyl-1-oxopropan-2-yl)-1H-indole-2-carboxamide (A198)

$^1$H NMR (500 MHz, Chloroform) δ 8.59 (s, 1H), 7.98 (s, 1H), 7.61 (d, J=10.9 Hz, 2H), 7.12 (d, J=16.2 Hz, 2H), 6.98 (s, 1H), 6.56 (s, 1H), 6.12 (s, 1H), 4.81 (s, 1H), 4.67 (s, 1H), 3.65 (s, 1H), 3.54 (s, 1H), 2.59 (s, 1H), 2.22 (s, 1H), 2.02 (s, 1H), 1.92 (s, 1H), 1.76 (s, 1H), 1.27 (s, 9H), 1.11 (s, 1H), 0.58 (s, 1H), 0.33 (s, 1H).

Example 199 N—((S)-1-((((S)-4-(cyclohexylamino)-3,4-dione-1-((S)-2-oxopyrrolidine-3-yl)but-2-yl)amino)-3-cyclopropyl-1-oxopropan-2-yl)-1H-indole-2-carboxamide (A199)

$^1$H NMR (500 MHz, Chloroform) δ 8.65 (s, 1H), 8.25 (s, 1H), 7.98 (s, 1H), 7.60 (s, 1H), 7.12 (d, J=24.7 Hz, 2H), 7.10-7.07 (m, 1H), 6.98 (s, 1H), 6.41 (s, 1H), 6.15 (s, 1H), 4.82 (s, 1H), 4.58 (s, 1H), 3.66 (d, J=5.6 Hz, 2H), 3.54 (s, 1H), 2.59 (s, 1H), 2.23 (s, 1H), 2.02 (s, 1H), 1.93 (s, 1H), 1.75 (d, "J=10.0 Hz, 3H), 1.46 (t, J=12.5 Hz, 3H), 1.21 (s, 2H), 1.11 (d, J=0.5 Hz, 2H), 0.57 (s, 21H), 0.28 (s, JH).

Example 200 N—((S)-1-((((S)-4-(benzylamino)-3,4-dione-1-((S)-2-oxopiperidine-3-yl)but-2-yl)amino)-3-cyclopropyl-1-oxopropan-2-yl)-1H-indole-2-carboxamide (A200)

¹H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.11 (s, 1H), 0.45 (s, 1H), 0.13 (s, 1H).

Example 201 N—((S)-1-((((S)-4-(benzylamino)-3,4-dione-1-((S)-2-oxopyrrolidine-3-yl)but-2-yl)amino)-3-cyclobutyl-1-oxopropan-2-yl)-1H-indole-2-carboxamide (A201)

¹H NMR (500 MHz, Chloroform) δ 7.98 (s, 1H), 7.60 (s, 1H), 7.29 (d, J=15.0 Hz, 5H), 7.10 (s, 1H), 6.98 (s, 1H), 4.34 (s, 2H), 2.75 (s, 1H), 2.67 (s, 1H), 2.09 (s, 1H), 2.03 (d, J=6.8 Hz, 4H), 1.94 (s, 1H), 1.92-1.82 (m, 3H), 1.76 (s, 1H), 1.66 (d, J=10.0 Hz, 2H), 1.61 (s, 1H), 0.45 (s, 1H), Example 202 N—((S)-1-((((S)-4-(tert-butylamino)-3,4-dione-1-((S)-2-oxopyrrolidine-3-yl)but-2-yl)amino)-3-cyclobutyl-1-oxopropan-2-yl)-1H-indole-2-carboxamide (A202)

¹H NMR (500 MHz, Chloroform) δ 7.98 (s, 1H), 7.60 (s, 1H), 7.29 (m, 3H), 7.10 (s, 1H), 6.98 (s, 1H), 6.29 (m, 3H), 2.75 (s, 1H), 2.67 (s, 1H), 2.09 (s, 2H), 2.03 (d, J=6.8 Hz, 3H), 1.94 (s, 1H), 1.92-1.82 (m, 3H), 1.76 (s, 1H), 1.66 (d, J=10.0 Hz, 2H), 1.61 (s, 1H), 1.27 (s, 9H), 0.45 (s, 1H)

Example 203 N—((S)-1-(((S)-4-(cyclohexylamino)-3,4-dione-1-((S)-2-oxopyrrolidine-3-yl)but-2-yl)amino)-3-cyclobutyl-1-oxopropan-2-yl)-1H-indole-2-carboxamide (A203)

1H NMR (500 MHz, Chloroform) δ 7.98 (s, 1H), 7.60 (s, 1H), 7.10 (s, 1H), 6.98 (s, 1H), 4.95 (s, 1H), 2.74 (s, 1H), 2.66 (s, 1H), 2.19 (s, 2H), 2.09 (s, 1H), 2.03 (d, J=6.9 Hz, 2H), 1.94 (s, 1H), 1.86 (dd, J=18.2, 10.2 Hz, 5H), 1.76 (s, 2H), 1.64 (dd, J=22.9, 7.1 Hz, 3H), 1.37 (s, 1H), 1.31 (s, 2H), 1.20 (s, 2H), 0.45 (s, 1H)

Example 204 N—((S)-1-(((S)-4-(benzylamino)-3,4-dione-1-((S)-2-oxopiperidine-3-yl)but-2-yl)amino)-3-cyclobutyl-1-oxopropan-2-yl)-1H-indole-2-carboxamide (A204)

¹H NMR (500 MHz, Chloroform) δ 7.98 (s, 1H), 7.60 (s, 1H), 7.29 (d, J=15.0 Hz, 4H), 7.10 (s, 1H), 6.98 (s, 1H), 6.05 (m, 2H), 4.34 (s, 2H), 3.21 (d, J=15.0 Hz, 2H), 2.09 (s, 1H), 2.06-1.69 (m, 9H), 1.76 (s, 2H), 1.76 (s, 2H), 1.65 (s, 1H), 1.61 (s, 1H), 0.53 (s, 1H), 0.39 (s, 1H).

Example 205 N—((S)-1-((((S)-4-(tert-butylamino)-3,4-dione-1-((S)-2-oxopiperidine-3-yl)but-2-yl)amino)-3-cyclobutyl-1-oxopropan-2-yl)-1H-indole-2-carboxamide (A205)

¹H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.27 (s, 9H), 1.11 (s, 3H), 0.45 (s, 1H), 0.13 (s, 1H).

Example 206 N—((S)-1-(((S)-4-(cyclohexylamino)-3,4-dione-1-((S)-2-oxopiperidine-3-yl)but-2-yl)amino)-3-cyclobutyl-1-oxopropan-2-yl)-1H-indole-2-carboxamide (A206)

¹H NMR (500 MHz, Chloroform) δ 8.62 (s, 1H), 8.00 (d, J=20.6 Hz, 2H), 7.60 (s, 1H), 7.30 (d, J=15.0 Hz, 5H), 7.18 (d, J=6.9 Hz, 2H), 7.10 (s, 1H), 6.98 (s, 1H), 6.09 (s, 1H), 4.85 (s, 1H), 4.33 (d, J=13.7 Hz, 3H), 3.21 (d, J=15.0 Hz, 2H), 2.91 (s, 1H), 2.62 (s, 1H), 2.54 (s, 1H), 2.01 (s, 1H), 1.92 (d, J=12.0 Hz, 1H), 1.76 (s, 2H), 1.59 (s, 1H), 1.11 (s, 1H), 0.45 (s, 21H), 0.13 (s, 1H).

Example 207 N—((S)-1-(((S)-4-(benzylamino)-3,4-dione-1-((S)-2-oxopyrrolidine-3-yl)but-2-yl)amino)-3-cyclopentyl-1-oxopropan-2-yl)-1H-indole-2-carboxamide (A207)

¹H NMR (500 MHz, Chloroform) δ 8.57 (s, 1H), 7.98 (s, 1H), 7.60 (s, 1H), 7.38 (s, 1H), 7.30 (d, J=15.0 Hz, 5H), 7.13-7.07 (m, 2H), 6.98 (d, J=4.1 Hz, 2H), 6.13 (s, 1H), 4.81 (d, J=3.3 Hz, 1H), 4.34 (s, 2H), 3.65 (s, 1H), 3.55 (s, 1H), 2.60 (s, 1H), 2.22 (s, 1H), 2.02 (s, 1H), 1.92 (s, 3H), 1.76 (s, 3H), 1.66 (d, J=4.7 Hz, 3H), 1.36 (s, 1H), 1.23 (s, 1H).

Example 208 N—((S)-1-((((S)-4-(tert-butylamino)-3,4-dione-1-((S)-2-oxopyrrolidine-3-yl)but-2-yl)amino)-3-cyclopentyl-1-oxopropan-2-yl)-1H-indole-2-carboxamide (A208)

¹H NMR (500 MHz, Chloroform) δ 8.60 (s, 1H), 7.98 (s, 1H), 7.77 (s, 1H), 7.60 (s, 1H), 7.11 (d, J=5.1 Hz, 82H), 6.98 (s, 1H), 6.57 (s, 1H), 6.14 (s, 1H), 4.83 (s, 1H), 4.61 (s, 1H), 3.66 (s, 1H), 3.54 (s, 1H), 2.59 (s, 1H), 2.22 (s, 1H), 2.02 (s, 1H), 1.93 (s, 1H), 1.76 (s, 3H), 1.65 (d, J=11.9 Hz, 5H), 1.34 (s, 4H), 1.26 (d, J=8.6 Hz, 9H).

Example 209 N—((S)-1-((((S)-4-(cyclohexylamino)-3,4-dione-1-((S)-2-oxopyrrolidine-3-yl)but-2-yl)amino)-3-cyclopentyl-1-oxopropan-2-yl)-1H-indole-2-carboxamide (A209)

¹H NMR (500 MHz, Chloroform) δ 8.54 (s, 1H), 7.98 (s, 1H), 7.60 (s, 1H), 7.28 (s, 1H), 7.08 (d, J=16.5 Hz, 2H), 6.98 (s, 1H), 6.46 (s, 1H), 6.14 (s, 1H), 4.80 (s, 1H), 4.75 (s, 1H), 3.64 (d, J=19.8 Hz, 2H), 3.54 (s, 1H), 2.59 (s, 1H), 2.22 (s, 1H), 2.02 (s, 1H), 1.93 (s, 1H), 1.75 (d, J=10.0 Hz, 6H), 1.65 (d, J=6.5 Hz, 63H), 1.46 (t, J=12.5 Hz, 4H), 1.35 (s, 3H), 1.27 (s, 1H), 1.21 (s, 2H), 1.11 (s, 1H).

Example 210 N—((S)-1-((((S)-4-(benzylamino)-3,4-dione-1-((S)-2-oxopiperidine-3-yl)but-2-yl)amino)-3-cyclopentyl-1-oxopropan-2-yl)-1H-indole-2-carboxamide (A210)

¹H NMR (500 MHz, Chloroform) δ 8.51 (s, 1H), 7.98 (s, 1H), 7.60 (s, 1H), 7.30 (d, J=15.0 Hz, 5H), 7.24 (s, 1H), 7.09 (d, J=13.7 Hz, 2H), 6.98 (s, 1H), 6.89 (s, 1H), 6.11 (s, 1H), 4.79 (s, 1H), 4.65 (s, 11H), 4.34 (s, 2H), 3.21 (d, J=15.0 Hz, 2H), 2.91 (s, 1H), 2.50 (d, J=13.8 Hz, 2H), 2.01 (s, 1H), 1.92

(d, J=5.3 Hz, 1H), 1.76 (s, 3H), 1.65 (d, J=5.8 Hz, 3H), 1.58 (s, 1H), 1.36 (s, 1H), 1.23 (s, 1H).

Example 211 N—((S)-1-((((S)-4-(tert-butylamino)-3,4-dione-1-((S)-2-oxopiperidine-3-yl)but-2-yl) amino)-3-cyclopentyl-1-oxopropan-2-yl)-1H-indole-2-carboxamide (A211)

$^1$H NMR (500 MHz, Chloroform) δ 8.45 (s, 1H), 7.98 (s, 1H), 7.60 (s, 1H), 7.10 (s, 1H), 7.00 (d, J=18.5 Hz, 2H), 6.89 (s, 1H), 6.53 (s, 1H), 6.10 (s, 1H), 4.78 (s, 1H), 4.65 (s, 1H), 3.21 (d, J=15.0 Hz, 2H), 2.90 (s, 1H), 2.49 (d, J=13.5 Hz, 2H), 2.01 (s, 1H), 1.91 (d, J=1.6 Hz, 1H), 1.76 (s, 3H), 1.63 (t, J=21.9 Hz, 4H), 1.55-1.52 (m, 1H), 1.37 (s, 1H), 1.27 (s, 9H), 1.22 (s, 1H).

Example 212 N—((S)-1-(((S)-4-(cyclohexylamino)-3,4-dione-1-((S)-2-oxopiperidine-3-yl)but-2-yl) amino)-3-cyclopentyl-1-oxopropan-2-yl)-1H-indole-2-carboxamide (A212)

$^1$H NMR (500 MHz, Chloroform) δ 8.45 (s, 1H), 7.98 (s, 1H), 7.60 (s, 1H), 7.10 (s, 1H), 7.00 (d, J=19.1 Hz, 42H), 6.88 (s, 1H), 6.44 (s, 1H), 6.10 (s, 1H), 4.95 (s, 1H), 4.77 (s, 1H), 4.64 (s, 1H), 3.21 (d, J=15.0 Hz, 2H), 2.90 (s, 1H), 2.49 (d, J=19.3 Hz, 2H), 2.19 (s, 2H), 2.01 (s, 1H), 1.93-1.89 (m, 1H), 1.84 (s, 2H), 1.76 (s, 3H), 1.73-1.60 (m, 6H), 1.57 (s, 1H), 1.37 (d, J=2.4 Hz, 3H), 1.31 (s, 1H)), 1.21 (d, J=13.0 Hz, 2H).

Example 213 N—((S)-1-(((S)-4-(benzylamino)-3,4-dione-1-((S)-2-oxopyrrolidine-3-yl)but-2-yl)amino)-3-cyclohexyl-1-oxopropan-2-yl)-2,2-difluorobenzo[d][1,3]dioxol-5-carboxamide (A213)

$^1$H NMR (500 MHz, Chloroform) δ 7.97 (s, 1H), 7.61 (s, 1H), 7.49 (s, 1H), 7.55-7.23 (m, 6H), 7.55-6.98 (m, 8H), 6.13 (s, 1H), 4.86 (s, 1H), 4.49 (s, 1H), 4.34 (s, 2H), 3.66 (s, 1H), 3.54 (s, 1H), 2.59 (s, 1H), 2.23 (s, 1H), 2.02 (s, 1H), 1.93 (s, 1H), 1.80 (s, 3H), 1.69 (d, J=10.0 Hz, 3H), 1.31 (s, 1H), 1.26 (s, 1H), 1.11 (s, 1H), 1.03 (s, 1H).

Example 214 N—((S)-1-((((S)-4-(tert-butylamino)-3,4-dione-1-((S)-2-oxopyrrolidine-3-yl)but-2-yl) amino)-3-cyclohexyl-1-oxopropan-2-yl)-2,2-difluorobenzo[d][1,3]dioxol-5-carboxamide (A214)

$^1$H NMR (500 MHz, Chloroform) δ 7.73 (s, 1H), 7.61 (s, 1H), 7.49 (s, 1H), 7.16 (s, 1H), 6.52 (s, 1H), 6.13 (s, 1H), 4.83 (s, 1H), 4.55 (s, 1H), 3.66 (s, 1H), 3.54 (s, 1H), 2.58 (s, 1H), 2.22 (s, 1H), 2.02 (s, 1H), 1.93 (s, 1H), 1.80 (s, 2H), 1.58 (s, 1H), 1.51 (d, J=15.0 Hz, 3H), 1.48-1.41 (m, 4H), 1.28 (d, J=5.4 Hz, 9H).

Example 215 N—((S)-1-(((S)-4-(cyclohexylamino)-3,4-dione-1-((S)-2-oxopyrrolidine-3-yl)but-2-yl) amino)-3-cyclohexyl-1-oxopropan-2-yl)-2,2-difluorobenzo[d][1,3]dioxol-5-carboxamide (A215)

$^1$H NMR (500 MHz, Chloroform) δ 7.55 (d, J=60.0 Hz, 2H), 7.16 (d, J=2.8 Hz, 2H), 6.45 (s, 1H), 6.14 (s, 1H), 4.95 (s, 1H), 4.77 (s, 1H), 4.66 (s, 1H), 3.66 (s, 1H), 3.54 (s, 1H), 2.58 (s, 1H), 2.21 (d, J=17.0 Hz, 2H), 2.02 (s, 1H), 1.92 (s, 1H), 1.84 (s, 2H), 1.80 (s, 1H), 1.64 (d, J=16.1 Hz, 3H), 1.51 (d, J=15.0 Hz, 1H), 1.44 (dd, J=12.8, 7.8 Hz, 6H), 1.37 (s, 3H), 1.31 (s, 1H), 1.20 (s, 2H).

Example 216 N—((S)-1-((((S)-4-(benzylamino)-3,4-dione-1-((S)-2-oxopiperidine-3-yl)but-2-yl)amino)-3-cyclohexyl-1-oxopropan-2-yl)-2,2-difluorobenzo[d][1,3]dioxol-5-carboxamide (A216)

$^1$H NMR (500 MHz, Chloroform δ 7.55 (d, J=60.0 Hz, 2H), 7.46-7.26 (m, 6H), 7.16 (s, 1H), 7.09 (s, 1H), 6.08 (s, 1H), 4.79 (s, 1H), 4.41 (s, 1H), 4.34 (s, 2H), 3.21 (d, J=15.0 Hz, 2H), 2.85 (s, 1H), 2.53 (d, J'''=12.1 Hz, 2H), 2.01 (s, JH), 1.91 (d, J'''=3.6 Hz, 1H), 1.80 (s, 1H), 1.72 (s, 1H), 1.58 (s, 1H), 1.52 (d, J=15.0 Hz, 2H), 1.48-1.41 (m, 4H), 1.34 (s, 1H).

Example 217 N—((S)-1-((((S)-4-(tert-butylamino)-3,4-dione-1-((S)-2-oxopiperidine-3-yl)but-2-yl) amino)-3-cyclohexyl-1-oxopropan-2-yl)-2,2-difluorobenzo[d][1,3]dioxol-5-carboxamide (A217)

$^1$H NMR (500 MHz, Chloroform) δ 7.61 (s, 2H), 7.49 (s, 2H), 7.16 (s, 2H), 6.89 (s, 2H), 6.53 (s, 2H), 6.09 (s, 2H), 4.76 (s, 1H), 4.44 (s, 1H), 3.21 (d, J=15.0 Hz, 4H), 2.88 (s, 2H), 2.49 (d, J=3.0 Hz, 4H), 2.01 (s, 1H), 1.93-1.89 (m, 2H), 1.80 (s, 3H), 1.69 (d, J=10.0 Hz, 2H), 1.57 (s, 1H), 1.31 (d, J=4.8 Hz, 2H), 1.27 (s, 9H), 1.11 (s, 1H), 1.03 (s, 3H).

Example 218 N—((S)-1-(((S)-4-(cyclohexylamino)-3,4-dione-1-((S)-2-oxopiperidine-3-yl)but-2-yl) amino)-3-cyclohexyl-1-oxopropan-2-yl)-2,2-difluorobenzo[d][1,3]dioxol-5-carboxamide (A218)

$^1$H NMR (500 MHz, Chloroform) δ 7.58 (s, 1H), 7.46 (s, 1H), 7.13 (s, 1H), 6.47 (d, J=5.5 Hz, 2H), 5.81 (s, 1H), 4.93 (d, J=6.0 Hz, 2H), 4.37 (s, 1H), 3.34 (s, 1H), 3.20 (d, J=15.0 Hz, 2H), 2.37 (d, J=18.2 Hz, 2H), 2.18 (s, 2H), 2.00 (s, 1H), 1.90 (d, J=0.5 Hz, 1H), 1.81 (d, J=19.9 Hz, 6H), 1.69 (s, 2H), 1.64 (d, J=29.9 Hz, 3H), 1.51 (s, 1H), 1.37 (s, 3H), 1.31 (s, 2H), 1.18 (d, J=16.6 Hz, 3H), 1.11 (s, 1H), 1.03 (s, 2H).

Example 219 N—((S)-1-(((S)-4-(cyclohexylamino)-3,4-dione-1-((S)-2-oxopiperidine-3-yl)but-2-yl) amino)-3-cyclohexyl-1-oxopropan-2-yl)-2,2-difluorobenzo[d][1,3]dioxol-5-carboxamide (A219)

1H NMR (500 MHz, Chloroform) δ 7.58 (s, 1H), 7.46 (s, 1H), 7.13 (s, 1H), 6.47 (d, J=5.5 Hz, 2H), 5.81 (s, 1H), 4.93 (d, J=6.0 Hz, 2H), 4.37 (s, 1H), 3.34 (s, 1H), 3.20 (d, J=15.0 Hz, 2H), 2.37 (d, J=18.2 Hz, 2H), 2.18 (s, 2H), 2.00 (s, 1H), 1.90 (d, J=0.5 Hz, 1H), 1.81 (d, J=19.9 Hz, 6H), 1.69 (s, 2H), 1.64 (d, J=29.9 Hz, 3H), 1.51 (s, 1H), 1.37 (s, 3H), 1.31 (s, 2H), 1.18 (d, J=16.6 Hz, 3H), 1.11 (s, 1H), 1.03 (s, 2H).

Example 220 N—((S)-1-((((S)-4-(benzylamino)-3,4-dione-1-((S)-2-oxopyrrolidine-3-yl)but-2-yl)amino)-1-oxo-3-phenylpropan-2-yl)-4,6-dimethoxy-1H-indole-2-carboxamide (A220)

1H NMR (500 MHz, Chloroform) δ 9.90 (s, 1H), 8.66 (s, 1H), 8.26 (s, 1H), 7.77 (s, 1H), 7.30 (d, J=15.0 Hz, 5H), 7.23-7.03 (m, 6H), 6.71 (s, 1H), 6.26 (s, 1H), 5.98 (s, 1H), 5.15 (s, 1H), 4.87 (s, 1H), 4.34 (s, 2H), 3.79 (s, 6H), 3.64 (s, 1H), 3.52 (s, 1H), 3.29 (s, 1H), 3.04 (s, 1H), 2.52 (s, 1H), 2.22 (s, 1H), 2.02 (s, 1H), 1.92 (s, 2H).

Example 221 N—((S)-1-((((S)-4-(tert-butylamino)-3,4-dione-1-((S)-2-oxopyrrolidine-3-yl)but-2-yl) amino)-1-oxo-3-phenylpropan-2-yl)-4,6-dimethoxy-1H-indole-2-carboxamide (A221)

1H NMR (500 MHz, Chloroform) δ 8.60 (s, 1H), 8.35 (s, 1H), 7.76 (s, 1H), 7.17 (d, J=25.0 Hz, 5H), 6.69 (s, 1H), 6.58

(s, 1H), 6.23 (s, 1H), 6.00 (s, 1H), 5.18 (s, 1H), 4.81 (s, 1H), 3.79 (s, 6H), 3.64 (s, 1H), 3.53 (s, 1H), 3.29 (s, 1H), 3.04 (s, 1H), 2.55 (s, 1H), 2.22 (s, 1H), 2.02 (s, 1H), 1.92 (s, 1H), 1.27 (s, 9H).

Example 222 N—((S)-1-((((S)-4-(cyclohexylamino)-3,4-dione-1-((S)-2-oxopyrrolidine-3-yl)but-2-yl)amino)-1-oxo-3-phenylpropan-2-yl)-4,6-dimethoxy-1H-indole-2-carboxamide (A222)

1H NMR (500 MHz, Chloroform) δ 8.59 (s, 1H), 8.10 (s, 1H), 7.68 (s, 1H), 7.15 (d, J=25.0 Hz, 5H), 6.67 (s, 1H), 6.45 (s, 1H), 6.21 (s, 1H), 6.07 (s, 1H), 5.18 (s, 1H), 4.94 (s, 1H), 4.80 (s, 1H), 3.78 (s, 6H), 3.64 (s, 1H), 3.53 (s, 1H), 3.28 (s, 1H), 3.03 (s, 1H), 2.56 (s, 1H), 2.20 (d, J=16.3 Hz, 3H), 2.02 (s, 1H)), 1.88 (d, J=41.4 Hz, 3H), 1.80 (s, 1H), 1.62 (s, 1H), 1.37 (s, 2H), 1.31 (s, 1H), 1.20 (s, 2H).

Example 223 N—((S)-1-(((S)-4-(benzylamino)-3,4-dione-1-((S)-2-oxopiperidine-3-yl)but-2-yl)amino)-1-oxo-3-phenylpropan-2-yl)-4,6-dimethoxy-1H-indole-2-carboxamide (A223)

1H NMR (500 MHz, Chloroform) δ 8.65 (s, 1H), 8.29 (s, 1H), 8.02 (s, 1H), 7.27 (d, J=15.0 Hz, 5H), 7.14 (d, J=24.9 Hz, 5H), 6.92 (s, 1H), 6.59 (s, 1H), 6.20 (s, 1H), 6.08 (s, 1H), 5.01 (s, 1H), 4.76 (s, 1H), 4.33 (s, 2H), 3.78 (s, 6H), 3.28 (s, 1H), 3.20 (d, J=15.0 Hz, 2H), 3.03 (s, 1H), 2.85 (d, J=1.0 Hz, 2H), 2.32 (s, 1H), 2.00 (s, 1H), 1.90 (d, J=1.3 Hz, 1H), 1.61 (s, 1H).

Example 224 N—((S)-1-((((S)-4-(tert-butylamino)-3,4-dione-1-((S)-2-oxopiperidine-3-yl)but-2-yl)amino)-1-oxo-3-phenylpropan-2-yl)-4,6-dimethoxy-1H-indole-2-carboxamide (A224)

1H NMR (500 MHz, Chloroform) δ 8.80 (d, J=11.2 Hz, 2H), 7.09 (t, J=61.7 Hz, 6H), 6.94 (s, 1H), 6.94 (s, 1H), 6.77 (s, 1H), 6.63 (s, 1H), 6.56 (s, 1H), 5.04 (d, J=1.0 Hz, 2H), 4.99 (s, 1H), 3.79 (s, 6H), 3.29 (s, 1H), 3.21 (d, J=15.0 Hz, 3H), 2.93 (d, J=106.3 Hz, 2H), 2.79-2.70 (m, 1H), 2.40 (s, 1H), 2.27 (s, 1H), 2.01 (s, 1H), 1.92 (d, J=8.4 Hz, 1H), 1.46 (s, 1H), 1.27 (s, 9H).

Example 225 N—((S)-1-(((S)-4-(cyclohexylamino)-3,4-dione-1-((S)-2-oxopiperidine-3-yl)but-2-yl)amino)-1-oxo-3-phenylpropan-2-yl)-4,6-dimethoxy-1H-indole-2-carboxamide (A225)

1H NMR (500 MHz, Chloroform) δ 8.67 (s, 1H), 7.80 (s, 1H), 7.65 (s, 1H), 7.08 (t, J=67.3 Hz, 6H), 6.91 (s, 1H), 6.91 (s, 1H), 6.55 (s, 1H), 6.49 (s, 1H), 6.07 (s, 1H), 5.09 (s, 1H), 4.95 (s, 1H), 4.69 (s, 1H), 3.79 (s, 6H), 3.29 (s, 1H), 3.21 (d, J=15.0 Hz, 2H), 3.04 (s, 1H), 2.93 (s, 1H), 2.42 (d, J=15.8 Hz, 2H), 2.19 (s, 2H), 2.03-1.73 (m, 5H), 1.84 (s, 3H), 1.84 (s, 2H), 1.60 (d, J=16.9 Hz, 2H), 1.37 (s, 2H), 1.31 (s, 1H), 1.20 (s, 2H).

Example 226 N—((S)-1-(((S)-4-(benzylamino)-3,4-dione-1-((S)-2-oxopyrrolidine-3-yl)but-2-yl)amino)-3-(3,4-difluorophenyl)-1-oxopropan-2-yl)-1H-indole-2-carboxamide (A226)

¹H NMR (500 MHz, Chloroform) δ 8.76 (s, 1H), 8.12 (s, 1H), 7.98 (s, 1H), 7.89 (s, 1H), 7.60 (s, 1H), 7.29 (d, J=15.0 Hz, 5H), 7.19 (d, J=17.1 Hz, 2H), 7.10 (d, J=2.2 Hz, 2H), 6.99 (d, J=15.0 Hz, 2H), 6.31 (s, 1H), 5.05 (s, 1H), 4.91 (s, 1H), 4.34 (s, 2H), 3.67 (s, 1H), 3.56 (s, 1H), 3.29 (s, 1H), 3.04 (s, 1H), 2.70 (s, 1H), 2.23 (s, 1H), 2.02 (s, 2H), 1.93 (s, 1H).

Example 227 N—((S)-1-((((S)-4-(tert-butylamino)-3,4-dione-1-((S)-2-oxopyrrolidine-3-yl)but-2-yl)amino)-3-(3,4-difluorophenyl)-1-oxopropan-2-yl)-1H-indole-2-carboxamide (A227)

¹H NMR (500 MHz, Chloroform) δ 8.72 (s, 1H), 8.44 (s, 1H), 7.96 (s, 1H), 7.59 (s, 1H), 7.25 (s, 1H), 7.16 (s, 1H), 7.09 (d, J=2.1 Hz, 2H), 6.98 (d, J=15.0 Hz, 2H), 6.60 (s, 1H), 5.97 (s, 1H), 5.12 (s, 1H), 4.82 (s, 1H), 3.64 (s, 1H), 3.52 (s, 1H), 3.28 (s, 1H), 3.03 (s, 1H), 2.54 (s, 1H), 2.22 (s, 1H), 2.02 (s, 1H), 1.92 (s, 1H), 1.27 (s, 9H).

Example 228 N—((S)-1-(((S)-4-(cyclohexylamino)-3,4-dione-1-((S)-2-oxopyrrolidine-3-yl)but-2-yl)amino)-3-(3,4-difluorophenyl)-1-oxopropan-2-yl)-1H-indole-2-carboxamide (A228)

¹H NMR (500 MHz, Chloroform) δ 8.69 (s, 1H), 8.41 (s, 1H), 7.94 (s, 1H), 7.56 (s, 1H), 7.23 (s, 1H), 7.13 (s, 1H), 7.06 (d, J=0.9 Hz, 2H), 6.96 (d, J=14.9 Hz, 2H), 6.65 (s, 1H), 5.95 (s, 1H), 5.11 (s, 1H), 4.92 (s, 1H), 4.81 (s, 1H), 3.63 (s, 1H), 3.51 (s, 1H), 3.27 (s, 1H), 3.02 (s, 1H), 2.53 (s, 1H), 2.19 (d, J=14.6 Hz, 2H), 2.01 (s, 1H), 1.87 (d, J=40.1 Hz, 3H), 1.79 (s, 1H), 1.61 (s, 1H), 1.36 (s, 2H), 1.30 (s, 1H), 1.19 (s, 2H).

Example 229 N—((S)-1-(((S)-4-(benzylamino)-3,4-dione-1-((S)-2-oxopiperidine-3-yl)but-2-yl)amino)-3-(3,4-difluorophenyl)-1-oxopropan-2-yl)-1H-indole-2-carboxamide (A229)

¹H NMR (500 MHz, Chloroform) δ 8.69 (s, 1H), 8.11 (s, 1H), 7.95 (s, 1H), 7.57 (s, 1H), 7.43 (s, 1H), 7.27 (d, J=15.0 Hz, 5H), 7.14 (s, 1H), 7.07 (s, 1H), 6.97 (d, J=15.0 Hz, 2H), 6.82 (s, 1H), 6.58 (s, 1H), 6.04 (s, 1H), 5.01 (s, 21H), 4.83 (s, 1H), 4.32 (s, 2H), 3.28 (s, 1H), 3.20 (d, J=15.0 Hz, 2H), 3.03 (s, 1H), 2.89 (s, 1H), 2.70 (s, 1H), 2.25 (s, 1H), 2.00 (s, 1H), 1.90 (d, J=2.9 Hz, 1H), 1.60 (s, 1H).

Example 230 N—((S)-1-((((S)-4-(tert-butylamino)-3,4-dione-1-((S)-2-oxopiperidine-3-yl)but-2-yl)amino)-3-(3, 4-difluorophenyl)-1-oxopropan-2-yl)-1H-indole-2-carboxamide (A230)

¹H NMR (500 MHz, Chloroform) δ 8.74 (s, 1H), 8.06 (s, 1H), 7.98 (s, 1H), 7.60 (s, 1H), 7.17 (s, 1H), 7.11 (d, J=8.4 Hz, 2H), 7.03-6.90 (m, 3H), 6.53 (s, 1H), 5.75 (s, 1H), 5.12 (s, 1H), 4.72 (s, 1H), 3.29 (s, 1H)), 3.21 (d, J=15.0 Hz, 2H), 3.04 (s, 1H), 2.75 (s, 1H), 2.43 (s, 1H), 2.33 (s, 1H), 2.01 (s, 1H), 1.96 (s, 1H), 1.91 (s, 1H), 1.52 (s, 1H), 1.27 (s, 9H).

Example 231 N—((S)-1-(((S)-4-(cyclohexylamino)-3,4-dione-1-((S)-2-oxopiperidine-3-yl)but-2-yl)amino)-3-(3,4-difluorophenyl)-1-oxopropan-2-yl)-1H-indole-2-carboxamide (A231)

¹H NMR (500 MHz, Chloroform) δ 8.72 (s, 1H), 7.99 (d, J=25.5 Hz, 2H), 7.59 (s, 1H), 7.16 (s, 1H), 7.09 (d, J=4.0 Hz, 2H), 6.97 (t, J=11.7 Hz, 3H), 6.45 (s, 1H), 6.07 (s, 1H), 5.09 (s, 1H), 4.94 (s, 1H), 4.68 (s, 1H), 3.28 (s, 1H), 3.21 (d, J=15.0 Hz, 2H), 3.03 (s, 1H), 2.95 (s, 1H), 2.44 (d, J=17.0

Hz, 2H), 2.19 (s, 2H), 2.03-1.73 (m, 5H), 1.84 (s, 2H), 1.84 (s, 2H), 1.60 (d, J=13.6 Hz, 2H), 1.37 (s, 2H), 1.31 (s, 1H), 1.20 (s, 2H).

Example 232 N—((S)-1-(((S)-4-(benzyl)-3,4-dione-1-(isopropylamino)-2-yl)amino)-3-(cyclohexyl)-1-oxopropan-2-yl)-1H-indole-2-carboxamide (A232)

¹H NMR (500 MHz, Chloroform) δ 8.57 (s, 1H), 7.94 (s, 1H), 7.57 (s, 1H), 7.40 (s, 1H), 7.26 (d, J=14.9 Hz, 4H), 7.16-7.03 (m, 3H), 6.95 (s, 1H), 6.45 (s, 1H), 5.67 (s, 1H), 4.95 (s, 1H), 4.48 (s, 1H), 4.32 (s, 2H), 3.79 (s, 1H), 2.20 (s, 1H), 2.15 (s, 1H), 2.04 (s, 2H), 1.77 (d, J=19.9 Hz, 3H), 1.68 (d, J=10.0 Hz, 4H), 1.37 (s, 1H), 1.30 (s, 1H), 1.11 (s, 1H), 1.01 (d, J=14.9 Hz, 6H).

Example 233 N—((S)-1-(((S)-4-(benzyl)-3,4-dione-1-(isopropylamino)-2-yl)amino)-3-(phenyl)-1-oxo-propan-2-yl)-1H-indole-2-carboxamide (A233)

1H NMR (500 MHz, Chloroform) δ 8.85 (s, 1H), 8.41 (s, 1H), 7.98 (s, 1H), 7.60 (s, 1H), 7.29 (d, J=15.0 Hz, 5H), 7.20 (d, J=16.0 Hz, 2H), 7.12 (d, J=20.0 Hz, 5H), 6.98 (s, 1H), 6.69 (s, 1H), 5.05 (s, 1H), 5.01 (s, 1H), 4.74 (s, 1H), 4.34 (s, 2H), 3.81 (s, 1H), 3.29 (s, 2H), 3.04 (s, 1H), 2.21 (d, J=5.4 Hz, 2H), 2.05 (s, 2H), 1.00 (s, 6H).

Example 234 N—((S)-1-((((S)-4-(cyclohexyl)-3,4-dione-1-(isopropylamino)-2-yl)amino)-3-(phenyl)-1-oxopropan-2-yl)-1H-indole-2-carboxamide (A234)

1H NMR (500 MHz, Chloroform) δ 8.73 (s, 1H), 8.16 (s, 1H), 7.98 (s, 1H), 7.60 (s, 1H), 7.27 (s, 1H), 7.19 (s, 1H), 7.12 (d, J=20.0 Hz, 5H), 7.07 (s, 1H), 6.98 (s, 1H), 6.53 (s, 1H), 5.87 (s, 1H), 5.64 (s, 1H), 4.92 (s, 1H), 4.86 (s, 1H), 3.81 (s, 1H), 3.29 (s, 3H), 3.02 (d, J=18.8 Hz, 3H), 2.19 (d, J=11.4 Hz, 2H), 2.05 (s, 2H), 1.80 (s, 1H), 1.69 (d, J=10.0 Hz, 3H), 1.58 (s, 1H), 1.31 (s, 1H), 1.11 (s, 1H), 1.01 (d, J=15.0 Hz, 8H).

Example 235 N—((S)-1-((((S)-4-(cyclohexyl)-3,4-dione-1-(cyclohexylamino)-2-yl)amino)-3-(phenyl)-1-oxopropan-2-yl)-1H-indole-2-carboxamide (A235)

1H NMR (500 MHz, Chloroform) δ 8.73 (s, 1H), 8.14 (s, 1H), 7.98 (s, 1H), 7.60 (s, 1H), 7.26 (s, 1H), 7.19 (s, 1H), 7.12 (d, J=20.0 Hz, 5H), 6.98 (s, 1H), 6.56 (s, 1H), 5.90 (s, 1H), 5.63 (s, 1H), 4.93 (d, J=16.9 Hz, 2H), 4.86 (s, 1H), 3.29 (s, 1H), 3.02 (d, J=18.8 Hz, 3H), 2.23-2.14 (m, 4H), 2.05 (s, 2H), 1.82 (d, J=20.0 Hz, 4H), 1.69 (d, J=10.0 Hz, 3H), 1.62 (s, 1H), 1.37 (d, J=0.9 Hz, 3H), 1.31 (s, 3H), 1.20 (s, 2H), 1.11 (s, 1H), 1.03 (s, 2H).

Example 236 N—((S)-1-(((S)-4-(benzyl)-3,4-dione-1-(isopropylamino)-2-yl)amino)-3-(cyclohexyl)-1-oxopropan-2-yl)-quinoxaline-2-carboxamide (A236)

¹H NMR (500 MHz, Chloroform) δ 9.45 (s, 1H), 7.80 (s, 2H), 7.67 (s, 2H), 7.35-7.26 (m, 6H), 7.11 (s, 1H), 6.67 (s, 1H), 5.75 (s, 1H), 5.11 (s, 1H), 4.33 (d, J=6.4 Hz, 3H), 3.81 (s, 1H), 2.16 (d, J=10.5 Hz, 2H), 2.05 (s, 1H), 1.76 (s, 1H), 1.60 (s, 1H), 1.51 (d, J=15.0 Hz, 2H), 1.48-1.41 (m, 4H), 1.32 (s, 1H), 1.00 (s, 6H).

Example 237 N—((S)-1-((((S)-4-(cyclohexyl)-3,4-dione-1-(isopropylamino)-2-yl)amino)-3-(cyclohexyl)-1-oxopropan-2-yl)-quinoxaline-2-carboxamide (A237)

¹H NMR (500 MHz, Chloroform) δ 9.32 (s, 1H), 8.17 (s, 1H), 8.12 (s, 1H), 7.76 (s, 1H), 7.66 (d, J=4.6 Hz, 2H), 7.33-7.27 (m, 4H), 7.19 (s, 1H), 5.70 (s, 1H), 4.93 (s, 1H), 4.80 (s, 1H), 4.75 (s, 1H), 4.03 (s, 1H), 3.98 (s, 1H), 3.24 (s, 1H), 3.02-2.98 (m, 3H), 2.30-2.26 (m, 2H), 2.18 (s, 1H), 2.10 (s, 1H), 1.82-1.75 (m, 2H), 1.75-1.71 (m, 2H), 1.67 (s, 1H), 1.45-1.41 (m, 2H), 1.33 (s, 1H), 1.30-1.20 (m, 6H), 1.14-1.07 (m, 3H).

Example 238 N—((S)-1-(((S)-4-(benzyl)-3,4-dione-1-(isopropylamino)-2-yl)amino)-3-(phenyl)-1-oxopropan-2-yl)-quinoxaline-2-carboxamide (A238)

¹H NMR (500 MHz, Chloroform) δ 9.34 (s, 1H), 8.08 (d, J=10.7 Hz, 2H), 7.62 (d, J=0.9 Hz, 2H), 7.30-7.21 (m, 8H), 7.19 (s, 1H), 7.14 (s, 1H), 6.23 (s, 1H), 6.03 (s, 1H), 5.22 (s, 1H), 5.08 (s, 1H), 4.95 (s, 1H), 4.88 (s, 1H), 4.33 (s, 1H), 4.28 (s, 1H), 3.96 (s, 1H), 3.22 (s, 1H), 2.99 (s, 1H), 2.38-2.34 (m, 2H), 2.21 (s, 1H), 2.16 (s, 1H), 1.33-1.20 (m, 6H).

Example 239 N—((S)-1-(((S)-4-(benzyl)-3,4-dione-1-(cyclohexylamino)-2-yl)amino)-3-(phenyl)-1-oxopropan-2-yl)-quinoxaline-2-carboxamide (A239)

1H NMR (500 MHz, Chloroform) δ 9.31 (s, 1H), 8.12 (d, J=31.2 Hz, 2H), 7.73 (s, 1H), 7.63 (d, J=6.0 Hz, 2H), 7.36-7.24 (m, 8H), 7.17 (d, J=11.8 Hz, 2H), 6.32 (s, 1H), 5.10 (s, 1H), 4.76 (s, 1H), 4.67 (s, 1H), 4.36 (s, 1H), 4.30 (d, J=18.6 Hz, 2H), 4.12 (s, 1H), 3.24 (s, 1H), 2.97 (s, 1H), 2.31-2.27 (m, 2H), 2.12 (d, J=3.2 Hz, 2H), 1.94-1.87 (m, 2H), 1.73-1.63 (m, 4H), 1.61-1.55 (m, 4H).

Example 240 N—((S)-1-((((S)-4-(benzylamino)-3,4-dione-1-((S)-2-oxopiperidine-3-yl)but-2-yl)amino)-3-cyclohexyl-1-oxopropan-2-yl)-1H-indole-6-fluoro-2-carboxamide (A240)

¹H NMR (500 MHz, Chloroform) δ 8.12 (s, 1H), 7.57 (s, 1H), 7.52 (s, 1H), 7.36-7.25 (m, 4H), 7.20 (d, J=7.7 Hz, 2H), 6.84 (s, 1H), 6.18 (s, 1H), 5.49 (d, J=11.0 Hz, 2H), 4.70 (s, 1H), 4.39 (d, J=17.7 Hz, 2H), 4.08 (s, 1H), 3.24 (d, J=17.5 Hz, 2H), 2.54 (s, 1H), 2.08-2.04 (m, 2H), 1.82 (s, 1H), 1.78-1.67 (m, 6H), 1.66-1.62 (m, 2H), 1.58 (dd, J=9.5, 3.3 Hz, 5H), 1.44 (s, 1H), 1.37-1.27 (m, 3H).

Example 241 N—((S)-1-((((S)-4-(benzylamino)-3,4-dione-1-((S)-2-oxopiperidine-3-yl)but-2-yl)amino)-3-cyclohexyl-1-oxopropan-2-yl)-5-methyloxazole-2-carboxamide (A241)

¹H NMR (500 MHz, Chloroform) δ 7.33-7.27 (m, 4H), 7.23 (s, 1H), 6.79 (d, J=13.7 Hz, 2H), 6.29 (s, 1H), 6.09 (s, 1H), 5.05 (s, 1H), 4.99 (d, J=9.8 Hz, 2H), 4.41 (s, 1H), 4.34 (s, 1H), 3.24 (d, J=14.9 Hz, 2H), 2.92 (s, 1H), 2.36-2.32 (m, 3H), 2.08-2.04 (m, 2H), 1.85 (s, 1H), 1.79 (s, 1H), 1.74-1.55 (m, 11H), 1.48 (s, 1H), 1.46-1.23 (m, 3H).

Example 242 N—((S)-1-(((S)-4-(benzylamino)-3,4-dione-1-((S)-2-oxopyrrolidine-3-yl)but-2-yl)amino)-3-cyclohexyl-1-oxopropan-2-yl)-5-methyloxazole-2-carboxamide (A242)

¹H NMR (500 MHz, Chloroform) δ 7.33-7.30 (m, 22H), 7.28 (t, J=15.0 Hz, 33H), 6.83 (s, 9H), 6.14 (s, 9H), 6.09 (s, 9H), 5.94 (s, 9H), 5.19 (s, 9H), 5.01 (s, 9H), 4.36 (d, J=0.5 Hz, 18H), 3.45 (s, 9H), 3.35 (s, 7H), 2.59 (s, 9H), 2.38-2.34 (m, 27H), 2.18 (s, 8H), 2.09-2.05 (m, 18H), 1.96-1.88 (m, 24H), 1.88 (s, 3H), 1.73-1.60 (m, 46H), 1.40-1.36 (m, 16H), 1.32 (s, 9H), 1.15 (s, 7H), 1.12-1.08 (m, 17H).

Example 243 N—((S)-1-(((((S)-4-(benzylamino)-3,4-dione-1-((S)-2-oxopiperidine-3-yl)but-2-yl)amino)-3-cyclohexyl-1-oxopropan-2-yl)-benzo[d]1,3-dioxole-5-carboxamide (A243)

$^1$H NMR (500 MHz, Chloroform) δ 7.54 (s, 6H), 7.45 (s, 6H), 7.29-7.18 (m, 30H), 6.96 (s, 6H), 6.49 (s, 6H), 6.01 (s, 6H), 5.92-5.88 (m, 12H), 5.58 (s, 6H), 5.11 (s, 6H), 4.93 (s, 6H), 4.63 (s, 6H), 4.29 (s, 6H), 4.24 (s, 6H), 3.24 (d, J=17.5 Hz, 11H), 2.86 (s, 6H), 2.05 (t, J=4.2 Hz, 18H), 1.95-1.87 (m, 12H), 1.84 (s, 6H), 1.76 (t, J=4.8 Hz, 17H), 1.63 (dd, J=40.8, 34.9 Hz, 22H), 1.51 (dd, J=4.6, 1.3 Hz, 1H), 1.40-1.36 (m, 10H), 1.32 (s, 6H), 1.17-1.09 (m, 17H).

Example 244 N—((S)-1-(((((S)-4-(benzylamino)-3,4-dione-1-((S)-2-oxopiperidine-3-yl)but-2-yl)amino)-3-cyclohexyl-1-oxopropan-2-yl)-1H-benzo[d]imidazole-2-carboxamide (A244)

$^1$H NMR (500 MHz, Chloroform) δ 7.84 (s, 1H), 7.73 (s, 1H), 7.62 (s, 1H), 7.38 (s, 1H), 7.31-7.23 (m, 6H), 7.16 (s, 1H), 6.17 (s, 1H), 5.59 (s, 1H), 5.10 (s, 1H), 4.75 (s, 1H), 4.53 (s, 1H), 4.36 (d, J=17.3 Hz, 2H), 3.24 (d, J=17.5 Hz, 2H), 2.88 (s, 1H), 2.06 (t, J=2.7 Hz, 3H), 1.96-1.81 (m, 3H), 1.77 (s, 1H), 1.73-1.60 (m, 5H), 1.53 (s, 1H), 1.40-1.36 (m, 2H), 1.32 (s, 1H), 1.22-1.15 (m, 3H).

Example 245 N—((S)-1-(((((S)-4-(benzylamino)-3,4-dione-1-((S)-2-oxopiperidine-3-yl)but-2-yl)amino)-3-cyclohexyl-1-oxopropan-2-yl)-7-methoxy-benzofuran-2-carboxamide (A245)

$^1$H NMR (500 MHz, Chloroform) δ 7.60 (s, 8H), 7.34-7.22 (m, 33H), 7.15 (d, J=10.0 Hz, 16H), 7.06 (s, 8H), 6.81 (s, 8H), 6.54 (s, 8H), 6.22 (s, 8H), 5.59 (s, 8H), 5.08 (s, 8H), 4.92 (s, 8H), 4.63 (s, 8H), 4.32 (d, J=1.1 Hz, 16H), 3.89-3.85 (m, 24H), 3.24 (d, J=17.4 Hz, 15H), 2.94 (s, 8H), 2.07 (t, J=5.1 Hz, 23H), 1.93-1.85 (m, 18H), 1.84 (s, 6H), 1.78 (s, 6H), 1.73-1.51 (m, 49H), 1.51 (d, J=5.5 Hz, 1H), 1.40-1.36 (m, 14H), 1.32 (s, 8H), 1.16-1.07 (m, 23H).

Example 246 N—((S)-1-(((((S)-4-(benzylamino)-3,4-dione-1-((S)-2-oxopiperidine-3-yl)but-2-yl)amino)-3-cyclohexyl-1-oxopropan-2-yl)-3-methyl-benzofuran-2-carboxamide (A246)

$^1$H NMR (500 MHz, Chloroform) δ 7.60-7.40 (m, 3H), 7.32-7.18 (m, 7H), 6.67 (s, 1H), 5.57 (s, 1H), 5.15 (s, 1H), 4.67 (s, 1H), 4.55 (s, 1H), 4.30 (d, J=14.7 Hz, 2H), 3.24 (d, J=17.3 Hz, 2H), 2.73 (s, 1H), 2.15-2.10 (m, 4H), 2.08-2.04 (m, 2H), 1.88-1.81 (m, 3H), 1.77 (s, 1H), 1.73-1.59 (m, 5H), 1.55 (s, 1H), 1.40-1.36 (m, 2H), 1.32 (s, 1H), 1.14-1.05 (m, 3H).

Example 247 N—((S)-1-(((((S)-4-(benzylamino)-3,4-dione-1-((S)-2-oxopiperidine-3-yl)but-2-yl)amino)-3-cyclohexyl-1-oxopropan-2-yl)-3,5-dimethyl-benzofuran-2-carboxamide (A247)

$^1$H NMR (500 MHz, Chloroform) δ 7.50-7.34 (m, 3H), 7.32-7.26 (m, 4H), 7.23 (s, 1H), 7.11 (s, 1H), 6.68 (s, 1H), 5.57 (s, 1H), 5.15 (s, 1H), 4.69 (s, 1H), 4.55 (s, 1H), 4.30 (d, J=14.8 Hz, 2H), 3.24 (d, J=17.3 Hz, 2H), 2.73 (s, 1H), 2.45-2.41 (m, 3H), 2.15-2.10 (m, 4H), 2.08-2.04 (m, 2H), 1.88-1.81 (m, 3H), 1.77 (s, 1H), 1.73-1.59 (m, 5H), 1.55 (s, 1H), 1.40-1.36 (m, 2H), 1.32 (s, 1H), 1.14-1.05 (m, 3H).

Example 248 N—((S)-1-(((((S)-4-(benzylamino)-3,4-dione-1-((S)-2-oxopiperidine-3-yl)but-2-yl)amino)-3-cyclohexyl-1-oxopropan-2-yl)-4,7-dimethoxy-benzofuran-2-carboxamide (A248)

$^1$H NMR (500 MHz, Chloroform) δ 7.59 (s, 1H), 7.34-7.27 (m, 2H), 7.27-7.22 (m, 2H), 7.10 (s, 1H), 6.86 (s, 1H), 6.82 (s, 1H), 6.38 (s, 1H), 6.32 (s, 1H), 5.56 (s, 1H), 5.35 (s, 1H), 4.66 (d, J=18.6 Hz, 2H), 4.28 (s, 1H), 4.17 (s, 1H), 3.91-3.87 (m, 3H), 3.85-3.81 (m, 3H), 3.24 (d, J=17.8 Hz, 2H), 3.06 (s, 1H), 2.05 (t, J=6.8 Hz, 3H), 1.96-1.88 (m, 2H), 1.84 (s, 1H), 1.77 (s, 1H), 1.73-1.54 (m, 5H), 1.52 (s, 1H), 1.40-1.36 (m, 2H), 1.32 (s, 1H), 1.17-1.08 (m, 3H).

Example 249 N—((S)-1-(((((S)-4-(benzylamino)-3,4-dione-1-((S)-2-oxopiperidine-3-yl)but-2-yl)amino)-3-cyclohexyl-1-oxopropan-2-yl)-benzofuran-3-carboxamide (A249)

$^1$H NMR (500 MHz, Chloroform) δ 8.07 (s, 91H), 7.62 (s, 92H), 7.58 (s, 94H), 7.47 (s, 94H), 7.27 (dd, J=9.9, 8.1 Hz, 379H), 7.20 (t, J=5.8 Hz, 274H), 6.24 (s, 91H), 5.61 (s, 91H), 5.16 (s, 90H), 4.93 (s, 91H), 4.52 (s, 89H)), 4.32 (d, J=0.6 Hz, 182H), 3.24 (d, J=17.5 Hz, 174H), 2.89 (s, 93H), 2.06 (t, J=2.7 Hz, 257H), 1.92-1.80 (m, 277H), 1.81 (s, 7H), 1.77 (s, 70H), 1.73-1.51 (m, 541H), 1.51 (d, J=1.8 Hz, 6H), 1.40-1.36 (m, 160H), 1.32 (s, 86H), 1.22-1.16 (m, 264H).

Example 250 N—((S)-1-(((((S)-4-(benzylamino)-3,4-dione-1-((S)-2-oxopiperidine-3-yl)but-2-yl)amino)-3-cyclohexyl-1-oxopropan-2-yl)-6-chloro-2H-chromene-3-carboxamide (A250)

$^1$H NMR (500 MHz, Chloroform) δ 8.16 (s, 1H), 7.32 (s, 1H), 7.32-7.24 (m, 4H), 7.23-7.09 (m, 3H), 6.84 (s, 1H), 6.05 (s, 1H), 5.64 (s, 1H), 5.33 (s, 1H), 5.06-5.02 (m, 2H), 4.50 (d, J=9.3 Hz, 2H), 4.39 (s, 1H), 4.32 (s, 1H), 3.24 (d, J=17.4 Hz, 2H), 2.99 (s, 1H), 2.15 (s, 1H), 2.08-2.04 (m, 2H), 1.85 (s, 1H), 1.79 (s, 1H), 1.73-1.69 (m, 2H), 1.69-1.62 (m, 5H), 1.55 (s, 1H), 1.39-1.35 (m, 2H), 1.31 (s, 1H), 1.23-1.19 (m, 2H), 1.17 (s, 1H).

Example 251 N—((S)-1-(((S)-4-(cyclohexylamino)-3,4-dione-1-((S)-2-oxopyrrolidine-3-yl)but-2-yl)amino)-3-cyclohexyl-1-oxopropan-2-yl)-6-chloro-2,3-dihydrobenzo[b]1,4-dioxin-6-carboxamide (A251)

$^1$H NMR (500 MHz, Chloroform) δ 8.51 (s, 1H), 7.66 (s, 1H), 7.55 (s, 1H), 7.11 (s, 1H), 5.40 (s, 1H), 5.16 (s, 1H), 4.65 (s, 1H), 4.52 (s, 1H), 4.38-4.34 (m, 4H), 3.45 (s, 1H), 3.36 (d, J=13.4 Hz, 2H), 2.68 (s, 1H)), 2.18 (s, 1H), 2.11-2.02 (m, 2H), 1.99-1.84 (m, 3H), 1.78-1.72 (m, 2H), 1.71-1.62 (m, 5H), 1.58 (dd, "J=9.0, 3.3 Hz, 5H), 1.55-1.50 (m, 2H), 1.48 (s, 1H), 1.43-1.39 (m, 4H), 1.37-1.29 (m, 3H).

Example 252 N—((S)-1-(((S)-4-(cyclohexylamino)-3,4-dione-1-((S)-2-oxopyrrolidine-3-yl)but-2-yl)amino)-3-phenyl-1-oxopropan-2-yl)-6-chloro-2,3-dihydrobenzo[b]1,4-dioxin-6-carboxamide (A252)

$^1$H NMR (500 MHz, Chloroform) δ 9.01 (s, 1H), 7.52 (s, 1H), 7.29-7.23 (m, 2H), 7.23-7.17 (m, 2H), 7.15 (s, 1H), 7.04 (s, 1H), 6.92 (s, 1H), 6.21 (s, 1H), 5.12 (s, 1H), 5.05 (s, 1H), 4.87 (s, 1H), 4.52 (s, 1H), 4.38-4.34 (m, 4H), 3.44 (d, J=12.5 Hz, 2H), 3.37-3.20 (m, 3H), 2.98 (s, 1H), 2.19 (s, 1H), 2.12-2.04 (m, 2H), 1.92 (s, 1H), 1.85-1.78 (m, 2H), 1.66 (s, 1H), 1.56-1.52 (m, 2H), 1.48-1.39 (m, 3H), 1.23-1.11 (m, 2H).

Example 253 N—((S)-1-(((S)-4-(cyclohexylamino)-3,4-dione-1-((S)-2-oxopyrrolidine-3-yl)but-2-yl)amino)-3-cyclohexyl-1-oxopropan-2-yl)-5-methoxy-indole-6-carboxamide (A253)

$^1$H NMR (500 MHz, Chloroform) δ 8.73 (s, 5H), 8.50 (s, 5H), 7.45 (s, 5H), 7.37 (s, 5H), 7.18 (s, 5H), 6.75 (s, 5H), 6.03 (s, 5H), 5.67 (s, 5H), 5.61 (s, 5H), 4.89 (s, 5H), 4.57 (s, 5H), 3.84-3.80 (m, 15H), 3.43 (d, " J=16.9 Hz, 10H), 3.35 (s, 4H), 2.70 (s, 5H), 2.19 (s, 5H), 2.09-2.06 (m, 9H), 2.06-2.04 (m, 1H), 2.06-1.91 (m, 16H), 1.73-1.61 (m, 35H), 1.60-1.46 (m, 47H), 1.46-1.39 (m, 11H), 1.35-1.26 (m, 9H), 1.22 (s, 4H).

Pharmacological Activity Test 1.1 Packaging of Pseudovirus

The packaging method of MERS-CoV pseudovirus was as follows:

a) 293T cells were digested 24 hours before transfection and they were plated in a 10 cm tissue culture dish (2×10$^6$/dish).

b) Medium for the cells was replaced with fresh pre-warmed DMEM medium (containing 10% FBS) 2 hours before transfection.

c) Two 1.5 mL EP tubes were used for transfection. 500 nt 0.9% NaCl solution was added into EP tube 1, which contained 20 μg of pcDNA3.1-S-IRES-GFP plasmid (or VSV-G expression plasmid) and pNL4-3.luc.RE plasmid; 500 μL 0.9% NaCl was also added into EP tube 2, then 10 nt of transfection reagents vigofect was added, and both EP tubes were allowed to stand for 5 minutes.

d) 500 μL of solution in EP tube 2 was added dropwise to EP tube 1, the reaction system was mixed with a pipette tip while adding, and was placed at room temperature for 15 minutes.

e) The above 1 mL mixed liquid was added dropwise and evenly into the culture dish having the previously plated 293T cells.

f) After 8 to 10 hours of transfection, it was replaced with 10 mL of fresh DMEM medium containing 10% FBS.

g) The supernatant containing pseudovirus was collected after 48 hours.

h) The supernatant was centrifuged at 4000 rpm for 4 min to remove cell debris, filtered with a 0.45 um sterile filter, aliquoted and stored at −80° C. for later use.

1.2 Detection of Pseudovirus Titer a) In MERS-CoV, HCoV-229E, VSV-G pseudovirus infection experiments, Huh-7 was used as the target cell. 12 hours before the infection experiment, the target cells were digested, the cell concentration was adjusted, and the cells were plated in a 96-well cell plate (10,000 cells per well) and cultivation was continued for 12 hours at 37° C. under 5% CO$_2$ for use.

b) 5-fold dilution of pseudovirus was conducted in a round bottom 96-well plate (system was 100 μL).

c) The target cell culture supernatant in the 96-well plate was discarded, and then the virus diluent (100 μL) was added.

d) After culturing for 12 hours, it was replaced with 100 μL of fresh DMEM medium (containing 10% FBS);

e) The cultivation was continued for 48 hours, then the supernatant was discarded, and the cells were washed twice with PBS gently to prevent the cells from falling off, and the PBS was removed as much as possible.

f) 50 μL of pre-diluted lysate was added (ddH$_2$O was used to dilute 5× cell lysate into 1× concentration) and then it was placed on a vortex mixer to shake and mix until the cells were completely lysed (1-2 h was sufficient).

g) 30 μL of lysate was taken into 96-well opaque white ELISA plate while paying attention to replace the pipette tip.

h) 50 μL of firefly enzyme detection reagent was added into each well, and then the fluorescence value was quickly detected by using the functional microplate reader. The general value was the 1000-fold virus dilution of the blank control, which was selected for the pseudovirus suppression experiment.

1.3 Pseudovirus Suppression Experiment a) DMEM was used to dilute the compound twice in a 96-well plate (50 μL system), while taking care to avoid the precipitation of the compound.

b) 50 μL of pseudovirus of a certain dilution was added into each well, DMEM (50 μL) was added into the blank control well. The virus and the compound were well mixed, and incubated at 37° C. for 30 min.

c) The target cell supernatant was removed, and the compound/virus mixture (100 μL) was added to the corresponding target cells.

The liquid was changed after 12 hours, and then the fluorescence value was detected after 48 hours.

The experimental results are shown in Table 2.

TABLE 2

| MERS-CoV pseudovirus inhibitory activity | | | |
|---|---|---|---|
| Compound number | IC$_{50}$ (μM) | Compound number | IC$_{50}$ (μM) |
| A5 | 0.0005 ± 0.0002 | A27 | 0.008 ± 0.004 |
| A15 | <0.0001 | A51 | <0.0001 |
| A39 | 0.0005 ± 0.0003 | A81 | 0.0002 ± 0.0001 |
| A232 | 0.0134 ± 0.003 | A236 | 0.0166 ± 0.004 |
| A21 | 0.0082 ± 0.0032 | A240 | 0.0159 ± 0.007 |
| A9 | 0.0010 ± 0.0007 | A214 | 0.0079 ± 0.0049 |
| A241 | 0.0025 ± 0.0013 | A242 | 0.0022 ± 0.0008 |
| A30 | 0.0162 ± 0.006 | A217 | 0.0079 ± 0.0053 |
| A243 | 0.0107 ± 0.0008 | A244 | 0.0126 ± 0.0122 |
| A245 | 0.0184 ± 0.008 | A246 | 0.0108 ± 0.0100 |
| A247 | 0.0017 ± 0.0004 | A248 | 0.0084 ± 0.0017 |
| A249 | 0.0006 ± 0.0002 | A250 | 0.0007 ± 0.0001 |
| A251 | 0.0808 ± 0.0213 | A42 | 0.0032 ± 0.0006 |
| A252 | 0.0264 ± 0.0176 | A43 | 0.7858 ± 0.4579 |
| A175 | 0.4356 ± 0.1807 | A26 | 0.0078 ± 0.0035 |
| A253 | 0.0225 ± 0.0042 | A68 | 0.0209 ± 0.0088 |
| A44 | 0.0180 ± 0.0056 | A176 | 0.0125 ± 0.0026 |
| A25 | 0.4070 ± 0.3520 | | |

2.1 In Vitro Inhibition of HCoV Live Virus Infection

Figure 1B:
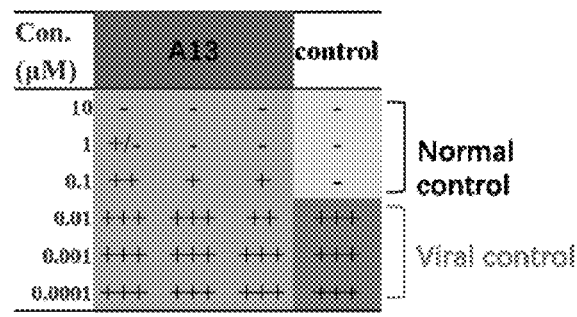
FIG. 1B shows the inhibitory effect of A13 at different concentrations on CPE in target cells, where "−" means no CPE, "+/−" means <10% CPE, "+" means 30% CPE, "++" means 60% CPE, and "+++" means >90% CPE.
Figure 1C:
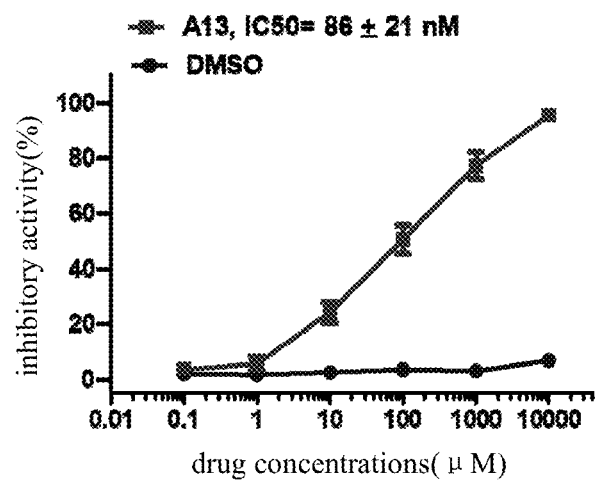
FIG. 1C shows evaluation of the inhibitory activity of A13 with different concentrations on HCoV-OC43 infection.

At present, we had HCoV-OC43 (ATCC-VR1558) live virus, and according to the virus culture conditions provided by ATCC, we had established an in vitro infection system. Using this system, we tested the inhibitory effect of compound A13 on HCoV-OC43 live virus infection. In HCT-8 cells infected with HCoV-OC43, a large number of vacuoles and other cytopathic phenomena (CPE) appeared, but in the presence of compound A13 (1 μM), it could effectively block the virus infection and the CPE caused by the infection (as shown in FIG. 1A), and the protective effect on target cells was obviously dose-dependent (as shown in FIG. 1B). We used the CCK8 method to detect the inhibitory effect of compound A13 on HCoV-OC43 live virus infection, and the results showed that its inhibitory activity was at a low nanomolar level ($IC_{50}$=86 nM), as shown in FIG. 1C.

Specifically, it can be seen from FIG. 1A that the compound A13 has a good inhibitory effect on HCoV-OC43 infection at a low concentration (1 μM); and it can be seen from FIG. 1B that the antiviral activity of the compound A13 shows obvious dose-dependence. As can be seen from FIG. 1C, as to the specific antiviral activity of compound A13, half of its inhibitory activity ($IC_{50}$) is at a low nanomolar level ($IC_{50}$=86 nM).

2.2 Evaluation of Broad-Spectrum of Compound A13 Antiviral Activity

Figure 2:
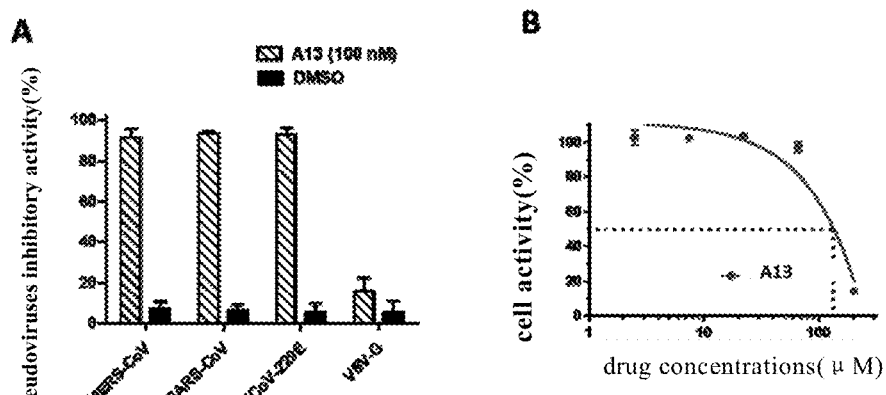
FIG. 2 shows the inhibitory activity of compound A13 on MERS-CoV, SARS-CoV, HCoV-229E and VSV-G pseudoviruses (A), and the cytotoxicity of compound A13 on target cells (Huh-7) (B).

We choose HCoV-229E as the representative among α-type human coronavirus, and MERS-CoV and SARS-CoV as representative β-type human coronavirus. On the pseudoviruses of these three HCoVs, A13 has shown highly effective anti-viral effect. At a concentration of 100 nM, it could achieve nearly 90% of the viral inhibitory effect. However, when using the control VSV-G-mediated pseudovirus infection system, the compound A13 did not show an effective inhibitory effect as shown in FIG. 2A. In addition, when using the system where Huh-7 was the target cell, the compound A13 showed less cytotoxicity, and its CC50 was greater than 100 μM (more than 1000 times of the detection dose, as shown in FIG. 2B).

2.3 Preliminary Evaluation of In Vivo Protective Activity of Compound A13

In order to preliminarily evaluate the stability and antiviral activity of the compound A13 in vivo, the compound (100 mg/kg) or 100 μL DMSO was administered intraperitoneally to the Balb/c mouse model. Blood was collected at 2 hours, 12 hours and 24 hours after the administration, and the serum was separated for detection of anti-MERS-CoV pseudovirus activity. The results showed that serum at 2 hours and 12 hours after administration had high viral inhibitory activity, which was 24 and 15 times of that of DMSO-base serum, respectively. The inhibitory activity of serum at 24 hours after administration was similar to that of DMSO-base serum. The results indicated that the compound A13 had better stability and antiviral activity in vivo, and implies that the compound had a better half-life in vivo, as shown in FIG. 3.

Figure 3A:
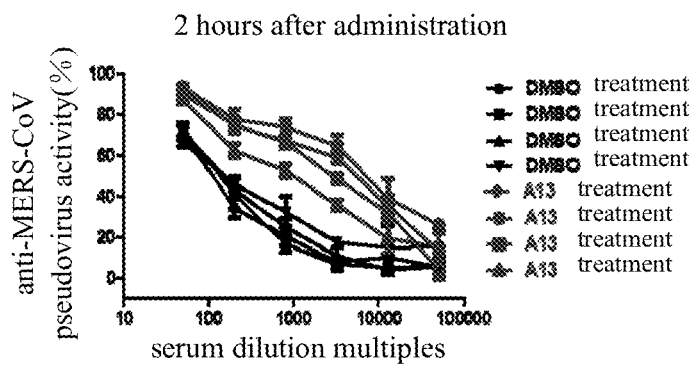
Figure 3B:
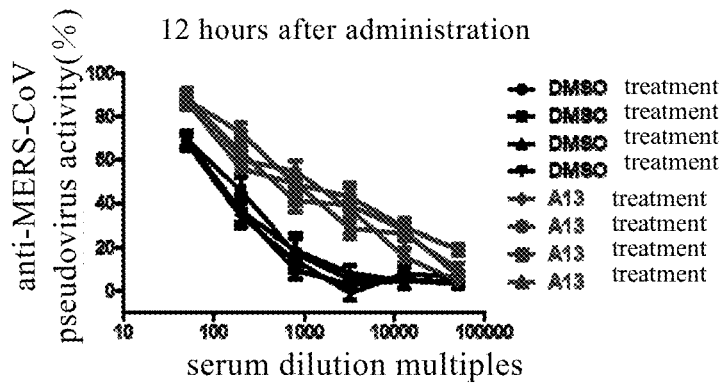

Specifically, it can be seen from FIG. 3D that in the Balb/c mouse model, the compound A13 (100 mg/kg) was administered intraperitoneally and showed good stability and antiviral activity in vivo. The median effective concentration (EC50) of the separated serum at 2 hours and 12 hours after administration was 3181 times and 1133 times of the serum dilution, much higher than the corresponding EC50 in the DMSO control group.

2.4 Preliminary Assessment of the Safety of Compound A13 In Vivo

Next, we further evaluated the safety of compound A13 in mice. The mice in the drug group (100 mg/kg) and the DMSO control group were administered intraperitoneally, once a day, for 7 consecutive days, and then the growth status and weight changes of the mice in each group were observed. The results are shown in FIG. 4. During the administration period, there was no difference of the body weight between the mice in the drug group and the mice in the PBS group, indicating that the compound A13 had better safety in vivo.

3.1 Rat Pharmacokinetic Study on Series of Compounds

Dosing Regimen

Nine CD-1 mice, male, weighing 18-22 g, were randomly divided into 3 groups with 3 mice in each group. The test compounds were administered by gavage, intravenously and intraperitoneally according to the following schemes.

Before the test, they were fasted for 12 hours and were allowed to drink water freely, and were fed uniformly 2 h after administration.

Experiment Grouping, Blood Sampling Time Point and Sample Processing:

There were 3 animals at each time point. Grouping and blood collection time points are shown in Table 3 below:

TABLE 3

| Group | Drug name | Administration mode | Dosage (mg/Kg) | Dosing volume (mL/Kg) | Sampling time (h) |
|---|---|---|---|---|---|
| 1 | A13 | Gavage | 20 | 10 | 0.25, 0.5, 1, 2, 4, 8, 24 h |
| 2 | | intravenous | 10 | 5 | 3 min, 0.25, 0.75, 2, 4, 8, 24 h |
| 3 | | intraperitoneally | 20 | 5 | 3 min, 0.25, 0.75, 2, 4, 8, 24 h |

The solution for gavage administration was formulated with DMSO/0.5% HPMC (5/95, v/v) into the final concentration. Intravenous and intraperitoneal administration were formulated with DMSO/PEG300/EtOH/NaCl (5/40/5/50, v/v/v). Retention samples of the dosing solution (50 μL of the drug solution was taken and mixed well with 50 μL of DMSO before and after the administration) for testing.

The drug was administered according to the above dosage, the time of administration were recorded, and 20 μL of blood was collected from the mouse femoral plexus at the above set time point and placed in a heparinized test tube and centrifuged immediately at 11000 rpm for 5 min. 10 μL of plasma was immediately and accurately drawn into a centrifuge tube pre-filled with 100 μL of PK-IS solution (prepared with methanol:acetonitrile (1:1, v/v)), mixed well, and frozen to store at −20° C. for testing.

The pharmacokinetic studies were conducted on compounds A9, A13, A42, A241 and A242. Among them, the oral exposure of Compound A9 was 584 h*ng/mL, and the exposure for intraperitoneal injection was 8191 h*ng/mL (as shown in Table 4). The oral exposure of compound A13 was 463 h*ng/mL, and the bioavailability was 7.99%; the exposure for intraperitoneal injection was 7298 h*ng/mL, and the bioavailability was 126% (as shown in Table 5). The oral exposure of A42 was 742 h*ng/mL, and the exposure of intraperitoneal injection was 5491 h*ng/mL (as shown in Table 6). The oral exposure of compound A241 was 663 h*ng/mL, and the exposure for intraperitoneal injection was 4163 h*ng/mL (as shown in Table 7). The oral exposure of compound A242 was 488 h*ng/mL, and the exposure for intraperitoneal injection was 6890 h*ng/mL (as shown in Table 8).

TABLE 4

Main pharmacokinetic parameters of A9

| Mode of administration | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $MRT_{INF\_obs}$ (h) |
|---|---|---|---|---|---|---|---|
| p.o. | 19 | 1.13 | 0.25 | 546 | 447 | 451 | 1.35 |
|  | 20 | 0.91 | 0.25 | 864 | 1143 | 1146 | 1.33 |
|  | 21 | 1.77 | 0.25 | 84 | 163 | 171 | 2.63 |
|  | Mean | 1.27 | 0.25 | 498 | 584 | 589 | 1.77 |
|  | SD | 0.44 | 0.00 | 392 | 504 | 502 | 0.75 |
| i.p. | 22 | 3.28 | 0.25 | 3515 | 7651 | 7674 | 2.70 |
|  | 23 | 3.67 | 0.25 | 2859 | 6786 | 6825 | 3.19 |
|  | 24 | 5.11 | 0.75 | 2364 | 10138 | 10574 | 6.07 |
|  | Mean | 4.02 | 0.42 | 2913 | 8191 | 8358 | 3.99 |
|  | SD | 0.96 | 0.29 | 577 | 1740 | 1966 | 1.82 |

TABLE 5

Main pharmacokinetic parameters of A13

|  | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $Cl_{\_obs}$ (mL/min/kg) | $MRT_{INF\_obs}$ (h) | $V_{SS\_obs}$ (mL/kg) | F (%) |
|---|---|---|---|---|---|---|---|---|---|---|
| p.o. | 1 | 0.619 | 0.250 | 493 | 690 | 700 | — | 1.37 | — |  |
|  | 2 | 2.15 | 0.250 | 259 | 458 | 499 | — | 3.08 | — |  |
|  | 3 | 1.18 | 0.250 | 118 | 241 | 263 | — | 1.88 | — | 7.99 |
|  | Mean | 1.32 | 0.250 | 290 | 463 | 488 | — | 2.11 | — |  |
|  | SD | 0.77 | 0.000 | 189 | 225 | 219 | — | 0.87 | — |  |
| i.v. | 4 | 6.09 | — | — | 3300 | 3411 | 48.9 | 3.11 | 9132 |  |
|  | 5 | 2.07 | — | — | 1734 | 1773 | 94.0 | 1.13 | 6389 |  |
|  | 6 | 1.87 | — | — | 3652 | 3745 | 44.5 | 1.40 | 3736 |  |
|  | Mean | 3.34 | — | — | 2896 | 2976 | 62.5 | 1.88 | 6419 |  |
|  | SD | 2.38 | — | — | 1021 | 1055 | 27.4 | 1.08 | 2698 |  |
| i.p. | 7 | 6.46 | 0.250 | 2856 | 6512 | 7002 | — | 6.69 | — |  |
|  | 8 | 5.90 | 0.050 | 3583 | 7304 | 7708 | — | 6.05 | — |  |
|  | 9 | 4.94 | 0.250 | 3372 | 8077 | 8196 | — | 3.28 | — | 126 |
|  | Mean | 5.77 | 0.183 | 3270 | 7298 | 7635 | — | 5.34 | — |  |
|  | SD | 0.77 | 0.115 | 374 | 782 | 600 | — | 1.81 | — |  |

TABLE 6

Main pharmacokinetic parameters of A42

| Mode of administration | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $MRT_{INF\_obs}$ (h) |
|---|---|---|---|---|---|---|---|
| p.o. | 1 | 4.19 | 0.25 | 1019 | 787 | 791 | 1.98 |
|  | 2 | 5.52 | 0.25 | 966 | 945 | 953 | 2.10 |
|  | 3 | 7.73 | 0.25 | 588 | 494 | 506 | 2.83 |
|  | Mean | 5.81 | 0.25 | 858 | 742 | 750 | 2.30 |
|  | SD | 1.79 | 0.00 | 235 | 229 | 226 | 0.46 |
| i.p. | 4 | 6.52 | 0.25 | 3843 | 12980 | 13715 | 6.38 |
|  | 5 | 3.67 | 0.25 | 3959 | 10576 | 10647 | 3.41 |
|  | 6 | 6.20 | 0.25 | 5038 | 11340 | 11768 | 4.99 |
|  | Mean | 5.46 | 0.25 | 4280 | 11632 | 12043 | 4.93 |
|  | SD | 1.57 | 0.00 | 659 | 1228 | 1553 | 1.49 |

TABLE 7

Main pharmacokinetic parameters of A241

| Mode of administration | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $MRT_{INF\_obs}$ (h) |
|---|---|---|---|---|---|---|---|
| p.o. | 13 | 3.84 | 0.25 | 707 | 467 | 469 | 2.12 |
|  | 14 | 3.85 | 0.25 | 942 | 945 | 947 | 1.68 |
|  | 15 | 4.96 | 0.25 | 651 | 576 | 579 | 1.64 |

TABLE 7-continued

Main pharmacokinetic parameters of A241

| Mode of administration | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $MRT_{INF\_obs}$ (h) |
|---|---|---|---|---|---|---|---|
| | Mean | 4.22 | 0.25 | 767 | 663 | 665 | 1.82 |
| | SD | 0.64 | 0.00 | 154 | 250 | 250 | 0.26 |
| i.p. | 16 | 4.78 | 0.25 | 4927 | 4874 | 4896 | 1.44 |
| | 17 | 3.59 | 0.05 | 4206 | 3514 | 3524 | 1.37 |
| | 18 | 4.72 | 0.25 | 4836 | 4100 | 4121 | 1.50 |
| | Mean | 4.36 | 0.18 | 4656 | 4163 | 4180 | 1.44 |
| | SD | 0.67 | 0.12 | 393 | 682 | 688 | 0.06 |

TABLE 8

Main pharmacokinetic parameters of A242

| Mode of administration | Animal number | $T_{1/2}$ (h) | $T_{max}$ (h) | $C_{max}$ (ng/mL) | $AUC_{last}$ (h * ng/mL) | $AUC_{INF\_obs}$ (h * ng/mL) | $MRT_{INF\_obs}$ (h) |
|---|---|---|---|---|---|---|---|
| p.o. | 7 | 4.00 | 0.25 | 499 | 434 | 436 | 2.13 |
| | 8 | 4.63 | 0.25 | 247 | 409 | 413 | 2.84 |
| | 9 | 4.91 | 0.25 | 482 | 622 | 629 | 2.71 |
| | Mean | 4.51 | 0.25 | 409 | 488 | 493 | 2.56 |
| | SD | 0.47 | 0.00 | 141 | 117 | 119 | 0.38 |
| i.p. | 10 | 4.85 | 0.25 | 6400 | 8263 | 8318 | 1.92 |
| | 11 | 4.37 | 0.25 | 4739 | 5779 | 5808 | 1.85 |
| | 12 | 6.75 | 0.25 | 5334 | 6628 | 6750 | 2.45 |
| | Mean | 5.32 | 0.25 | 5491 | 6890 | 6958 | 2.07 |
| | SD | 1.26 | 0.00 | 842 | 1262 | 1268 | 0.33 |

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound represented by formula A, or a racemate, an enantiomer, a diastereomer, or a mixture thereof, or a pharmaceutically active metabolite, or a pharmaceutically acceptable salt, a solvate or a prodrug thereof:

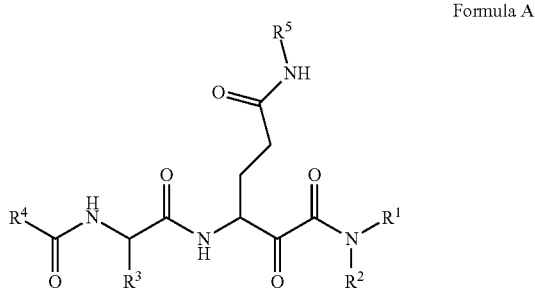

Formula A wherein:
$R^1$ and $R^2$ are each independently selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 cycloalkyl C1-C10 alkylene, substituted or unsubstituted C3-C10 heterocycloalkyl, substituted or unsubstituted C3-C10 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C10 alkenylene, substituted or unsubstituted C3-C20 heteroaryl C2-C10 alkenylene, acyl, and sulfonyl;

$R^3$ is selected from the group consisting of substituted or unsubstituted C1-C10 alkyl, substituted or unsubstituted C2-C10 alkenyl, substituted or unsubstituted C2-C10 alkynyl, substituted or unsubstituted C3-C8 cycloalkyl, substituted or unsubstituted C3-C8 cycloalkyl C1-C10 alkylene, substituted or unsubstituted C3-C8 heterocycloalkyl, substituted or unsubstituted C3-C8 heterocycloalkyl C1-C10 alkylene, substituted or unsubstituted C6-C20 aryl, substituted or unsubstituted C3-C20 heteroaryl, substituted or unsubstituted C6-C20 aryl C1-C10 alkylene, substituted or unsubstituted C3-C20 heteroaryl C1-C10 alkylene, substituted or unsubstituted C6-C20 aryl C2-C6 alkenylene, substituted or unsubstituted C3-C20 heteroaryl C2-C6 alkenylene, substituted or unsubstituted C6-C20 aryl C2-C6 alkynylene, and substituted or unsubstituted C3-C20 heteroaryl C2-C6 alkynylene;

$R^4$ is selected from the group consisting of substituted or unsubstituted indole, benzofuran, benzothiophene, quinoxaline, quinoline, and benzopyran;

when —$NHR^5$ and its adjacent —(C=O)—$CH_2$— form a ring, $R^5$ is —$(CH_2)_n$—, and n is 2 or 3;

when —$NHR^5$ does not form a ring with its adjacent —(C=O)—$CH_2$—, $R^5$ is selected from the group consisting of hydrogen, deuterium, tritium, amino, hydroxyl, substituted or unsubstituted C1-C10 alkyl, substituted or unsubstituted C3-C10 cycloalkyl, substituted or unsubstituted C3-C10 heterocycloalkyl, substituted or unsubstituted C6-C20 aryl, substituted or unsubstituted C3-C20 heteroaryl, substituted or unsubstituted C6-C20 aryl C1-C6 alkylene, substituted or unsubstituted C6-C20 aryl C2-C6 alkenylene, substituted or unsubstituted C3-C20 heteroaryl C1-C9 alkylene, substituted or unsubstituted C3-C20 heteroaryl C2-C9 alkenylene, acyl, and sulfonyl;

wherein, in $R^1$, $R^2$, $R^3$, $R^4$ and $R^5$, each of the term "substituted" independently refers to substitution by 1, 2, 3 or 4 substituents selected from the group consisting of halogen, hydroxyl, mercapto, nitro, cyano, amino, imino, tertiary amino, azido, C1-C8 alkyl, halogenated C1-C8 alkyl, C1-C8 alkoxy, halogenated C1-C8 alkoxy, C1-C6 alkylcarbonyl, C1-C6 alkylthio, C1-C8 alkoxycarbonyl, and trifluoromethyl; wherein the heterocycloalkyl and the heteroaryl each independently comprise 1, 2, 3 or 4 heteroatoms selected from N, O, and S.

2. The compound, or the racemate, the enantiomer, the diastereomer, or the mixture thereof, or the pharmaceutically active metabolite, or the pharmaceutically acceptable salt, the solvate or the prodrug thereof according to claim 1, wherein the compound is a compound represented by formula AA,

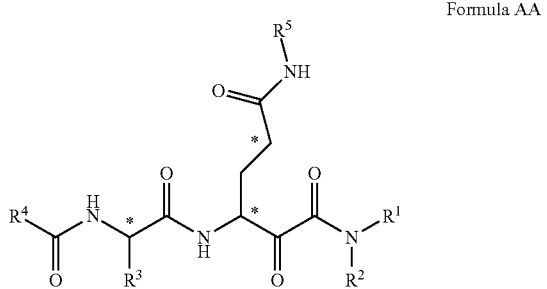

Formula AA wherein $R^1$, $R^2$, $R^3$, $R^4$, $R^5$ and n are as defined in claim 1;
* indicates that the stereochemical isomerism of carbon atoms can independently be R or S.

3. The compound, or the racemate, the enantiomer, the diastereomer, or the mixture thereof, or the pharmaceutically active metabolite, or the pharmaceutically acceptable salt, the solvate or the prodrug thereof according to claim 1, wherein $R^4$ is selected from the group consisting of substituted or unsubstituted benzofuran, benzothiophene, quinoxaline and quinoline.

4. The compound, or the racemate, the enantiomer, the diastereomer, or the mixture thereof, or the pharmaceutically active metabolite, or the pharmaceutically acceptable salt, the solvate or the prodrug thereof according to claim 1, wherein $R^4$ is selected from the group consisting of:
substituted or unsubstituted quinolinyl,
substituted or unsubstituted benzothienyl; and
substituted or unsubstituted benzofuranyl.

5. The compound, or the racemate, the enantiomer, the diastereomer, or the mixture thereof, or the pharmaceutically active metabolite, or the pharmaceutically acceptable salt, the solvate or the prodrug thereof according to claim 1, wherein:
when —NHR$^5$ and its adjacent —(C=O)—CH$_2$— form a ring, R$^5$ is —(CH$_2$)$_n$—, and n is 3;
when —NHR$^5$ does not form a ring with its adjacent —(C=O)—CH$_2$—, R$^5$ is selected from the group consisting of hydrogen, deuterium, tritium, hydroxyl, substituted or unsubstituted C1-C6 alkyl, substituted or unsubstituted C3-C8 cycloalkyl, substituted or unsubstituted C3-C8 heterocycloalkyl, substituted or unsubstituted C6-C10 aryl, substituted or unsubstituted C3-C10 heteroaryl, substituted or unsubstituted C6-C10 aryl C1-C4 alkylene, substituted or unsubstituted C6-C10 aryl C2-C4 alkenylene, substituted or unsubstituted C3-C10 heteroaryl C1-C4 alkylene, and substituted or unsubstituted C3-C10 heteroaryl C2-C4 alkenylene;
wherein the term "substituted" each independently refer to substitution by 1, 2, or 3 substituents selected from the group consisting of F, Cl, Br, I, hydroxyl, C1-C6 alkyl, C1-C6 alkoxy, C1-C6 alkylthio; and the heterocycloalkyl and the heteroaryl each independently contain 1, 2 or 3 heteroatoms selected from N, O, and S.

6. A compound selected from the group consisting of:

| number | structure |
|---|---|
| A1 | 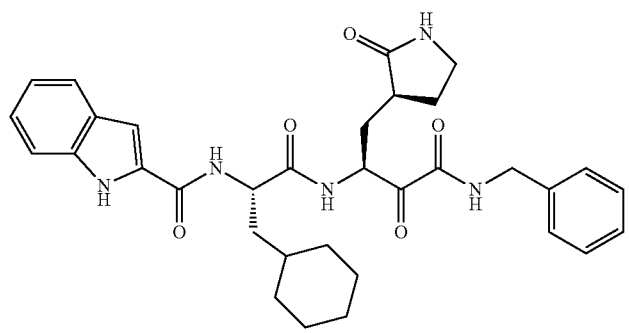 [SMILES: O=C(NCc1ccccc1)C(=O)[C@H](C[C@@H]1CCNC1=O)NC(=O)[C@H](CC1CCCCC1)NC(=O)c1cc2ccccc2[nH]1] |

-continued
| number | structure |
|---|---|
| A2 | 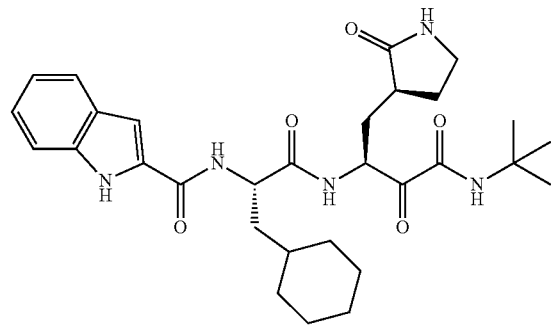 [SMILES: CC(C)(C)NC(=O)C(=O)[C@H](C[C@@H]1CCNC1=O)NC(=O)[C@H](CC1CCCCC1)NC(=O)c1cc2ccccc2[nH]1] |
| A3 | 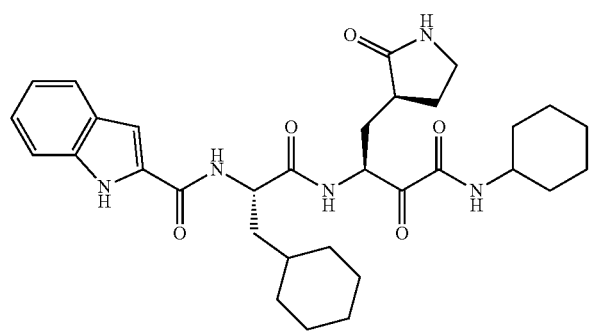 [SMILES: O=C(NC1CCCCC1)C(=O)[C@H](C[C@@H]1CCNC1=O)NC(=O)[C@H](CC1CCCCC1)NC(=O)c1cc2ccccc2[nH]1] |
| A4 | 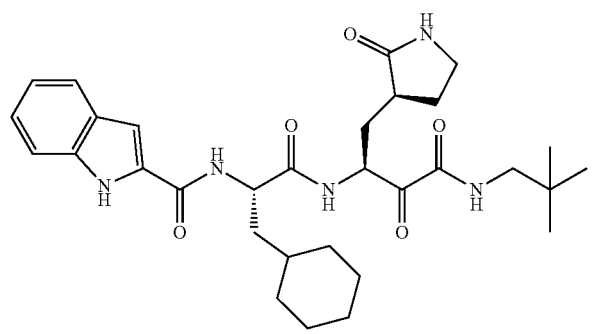 [SMILES: CC(C)(C)CNC(=O)C(=O)[C@H](C[C@@H]1CCNC1=O)NC(=O)[C@H](CC1CCCCC1)NC(=O)c1cc2ccccc2[nH]1] |

-continued
| number | structure |
|---|---|
| A5 | 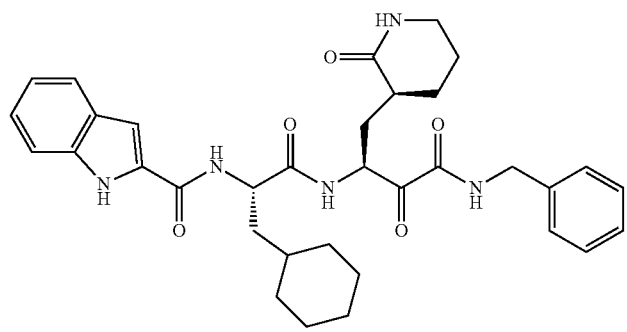 [SMILES: O=C(NCc1ccccc1)C(=O)[C@H](C[C@@H]1CCCNC1=O)NC(=O)[C@H](CC1CCCCC1)NC(=O)c1cc2ccccc2[nH]1] |
| A6 | 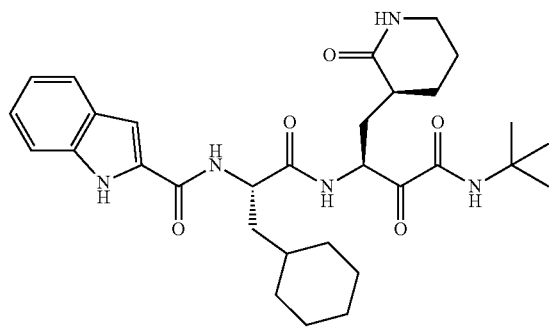 [SMILES: CC(C)(C)NC(=O)C(=O)[C@H](C[C@@H]1CCCNC1=O)NC(=O)[C@H](CC1CCCCC1)NC(=O)c1cc2ccccc2[nH]1] |
| A7 | 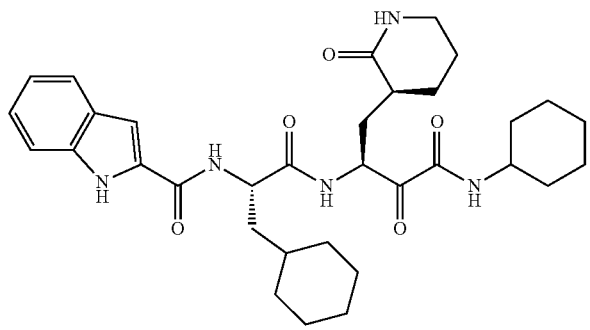 [SMILES: O=C(NC1CCCCC1)C(=O)[C@H](C[C@@H]1CCCNC1=O)NC(=O)[C@H](CC1CCCCC1)NC(=O)c1cc2ccccc2[nH]1] |
| A8 | 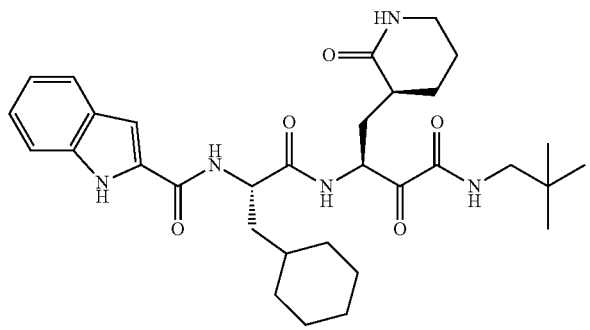 [SMILES: CC(C)(C)CNC(=O)C(=O)[C@H](C[C@@H]1CCCNC1=O)NC(=O)[C@H](CC1CCCCC1)NC(=O)c1cc2ccccc2[nH]1] |

| number | structure |
|---|---|
| A9 | 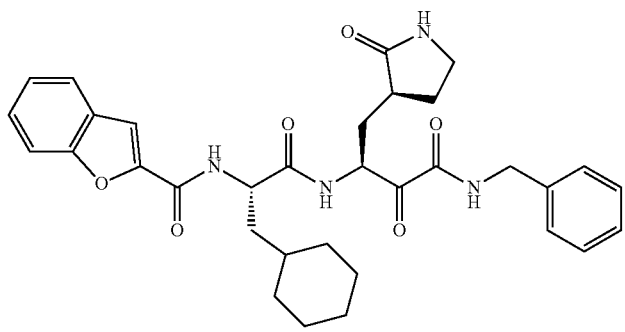 [SMILES: O=C(NCc1ccccc1)C(=O)[C@H](C[C@@H]1CCNC1=O)NC(=O)[C@H](CC1CCCCC1)NC(=O)c1cc2ccccc2o1] |
| A10 | 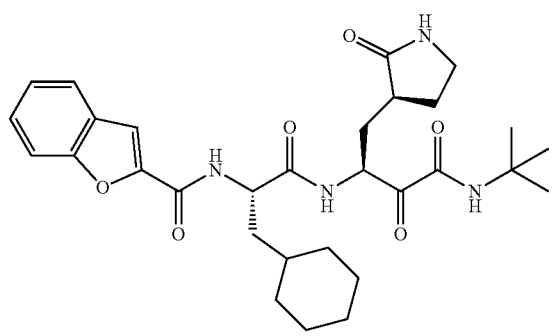 [SMILES: CC(C)(C)NC(=O)C(=O)[C@H](C[C@@H]1CCNC1=O)NC(=O)[C@H](CC1CCCCC1)NC(=O)c1cc2ccccc2o1] |
| A11 | 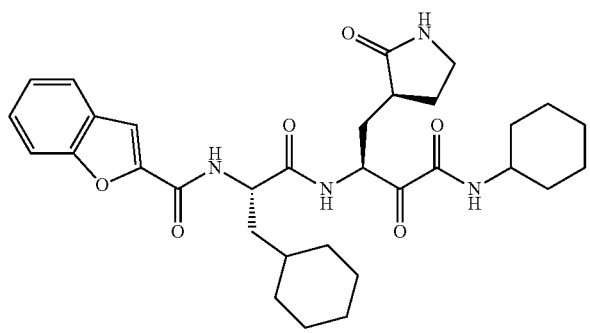 [SMILES: O=C(NC1CCCCC1)C(=O)[C@H](C[C@@H]1CCNC1=O)NC(=O)[C@H](CC1CCCCC1)NC(=O)c1cc2ccccc2o1] |

| number | structure |
|---|---|
| A12 | 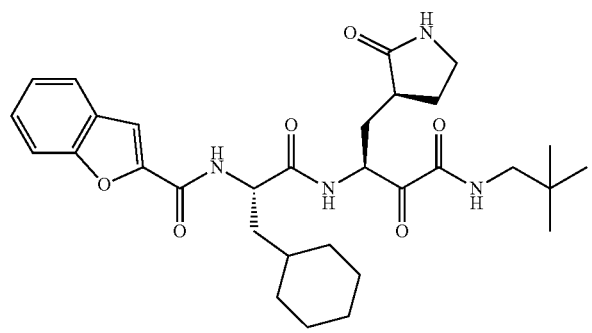 [SMILES: CC(C)(C)CNC(=O)C(=O)[C@H](C[C@@H]1CCNC1=O)NC(=O)[C@H](CC1CCCCC1)NC(=O)c1cc2ccccc2o1] |
| A13 | 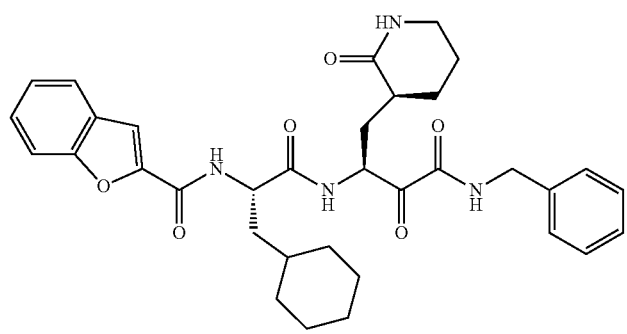 [SMILES: O=C(NCc1ccccc1)C(=O)[C@H](C[C@@H]1CCCNC1=O)NC(=O)[C@H](CC1CCCCC1)NC(=O)c1cc2ccccc2o1] |
| A14 | 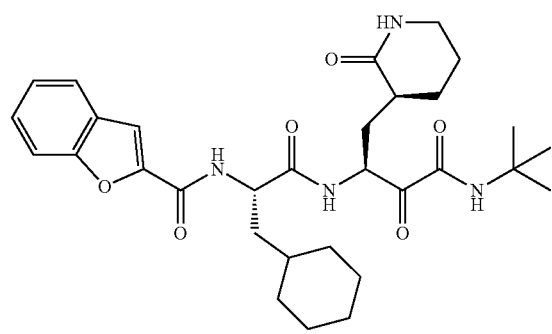 [SMILES: CC(C)(C)NC(=O)C(=O)[C@H](C[C@@H]1CCCNC1=O)NC(=O)[C@H](CC1CCCCC1)NC(=O)c1cc2ccccc2o1] |

| number | structure |
|---|---|
| A15 | 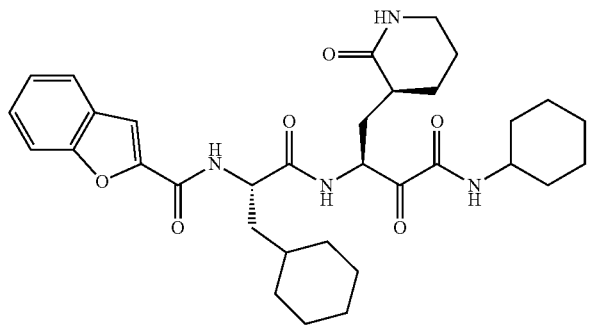 [SMILES: O=C(NC1CCCCC1)C(=O)[C@H](C[C@@H]1CCCNC1=O)NC(=O)[C@H](CC1CCCCC1)NC(=O)c1cc2ccccc2o1] |
| A16 | 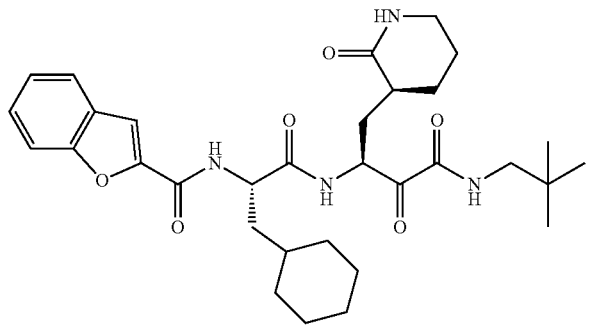 [SMILES: CC(C)(C)CNC(=O)C(=O)[C@H](C[C@@H]1CCCNC1=O)NC(=O)[C@H](CC1CCCCC1)NC(=O)c1cc2ccccc2o1] |
| A17 | 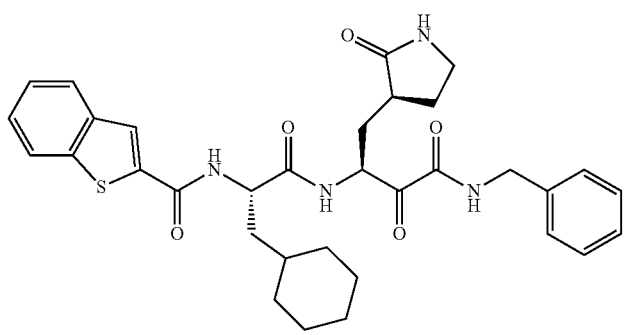 [SMILES: O=C(NCc1ccccc1)C(=O)[C@H](C[C@@H]1CCNC1=O)NC(=O)[C@H](CC1CCCCC1)NC(=O)c1cc2ccccc2s1] |

-continued
| number | structure |
|---|---|
| A18 | 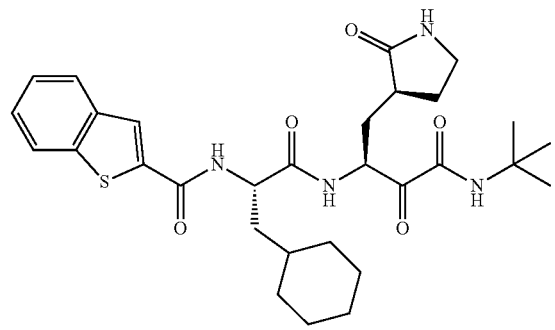 [SMILES: CC(C)(C)NC(=O)C(=O)[C@H](C[C@@H]1CCNC1=O)NC(=O)[C@H](CC1CCCCC1)NC(=O)c1cc2ccccc2s1] |
| A19 | 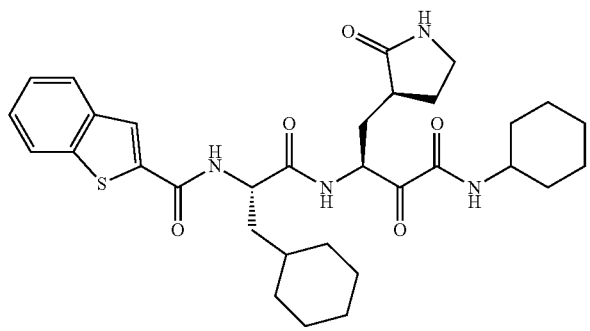 [SMILES: O=C(NC1CCCCC1)C(=O)[C@H](C[C@@H]1CCNC1=O)NC(=O)[C@H](CC1CCCCC1)NC(=O)c1cc2ccccc2s1] |
| A20 | 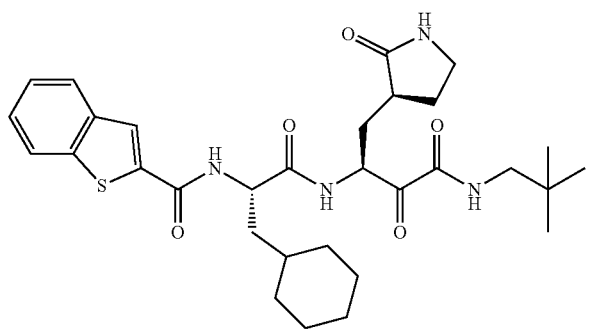 [SMILES: CC(C)(C)CNC(=O)C(=O)[C@H](C[C@@H]1CCNC1=O)NC(=O)[C@H](CC1CCCCC1)NC(=O)c1cc2ccccc2s1] |
| A21 | 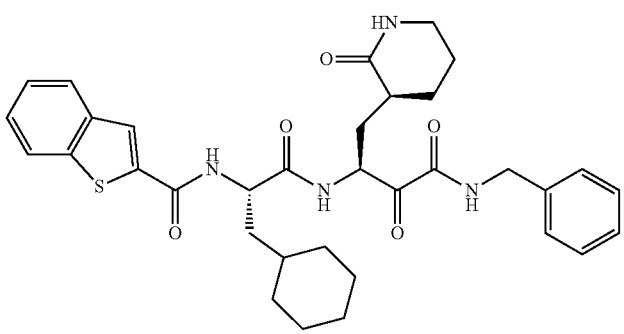 [SMILES: O=C(NCc1ccccc1)C(=O)[C@H](C[C@@H]1CCCNC1=O)NC(=O)[C@H](CC1CCCCC1)NC(=O)c1cc2ccccc2s1] |

| number | structure |
|---|---|
| A22 | 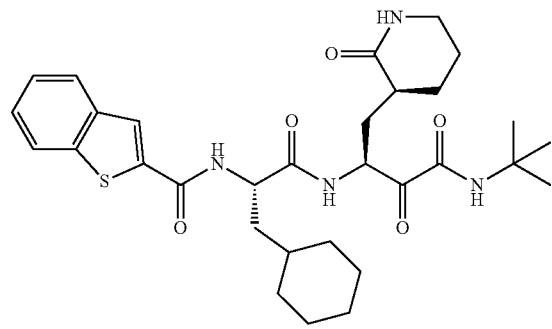 [SMILES: CC(C)(C)NC(=O)C(=O)[C@H](C[C@@H]1CCCNC1=O)NC(=O)[C@H](CC1CCCCC1)NC(=O)c1cc2ccccc2s1] |
| A23 | 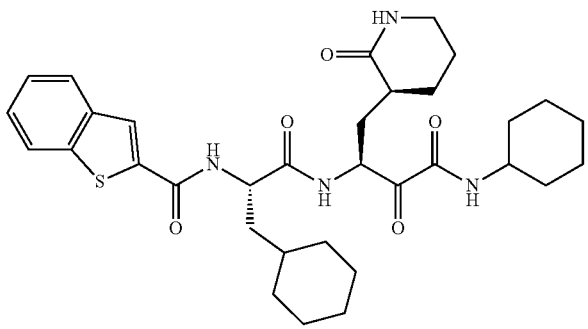 [SMILES: O=C(NC1CCCCC1)C(=O)[C@H](C[C@@H]1CCCNC1=O)NC(=O)[C@H](CC1CCCCC1)NC(=O)c1cc2ccccc2s1] |
| A24 | 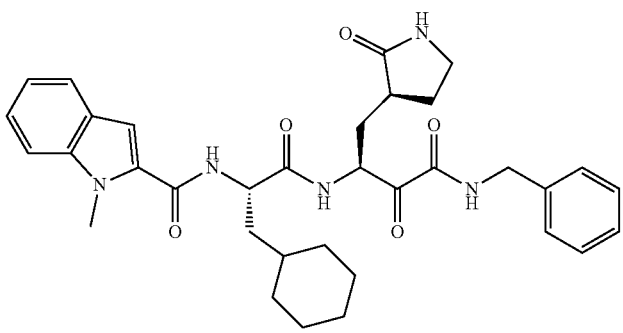 [SMILES: Cn1c(C(=O)N[C@@H](CC2CCCCC2)C(=O)N[C@@H](C[C@@H]2CCNC2=O)C(=O)C(=O)NCc2ccccc2)cc2ccccc21] |
| A25 | 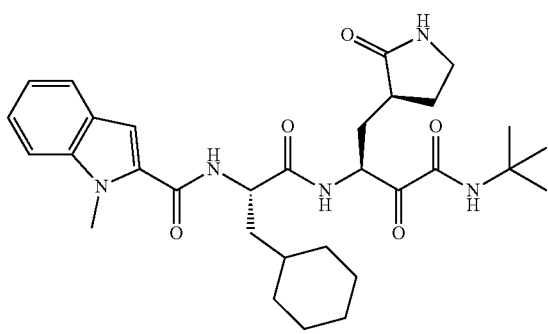 [SMILES: Cn1c(C(=O)N[C@@H](CC2CCCCC2)C(=O)N[C@@H](C[C@@H]2CCNC2=O)C(=O)C(=O)NC(C)(C)C)cc2ccccc21] |

| number | structure |
|---|---|
| A26 | 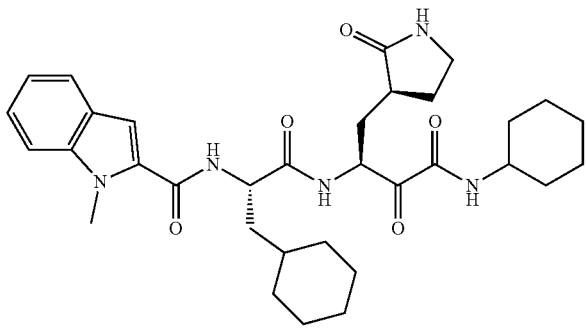 [SMILES: Cn1c(C(=O)N[C@@H](CC2CCCCC2)C(=O)N[C@@H](C[C@@H]2CCNC2=O)C(=O)C(=O)NC2CCCCC2)cc2ccccc21] |
| A27 | 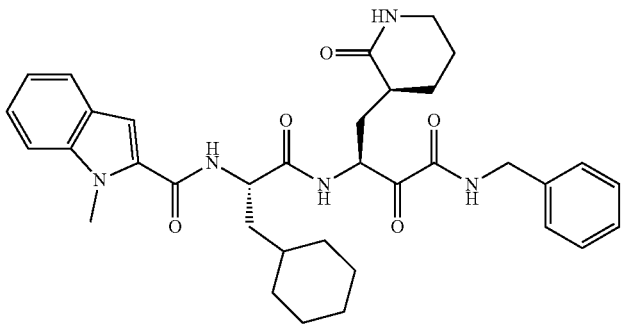 [SMILES: Cn1c(C(=O)N[C@@H](CC2CCCCC2)C(=O)N[C@@H](C[C@@H]2CCCNC2=O)C(=O)C(=O)NCc2ccccc2)cc2ccccc21] |
| A28 | 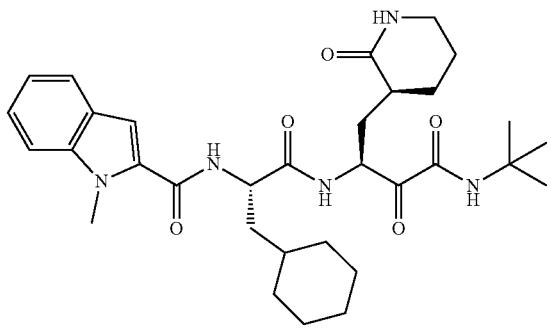 [SMILES: Cn1c(C(=O)N[C@@H](CC2CCCCC2)C(=O)N[C@@H](C[C@@H]2CCCNC2=O)C(=O)C(=O)NC(C)(C)C)cc2ccccc21] |
| A29 | 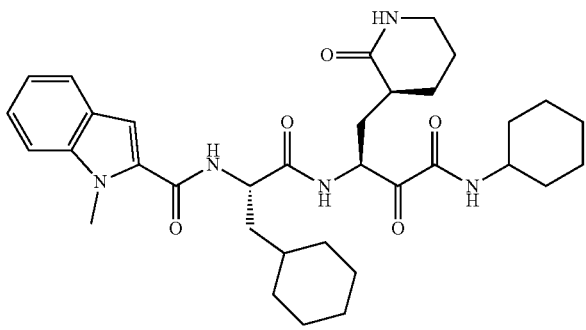 [SMILES: Cn1c(C(=O)N[C@@H](CC2CCCCC2)C(=O)N[C@@H](C[C@@H]2CCCNC2=O)C(=O)C(=O)NC2CCCCC2)cc2ccccc21] |

| number | structure |
|---|---|
| A30 | 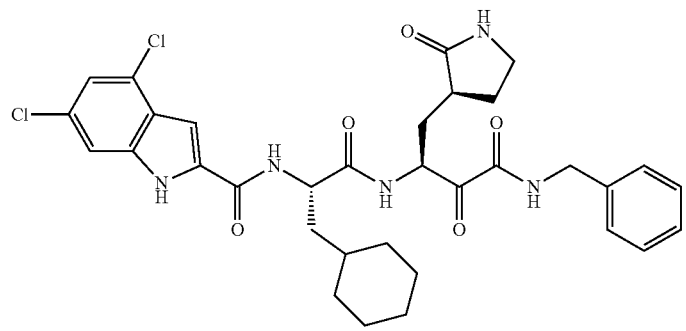 [SMILES: O=C(NCc1ccccc1)C(=O)[C@H](C[C@@H]1CCNC1=O)NC(=O)[C@H](CC1CCCCC1)NC(=O)c1cc2c(Cl)cc(Cl)cc2[nH]1] |
| A31 | 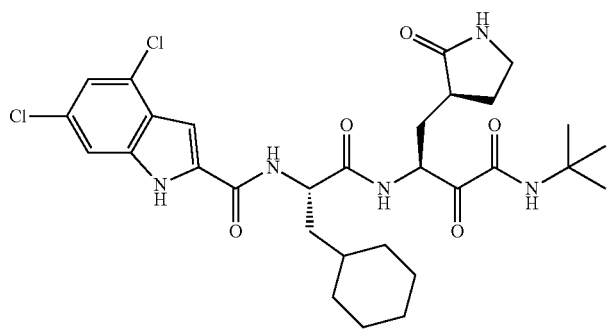 [SMILES: CC(C)(C)NC(=O)C(=O)[C@H](C[C@@H]1CCNC1=O)NC(=O)[C@H](CC1CCCCC1)NC(=O)c1cc2c(Cl)cc(Cl)cc2[nH]1] |
| A32 | 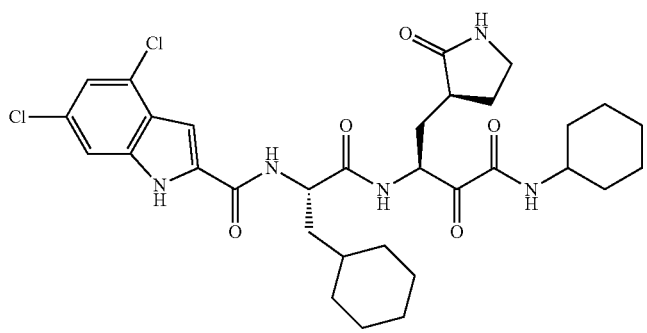 [SMILES: O=C(NC1CCCCC1)C(=O)[C@H](C[C@@H]1CCNC1=O)NC(=O)[C@H](CC1CCCCC1)NC(=O)c1cc2c(Cl)cc(Cl)cc2[nH]1] |
| A33 | 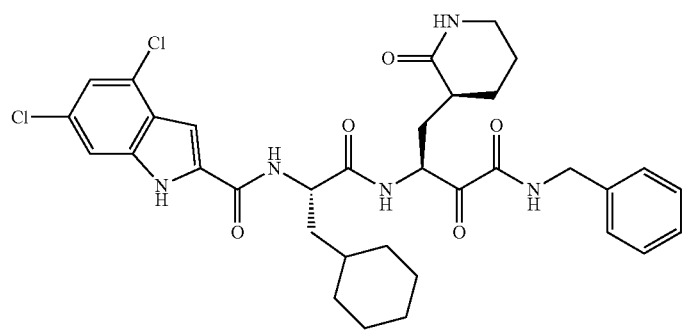 [SMILES: O=C(NCc1ccccc1)C(=O)[C@H](C[C@@H]1CCCNC1=O)NC(=O)[C@H](CC1CCCCC1)NC(=O)c1cc2c(Cl)cc(Cl)cc2[nH]1] |

-continued
| number | structure |
|---|---|
| A34 | 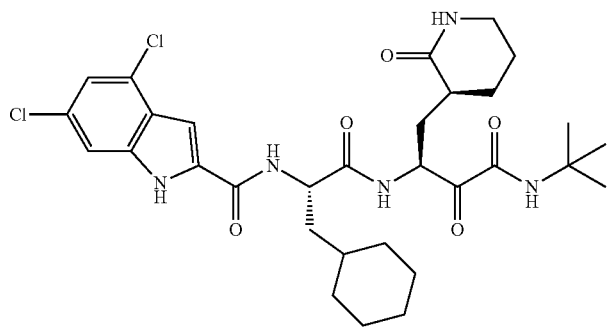 [SMILES: CC(C)(C)NC(=O)C(=O)[C@H](C[C@@H]1CCCNC1=O)NC(=O)[C@H](CC1CCCCC1)NC(=O)c1cc2c(Cl)cc(Cl)cc2[nH]1] |
| A35 | 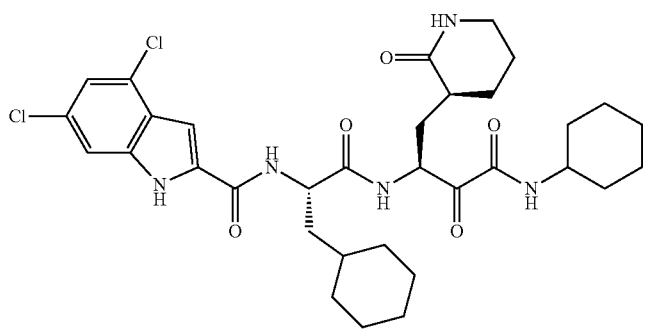 [SMILES: O=C(NC1CCCCC1)C(=O)[C@H](C[C@@H]1CCCNC1=O)NC(=O)[C@H](CC1CCCCC1)NC(=O)c1cc2c(Cl)cc(Cl)cc2[nH]1] |
| A36 | 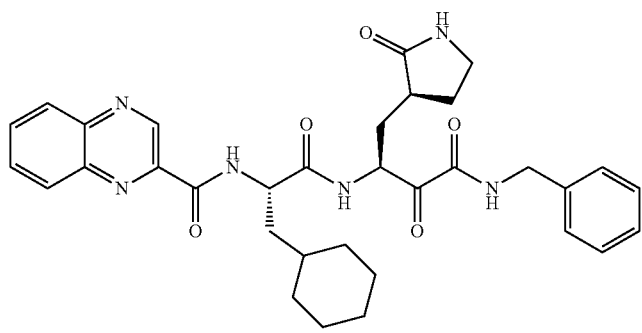 [SMILES: O=C(NCc1ccccc1)C(=O)[C@H](C[C@@H]1CCNC1=O)NC(=O)[C@H](CC1CCCCC1)NC(=O)c1cnc2ccccc2n1] |
| A37 | 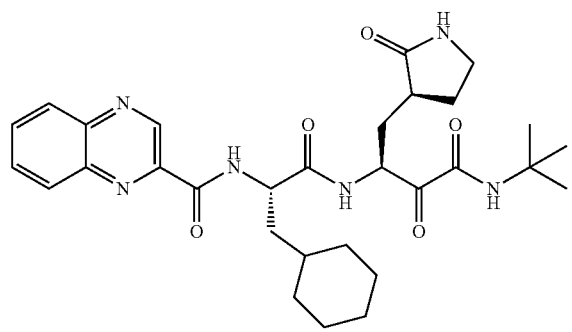 [SMILES: CC(C)(C)NC(=O)C(=O)[C@H](C[C@@H]1CCNC1=O)NC(=O)[C@H](CC1CCCCC1)NC(=O)c1cnc2ccccc2n1] |

-continued
| number | structure |
|---|---|
| A38 | 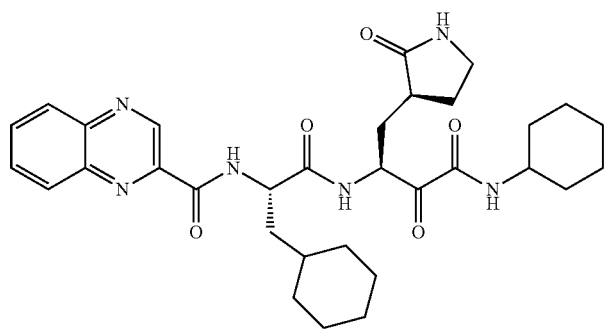 [SMILES: O=C(NC1CCCCC1)C(=O)[C@H](C[C@@H]1CCNC1=O)NC(=O)[C@H](CC1CCCCC1)NC(=O)c1cnc2ccccc2n1] |
| A39 | 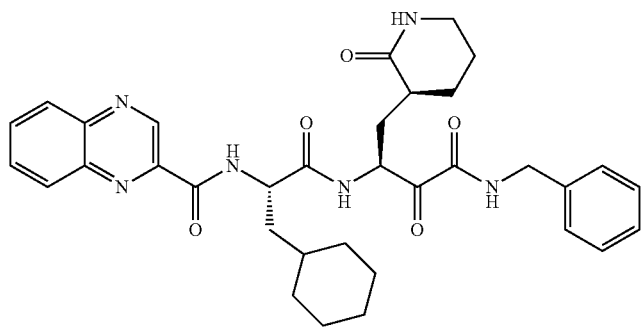 [SMILES: O=C(NCc1ccccc1)C(=O)[C@H](C[C@@H]1CCCNC1=O)NC(=O)[C@H](CC1CCCCC1)NC(=O)c1cnc2ccccc2n1] |
| A40 | 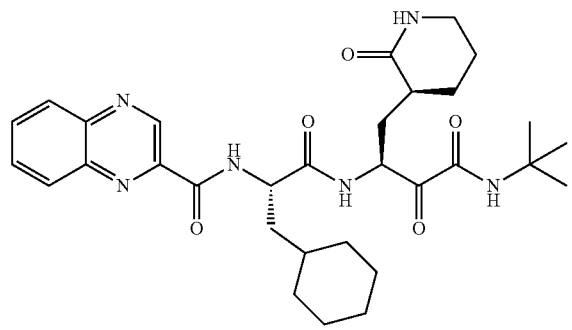 [SMILES: CC(C)(C)NC(=O)C(=O)[C@H](C[C@@H]1CCCNC1=O)NC(=O)[C@H](CC1CCCCC1)NC(=O)c1cnc2ccccc2n1] |
| A41 | 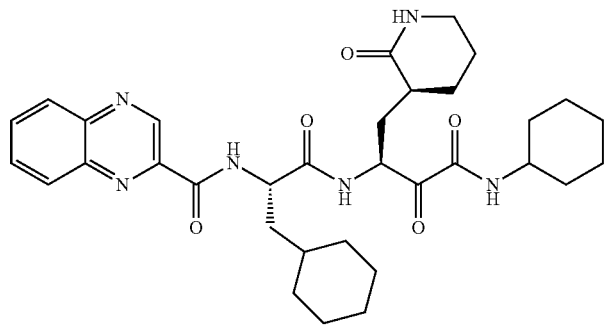 [SMILES: O=C(NC1CCCCC1)C(=O)[C@H](C[C@@H]1CCCNC1=O)NC(=O)[C@H](CC1CCCCC1)NC(=O)c1cnc2ccccc2n1] |

| number | structure |
|---|---|
| A42 | 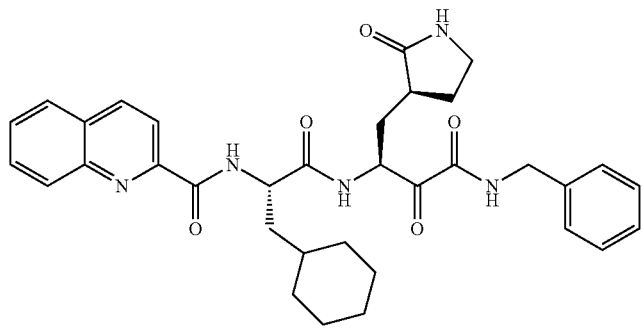 [SMILES: O=C(NCc1ccccc1)C(=O)[C@H](C[C@@H]1CCNC1=O)NC(=O)[C@H](CC1CCCCC1)NC(=O)c1ccc2ccccc2n1] |
| A43 | 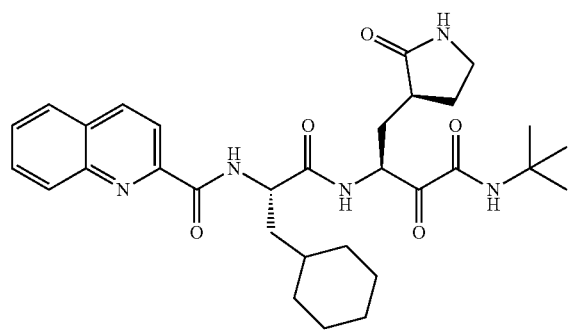 [SMILES: CC(C)(C)NC(=O)C(=O)[C@H](C[C@@H]1CCNC1=O)NC(=O)[C@H](CC1CCCCC1)NC(=O)c1ccc2ccccc2n1] |
| A44 | 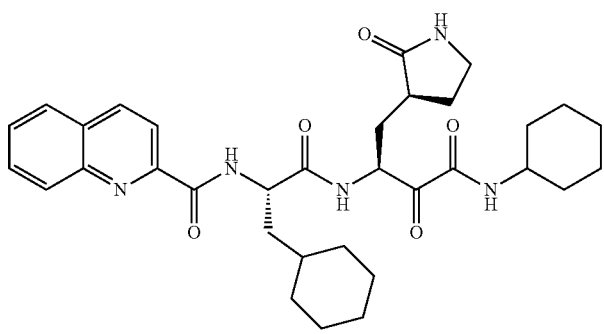 [SMILES: O=C(NC1CCCCC1)C(=O)[C@H](C[C@@H]1CCNC1=O)NC(=O)[C@H](CC1CCCCC1)NC(=O)c1ccc2ccccc2n1] |
| A45 | 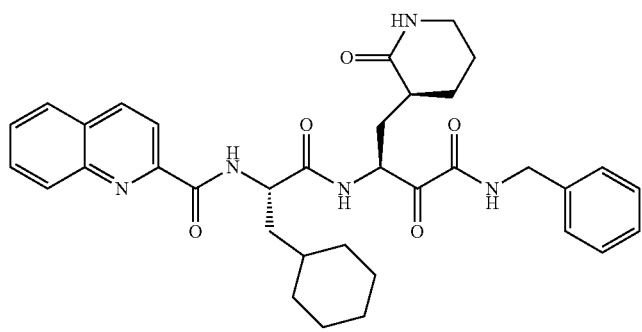 [SMILES: O=C(NCc1ccccc1)C(=O)[C@H](C[C@@H]1CCCNC1=O)NC(=O)[C@H](CC1CCCCC1)NC(=O)c1ccc2ccccc2n1] |

| number | structure |
|---|---|
| A46 | 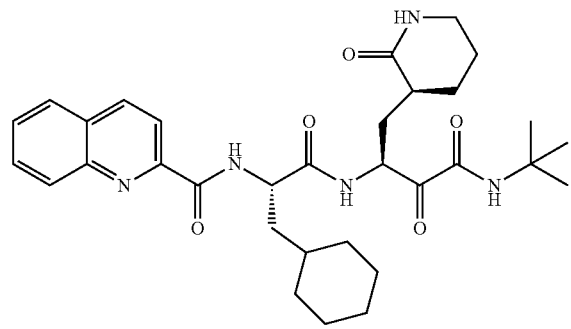 [SMILES: CC(C)(C)NC(=O)C(=O)[C@H](C[C@@H]1CCCNC1=O)NC(=O)[C@H](CC1CCCCC1)NC(=O)c1ccc2ccccc2n1] |
| A47 | 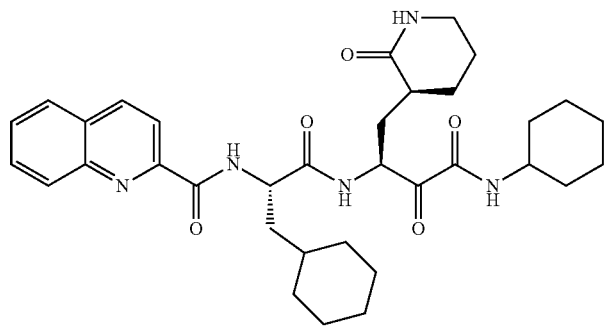 [SMILES: O=C(NC1CCCCC1)C(=O)[C@H](C[C@@H]1CCCNC1=O)NC(=O)[C@H](CC1CCCCC1)NC(=O)c1ccc2ccccc2n1] |
| A48 | 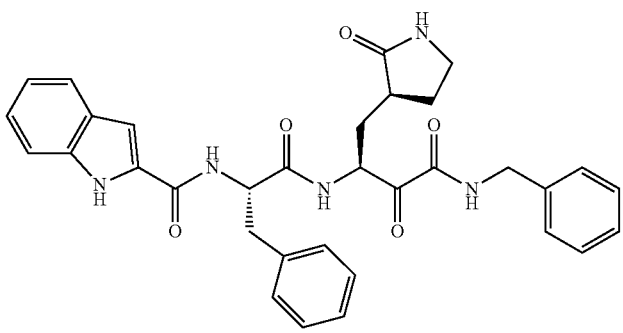 [SMILES: O=C(NCc1ccccc1)C(=O)[C@H](C[C@@H]1CCNC1=O)NC(=O)[C@H](Cc1ccccc1)NC(=O)c1cc2ccccc2[nH]1] |
| A49 | 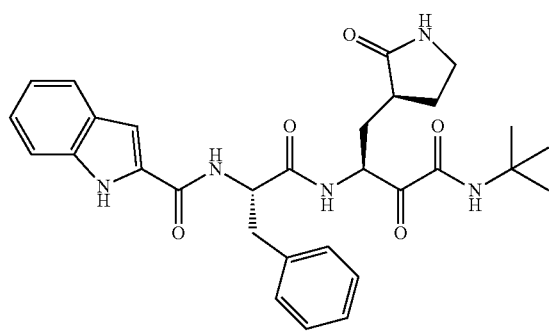 [SMILES: CC(C)(C)NC(=O)C(=O)[C@H](C[C@@H]1CCNC1=O)NC(=O)[C@H](Cc1ccccc1)NC(=O)c1cc2ccccc2[nH]1] |

| number | structure |
|---|---|
| A50 | 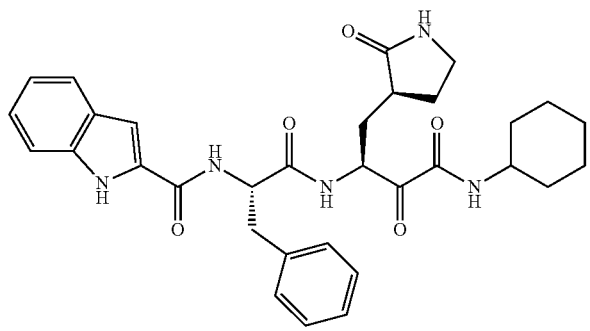 [SMILES: O=C(NC1CCCCC1)C(=O)[C@H](C[C@@H]1CCNC1=O)NC(=O)[C@H](Cc1ccccc1)NC(=O)c1cc2ccccc2[nH]1] |
| A51 | 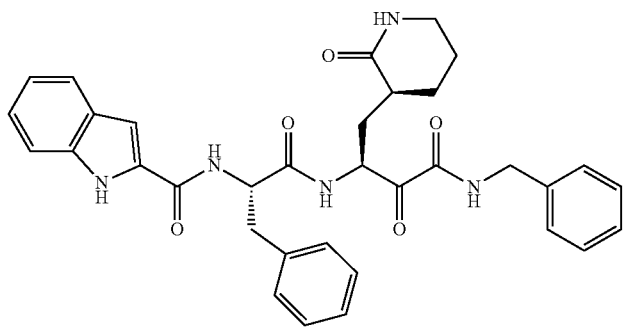 [SMILES: O=C(NCc1ccccc1)C(=O)[C@H](C[C@@H]1CCCNC1=O)NC(=O)[C@H](Cc1ccccc1)NC(=O)c1cc2ccccc2[nH]1] |
| A52 | 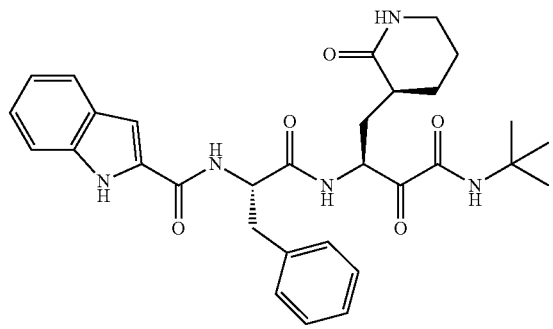 [SMILES: CC(C)(C)NC(=O)C(=O)[C@H](C[C@@H]1CCCNC1=O)NC(=O)[C@H](Cc1ccccc1)NC(=O)c1cc2ccccc2[nH]1] |
| A53 | 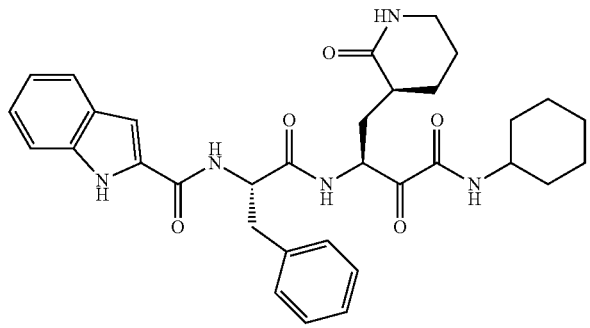 [SMILES: O=C(NC1CCCCC1)C(=O)[C@H](C[C@@H]1CCCNC1=O)NC(=O)[C@H](Cc1ccccc1)NC(=O)c1cc2ccccc2[nH]1] |

| number | structure |
|---|---|
| A54 | 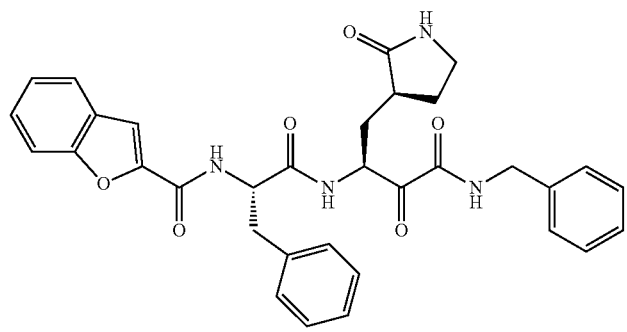 [SMILES: O=C(NCc1ccccc1)C(=O)[C@H](C[C@@H]1CCNC1=O)NC(=O)[C@H](Cc1ccccc1)NC(=O)c1cc2ccccc2o1] |
| A55 | 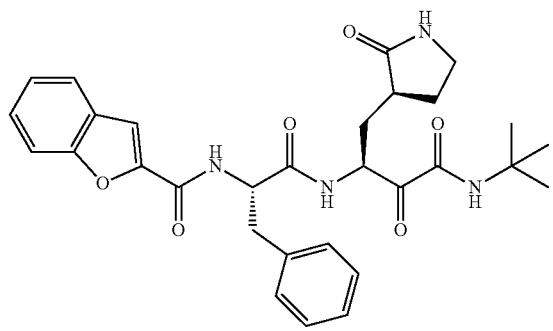 [SMILES: CC(C)(C)NC(=O)C(=O)[C@H](C[C@@H]1CCNC1=O)NC(=O)[C@H](Cc1ccccc1)NC(=O)c1cc2ccccc2o1] |
| A56 | 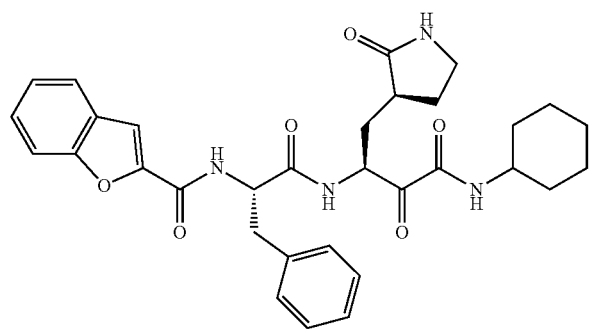 [SMILES: O=C(NC1CCCCC1)C(=O)[C@H](C[C@@H]1CCNC1=O)NC(=O)[C@H](Cc1ccccc1)NC(=O)c1cc2ccccc2o1] |
| A57 | 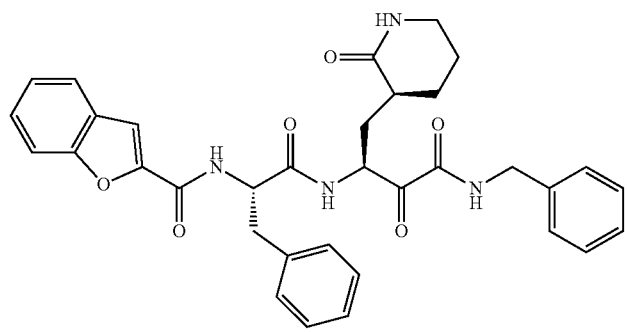 [SMILES: O=C(NCc1ccccc1)C(=O)[C@H](C[C@@H]1CCCNC1=O)NC(=O)[C@H](Cc1ccccc1)NC(=O)c1cc2ccccc2o1] |

-continued
| number | structure |
|---|---|
| A58 | 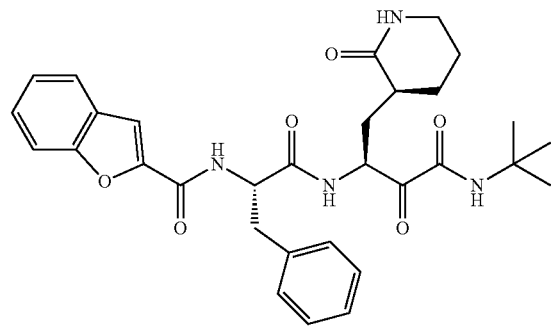 [SMILES: CC(C)(C)NC(=O)C(=O)[C@H](C[C@@H]1CCCNC1=O)NC(=O)[C@H](Cc1ccccc1)NC(=O)c1cc2ccccc2o1] |
| A59 | 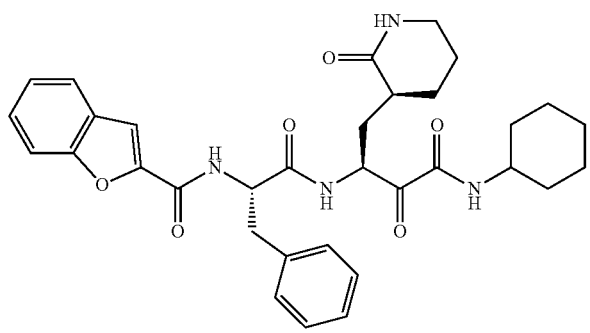 [SMILES: O=C(NC1CCCCC1)C(=O)[C@H](C[C@@H]1CCCNC1=O)NC(=O)[C@H](Cc1ccccc1)NC(=O)c1cc2ccccc2o1] |
| A60 | 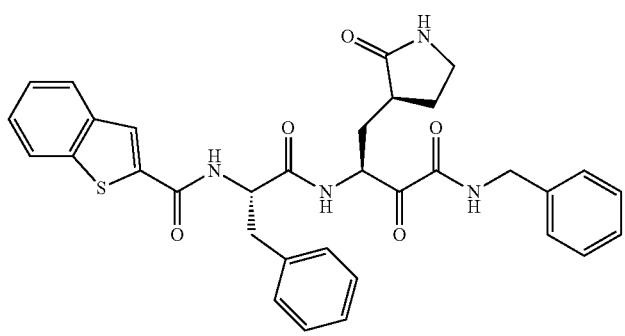 [SMILES: O=C(NCc1ccccc1)C(=O)[C@H](C[C@@H]1CCNC1=O)NC(=O)[C@H](Cc1ccccc1)NC(=O)c1cc2ccccc2s1] |
| A61 | 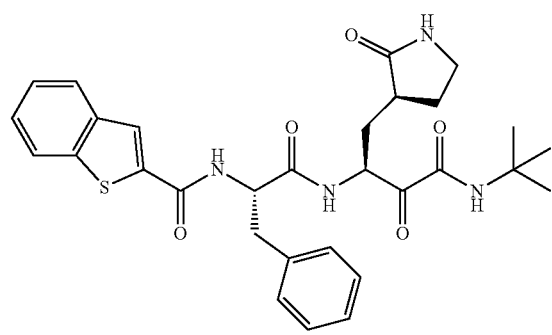 [SMILES: CC(C)(C)NC(=O)C(=O)[C@H](C[C@@H]1CCNC1=O)NC(=O)[C@H](Cc1ccccc1)NC(=O)c1cc2ccccc2s1] |

| number | structure |
|--------|-----------|
| A62 | 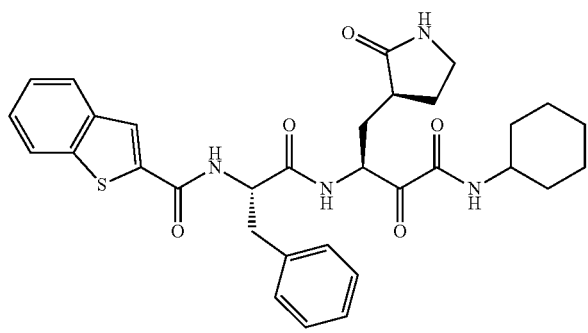 [SMILES: O=C(NC1CCCCC1)C(=O)[C@H](C[C@@H]1CCNC1=O)NC(=O)[C@H](Cc1ccccc1)NC(=O)c1cc2ccccc2s1] |
| A63 | 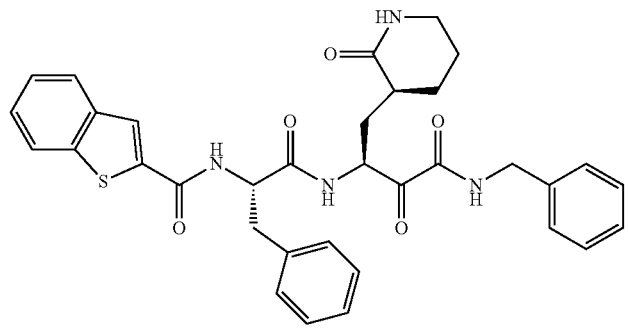 [SMILES: O=C(NCc1ccccc1)C(=O)[C@H](C[C@@H]1CCCNC1=O)NC(=O)[C@H](Cc1ccccc1)NC(=O)c1cc2ccccc2s1] |
| A64 | 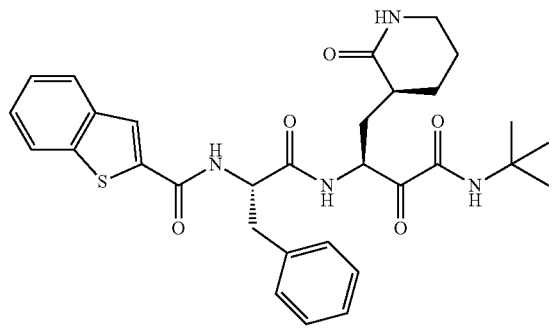 [SMILES: CC(C)(C)NC(=O)C(=O)[C@H](C[C@@H]1CCCNC1=O)NC(=O)[C@H](Cc1ccccc1)NC(=O)c1cc2ccccc2s1] |
| A65 | 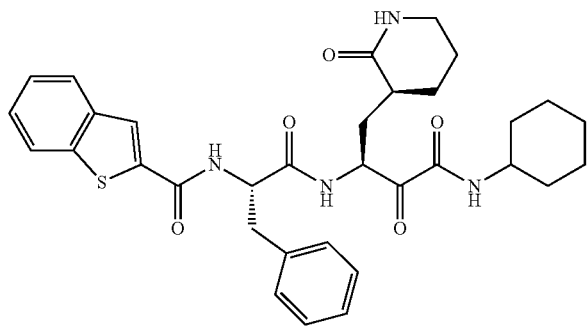 [SMILES: O=C(NC1CCCCC1)C(=O)[C@H](C[C@@H]1CCCNC1=O)NC(=O)[C@H](Cc1ccccc1)NC(=O)c1cc2ccccc2s1] |

| number | structure |
|---|---|
| A66 | 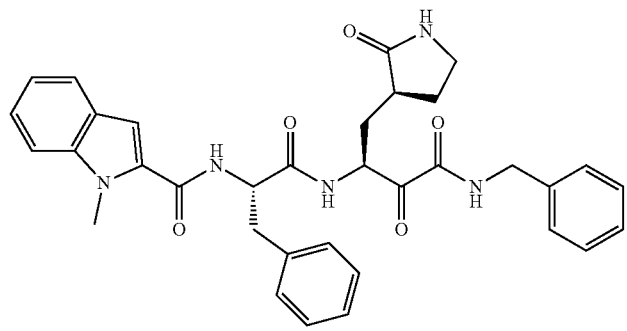 [SMILES: Cn1c(C(=O)N[C@@H](Cc2ccccc2)C(=O)N[C@@H](C[C@@H]2CCNC2=O)C(=O)C(=O)NCc2ccccc2)cc2ccccc21] |
| A67 | 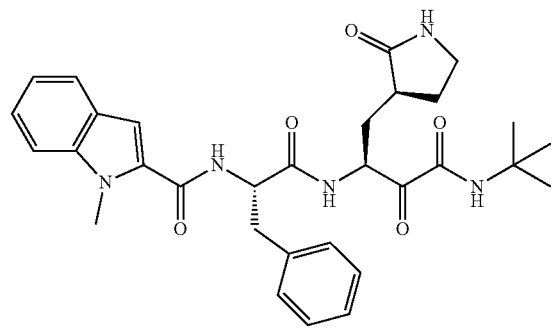 [SMILES: Cn1c(C(=O)N[C@@H](Cc2ccccc2)C(=O)N[C@@H](C[C@@H]2CCNC2=O)C(=O)C(=O)NC(C)(C)C)cc2ccccc21] |
| A68 | 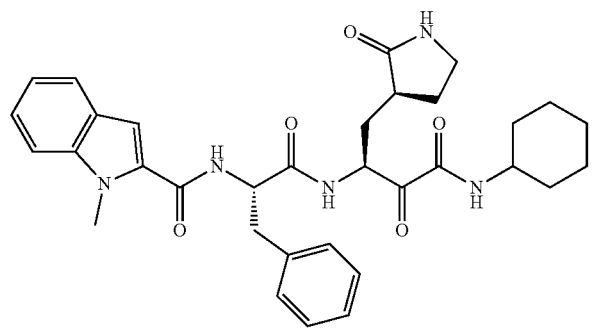 [SMILES: Cn1c(C(=O)N[C@@H](Cc2ccccc2)C(=O)N[C@@H](C[C@@H]2CCNC2=O)C(=O)C(=O)NC2CCCCC2)cc2ccccc21] |
| A69 | 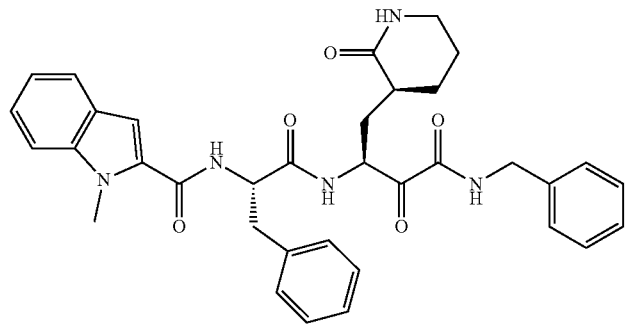 [SMILES: Cn1c(C(=O)N[C@@H](Cc2ccccc2)C(=O)N[C@@H](C[C@@H]2CCCNC2=O)C(=O)C(=O)NCc2ccccc2)cc2ccccc21] |

| number | structure |
|---|---|
| A70 | 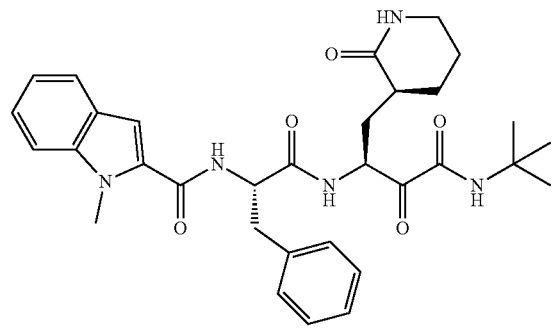 [SMILES: Cn1c(C(=O)N[C@@H](Cc2ccccc2)C(=O)N[C@@H](C[C@@H]2CCCNC2=O)C(=O)C(=O)NC(C)(C)C)cc2ccccc21] |
| A71 | 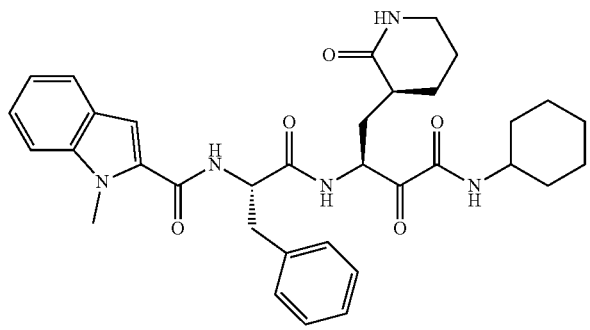 [SMILES: Cn1c(C(=O)N[C@@H](Cc2ccccc2)C(=O)N[C@@H](C[C@@H]2CCCNC2=O)C(=O)C(=O)NC2CCCCC2)cc2ccccc21] |
| A72 | 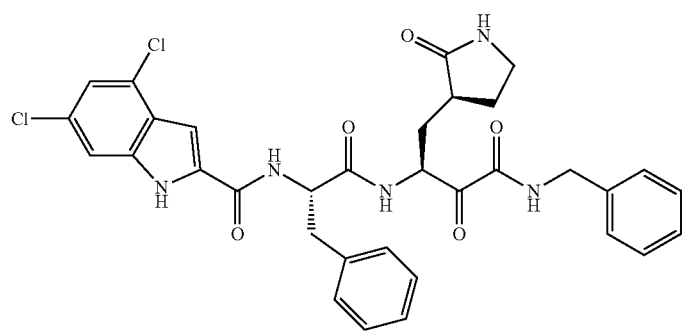 [SMILES: O=C(NCc1ccccc1)C(=O)[C@H](C[C@@H]1CCNC1=O)NC(=O)[C@H](Cc1ccccc1)NC(=O)c1cc2c(Cl)cc(Cl)cc2[nH]1] |
| A73 | 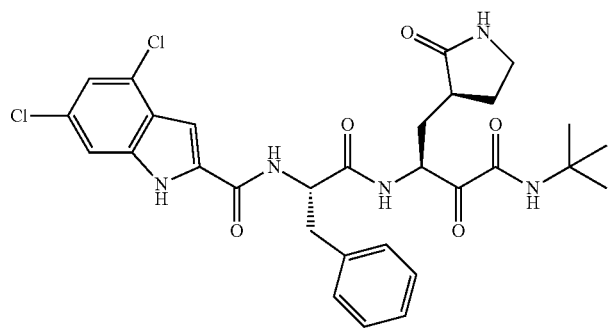 [SMILES: CC(C)(C)NC(=O)C(=O)[C@H](C[C@@H]1CCNC1=O)NC(=O)[C@H](Cc1ccccc1)NC(=O)c1cc2c(Cl)cc(Cl)cc2[nH]1] |

| number | structure |
|---|---|
| A74 | 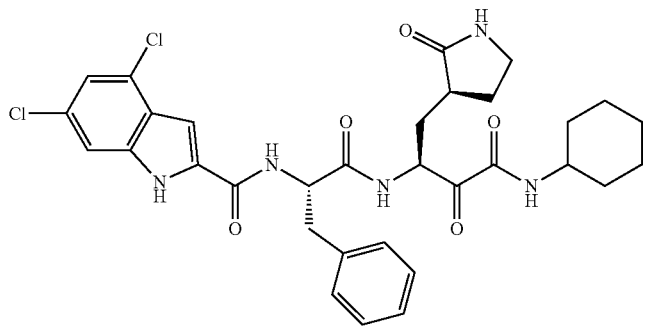 [SMILES: O=C(NC1CCCCC1)C(=O)[C@H](C[C@@H]1CCNC1=O)NC(=O)[C@H](Cc1ccccc1)NC(=O)c1cc2c(Cl)cc(Cl)cc2[nH]1] |
| A75 | 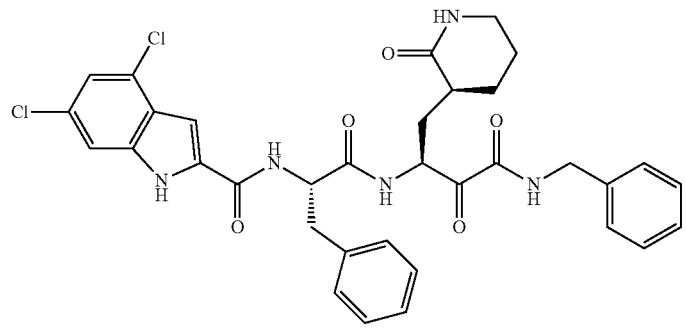 [SMILES: O=C(NCc1ccccc1)C(=O)[C@H](C[C@@H]1CCCNC1=O)NC(=O)[C@H](Cc1ccccc1)NC(=O)c1cc2c(Cl)cc(Cl)cc2[nH]1] |
| A76 | 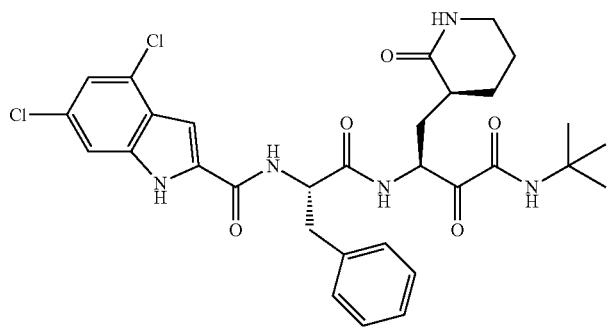 [SMILES: CC(C)(C)NC(=O)C(=O)[C@H](C[C@@H]1CCCNC1=O)NC(=O)[C@H](Cc1ccccc1)NC(=O)c1cc2c(Cl)cc(Cl)cc2[nH]1] |
| A77 | 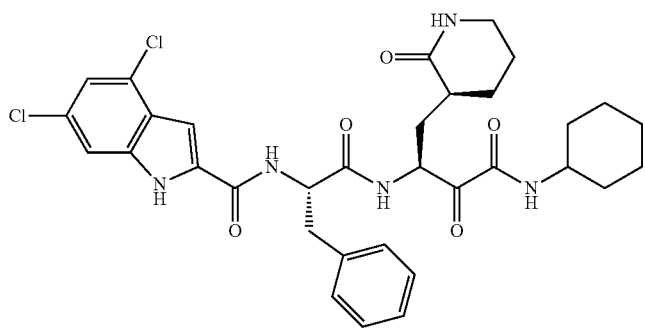 [SMILES: O=C(NC1CCCCC1)C(=O)[C@H](C[C@@H]1CCCNC1=O)NC(=O)[C@H](Cc1ccccc1)NC(=O)c1cc2c(Cl)cc(Cl)cc2[nH]1] |

| number | structure |
|---|---|
| A78 | 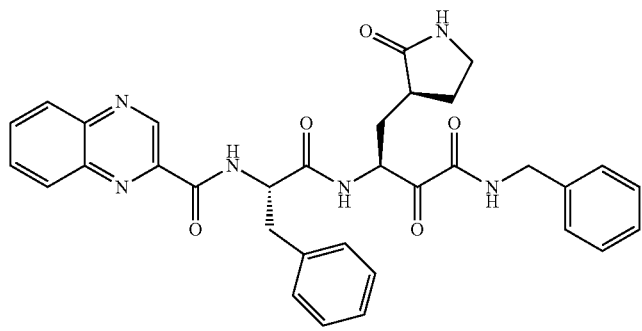 [SMILES: O=C(NCc1ccccc1)C(=O)[C@H](C[C@@H]1CCNC1=O)NC(=O)[C@H](Cc1ccccc1)NC(=O)c1cnc2ccccc2n1] |
| A79 | 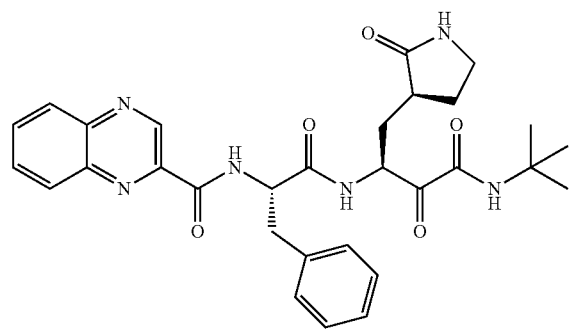 [SMILES: CC(C)(C)NC(=O)C(=O)[C@H](C[C@@H]1CCNC1=O)NC(=O)[C@H](Cc1ccccc1)NC(=O)c1cnc2ccccc2n1] |
| A80 | 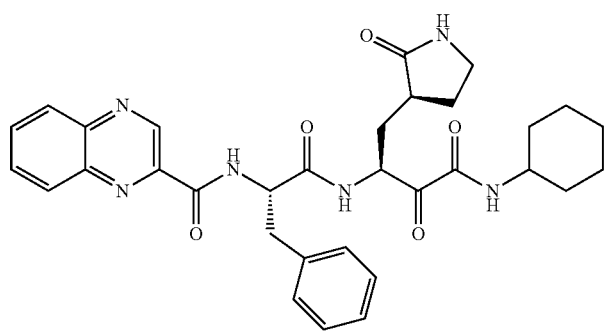 [SMILES: O=C(NC1CCCCC1)C(=O)[C@H](C[C@@H]1CCNC1=O)NC(=O)[C@H](Cc1ccccc1)NC(=O)c1cnc2ccccc2n1] |
| A81 | 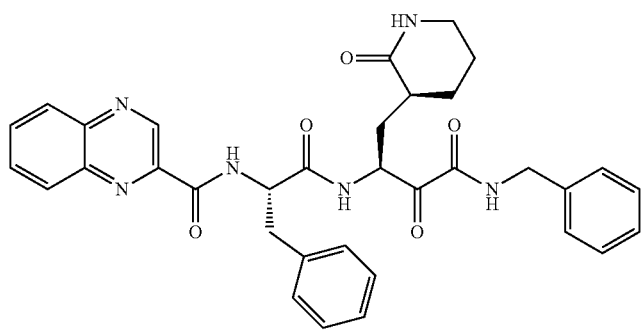 [SMILES: O=C(NCc1ccccc1)C(=O)[C@H](C[C@@H]1CCCNC1=O)NC(=O)[C@H](Cc1ccccc1)NC(=O)c1cnc2ccccc2n1] |

| number | structure |
|---|---|
| A82 | 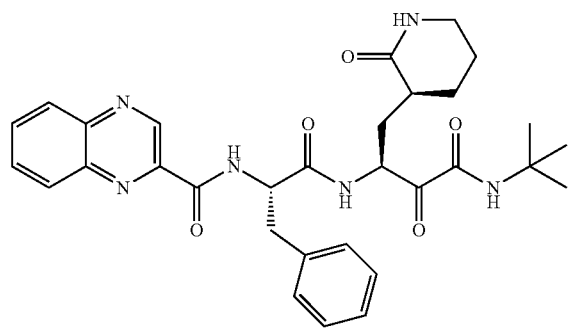 [SMILES: CC(C)(C)NC(=O)C(=O)[C@H](C[C@@H]1CCCNC1=O)NC(=O)[C@H](Cc1ccccc1)NC(=O)c1cnc2ccccc2n1] |
| A83 | 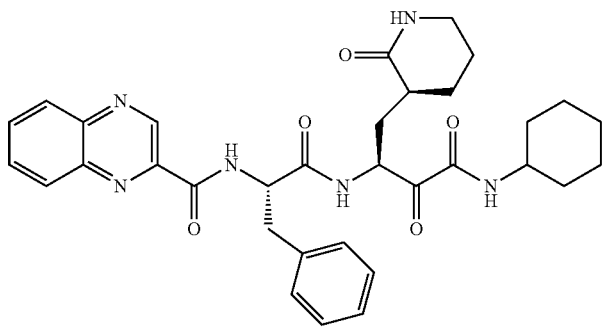 [SMILES: O=C(NC1CCCCC1)C(=O)[C@H](C[C@@H]1CCCNC1=O)NC(=O)[C@H](Cc1ccccc1)NC(=O)c1cnc2ccccc2n1] |
| A84 | 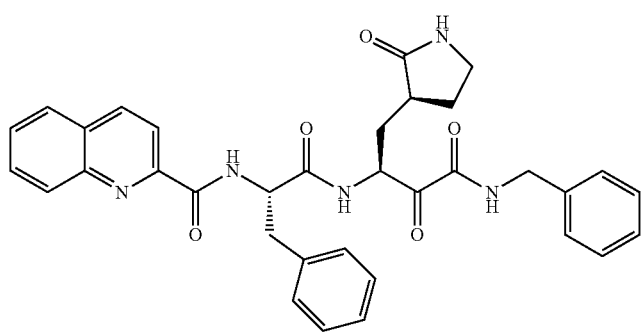 [SMILES: O=C(NCc1ccccc1)C(=O)[C@H](C[C@@H]1CCNC1=O)NC(=O)[C@H](Cc1ccccc1)NC(=O)c1ccc2ccccc2n1] |
| A85 | 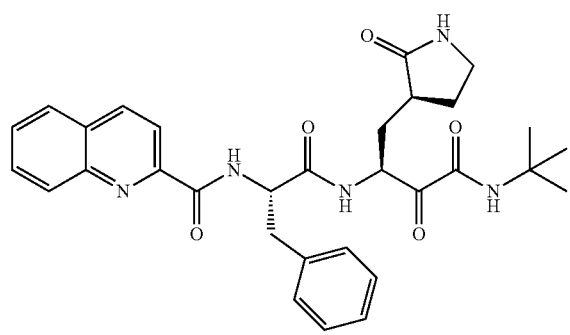 [SMILES: CC(C)(C)NC(=O)C(=O)[C@H](C[C@@H]1CCNC1=O)NC(=O)[C@H](Cc1ccccc1)NC(=O)c1ccc2ccccc2n1] |

| number | structure |
|---|---|
| A86 | 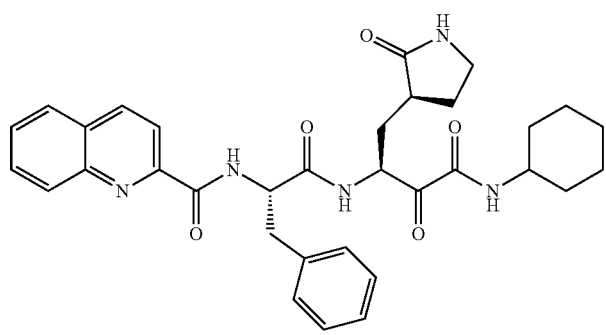 [SMILES: O=C(NC1CCCCC1)C(=O)[C@H](C[C@@H]1CCNC1=O)NC(=O)[C@H](Cc1ccccc1)NC(=O)c1ccc2ccccc2n1] |
| A87 | 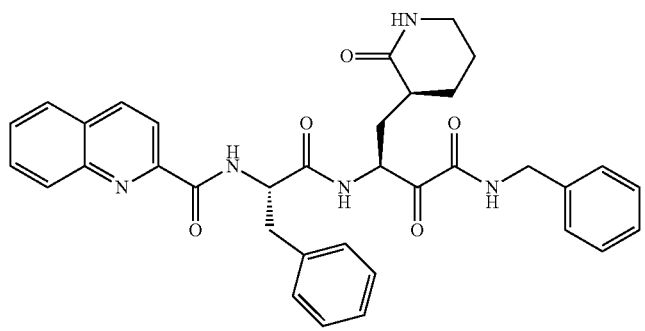 [SMILES: O=C(NCc1ccccc1)C(=O)[C@H](C[C@@H]1CCCNC1=O)NC(=O)[C@H](Cc1ccccc1)NC(=O)c1ccc2ccccc2n1] |
| A88 | 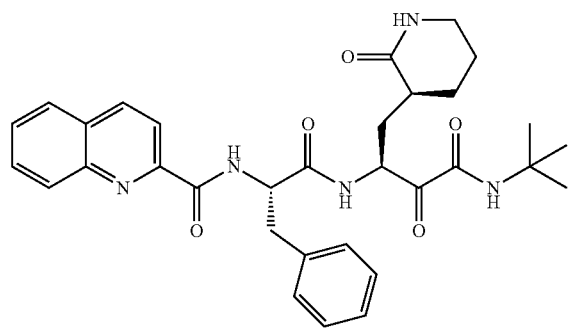 [SMILES: CC(C)(C)NC(=O)C(=O)[C@H](C[C@@H]1CCCNC1=O)NC(=O)[C@H](Cc1ccccc1)NC(=O)c1ccc2ccccc2n1] |
| A89 | 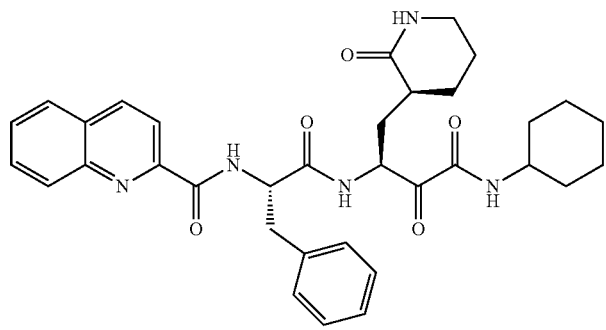 [SMILES: O=C(NC1CCCCC1)C(=O)[C@H](C[C@@H]1CCCNC1=O)NC(=O)[C@H](Cc1ccccc1)NC(=O)c1ccc2ccccc2n1] |

-continued
| number | structure |
|---|---|
| A90 | 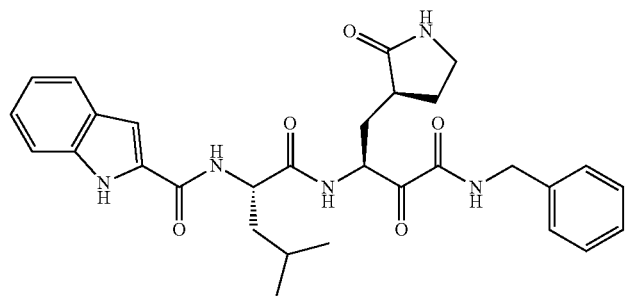 [SMILES: CC(C)C[C@H](NC(=O)c1cc2ccccc2[nH]1)C(=O)N[C@@H](C[C@@H]1CCNC1=O)C(=O)C(=O)NCc1ccccc1] |
| A91 | 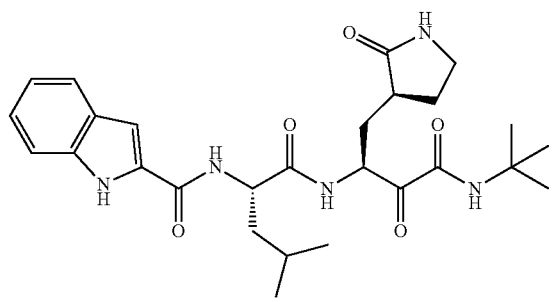 [SMILES: CC(C)C[C@H](NC(=O)c1cc2ccccc2[nH]1)C(=O)N[C@@H](C[C@@H]1CCNC1=O)C(=O)C(=O)NC(C)(C)C] |
| A92 | 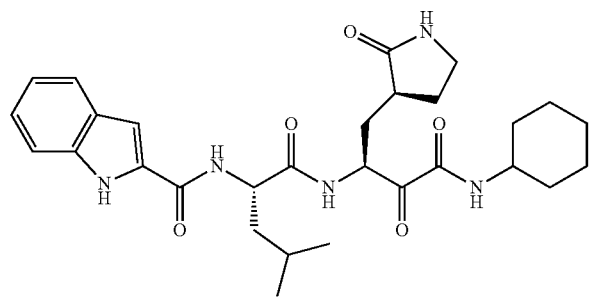 |
| A93 | 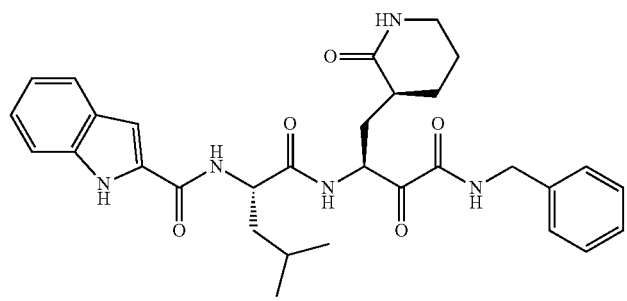 [SMILES: CC(C)C[C@H](NC(=O)c1cc2ccccc2[nH]1)C(=O)N[C@@H](C[C@@H]1CCCNC1=O)C(=O)C(=O)NCc1ccccc1] |
| A94 | 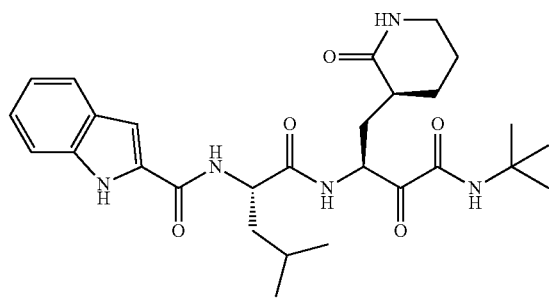 [SMILES: CC(C)C[C@H](NC(=O)c1cc2ccccc2[nH]1)C(=O)N[C@@H](C[C@@H]1CCCNC1=O)C(=O)C(=O)NC(C)(C)C] |

| number | structure |
|---|---|
| A95 | 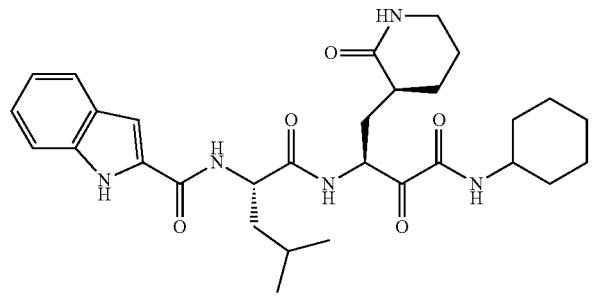 |
| A96 | 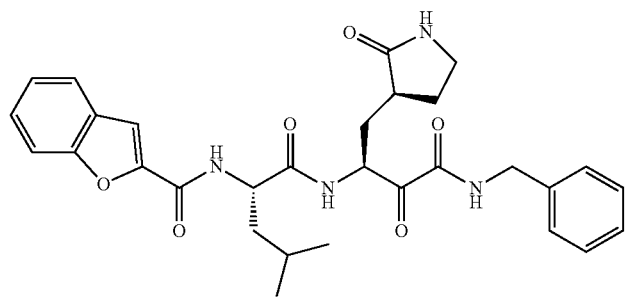 [SMILES: CC(C)C[C@H](NC(=O)c1cc2ccccc2o1)C(=O)N[C@@H](C[C@@H]1CCNC1=O)C(=O)C(=O)NCc1ccccc1] |
| A97 | 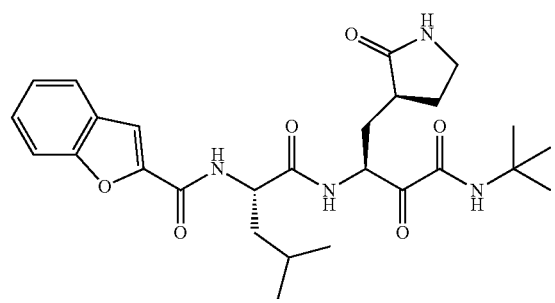 |
| A98 | 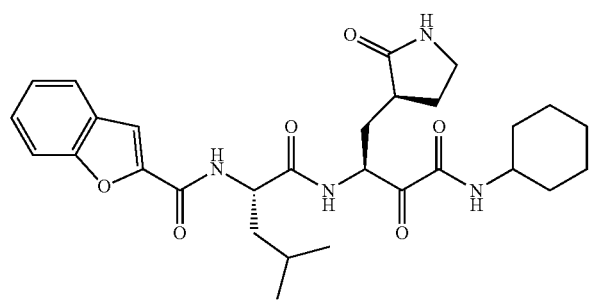 [SMILES: CC(C)C[C@H](NC(=O)c1cc2ccccc2o1)C(=O)N[C@@H](C[C@@H]1CCNC1=O)C(=O)C(=O)NC1CCCCC1] |
| A99 | 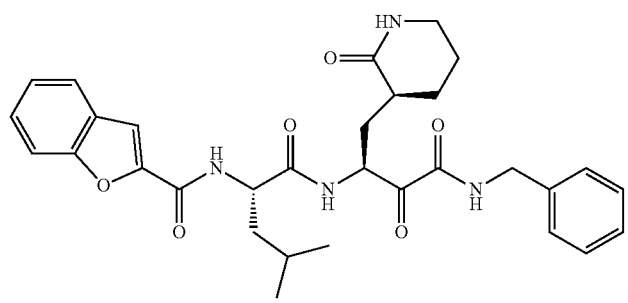 [SMILES: CC(C)C[C@H](NC(=O)c1cc2ccccc2s1)C(=O)N[C@@H](C[C@@H]1CCCNC1=O)C(=O)C(=O)NCc1ccccc1] |

| number | structure |
|---|---|
| A100 | 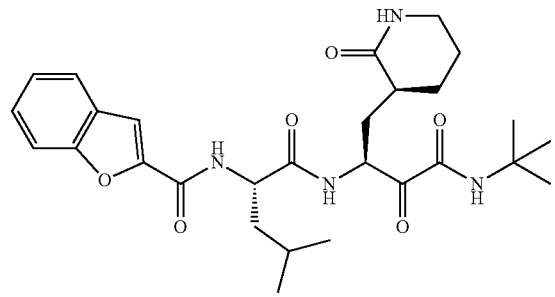 [SMILES: CC(C)C[C@H](NC(=O)c1cc2ccccc2s1)C(=O)N[C@@H](C[C@@H]1CCCNC1=O)C(=O)C(=O)NC(C)(C)C] |
| A101 | 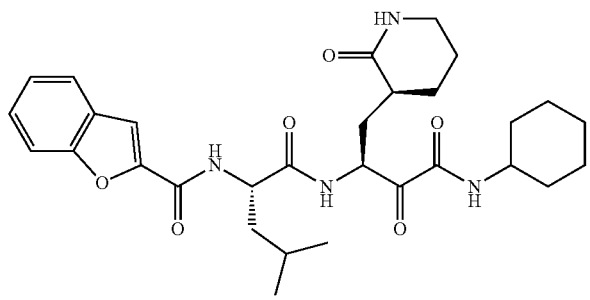 [SMILES: CC(C)C[C@H](NC(=O)c1cc2ccccc2s1)C(=O)N[C@@H](C[C@@H]1CCCNC1=O)C(=O)C(=O)NC1CCCCC1] |
| A102 | 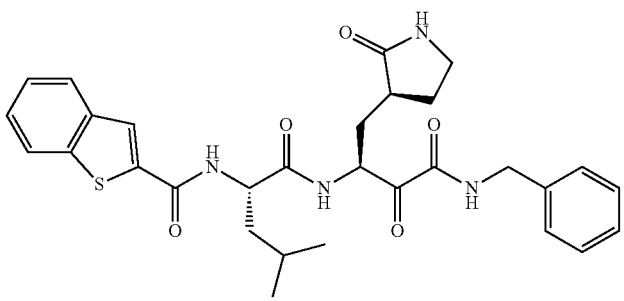 |
| A103 | 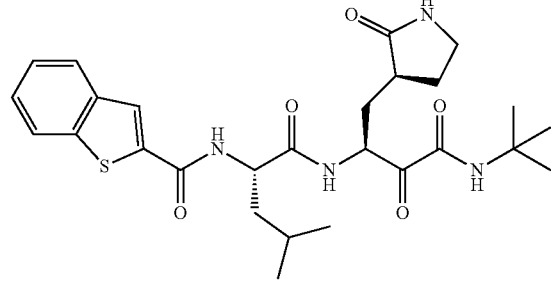 |
| A104 | 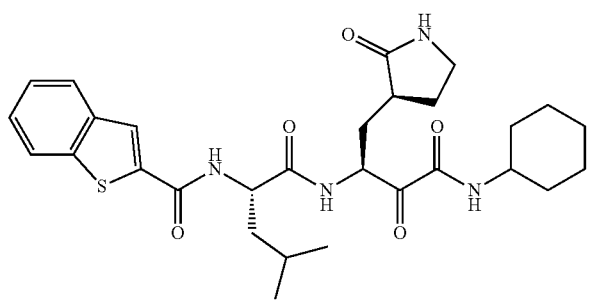 |

| number | structure |
|---|---|
| A105 | 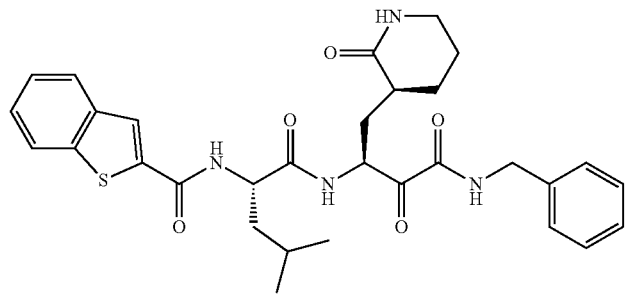 |
| A106 | 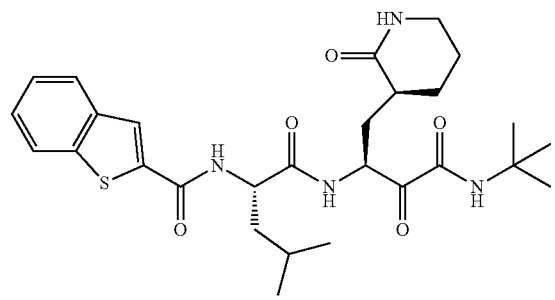 |
| A107 | 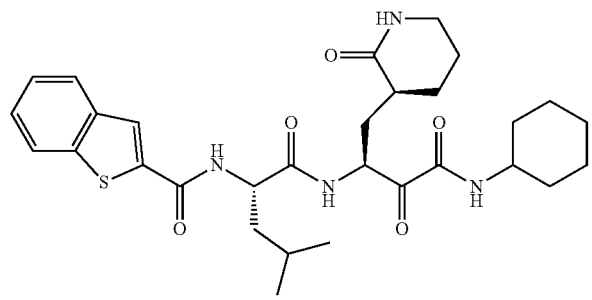 |
| A108 | 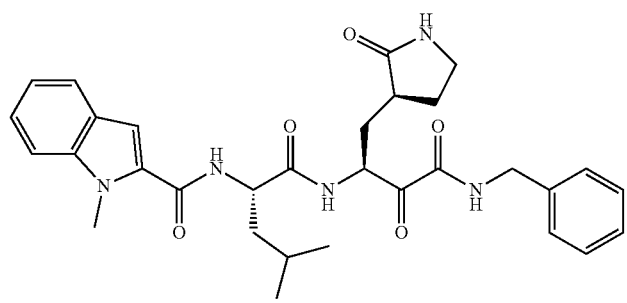 [SMILES: CC(C)C[C@H](NC(=O)c1cc2ccccc2n1C)C(=O)N[C@@H](C[C@@H]1CCNC1=O)C(=O)C(=O)NCc1ccccc1] |
| A109 | 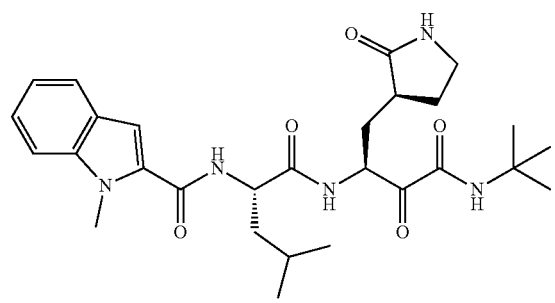 [SMILES: CC(C)C[C@H](NC(=O)c1cc2ccccc2n1C)C(=O)N[C@@H](C[C@@H]1CCNC1=O)C(=O)C(=O)NC(C)(C)C] |

| number | structure |
|---|---|
| A110 | 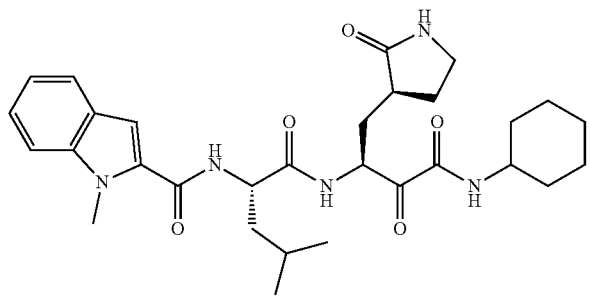 [SMILES: CC(C)C[C@H](NC(=O)c1cc2ccccc2n1C)C(=O)N[C@@H](C[C@@H]1CCNC1=O)C(=O)C(=O)NC1CCCCC1] |
| A111 | 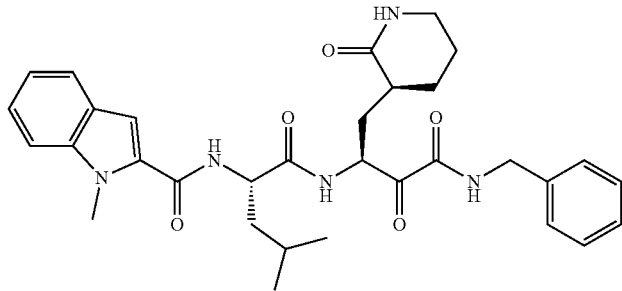 [SMILES: CC(C)C[C@H](NC(=O)c1cc2ccccc2n1C)C(=O)N[C@@H](C[C@@H]1CCCNC1=O)C(=O)C(=O)NCc1ccccc1] |
| A112 | 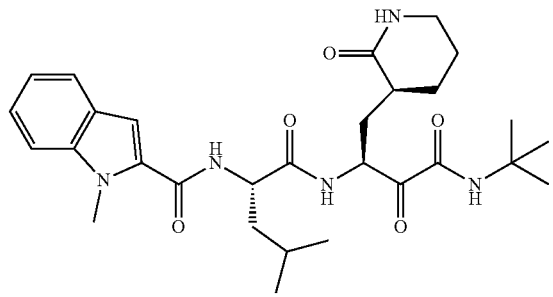 [SMILES: CC(C)C[C@H](NC(=O)c1cc2ccccc2n1C)C(=O)N[C@@H](C[C@@H]1CCCNC1=O)C(=O)C(=O)NC(C)(C)C] |
| A113 | 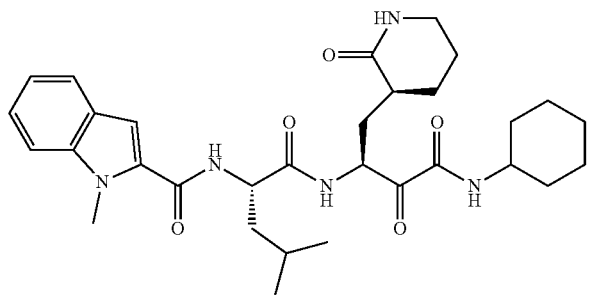 [SMILES: CC(C)C[C@H](NC(=O)c1cc2ccccc2n1C)C(=O)N[C@@H](C[C@@H]1CCCNC1=O)C(=O)C(=O)NC1CCCCC1] |
| A114 | 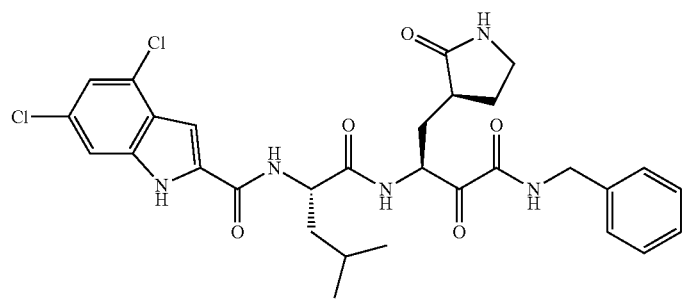 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NCc1ccccc1] |

-continued

| number | structure |
|---|---|
| A115 | 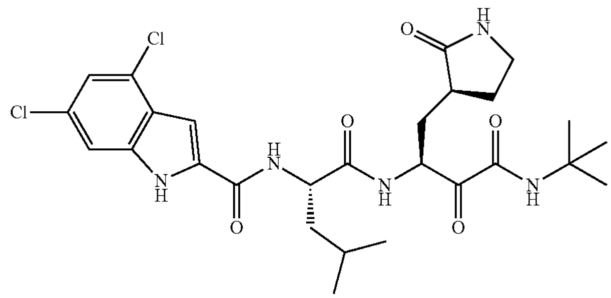 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC(C)(C)C] |
| A116 | 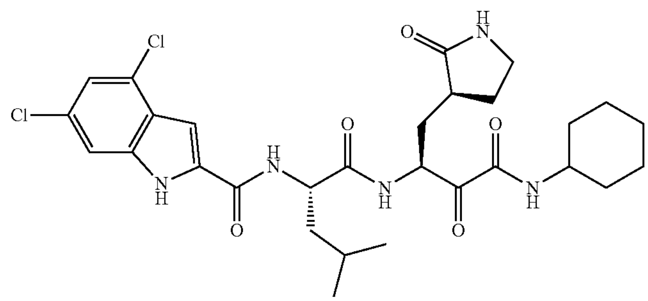 [SMILES: CC(C)C[C@H](NC(=O)c1cc2c(Cl)cc(Cl)cc2[nH]1)C(=O)N[C@@H](C[C@@H]1CCNC1=O)C(=O)C(=O)NC1CCCCC1] |
| A117 | 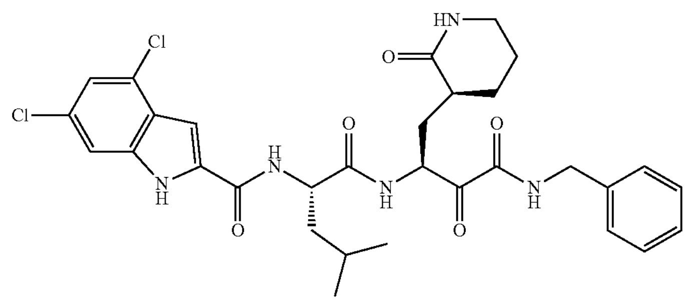 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NCc1ccccc1] |
| A118 | 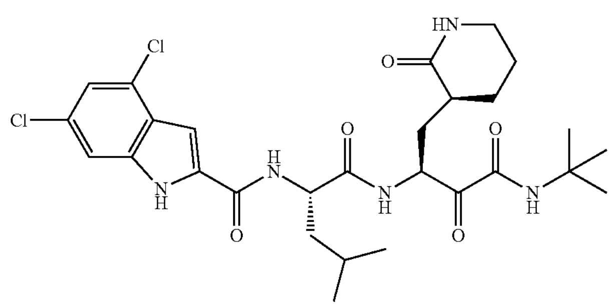 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC(C)(C)C] |
| A119 | 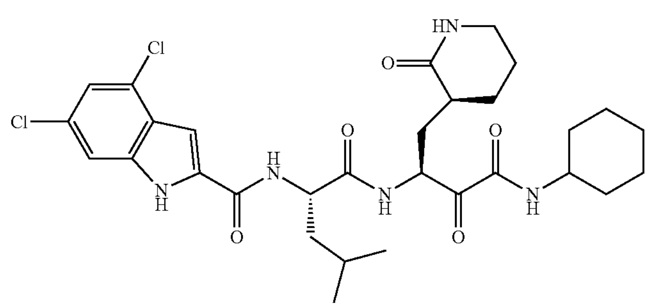 [SMILES: CC(C)C[C@H](NC(=O)c1cc2c(Cl)cc(Cl)cc2[nH]1)C(=O)N[C@@H](C[C@@H]1CCCNC1=O)C(=O)C(=O)NC1CCCCC1] |

| number | structure |
|---|---|
| A120 | 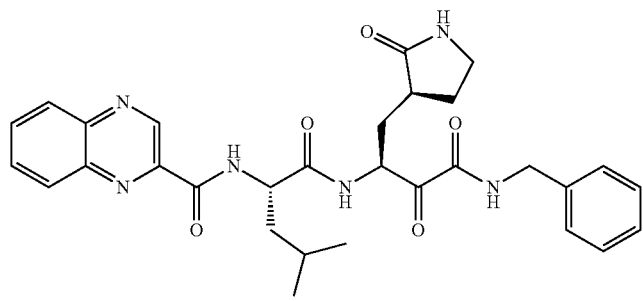 [SMILES: CC(C)C[C@H](NC(=O)c1cnc2ccccc2n1)C(=O)N[C@@H](C[C@@H]1CCNC1=O)C(=O)C(=O)NCc1ccccc1] |
| A121 | 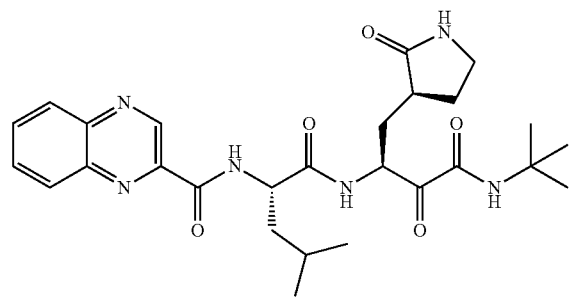 [SMILES: CC(C)C[C@H](NC(=O)c1cnc2ccccc2n1)C(=O)N[C@@H](C[C@@H]1CCNC1=O)C(=O)C(=O)NC(C)(C)C] |
| A122 | 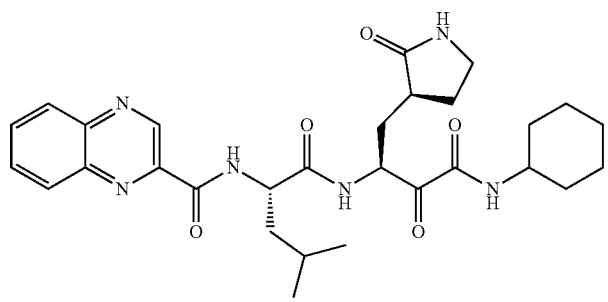 [SMILES: CC(C)C[C@H](NC(=O)c1cnc2ccccc2n1)C(=O)N[C@@H](C[C@@H]1CCNC1=O)C(=O)C(=O)NC1CCCCC1] |
| A123 | 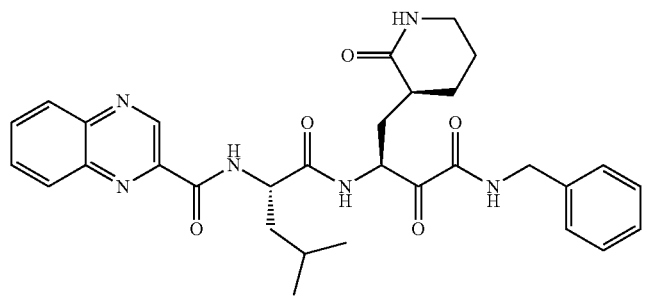 [SMILES: CC(C)C[C@H](NC(=O)c1cnc2ccccc2n1)C(=O)N[C@@H](C[C@@H]1CCCNC1=O)C(=O)C(=O)NCc1ccccc1] |
| A124 | 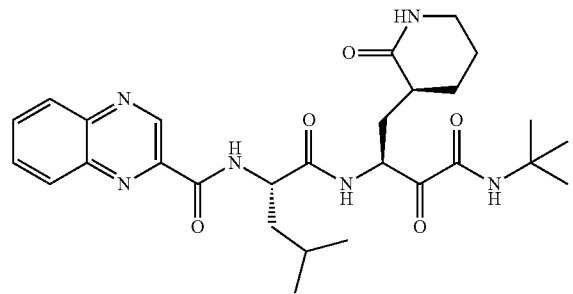 [SMILES: CC(C)C[C@H](NC(=O)c1cnc2ccccc2n1)C(=O)N[C@@H](C[C@@H]1CCCNC1=O)C(=O)C(=O)NC(C)(C)C] |

-continued
| number | structure |
|---|---|
| A125 | 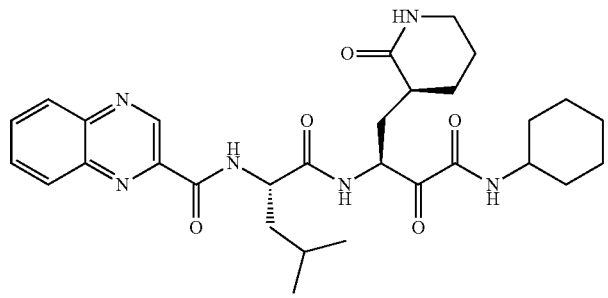 [SMILES: CC(C)C[C@H](NC(=O)c1cnc2ccccc2n1)C(=O)N[C@@H](C[C@@H]1CCCNC1=O)C(=O)C(=O)NC1CCCCC1] |
| A126 | 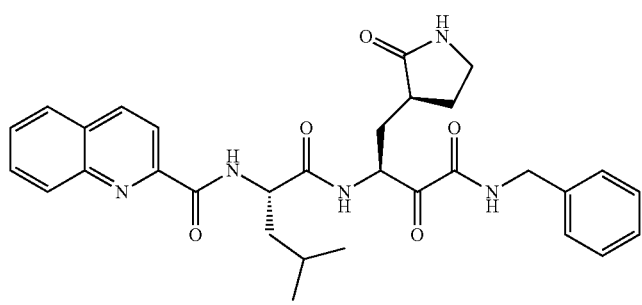 [SMILES: CC(C)C[C@H](NC(=O)c1ccc2ccccc2n1)C(=O)N[C@@H](C[C@@H]1CCNC1=O)C(=O)C(=O)NCc1ccccc1] |
| A127 | 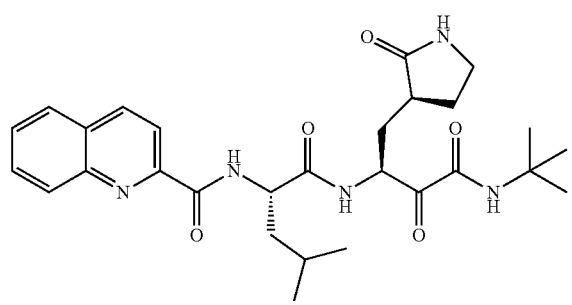 [SMILES: CC(C)C[C@H](NC(=O)c1ccc2ccccc2n1)C(=O)N[C@@H](C[C@@H]1CCNC1=O)C(=O)C(=O)NC(C)(C)C] |
| A128 | 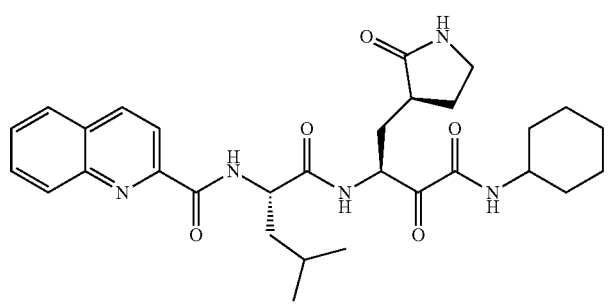 [SMILES: CC(C)C[C@H](NC(=O)c1ccc2ccccc2n1)C(=O)N[C@@H](C[C@@H]1CCNC1=O)C(=O)C(=O)NC1CCCCC1] |
| A129 | 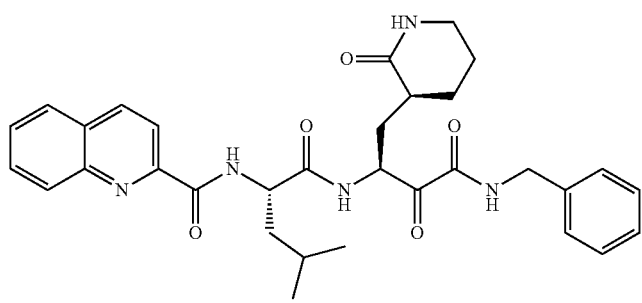 [SMILES: CC(C)C[C@H](NC(=O)c1ccc2ccccc2n1)C(=O)N[C@@H](C[C@@H]1CCCNC1=O)C(=O)C(=O)NCc1ccccc1] |

| number | structure |
|---|---|
| A130 | 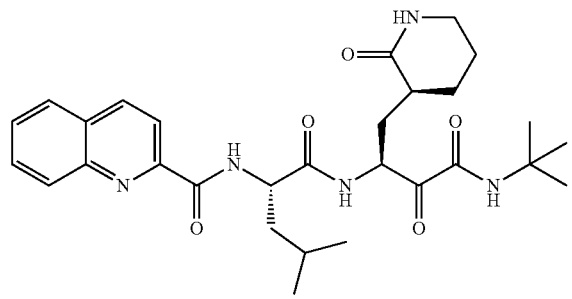 [SMILES: CC(C)C[C@H](NC(=O)c1ccc2ccccc2n1)C(=O)N[C@@H](C[C@@H]1CCCNC1=O)C(=O)C(=O)NC(C)(C)C] |
| A131 | 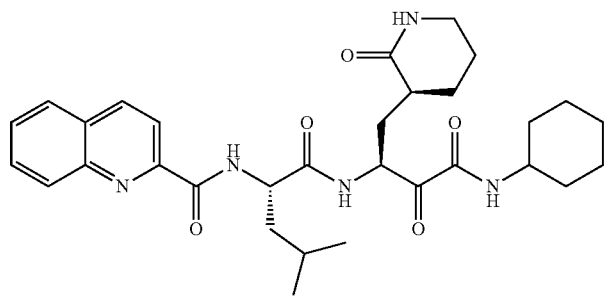 [SMILES: CC(C)C[C@H](NC(=O)c1ccc2ccccc2n1)C(=O)N[C@@H](C[C@@H]1CCCNC1=O)C(=O)C(=O)NC1CCCCC1] |
| A132 | 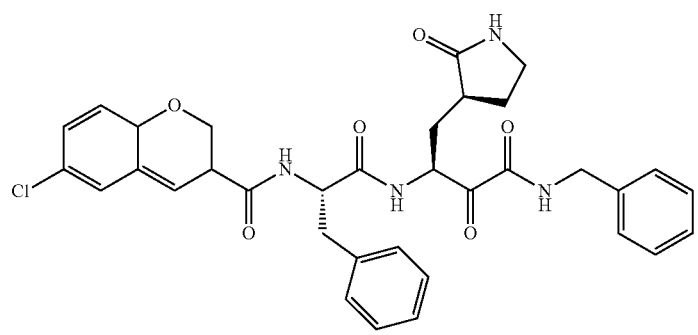 [SMILES: O=C(NCc1ccccc1)C(=O)[C@H](C[C@@H]1CCNC1=O)NC(=O)[C@H](Cc1ccccc1)NC(=O)C1C=C2C=C(Cl)C=CC2OC1] |
| A133 | 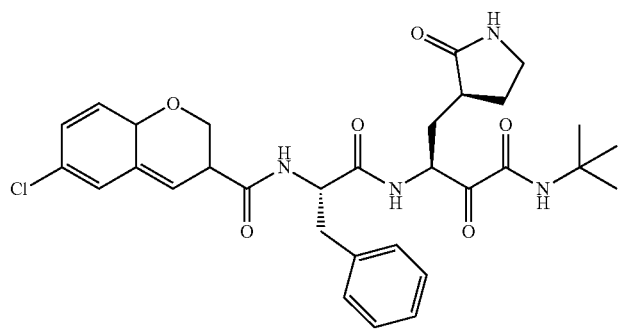 [SMILES: CC(C)(C)NC(=O)C(=O)[C@H](C[C@@H]1CCNC1=O)NC(=O)[C@H](Cc1ccccc1)NC(=O)C1C=C2C=C(Cl)C=CC2OC1] |

| number | structure |
|---|---|
| A134 | 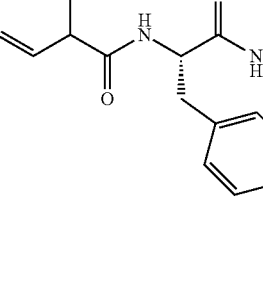 |
| A135 | 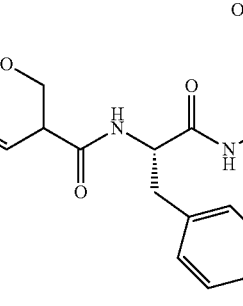 |
| A136 | 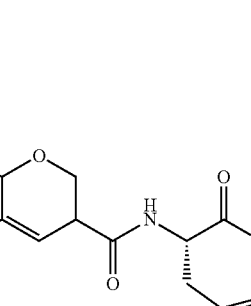 |
| A137 | 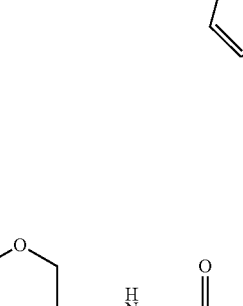 |

| number | structure |
|---|---|
| A168 | 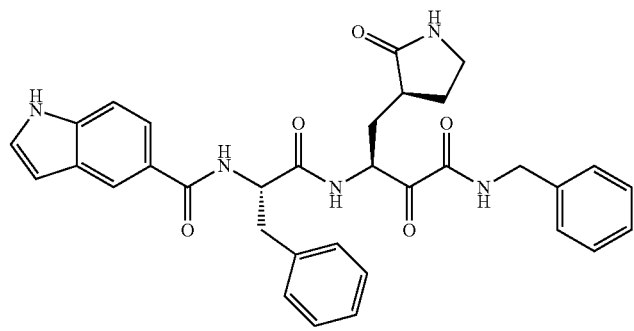 [SMILES: O=C(NCc1ccccc1)C(=O)[C@H](C[C@@H]1CCNC1=O)NC(=O)[C@H](Cc1ccccc1)NC(=O)c1ccc2[nH]ccc2c1] |
| A169 | 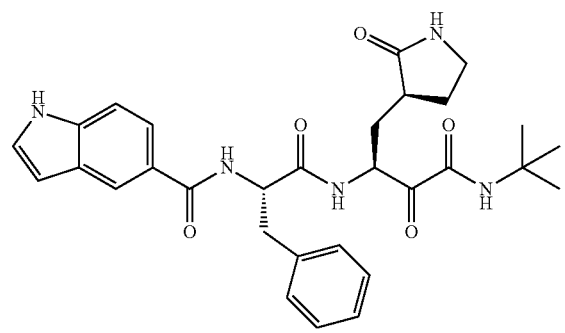 [SMILES: CC(C)(C)NC(=O)C(=O)[C@H](C[C@@H]1CCNC1=O)NC(=O)[C@H](Cc1ccccc1)NC(=O)c1ccc2[nH]ccc2c1] |
| A170 | 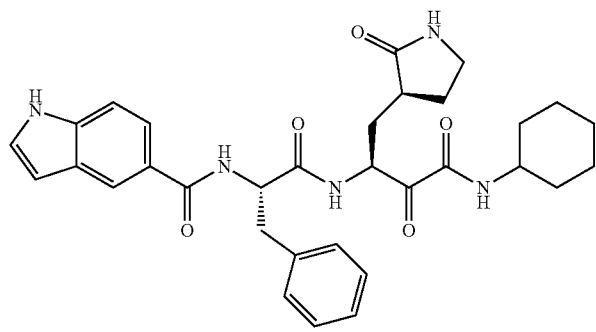 [SMILES: O=C(NC1CCCCC1)C(=O)[C@H](C[C@@H]1CCNC1=O)NC(=O)[C@H](Cc1ccccc1)NC(=O)c1ccc2[nH]ccc2c1] |
| A171 | 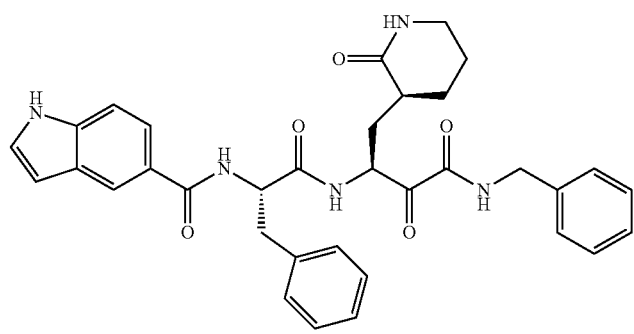 [SMILES: O=C(NCc1ccccc1)C(=O)[C@H](C[C@@H]1CCCNC1=O)NC(=O)[C@H](Cc1ccccc1)NC(=O)c1ccc2[nH]ccc2c1] |

| number | structure |
|---|---|
| A172 | 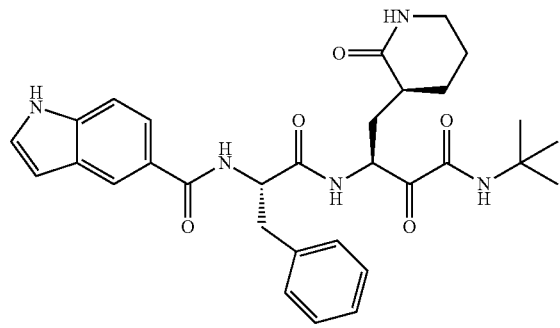 [SMILES: CC(C)(C)NC(=O)C(=O)[C@H](C[C@@H]1CCCNC1=O)NC(=O)[C@H](Cc1ccccc1)NC(=O)c1ccc2[nH]ccc2c1] |
| A173 | 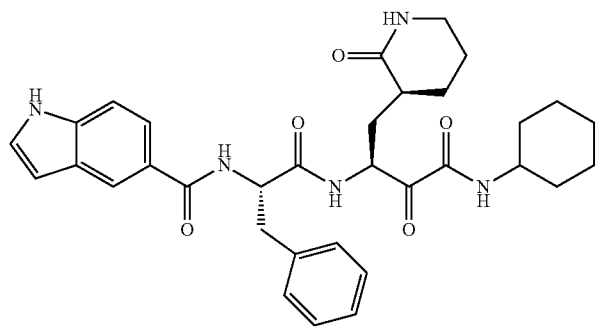 [SMILES: O=C(NC1CCCCC1)C(=O)[C@H](C[C@@H]1CCCNC1=O)NC(=O)[C@H](Cc1ccccc1)NC(=O)c1ccc2[nH]ccc2c1] |
| A174 | 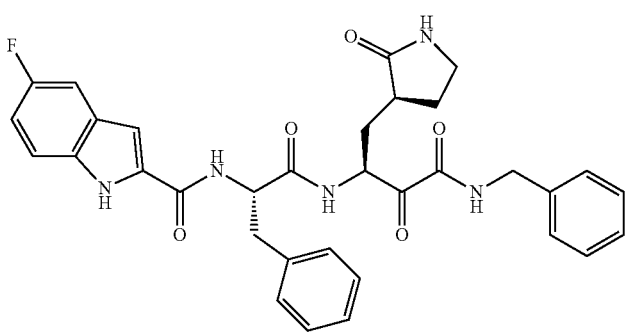 [SMILES: O=C(NCc1ccccc1)C(=O)[C@H](C[C@@H]1CCNC1=O)NC(=O)[C@H](Cc1ccccc1)NC(=O)c1cc2cc(F)ccc2[nH]1] |
| A175 | 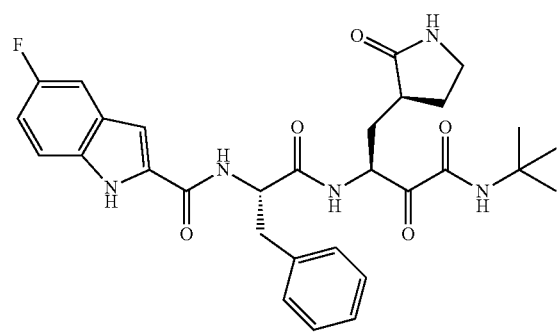 [SMILES: CC(C)(C)NC(=O)C(=O)[C@H](C[C@@H]1CCNC1=O)NC(=O)[C@H](Cc1ccccc1)NC(=O)c1cc2cc(F)ccc2[nH]1] |

| number | structure |
|---|---|
| A176 | 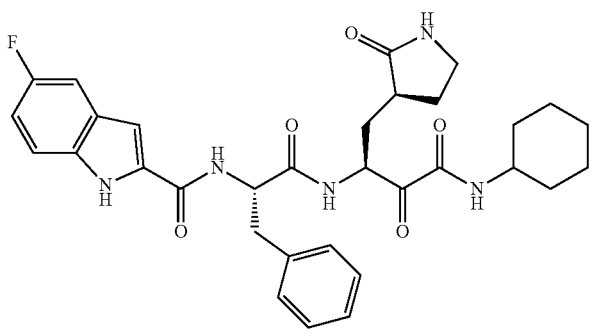 [SMILES: O=C(NC1CCCCC1)C(=O)[C@H](C[C@@H]1CCNC1=O)NC(=O)[C@H](Cc1ccccc1)NC(=O)c1cc2cc(F)ccc2[nH]1] |
| A177 | 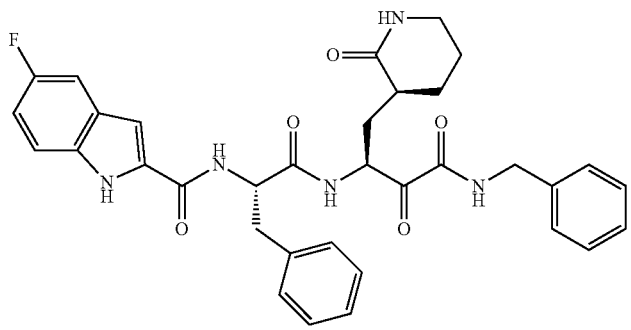 [SMILES: O=C(NCc1ccccc1)C(=O)[C@H](C[C@@H]1CCCNC1=O)NC(=O)[C@H](Cc1ccccc1)NC(=O)c1cc2cc(F)ccc2[nH]1] |
| A178 | 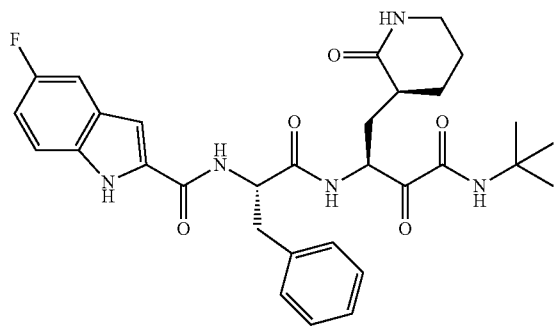 [SMILES: CC(C)(C)NC(=O)C(=O)[C@H](C[C@@H]1CCCNC1=O)NC(=O)[C@H](Cc1ccccc1)NC(=O)c1cc2cc(F)ccc2[nH]1] |
| A179 | 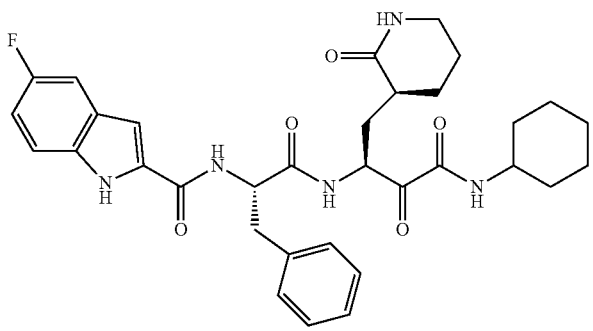 [SMILES: O=C(NC1CCCCC1)C(=O)[C@H](C[C@@H]1CCCNC1=O)NC(=O)[C@H](Cc1ccccc1)NC(=O)c1cc2cc(F)ccc2[nH]1] |

| number | structure |
|---|---|
| A180 | 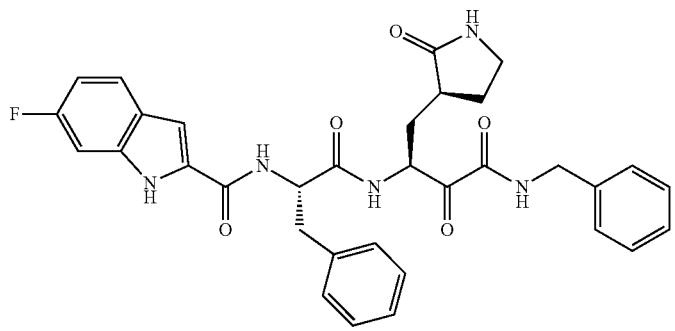 [SMILES: O=C(NCc1ccccc1)C(=O)[C@H](C[C@@H]1CCNC1=O)NC(=O)[C@H](Cc1ccccc1)NC(=O)c1cc2ccc(F)cc2[nH]1] |
| A181 | 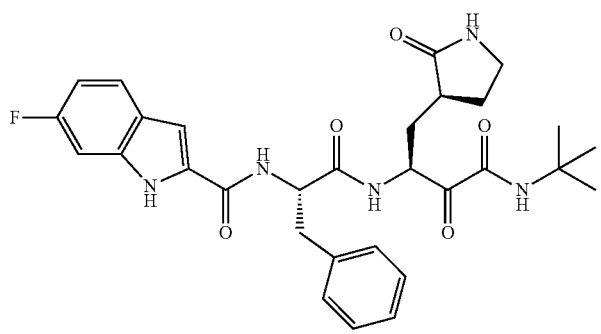 [SMILES: CC(C)(C)NC(=O)C(=O)[C@H](C[C@@H]1CCNC1=O)NC(=O)[C@H](Cc1ccccc1)NC(=O)c1cc2ccc(F)cc2[nH]1] |
| A182 | 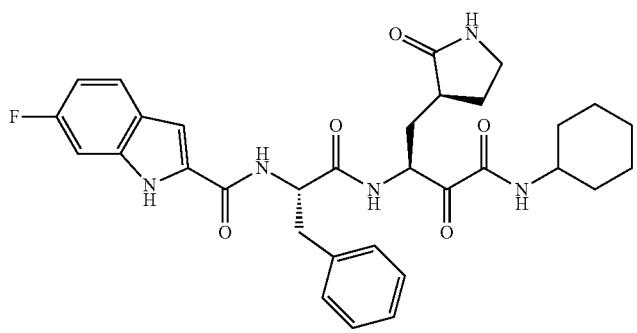 [SMILES: O=C(NC1CCCCC1)C(=O)[C@H](C[C@@H]1CCNC1=O)NC(=O)[C@H](Cc1ccccc1)NC(=O)c1cc2ccc(F)cc2[nH]1] |
| A183 | 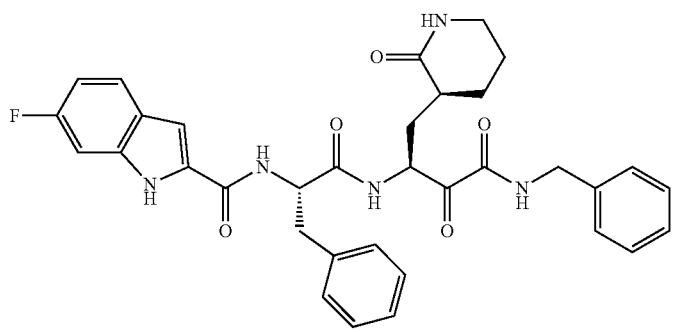 [SMILES: O=C(NCc1ccccc1)C(=O)[C@H](C[C@@H]1CCCNC1=O)NC(=O)[C@H](Cc1ccccc1)NC(=O)c1cc2ccc(F)cc2[nH]1] |

-continued
| number | structure |
|---|---|
| A184 | 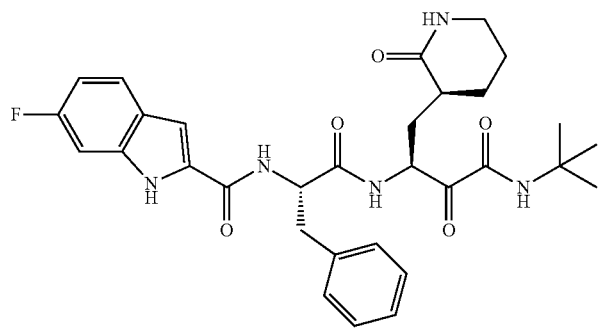 [SMILES: CC(C)(C)NC(=O)C(=O)[C@H](C[C@@H]1CCCNC1=O)NC(=O)[C@H](Cc1ccccc1)NC(=O)c1cc2ccc(F)cc2[nH]1] |
| A185 | 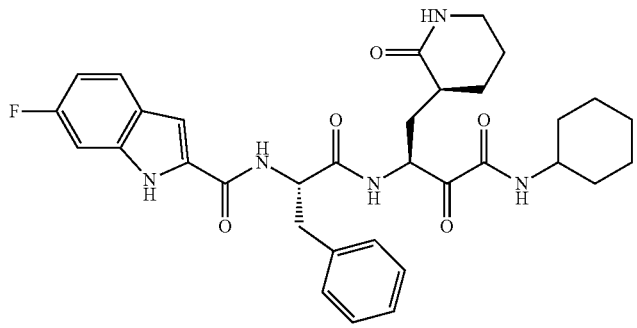 [SMILES: O=C(NC1CCCCC1)C(=O)[C@H](C[C@@H]1CCCNC1=O)NC(=O)[C@H](Cc1ccccc1)NC(=O)c1cc2ccc(F)cc2[nH]1] |
| A186 | 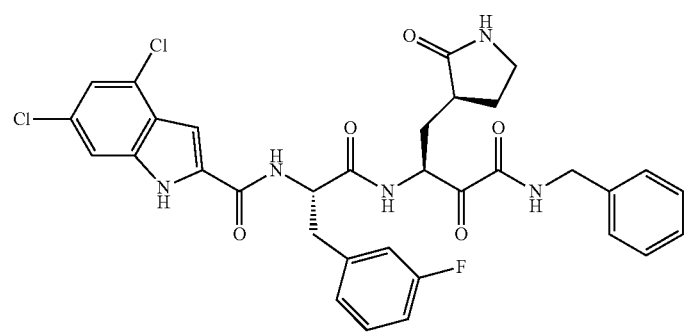 [SMILES: O=C(NCc1ccccc1)C(=O)[C@H](C[C@@H]1CCNC1=O)NC(=O)[C@H](Cc1cccc(F)c1)NC(=O)c1cc2c(Cl)cc(Cl)cc2[nH]1] |
| A187 | 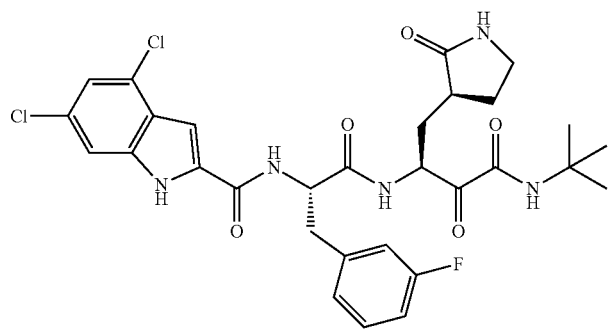 [SMILES: CC(C)(C)NC(=O)C(=O)[C@H](C[C@@H]1CCNC1=O)NC(=O)[C@H](Cc1cccc(F)c1)NC(=O)c1cc2c(Cl)cc(Cl)cc2[nH]1] |

| number | structure |
|---|---|
| A188 | 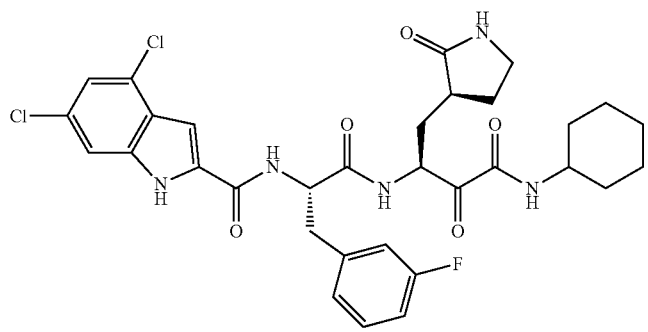 [SMILES: O=C(NC1CCCCC1)C(=O)[C@H](C[C@@H]1CCNC1=O)NC(=O)[C@H](Cc1cccc(F)c1)NC(=O)c1cc2c(Cl)cc(Cl)cc2[nH]1] |
| A189 | 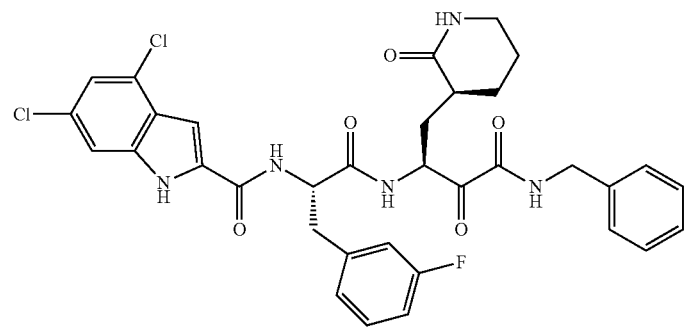 [SMILES: O=C(NCc1ccccc1)C(=O)[C@H](C[C@@H]1CCCNC1=O)NC(=O)[C@H](Cc1cccc(F)c1)NC(=O)c1cc2c(Cl)cc(Cl)cc2[nH]1] |
| A190 | 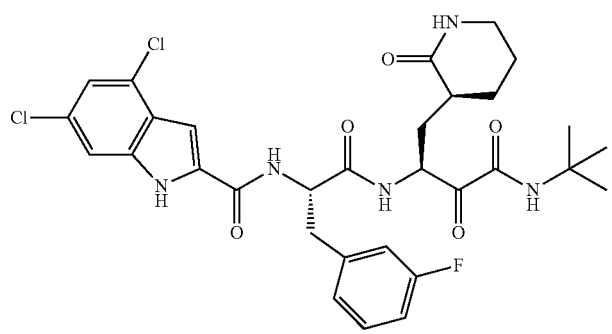 [SMILES: CC(C)(C)NC(=O)C(=O)[C@H](C[C@@H]1CCCNC1=O)NC(=O)[C@H](Cc1cccc(F)c1)NC(=O)c1cc2c(Cl)cc(Cl)cc2[nH]1] |
| A191 | 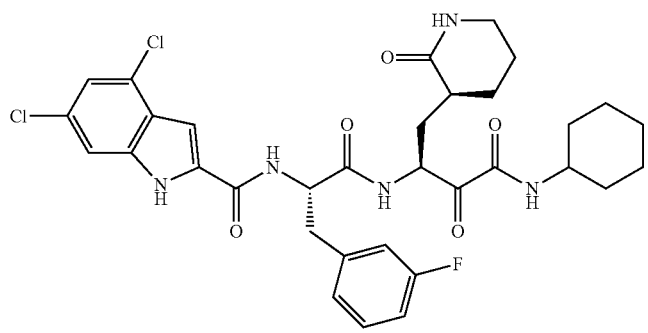 [SMILES: O=C(NC1CCCCC1)C(=O)[C@H](C[C@@H]1CCCNC1=O)NC(=O)[C@H](Cc1cccc(F)c1)NC(=O)c1cc2c(Cl)cc(Cl)cc2[nH]1] |

| number | structure |
|---|---|
| A192 | 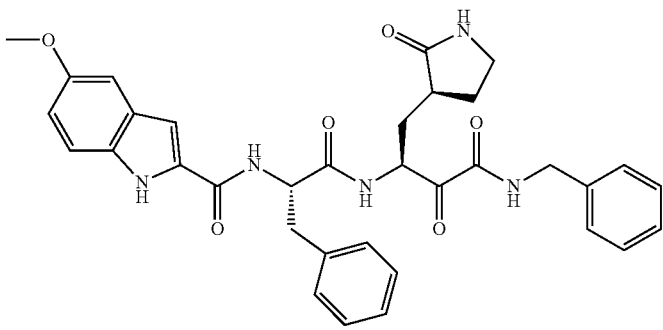 [SMILES: COc1ccc2[nH]c(C(=O)N[C@@H](Cc3ccccc3)C(=O)N[C@@H](C[C@@H]3CCNC3=O)C(=O)C(=O)NCc3ccccc3)cc2c1] |
| A193 | 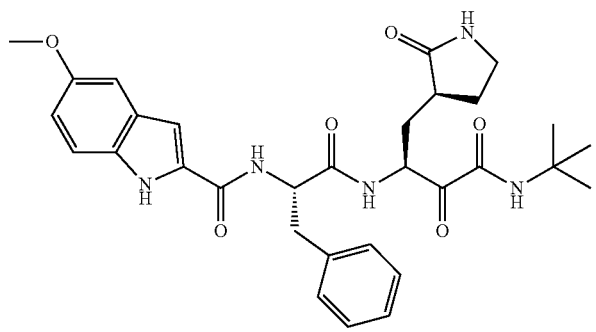 [SMILES: COc1ccc2[nH]c(C(=O)N[C@@H](Cc3ccccc3)C(=O)N[C@@H](C[C@@H]3CCNC3=O)C(=O)C(=O)NC(C)(C)C)cc2c1] |
| A194 | 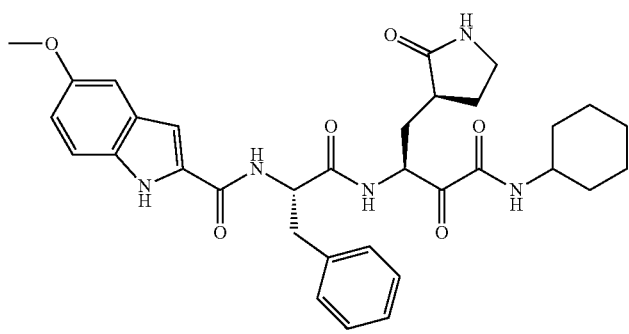 [SMILES: COc1ccc2[nH]c(C(=O)N[C@@H](Cc3ccccc3)C(=O)N[C@@H](C[C@@H]3CCNC3=O)C(=O)C(=O)NC3CCCCC3)cc2c1] |
| A195 | 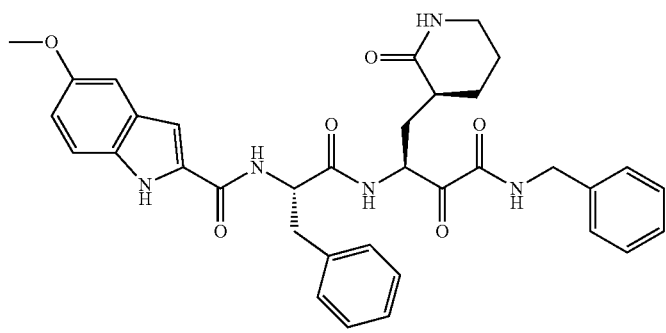 [SMILES: COc1ccc2[nH]c(C(=O)N[C@@H](Cc3ccccc3)C(=O)N[C@@H](C[C@@H]3CCCNC3=O)C(=O)C(=O)NCc3ccccc3)cc2c1] |

| number | structure |
|---|---|
| A196 | 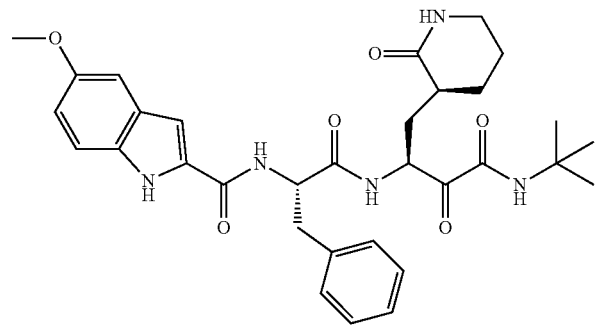 [SMILES: COc1ccc2[nH]c(C(=O)N[C@@H](Cc3ccccc3)C(=O)N[C@@H](C[C@@H]3CCCNC3=O)C(=O)C(=O)NC(C)(C)C)cc2c1] |
| A197 | 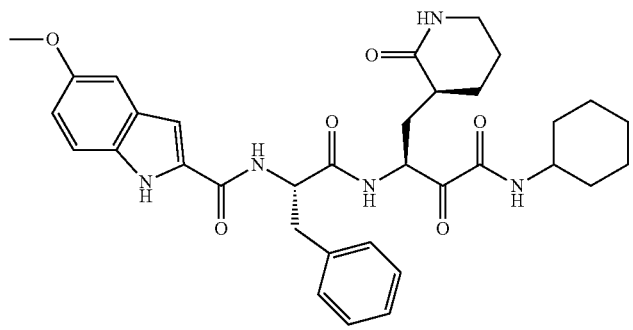 [SMILES: COc1ccc2[nH]c(C(=O)N[C@@H](Cc3ccccc3)C(=O)N[C@@H](C[C@@H]3CCCNC3=O)C(=O)C(=O)NC3CCCCC3)cc2c1] |
| A198 | 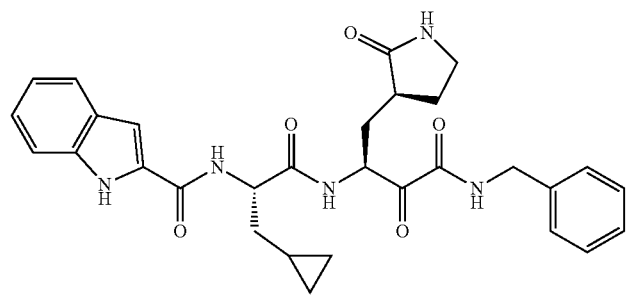 [SMILES: O=C(NCc1ccccc1)C(=O)[C@H](C[C@@H]1CCNC1=O)NC(=O)[C@H](CC1CC1)NC(=O)c1cc2ccccc2[nH]1] |
| A199 | 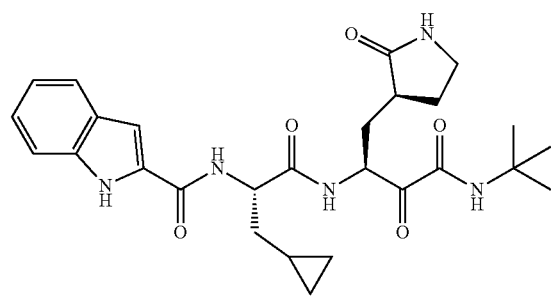 [SMILES: CC(C)(C)NC(=O)C(=O)[C@H](C[C@@H]1CCNC1=O)NC(=O)[C@H](CC1CC1)NC(=O)c1cc2ccccc2[nH]1] |
| A200 | 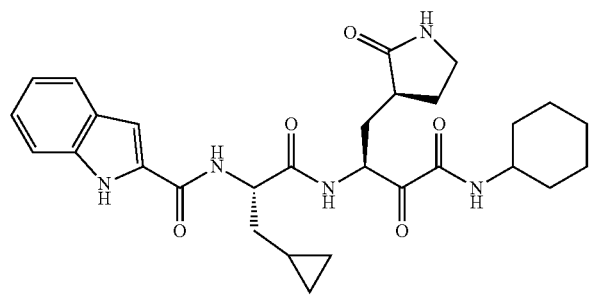 [SMILES: O=C(NC1CCCCC1)C(=O)[C@H](C[C@@H]1CCNC1=O)NC(=O)[C@H](CC1CC1)NC(=O)c1cc2ccccc2[nH]1] |

-continued
| number | structure |
|---|---|
| A201 | 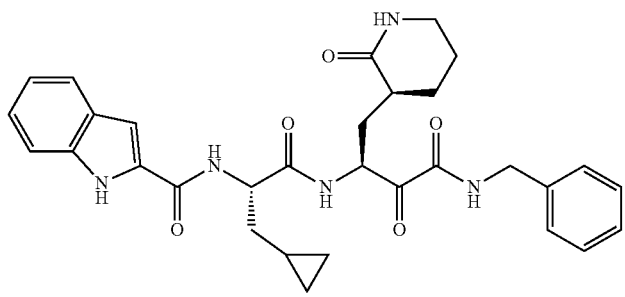 [SMILES: O=C(NCc1ccccc1)C(=O)[C@H](C[C@@H]1CCCNC1=O)NC(=O)[C@H](CC1CC1)NC(=O)c1cc2ccccc2[nH]1] |
| A202 | 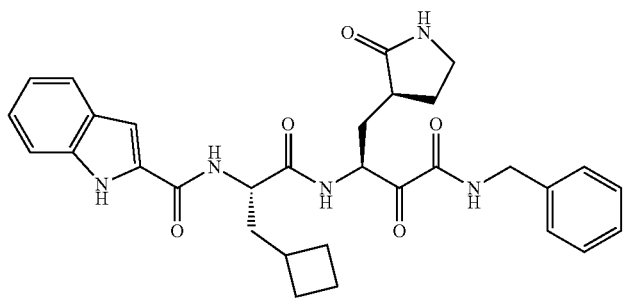 [SMILES: O=C(NCc1ccccc1)C(=O)[C@H](C[C@@H]1CCNC1=O)NC(=O)[C@H](CC1CCC1)NC(=O)c1cc2ccccc2[nH]1] |
| A203 | 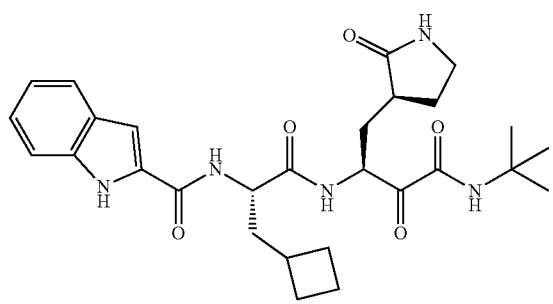 [SMILES: CC(C)(C)NC(=O)C(=O)[C@H](C[C@@H]1CCNC1=O)NC(=O)[C@H](CC1CCC1)NC(=O)c1cc2ccccc2[nH]1] |
| A204 | 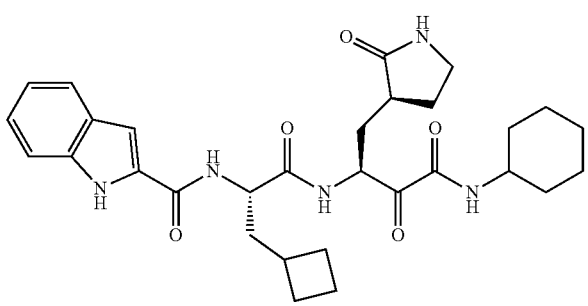 [SMILES: O=C(NC1CCCCC1)C(=O)[C@H](C[C@@H]1CCNC1=O)NC(=O)[C@H](CC1CCC1)NC(=O)c1cc2ccccc2[nH]1] |
| A205 | 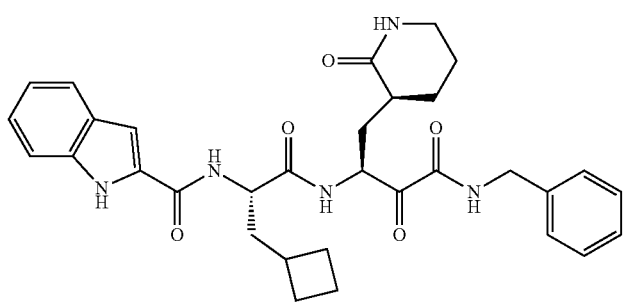 [SMILES: O=C(NCc1ccccc1)C(=O)[C@H](C[C@@H]1CCCNC1=O)NC(=O)[C@H](CC1CCC1)NC(=O)c1cc2ccccc2[nH]1] |

| number | structure |
|---|---|
| A206 | 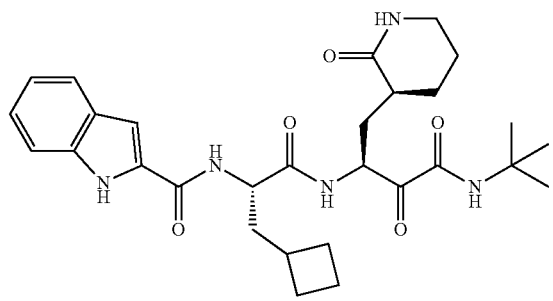 [SMILES: CC(C)(C)NC(=O)C(=O)[C@H](C[C@@H]1CCCNC1=O)NC(=O)[C@H](CC1CCC1)NC(=O)c1cc2ccccc2[nH]1] |
| A207 | 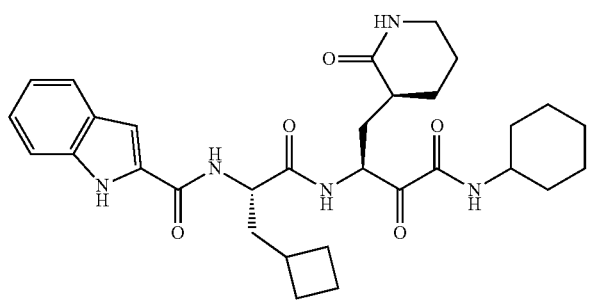 [SMILES: O=C(NC1CCCCC1)C(=O)[C@H](C[C@@H]1CCCNC1=O)NC(=O)[C@H](CC1CCC1)NC(=O)c1cc2ccccc2[nH]1] |
| A208 | 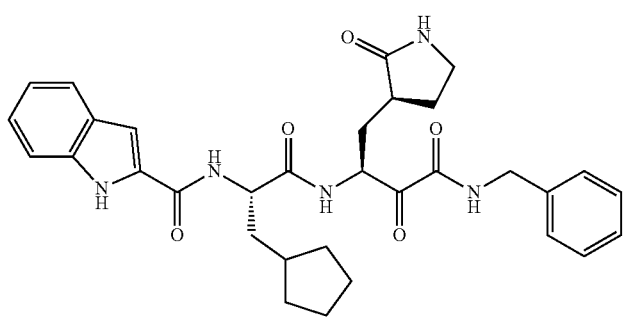 [SMILES: O=C(NCc1ccccc1)C(=O)[C@H](C[C@@H]1CCNC1=O)NC(=O)[C@H](CC1CCCC1)NC(=O)c1cc2ccccc2[nH]1] |
| A209 | 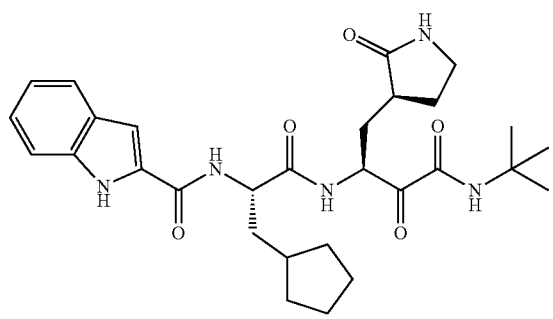 [SMILES: CC(C)(C)NC(=O)C(=O)[C@H](C[C@@H]1CCNC1=O)NC(=O)[C@H](CC1CCCC1)NC(=O)c1cc2ccccc2[nH]1] |
| A210 | 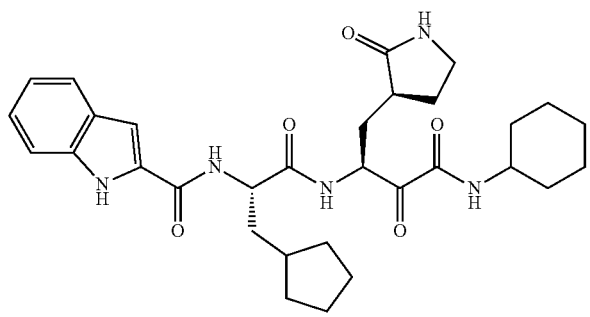 [SMILES: O=C(NC1CCCCC1)C(=O)[C@H](C[C@@H]1CCNC1=O)NC(=O)[C@H](CC1CCCC1)NC(=O)c1cc2ccccc2[nH]1] |

| number | structure |
|---|---|
| A211 | 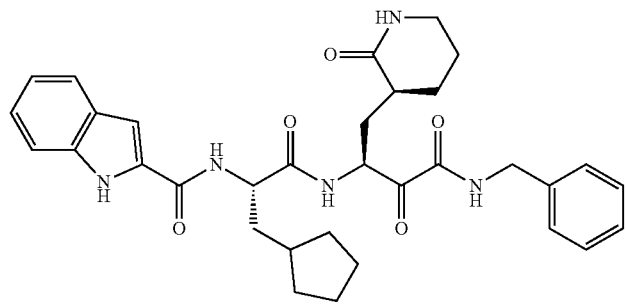 [SMILES: O=C(NCc1ccccc1)C(=O)[C@H](C[C@@H]1CCCNC1=O)NC(=O)[C@H](CC1CCCC1)NC(=O)c1cc2ccccc2[nH]1] |
| A212 | 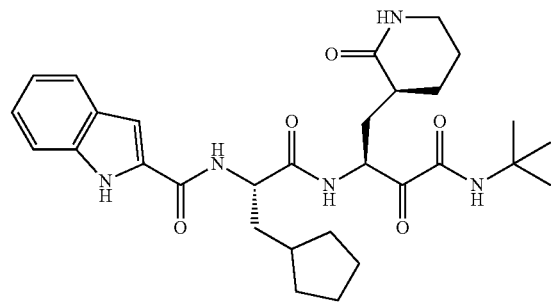 [SMILES: CC(C)(C)NC(=O)C(=O)[C@H](C[C@@H]1CCCNC1=O)NC(=O)[C@H](CC1CCCC1)NC(=O)c1cc2ccccc2[nH]1] |
| A213 | 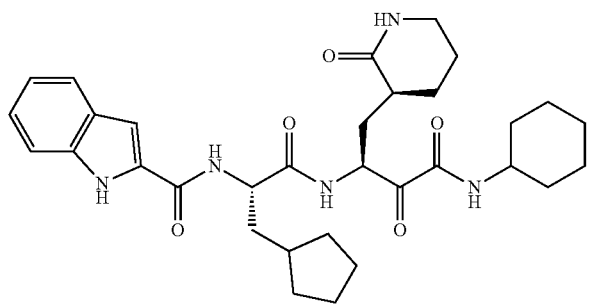 [SMILES: O=C(NC1CCCCC1)C(=O)[C@H](C[C@@H]1CCCNC1=O)NC(=O)[C@H](CC1CCCC1)NC(=O)c1cc2ccccc2[nH]1] |
| A220 | 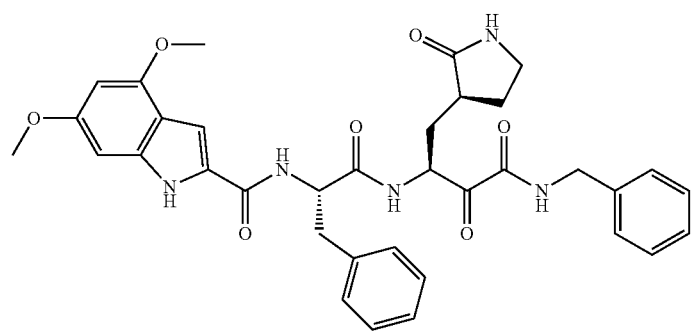 [SMILES: COc1cc(OC)c2cc(C(=O)N[C@@H](Cc3ccccc3)C(=O)N[C@@H](C[C@@H]3CCNC3=O)C(=O)C(=O)NCc3ccccc3)[nH]c2c1] |

| number | structure |
|---|---|
| A221 | 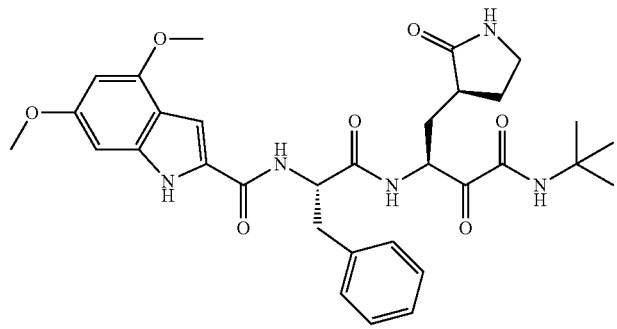 [SMILES: COc1cc(OC)c2cc(C(=O)N[C@@H](Cc3ccccc3)C(=O)N[C@@H](C[C@@H]3CCNC3=O)C(=O)C(=O)NC(C)(C)C)[nH]c2c1] |
| A222 | 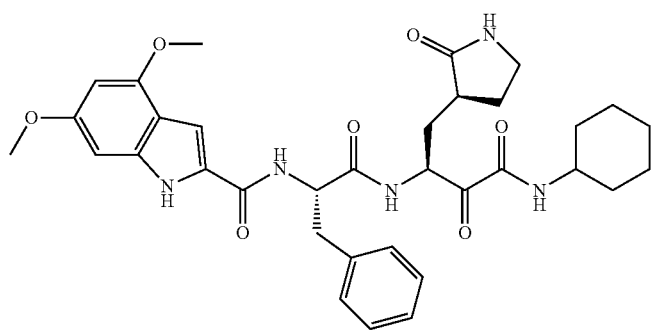 [SMILES: COc1cc(OC)c2cc(C(=O)N[C@@H](Cc3ccccc3)C(=O)N[C@@H](C[C@@H]3CCNC3=O)C(=O)C(=O)NC3CCCCC3)[nH]c2c1] |
| A223 | 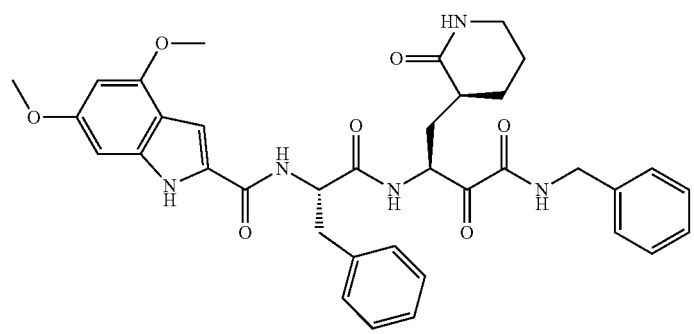 [SMILES: COc1cc(OC)c2cc(C(=O)N[C@@H](Cc3ccccc3)C(=O)N[C@@H](C[C@@H]3CCCNC3=O)C(=O)C(=O)NCc3ccccc3)[nH]c2c1] |
| A224 | 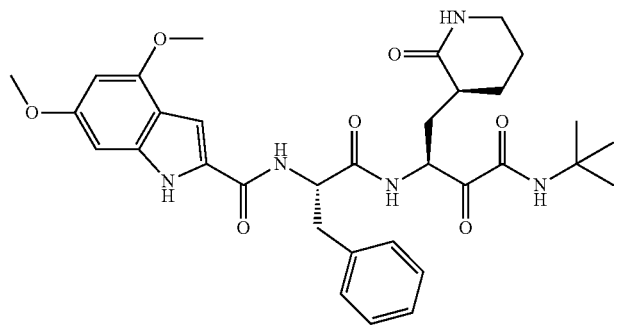 [SMILES: COc1cc(OC)c2cc(C(=O)N[C@@H](Cc3ccccc3)C(=O)N[C@@H](C[C@@H]3CCCNC3=O)C(=O)C(=O)NC(C)(C)C)[nH]c2c1] |

| number | structure |
|---|---|
| A225 | 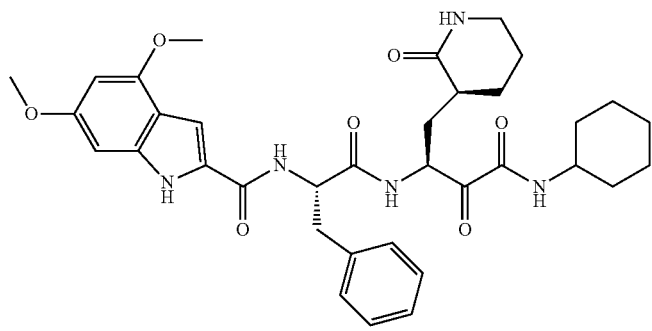 [SMILES: COc1cc(OC)c2cc(C(=O)N[C@@H](Cc3ccccc3)C(=O)N[C@@H](C[C@@H]3CCCNC3=O)C(=O)C(=O)NC3CCCCC3)[nH]c2c1] |
| A226 | 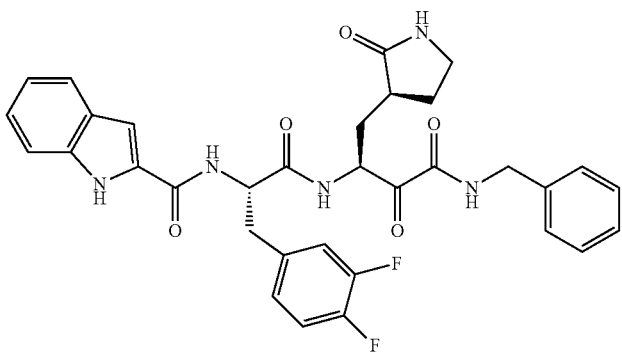 [SMILES: O=C(NCc1ccccc1)C(=O)[C@H](C[C@@H]1CCNC1=O)NC(=O)[C@H](Cc1ccc(F)c(F)c1)NC(=O)c1cc2ccccc2[nH]1] |
| A227 | 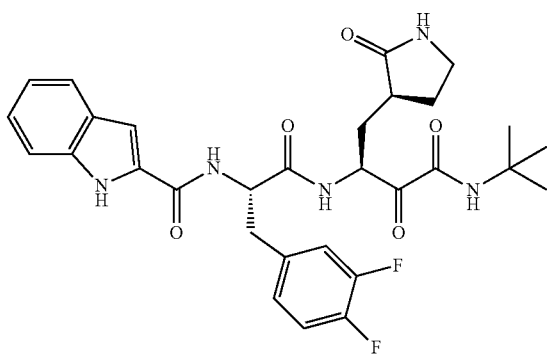 [SMILES: CC(C)(C)NC(=O)C(=O)[C@H](C[C@@H]1CCNC1=O)NC(=O)[C@H](Cc1ccc(F)c(F)c1)NC(=O)c1cc2ccccc2[nH]1] |
| A228 | 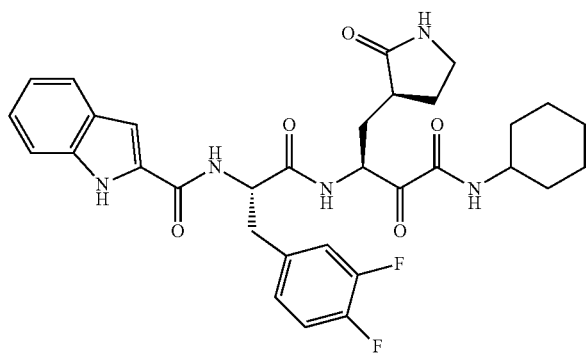 [SMILES: O=C(NC1CCCCC1)C(=O)[C@H](C[C@@H]1CCNC1=O)NC(=O)[C@H](Cc1ccc(F)c(F)c1)NC(=O)c1cc2ccccc2[nH]1] |

| number | structure |
|---|---|
| A229 | 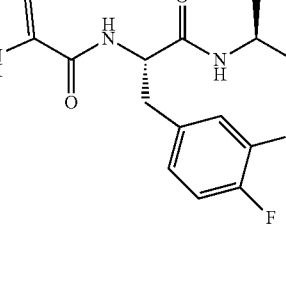 |
| A230 | 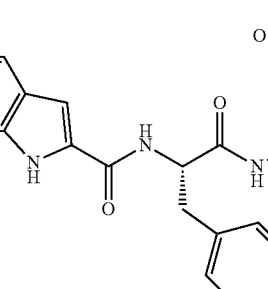 |
| A231 | 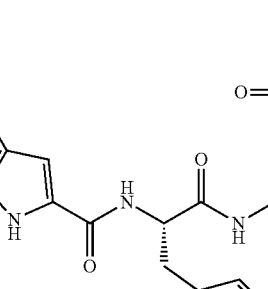 |
| A232 | 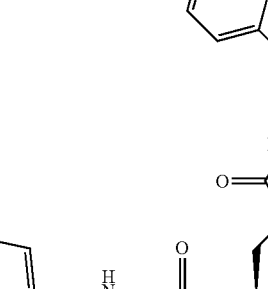 |

| number | structure |
|---|---|
| A233 | 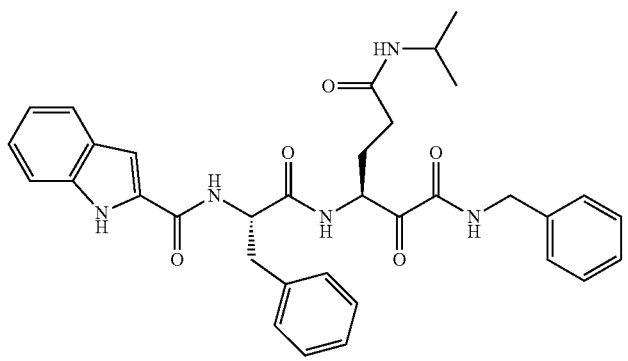 [SMILES: CC(C)NC(=O)CC[C@H](NC(=O)[C@H](Cc1ccccc1)NC(=O)c1cc2ccccc2[nH]1)C(=O)C(=O)NCc1ccccc1] |
| A234 | 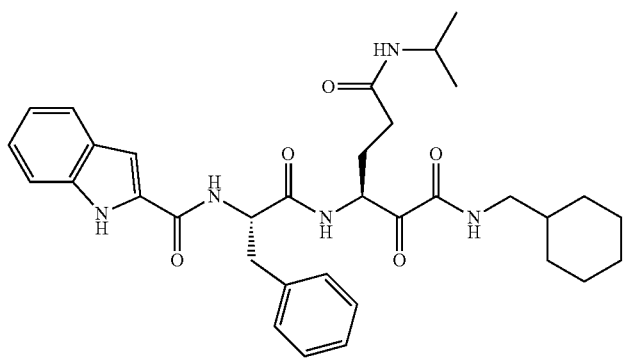 [SMILES: CC(C)NC(=O)CC[C@H](NC(=O)[C@H](Cc1ccccc1)NC(=O)c1cc2ccccc2[nH]1)C(=O)C(=O)NCC1CCCCC1] |
| A235 | 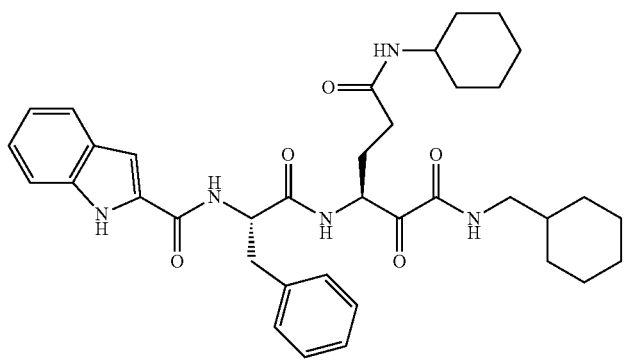 [SMILES: O=C(CC[C@H](NC(=O)[C@H](Cc1ccccc1)NC(=O)c1cc2ccccc2[nH]1)C(=O)C(=O)NCC1CCCCC1)NC1CCCCC1] |
| A236 | 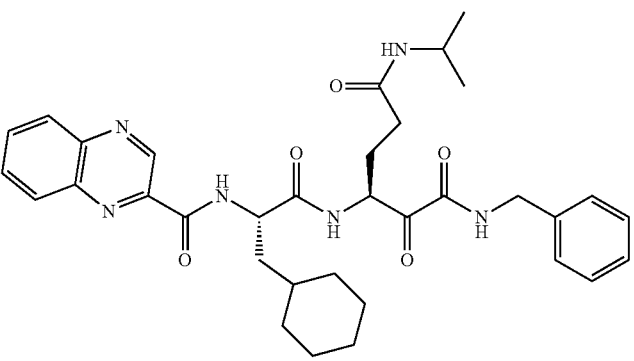 [SMILES: CC(C)NC(=O)CC[C@H](NC(=O)[C@H](CC1CCCCC1)NC(=O)c1cnc2ccccc2n1)C(=O)C(=O)NCc1ccccc1] |

| number | structure |
|---|---|
| A237 | 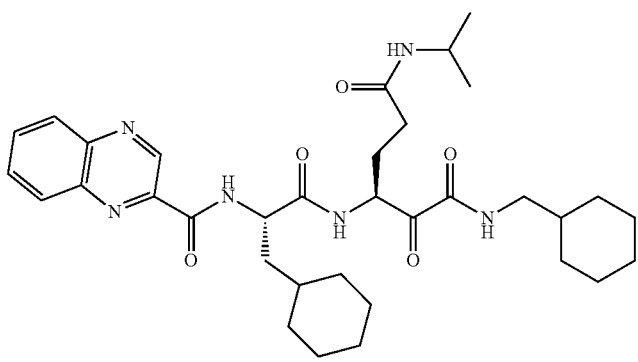 [SMILES: CC(C)NC(=O)CC[C@H](NC(=O)[C@H](CC1CCCCC1)NC(=O)c1cnc2ccccc2n1)C(=O)C(=O)NCC1CCCCC1] |
| A238 | 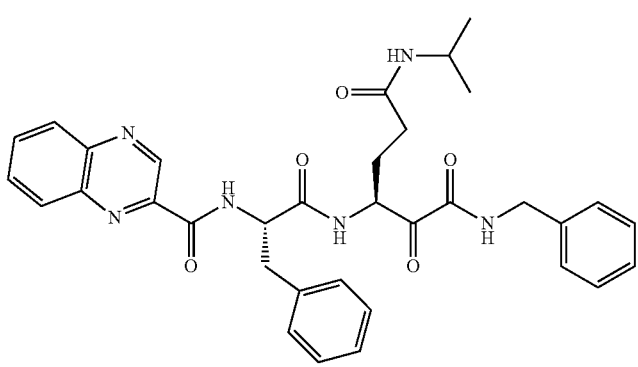 [SMILES: CC(C)NC(=O)CC[C@H](NC(=O)[C@H](Cc1ccccc1)NC(=O)c1cnc2ccccc2n1)C(=O)C(=O)NCc1ccccc1] |
| A239 | 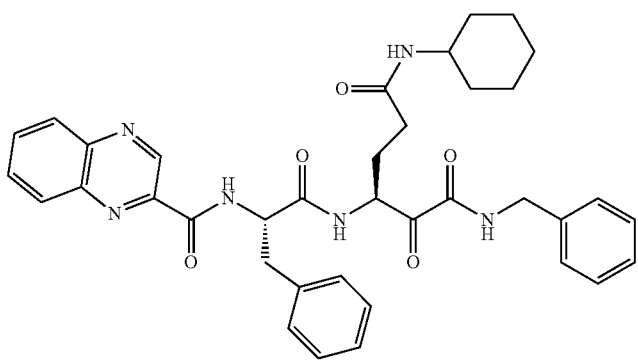 [SMILES: O=C(CC[C@H](NC(=O)[C@H](Cc1ccccc1)NC(=O)c1cnc2ccccc2n1)C(=O)C(=O)NCc1ccccc1)NC1CCCCC1] |
| A240 | 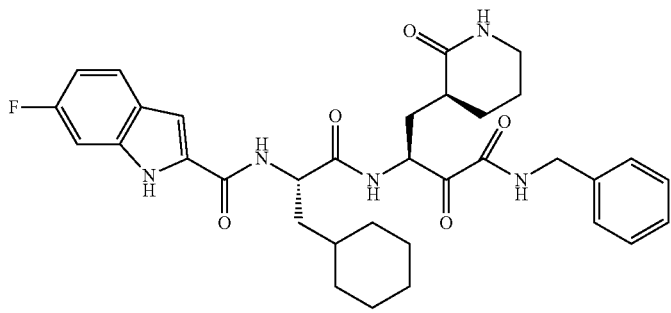 [SMILES: O=C(NCc1ccccc1)C(=O)[C@H](C[C@@H]1CCCNC1=O)NC(=O)[C@H](CC1CCCCC1)NC(=O)c1cc2ccc(F)cc2[nH]1] |

| number | structure |
|---|---|
| A245 | 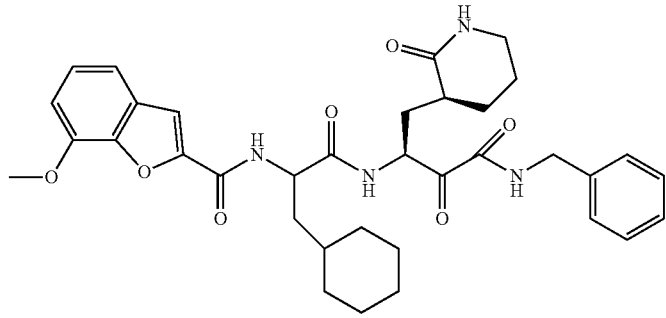 [SMILES: COc1cccc2cc(C(=O)NC(CC3CCCCC3)C(=O)N[C@@H](C[C@@H]3CCCNC3=O)C(=O)C(=O)NCc3ccccc3)oc12] |
| A246 | 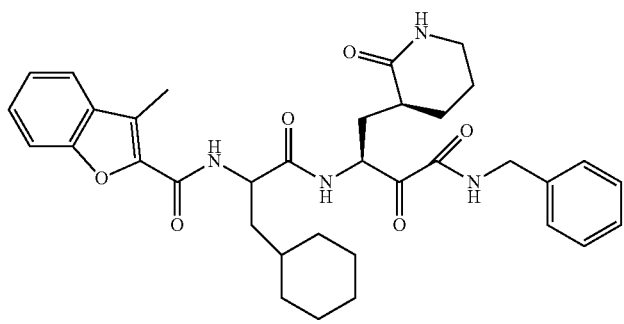 [SMILES: Cc1c(C(=O)NC(CC2CCCCC2)C(=O)N[C@@H](C[C@@H]2CCCNC2=O)C(=O)C(=O)NCc2ccccc2)oc2ccccc12] |
| A247 | 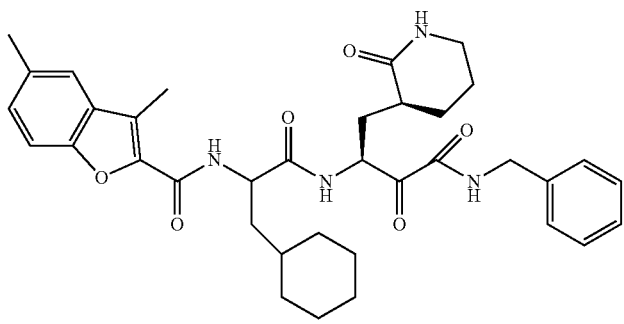 [SMILES: Cc1ccc2oc(C(=O)NC(CC3CCCCC3)C(=O)N[C@@H](C[C@@H]3CCCNC3=O)C(=O)C(=O)NCc3ccccc3)c(C)c2c1] |
| A248 | 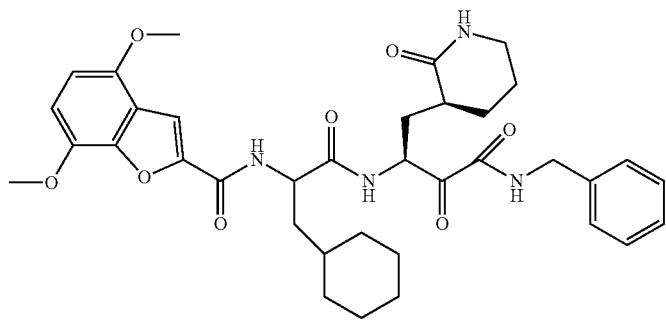 [SMILES: COc1ccc(OC)c2oc(C(=O)NC(CC3CCCCC3)C(=O)N[C@@H](C[C@@H]3CCCNC3=O)C(=O)C(=O)NCc3ccccc3)cc12] |

| number | structure |
|---|---|
| A249 | 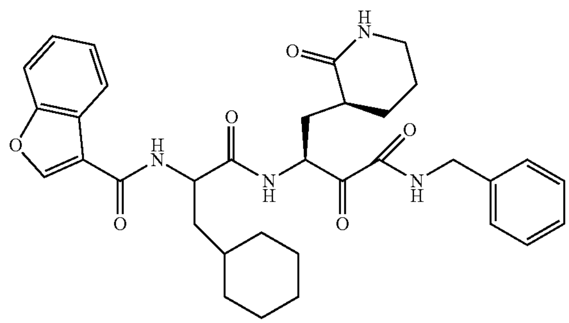 [SMILES: O=C(NCc1ccccc1)C(=O)[C@H](C[C@@H]1CCCNC1=O)NC(=O)C(CC1CCCCC1)NC(=O)c1coc2ccccc12] |
| A250 | 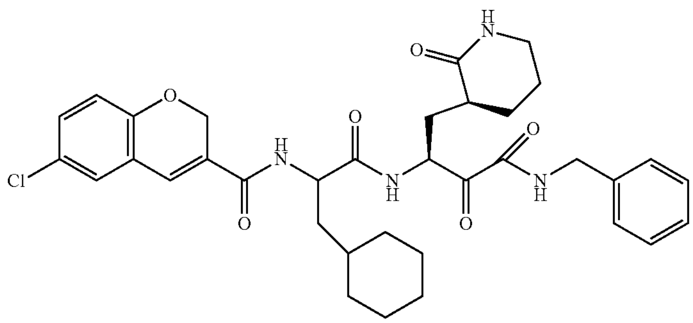 [SMILES: O=C(NCc1ccccc1)C(=O)[C@H](C[C@@H]1CCCNC1=O)NC(=O)C(CC1CCCCC1)NC(=O)C1=Cc2cc(Cl)ccc2OC1] |
| A253 | | or a racemate, an enantiomer, a diastereomer, or a mixture thereof, or a pharmaceutically active metabolite, or a pharmaceutically acceptable salt, a solvate or a prodrug thereof.

7. A method for preparing the compound, or the racemate, the enantiomer, the diastereomer, or the mixture thereof, or the pharmaceutically active metabolite, or the pharmaceutically acceptable salt, the solvate or the prodrug thereof according to claim 1, which comprises the following step:

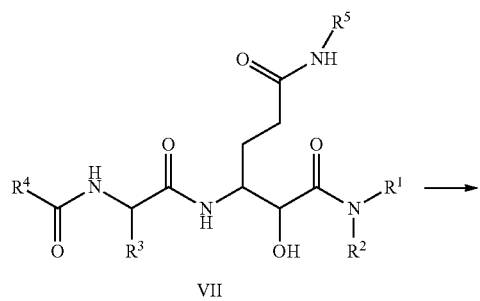

VII

→

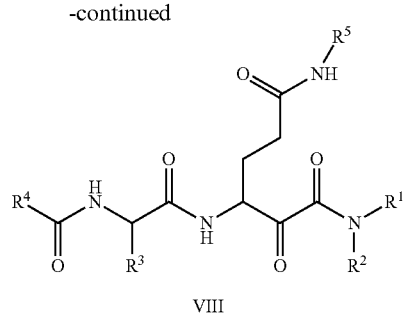

VIII in an inert solvent, oxidizing compound VII with an oxidant to obtain compound VIII;
in the above formulas, $R^1$, $R^2$, $R^3$, $R^4$, $R^5$ and n are as defined in claim 1.

8. A pharmaceutical composition, which comprises the following components:
i) a therapeutically effective amount of one or more of the compound, or the racemate, the enantiomer, the diastereomer, or the mixture thereof, or the pharmaceutically active metabolite, or the pharmaceutically acceptable salt, the solvate or the prodrug thereof according to claim 1; and ii) a pharmaceutically acceptable carrier or excipient.

9. A method for the treatment of a disease related to coronavirus or a disease related to Ebola virus comprising a step of administrating a therapeutically effective amount of the compound, or the racemate, the enantiomer, the diastereomer, or the mixture thereof, or the pharmaceutically active metabolite, or the pharmaceutically acceptable salt, the solvate or the prodrug thereof according to claim 1 to a subject in need thereof;

wherein the disease related to coronavirus is selected from the group consisting of common cold, upper respiratory tract infection, severe acute respiratory syndrome, multiple sclerosis, otitis media and gastrointestinal disorder;

the disease related to Ebola virus is selected from the group consisting of hemorrhagic fever, acute onset fever, myalgia and bleeding rash.

10. The method of claim 9, wherein the coronavirus is selected from the group consisting of SARS virus and MERS virus.

\* \* \* \* \*